(12) United States Patent
Lowery, Jr. et al.

(10) Patent No.: US 9,714,940 B2
(45) Date of Patent: *Jul. 25, 2017

(54) NMR SYSTEMS AND METHODS FOR THE RAPID DETECTION OF ANALYTES

(75) Inventors: Thomas Jay Lowery, Jr., Belmont, MA (US); Mark John Audeh, Brighton, MA (US); Matthew Blanco, Brookline, MA (US); James Franklin Chepin, San Diego, CA (US); Vasiliki Demas, Arlington, MA (US); Rahul Dhanda, Needham, MA (US); Lori Anne Neely, Reading, MA (US)

(73) Assignee: T2 Biosystems, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/384,051

(22) PCT Filed: Oct. 19, 2011

(86) PCT No.: PCT/US2011/056936
§ 371 (c)(1),
(2), (4) Date: Jun. 20, 2013

(87) PCT Pub. No.: WO2012/054639
PCT Pub. Date: Apr. 26, 2012

(65) Prior Publication Data
US 2013/0260367 A1   Oct. 3, 2013

Related U.S. Application Data

(63) Continuation-in-part of application No. 12/910,594, filed on Oct. 22, 2010, now Pat. No. 8,563,298.

(60) Provisional application No. 61/414,141, filed on Nov. 16, 2010, provisional application No. 61/418,465, filed on Dec. 1, 2010, provisional application No. 61/497,374, filed on Jun. 15, 2011.

(51) Int. Cl.
| | | |
|---|---|---|
| G01N 33/543 | (2006.01) | |
| G01N 33/94 | (2006.01) | |
| G01N 24/08 | (2006.01) | |
| G01N 27/74 | (2006.01) | |
| B82Y 25/00 | (2011.01) | |
| C12Q 1/68 | (2006.01) | |
| C12Q 1/70 | (2006.01) | |
| G01R 33/09 | (2006.01) | |
| G01R 33/12 | (2006.01) | |
| G01R 33/28 | (2006.01) | |
| G01R 33/30 | (2006.01) | |
| G01R 33/44 | (2006.01) | |

(52) U.S. Cl.
CPC ........ *G01N 33/54326* (2013.01); *B82Y 25/00* (2013.01); *C12Q 1/689* (2013.01); *C12Q 1/6825* (2013.01); *C12Q 1/6827* (2013.01); *C12Q 1/6895* (2013.01); *C12Q 1/70* (2013.01); *C12Q 1/701* (2013.01); *G01N 24/08* (2013.01); *G01N 27/745* (2013.01); *G01N 33/5434* (2013.01); *G01N 33/9493* (2013.01); *G01R 33/093* (2013.01); *G01R 33/1269* (2013.01); *G01R 33/281* (2013.01); *G01R 33/302* (2013.01); *G01R 33/448* (2013.01)

(58) Field of Classification Search
None
See application file for complete search history.

(56) References Cited

U.S. PATENT DOCUMENTS

| | | |
|---|---|---|
| 4,101,435 A | 7/1978 | Hasegawa et al. |
| 4,295,613 A | 10/1981 | Moore et al. |
| 4,374,360 A | 2/1983 | Sepponen |
| 4,452,773 A | 6/1984 | Molday |
| 4,471,306 A | 9/1984 | Edelstein et al. |
| 4,485,177 A | 11/1984 | Siedel et al. |
| 4,578,361 A | 3/1986 | Siedel et al. |
| 4,683,195 A | 7/1987 | Mullis et al. |
| 4,683,202 A | 7/1987 | Mullis |
| 4,745,077 A | 5/1988 | Holian et al. |
| 4,875,486 A | 10/1989 | Rapoport et al. |
| 4,889,818 A | 12/1989 | Gelfand et al. |
| 4,920,061 A | 4/1990 | Poynton et al. |
| 4,965,188 A | 10/1990 | Mullis et al. |
| 5,038,852 A | 8/1991 | Johnson et al. |
| 5,049,819 A | 9/1991 | Dechene et al. |
| 5,066,584 A | 11/1991 | Gyllensten et al. |
| 5,079,352 A | 1/1992 | Gelfand et al. |
| 5,135,875 A | 8/1992 | Meucci et al. |
| 5,136,095 A | 8/1992 | Tarnowski et al. |
| 5,164,297 A | 11/1992 | Josephson et al. |
| 5,164,495 A | 11/1992 | Lunetta |
| 5,204,457 A | 4/1993 | Maruno et al. |
| 5,229,297 A | 7/1993 | Schnipelsky et al. |

(Continued)

FOREIGN PATENT DOCUMENTS

| | | |
|---|---|---|
| BY | 6388 C1 | 9/2004 |
| EP | 0574267 A2 | 12/1993 |

(Continued)

OTHER PUBLICATIONS

Liu et al. Analytical Chemistry (2004) 76: 1824-1831.*
Khlif et al. Journal of Medical Mycology (2007) 17: 256-260.*
Extended European Search Report for European Application No. 11835088.3, dated Mar. 19, 2014 (11 pages).
Tsukamoto et al., "Development of a SQUID system using field reversal for rapidly detecting bacteria," IEEE Transactions on Applied Superconductivity. 19(3):853-856 (2009).
U.S. Appl. No. 13/646,402, filed Jan. 31, 2013, Neely et al.
U.S. Appl. No. 13/649,839, Neely et al.
U.S. Appl. No. 13/846,411, Neely et al.
U.S. Appl. No. 13/852,739, Neely et al.

(Continued)

*Primary Examiner* — Angela M Bertagna
(74) *Attorney, Agent, or Firm* — Clark & Elbing LLP

(57) ABSTRACT

This invention features systems and methods for the detection of analytes, and their use in the treatment and diagnosis of disease.

18 Claims, 57 Drawing Sheets

(56) References Cited

U.S. PATENT DOCUMENTS

| | | |
|---|---|---|
| 5,247,076 A | 9/1993 | Goulet et al. |
| 5,252,732 A | 10/1993 | Sinclair et al. |
| 5,254,460 A | 10/1993 | Josephson et al. |
| 5,262,176 A | 11/1993 | Palmacci et al. |
| 5,333,675 A | 8/1994 | Mullis et al. |
| 5,338,684 A | 8/1994 | Grenier et al. |
| 5,352,600 A | 10/1994 | Gelfand et al. |
| 5,424,419 A | 6/1995 | Hasegawa et al. |
| 5,426,026 A | 6/1995 | Jordan |
| 5,426,027 A | 6/1995 | Lott et al. |
| 5,436,149 A | 7/1995 | Barnes |
| 5,445,970 A | 8/1995 | Rohr |
| 5,445,971 A | 8/1995 | Rohr |
| 5,475,610 A | 12/1995 | Atwood et al. |
| 5,492,814 A | 2/1996 | Weissleder |
| 5,508,164 A | 4/1996 | Kausch et al. |
| 5,512,439 A | 4/1996 | Hornes et al. |
| 5,532,137 A | 7/1996 | Niwa et al. |
| 5,543,305 A | 8/1996 | Cummins et al. |
| 5,578,325 A | 11/1996 | Domb et al. |
| 5,599,498 A | 2/1997 | Oh |
| 5,618,926 A | 4/1997 | Salamone et al. |
| 5,635,353 A | 6/1997 | Lott et al. |
| 5,635,406 A | 6/1997 | Grenier et al. |
| 5,637,469 A | 6/1997 | Wilding et al. |
| 5,650,288 A | 7/1997 | MacFarlane et al. |
| 5,656,493 A | 8/1997 | Mullis et al. |
| 5,677,133 A | 10/1997 | Oberhardt |
| 5,688,644 A | 11/1997 | Lott et al. |
| 5,698,448 A | 12/1997 | Soldin |
| 5,705,628 A | 1/1998 | Hawkins |
| 5,708,159 A | 1/1998 | Ohno et al. |
| 5,711,871 A | 1/1998 | Miltenyi |
| 5,773,307 A | 6/1998 | Colin et al. |
| 5,776,696 A | 7/1998 | Salowe |
| 5,801,003 A | 9/1998 | Shimamura et al. |
| 5,804,375 A | 9/1998 | Gelfand et al. |
| 5,837,501 A | 11/1998 | Beumer et al. |
| 5,858,534 A | 1/1999 | Sucholeiki |
| 5,898,071 A | 4/1999 | Hawkins |
| 5,910,409 A | 6/1999 | Bhattacharjee et al. |
| 5,935,825 A | 8/1999 | Nishimura et al. |
| 5,973,138 A | 10/1999 | Collis et al. |
| 5,994,056 A | 11/1999 | Higuchi et al. |
| 6,007,845 A | 12/1999 | Domb et al. |
| 6,013,188 A | 1/2000 | Terstappen et al. |
| 6,020,211 A | 2/2000 | Tuunanen |
| 6,030,845 A | 2/2000 | Yamao et al. |
| 6,040,166 A | 3/2000 | Erlich et al. |
| 6,097,188 A | 8/2000 | Sweedler et al. |
| 6,123,902 A | 9/2000 | Koch et al. |
| 6,127,155 A | 10/2000 | Gelfand et al. |
| 6,130,045 A | 10/2000 | Wurst et al. |
| 6,136,549 A | 10/2000 | Feistel |
| 6,143,578 A | 11/2000 | Bendele et al. |
| 6,159,378 A | 12/2000 | Holman et al. |
| 6,165,378 A | 12/2000 | Maruno et al. |
| 6,187,547 B1 | 2/2001 | Legay et al. |
| 6,194,900 B1 | 2/2001 | Freeman et al. |
| 6,197,563 B1 | 3/2001 | Erlich et al. |
| 6,235,890 B1 | 5/2001 | Morrison et al. |
| 6,294,342 B1 | 9/2001 | Rohr et al. |
| 6,297,062 B1 | 10/2001 | Gombinski |
| 6,338,946 B1 | 1/2002 | Kobayashi et al. |
| 6,342,396 B1 | 1/2002 | Perrin et al. |
| 6,346,813 B1 | 2/2002 | Kleinberg |
| 6,361,944 B1 | 3/2002 | Mirkin et al. |
| 6,423,490 B1 | 7/2002 | Takama |
| 6,456,072 B1 | 9/2002 | Webb et al. |
| 6,489,767 B1 | 12/2002 | Prado et al. |
| 6,500,343 B2 | 12/2002 | Siddiqi |
| 6,514,736 B1 | 2/2003 | Erlich et al. |
| 6,548,311 B1 | 4/2003 | Knoll |
| 6,566,086 B1 | 5/2003 | Al Athel et al. |
| 6,599,498 B1 | 7/2003 | Groman et al. |
| 6,605,439 B2 | 8/2003 | Einsele |
| 6,630,355 B1 | 10/2003 | Pivarnik et al. |
| 6,654,636 B1 | 11/2003 | Dev et al. |
| 6,686,195 B1 | 2/2004 | Colin et al. |
| 6,686,454 B1 | 2/2004 | Yatscoff et al. |
| 6,767,635 B1 | 7/2004 | Bahr et al. |
| 6,768,305 B1 | 7/2004 | Keifer |
| 6,788,061 B1 | 9/2004 | Sweedler et al. |
| 6,822,452 B2 | 11/2004 | Ham et al. |
| 6,822,454 B2 | 11/2004 | Peck et al. |
| 6,866,838 B1 | 3/2005 | Mondain-Monval et al. |
| 6,872,523 B1 | 3/2005 | Iwen et al. |
| 6,884,357 B2 | 4/2005 | Siddiqi |
| 6,890,765 B2 | 5/2005 | Lawrence et al. |
| 6,940,378 B2 | 9/2005 | Miller et al. |
| 6,958,609 B2 | 10/2005 | Raftery et al. |
| 7,001,589 B2 | 2/2006 | Mondain-Monval et al. |
| 7,018,849 B2 | 3/2006 | Piasio et al. |
| 7,037,688 B2 | 5/2006 | Salituro et al. |
| 7,049,558 B2 | 5/2006 | Baer et al. |
| 7,078,495 B1 | 7/2006 | Kasper et al. |
| 7,164,077 B2 | 1/2007 | Venkatasubramanian |
| 7,169,556 B2 | 1/2007 | Park et al. |
| 7,186,518 B2 | 3/2007 | Wang et al. |
| 7,200,430 B2 | 4/2007 | Thomas et al. |
| 7,217,457 B2 | 5/2007 | Elaissari et al. |
| 7,217,542 B2 | 5/2007 | Tyvoll et al. |
| 7,274,191 B2 | 9/2007 | Park et al. |
| D556,338 S | 11/2007 | Coulling et al. |
| 7,332,353 B2 | 2/2008 | Baudry et al. |
| 7,397,241 B2 | 7/2008 | Gauthausen et al. |
| 7,459,145 B2 | 12/2008 | Bao et al. |
| 7,462,475 B2 | 12/2008 | Kermekchiev et al. |
| 7,494,771 B2 | 2/2009 | Picard et al. |
| 7,517,457 B2 | 4/2009 | Siddiqi |
| 7,553,542 B2 | 6/2009 | Ou et al. |
| 7,560,923 B2 | 7/2009 | Viswanathan |
| 7,564,245 B2 | 7/2009 | Lee |
| 7,575,875 B2 | 8/2009 | Konrath et al. |
| 7,615,381 B2 | 11/2009 | Masters et al. |
| 7,651,837 B2 | 1/2010 | Ohno et al. |
| 7,670,780 B2 | 3/2010 | Hogan et al. |
| 7,723,095 B2 | 5/2010 | Cleuziat et al. |
| 7,781,228 B2 | 8/2010 | Menon et al. |
| D628,306 S | 11/2010 | Blanc et al. |
| 7,829,350 B2 | 11/2010 | Josephson et al. |
| 7,906,286 B2 | 3/2011 | Fukui et al. |
| 8,044,001 B2 | 10/2011 | Putzig |
| 8,049,001 B2 | 11/2011 | Tomatsu et al. |
| 8,409,807 B2 | 4/2013 | Neely et al. |
| 8,563,298 B2 * | 10/2013 | Lowery, Jr. .......... C12Q 1/6895 422/68.1 |
| 9,046,493 B2 | 6/2015 | Neely et al. |
| 9,488,648 B2 * | 11/2016 | Neely .................... B82Y 25/00 |
| 2002/0051974 A1 | 5/2002 | Dodge et al. |
| 2003/0054370 A1 | 3/2003 | Zeng et al. |
| 2003/0069180 A1 | 4/2003 | Jiang et al. |
| 2003/0092029 A1 | 5/2003 | Josephson et al. |
| 2003/0207296 A1 | 11/2003 | Park et al. |
| 2003/0216638 A1 | 11/2003 | Dharmakumar et al. |
| 2003/0222648 A1 | 12/2003 | Fan |
| 2004/0018611 A1 | 1/2004 | Ward et al. |
| 2004/0076990 A1 * | 4/2004 | Picard et al. .................. 435/6 |
| 2004/0166492 A1 | 8/2004 | Engel et al. |
| 2005/0176080 A1 | 8/2005 | Bodepudi et al. |
| 2006/0051770 A1 | 3/2006 | Makeev |
| 2006/0269965 A1 | 11/2006 | Josephson et al. |
| 2007/0027309 A1 | 2/2007 | Weinstock et al. |
| 2007/0083945 A1 | 4/2007 | Byrum et al. |
| 2007/0111330 A1 | 5/2007 | Hong et al. |
| 2007/0116602 A1 | 5/2007 | Lee |
| 2007/0166730 A1 | 7/2007 | Menon et al. |
| 2007/0190543 A1 | 8/2007 | Livak |
| 2007/0292891 A1 | 12/2007 | Wei et al. |
| 2008/0008996 A1 | 1/2008 | Byrum |
| 2008/0020401 A1 | 1/2008 | Grenier et al. |
| 2008/0081379 A1 | 4/2008 | Sigler et al. |
| 2008/0102449 A1 | 5/2008 | Trama et al. |
| 2008/0124722 A1 | 5/2008 | Dromaretsky et al. |

(56) References Cited

U.S. PATENT DOCUMENTS

| | | |
|---|---|---|
| 2008/0160499 A1 | 7/2008 | Grenier et al. |
| 2008/0176756 A1 | 7/2008 | Siegel et al. |
| 2008/0204022 A1 | 8/2008 | Sillerud et al. |
| 2008/0248970 A1 | 10/2008 | Morrison et al. |
| 2008/0305048 A1 | 12/2008 | Josephson et al. |
| 2008/0311676 A1 | 12/2008 | Brate et al. |
| 2009/0042223 A1 | 2/2009 | Wei et al. |
| 2009/0054741 A1 | 2/2009 | McAleer |
| 2009/0077685 A1 | 3/2009 | Buehler et al. |
| 2009/0087865 A1 | 4/2009 | Kasper et al. |
| 2009/0099342 A1 | 4/2009 | Braconnot et al. |
| 2009/0119022 A1 | 5/2009 | Timberlake et al. |
| 2009/0134869 A1 | 5/2009 | Lee |
| 2009/0155929 A1 | 6/2009 | Wei et al. |
| 2009/0170060 A1 | 7/2009 | Kermechiev et al. |
| 2009/0253210 A1 | 10/2009 | Kobold et al. |
| 2009/0298090 A1 | 12/2009 | Drengler et al. |
| 2009/0325193 A1 | 12/2009 | Grenier et al. |
| 2009/0325197 A1 | 12/2009 | Drengler et al. |
| 2009/0325198 A1 | 12/2009 | Holets-Mccormack |
| 2010/0062090 A1 | 3/2010 | Kim et al. |
| 2010/0072994 A1 | 3/2010 | Lee et al. |
| 2010/0092979 A1 | 4/2010 | Kelso et al. |
| 2010/0099746 A1 | 4/2010 | Yamada et al. |
| 2010/0120174 A1 | 5/2010 | Josephson et al. |
| 2010/0129821 A1 | 5/2010 | Fredricks et al. |
| 2010/0180980 A1 | 7/2010 | Lee et al. |
| 2010/0219824 A1 | 9/2010 | Sillerud et al. |
| 2010/0233035 A1 | 9/2010 | Denawa et al. |
| 2010/0239504 A1 | 9/2010 | Liu et al. |
| 2010/0259259 A1 | 10/2010 | Zahn et al. |
| 2011/0245094 A1 | 10/2011 | Washburn et al. |
| 2012/0100546 A1 | 4/2012 | Lowery, Jr. et al. |

FOREIGN PATENT DOCUMENTS

| | | |
|---|---|---|
| EP | 0864863 A2 | 9/1998 |
| EP | 1870449 A1 | 12/2007 |
| EP | 2410052 A1 | 1/2012 |
| JP | 2009-506345 A | 2/2009 |
| JP | 2009-529883 A | 8/2009 |
| JP | 2009-537167 A | 10/2009 |
| RU | 2176393 C2 | 11/2001 |
| WO | WO 90/06045 | 6/1990 |
| WO | WO 91/17428 | 11/1991 |
| WO | WO 97/40181 | 10/1997 |
| WO | WO-97/40377 A1 | 10/1997 |
| WO | WO 98/04740 | 2/1998 |
| WO | WO 01/00876 | 1/2001 |
| WO | WO 01/11360 | 2/2001 |
| WO | WO 01/19405 | 3/2001 |
| WO | WO 01/55719 | 8/2001 |
| WO | WO 02/098364 | 12/2002 |
| WO | WO 2004/029216 | 4/2004 |
| WO | WO 2005/061724 | 7/2005 |
| WO | WO 2005/099419 | 10/2005 |
| WO | WO 2005/111596 | 11/2005 |
| WO | WO 2006/013844 | 2/2006 |
| WO | WO-2006/013844 A1 | 2/2006 |
| WO | WO 2006/122083 | 11/2006 |
| WO | WO 2007/023461 | 3/2007 |
| WO | WO-2007/027843 A2 | 3/2007 |
| WO | WO-2007/106579 A2 | 9/2007 |
| WO | WO 2007/106765 | 9/2007 |
| WO | WO 2007/134294 | 11/2007 |
| WO | WO-2007/135332 A1 | 11/2007 |
| WO | WO-2008/003114 A2 | 1/2008 |
| WO | WO 2008/003451 | 1/2008 |
| WO | WO 2008/007270 | 1/2008 |
| WO | WO 2008/010111 | 1/2008 |
| WO | WO 2008/054517 | 5/2008 |
| WO | WO 2008/072156 | 6/2008 |
| WO | WO-2008/078579 A1 | 7/2008 |
| WO | WO 2008/119054 | 10/2008 |
| WO | WO 2008/137721 | 11/2008 |
| WO | WO-2009/004551 A1 | 1/2009 |
| WO | WO 2009/005178 | 1/2009 |
| WO | WO 2009/017697 | 2/2009 |
| WO | WO 2009/025475 | 2/2009 |
| WO | WO-2009/026164 A1 | 2/2009 |
| WO | WO 2009/026251 | 2/2009 |
| WO | WO 2009/045354 | 4/2009 |
| WO | WO 2009/045551 | 4/2009 |
| WO | WO 2009/055587 | 4/2009 |
| WO | WO 2009/061481 | 5/2009 |
| WO | WO 2009/078875 | 6/2009 |
| WO | WO 2009/085214 | 7/2009 |
| WO | WO 2010/002479 | 1/2010 |
| WO | WO-2010/034846 A1 | 4/2010 |
| WO | WO 2010/051362 | 5/2010 |
| WO | WO-2010/062909 A1 | 6/2010 |
| WO | WO-2011/030091 A1 | 3/2011 |
| WO | WO-2011/053241 A1 | 5/2011 |
| WO | WO-2011/121288 A2 | 10/2011 |

OTHER PUBLICATIONS

U.S. Appl. No. 13/852,613, Neely et al.
U.S. Appl. No. 13/852,709, Lowery Jr. et al.
Bergman et al., "Rapid identification of pathogenic yeast isolates by real-time PCR and two-dimensional melting point analysis," Euro J of Clinical Microbiology & Infectious Diseases. 26:813-818 (2007).
NCBI Blast for Accession No. X53497. Retrieved on Apr. 14, 2012 (4 pages).
NCBI Blast for Accession No. AY198398.1. Retrieved on Apr. 14, 2012 (3 pages).
Buck et al., "Design strategies and performance of custom DNA sequencing primers," BioTechniques. 27:528-536 (1999).
Ferrer et al., "Detection and identification of fungal pathogens by PCR and by ITS2 and 5.8S ribosomal DNA typing in ocular infections," J Clin Microbiol. 39(8):2873-2879 (2001).
Fredricks et al., "Comparison of six DNA extraction methods for recovery of fungal DNA as assessed by quantitative PCR," J Clin Microbiol. 43(10):5122-5128 (2005).
Fujita et al., "Microtitration plate enzyme immunoassay to detect PCR-amplified DNA from *Candida* species in blood," J Clin Microbiol. 33(4):962-967 (1995).
Lee et al., "Sequence-specific electrochemical detection of asymmetric PCR amplicons of traditional Chinese medicinal plant DNA," Anal Chem. 74:5057-5062 (2002).
Martin et al., "Development of a PCR-based line probe assay for identification of fungal pathogens," J Clin Microbiol. 38(10):3735-3742 (2000).
International Search Report and Written Opinion of the International Searching Authority for International Application No. PCT/US11/56933, dated May 10, 2012 (23 pages).
International Search Report and Written Opinion of the International Searching Authority for International Application No. PCT/US11/56936, dated May 17, 2012 (18 pages).
International Preliminary Report on Patentability for International Patent Application No. PCT/US2011/056933, dated Apr. 23, 2013 (16 pages).
International Preliminary Report on Patentability issued for International Patent Application No. PCT/US2011/056936, dated Jun. 18, 2013 (11 pages).
Office Action for U.S. Appl. No. 13/363,916, dated Aug. 2, 2012 (65 pages).
Office Action for U.S. Appl. No. 13/402,566, dated Oct. 29, 2012 (61 pages).
Office Action for U.S. Appl. No. 13/646,402, dated Mar. 14, 2013 (54 pages).
Office Action for U.S. Appl. No. 13/402,566, dated Jan. 22, 2013 (28 pages).
Office Action for U.S. Appl. No. 13/649,839, dated Mar. 14, 2013 (49 pages).
Office Action for U.S. Appl. No. 13/402,566, dated May 30, 2013 (33 pages).
U.S. Appl. No. 12/910,594, Lowery Jr. et al.
U.S. Appl. No. 13/363,916, Lowery Jr. et al.

(56) References Cited

OTHER PUBLICATIONS

U.S. Appl. No. 13/402,566, Neely et al.
George et al., "Effect of Inoculum Size on Detection of *Candida* Growth by the BACTEC 9240 Automated Blood Culture System Using Aerobic and Anaerobic Media," *J. Clin. Microbiol.* 43:433-435 (2005).
Lee et al., "Rapid Detection and Profiling of Cancer Cells in Fine-needle Aspirates" *Proc Natl Acad Sci U.S.A.* 106:12459-12464 and supporting information (2 pages) (2009).
Ling et al., "Magnetic Relaxation-Based Platform for Multiplexed Assays," *Analyst* 135:2360-2364 (2010).
Moser et al., "On-Chip Immune-Agglutination Assay with Analyte Capture by Dynamic Manipulation of Superparamagnetic Beads," *Lab Chip* 9:3261-3267 (2009).
International Search Report for International Application No. PCT/US08/73346, completed Oct. 23, 2008, mailed Nov. 7, 2008.
International Search Report for International Application No. PCT/IB2008/052597; completed Oct. 31, 2008, mailed Nov. 11, 2008.
Ahmad et al., "Seminested PCR for Diagnosis of Candidemia: Comparison with Culture, Antigen Detection, and Biochemical Methods for Species Identification," *J. Clin. Microbiol.* 40:2483-2489 (2002).
Alhassan et al., "Comparison of Polymerase Chain Reaction Methods for the Detection of Theileria Equi Infection Using Whole Blood Compared with Pre-Extracted DNA Samples as PCR Templates," *Trop. Anim. Health Prod.* 39:369-374 (2007).
Allice et al., "Evaluation of a Novel Real-Time PCR System for Cytomegalovirus DNA Quantitation on Whole Blood and Correlation with PP65-Antigen Test in Guiding Pre-Emptive Antiviral Treatment," *J. Virol. Methods* 148:9-16 (2008).
Altschul et al., "Basic Local Alignment Search Tool," *J. Mol. Biol.* 215:403-410 (1990).
Amaral et al., "Coagulation in Sepsis" *Intensive. Care Med.* 30:1032-1040 (2004).
Aoki et al., "Detection of Legionella DNA by PCR of Whole-Blood Samples in a Mouse Model," *J. Med. Microbiol.* 52:325-329 (2003).
Atanasijevic et al., "Calcium-sensitive MRI Contrast Agents Based on Superparamagnetic Iron Oxide Nanoparticles and Calmodulin" *Proc Natl Acad Sci. U.S.A.* 103:14707-14712 (2006).
Attal et al., "A Simple Method of DNA Extraction from Whole Tissues and Blood Using Glass Powder for Detection of Transgenic Animals by PCR," *Transgenic Res.* 4:149-150 (1995).
Awduche et al., "RSVP-TE: Extensions to RSVP for LSP Tunnels" IETF Standard, Internet Engineering Task Force, IETF, CH. (Dec. 2001).
Barany, "Genetic Disease Detection and DNA Amplification Using Cloned Thermostable Ligase," *Proc. Natl. Acad. Sci.* 88:189-193 (1991).
Baudry et al., "Acceleration of the Recognition Rate Between Grafted Ligands and Receptors with Magnetic Forces," *Proc. Natl. Acad. Sci.* 103:16076-16078 (2006).
Baugher et al., "Evaluation of the Tacrolimus Assay on the Abbott ARCHITECT Analyzer," American Association for Clinical Chemistry Annual Meeting, Chicago, Illinois on Jul. 23-27, 2006 (4 pages).
Benkert et al., "Development of a Creatinine ELISA and Amperometric Antibody-Based Creatinine Sensor with a Detection Limit in the Nanomolar Range," *Anal. Chem.* 72:916-921 (2000).
Boero et al., "An NMR Magnetometer with Planar Microcoils and Integrated Electronics for Signal Detection and Amplification" *Sens Actuators, A Phys.* 67:18-23 (1998).
Bougnoux et al., "Serum is More Suitable than Whole Blood for Diagnosis of Systematic Candidiasis by Nested PCR," *J. Clin. Microbiol.* 37:925-930(1999).
Brown et al., "Scaling of Transverse Nuclear Magnetic Relaxation due to Magnetic Nanoparticle Aggregation" *J. Magn Magn Mater.* 322:3122-3126 (2010).
Bu et al., "Direct Polymerase Chain Reaction (PCR) from Human Whole Blood and Filter-Paper-Dried Blood by Using a PCR Buffer with a Higher pH," *Anal. Biochem.* 375:370-372 (2008).

Burckhardt, "Amplification of DNA from Whole Blood," *Genome Res.* 3:239-243 (1994).
Castley et al., "Clinical Application of Whole-Blood PCR with Real-Time Instrumentation," *Clin. Chem.* 51:2025-2030 (2005).
Cedervall et al., "Understanding the Nanoparticle-Protein Corona Using Methods to Quantify Exchange Rates and Affinities of Proteins for Nanoparticles," *Proc. Natl. Acad. Sci. USA* 104:2050-2055 (2007).
Cerikcioglu et al., "Seminested PCR for Detection and Identification of *Candida* Species Directly from Blood Culture Bottles," *New Microbiologica* 33:57-62 (2010).
Chaffin et al., "Cell Wall and Secreted Proteins of *Candida albicans*: Identification, Function, and Expression," *Microbiol. Mol. Biol. Rev.* 62:130-180 (1998).
Chisti and Moo-Young, Chapter 13: Fermentation Technology, Bioprocessing, Scale-Up and Manufacture *Biotechnology:The Science and the Business* pp. 177-222 (1999).
Chomczynski and Rymaszewski, "Alkaline Polyethylene Glycol-Based Method for Direct PCR from Bacteria, Eukaryotic Tissue Samples, and Whole Blood," *BioTechniques* 40:454,456,458 (2006).
Christians et al., "Tacrolimus," in *Applied Pharmacokinetics and Pharmacodynamics*, Burton, Schentag, Shaw, and Evans, 4$^{th}$ Edition, Lippincott Williams & Wilkins, pp. 529-562 (2006).
Cohen-Tannoudji et al., "Measuring the Kinetics of Biomolecular Recognition with Magnetic Colloids," *Phys. Rev. Letters* 100:108301 (2008) (4 pages).
Colombo et al., Femtomolar Detection of Autoantibodies by Magnetic Relaxation, *Anal. Biochem.* 392:96-102 (2009).
Costanzo et al., "Protein-Ligand Mediated Aggregation of Nanoparticles: A Study of Synthesis and Assembly Mechanism," *Chem. Mater.* 16:1775-1785 (2004).
Curran and Evans, "The Killing of Bacterial Spores in Fluids by Agitation with Small Inert Particles," *J. Bacteriol.* 43:125-139 (1942).
D'Ambrosio et al., "Improved Procedures for Enzyme Immunoassay of Tacrolimus (FK506) in Whole Blood," *Clin. Chem.* 40:159-160 (1994).
Daniel et al., "Multi-Reservoir Device for Detecting a Soluble Cancer Biomarker," *Lab Chip* 7:1288-1293 (2007).
Deak et al., "Utility of a Luminex-based Assay for Multiplexed, Rapid Species Identification of *Candida* isolates from an Ongoing Candidemia Surveillance" *Can. J. Microbiol.* 56:348-351 (2010).
Deback et al., "Monitoring of Human Cytomegalovirus Infection in Immunosuppressed Patients Using Real-Time PCR on Whole Blood," *J. Clin. Virol.* 40:173-179 (2007).
Delgado et al.., "Surface Properties of Polystyrene Nanoparticles Coated with Dextrans and Dextran-PEO Copolymers. Effect of Polymer Architecture on Protein Adsorption," *Langmuir* 17:4386-4391 (2001).
Demas et al., "Electronic Characterization of Lithographically Patterned Microcoils for High Sensitivity NMR Detection" *J. Magn Reson.* 200:56-63 (2009).
Demas et al., "Portable, Low-Cost NMR with Laser-Lathe Lithography Produced Microcoils," *J. Mag. Reson.* 189:121-129 (2007).
Demas and Lowery, "Magnetic Resonance for in Vitro Medical Diagnostics: Superparamagnetic Nanoparticle Based Magnetic Relaxation Switches," *New J. Phys.* 13:025005 (2011) (17 pages).
De Paula et al., "Optimizing Dengue Diagnosis by RT-PCR in IgM-Positive Samples: Comparison of Whole Blood, Buffy-Coat and Serum as Clinical Samples," *J. Virol. Methods* 102:113-117 (2002).
de Vries et al., "PCR on Cell Lysates Obtained from Whole Blood Circumvents DNA Isolation," *Clin. Chem.* 47:1701-1702 (2001).
Dreyfus et al., "Microscopic Artificial Swimmers," *Nature* 437:862-865 (2005).
Elie et al., "Rapid Identification of *Candida* Species with Species-Specific DNA Probes," *J. Clin. Microbiol.* 36:3260-3265 (1998).
Espy et al., "Real-Time PCR in Clinical Microbiology: Applications for Routine Laboratory Testing," *Clin. Microbiol. Rev.* 19:165-256 (2006).

(56) References Cited

OTHER PUBLICATIONS

Fossati et al. "Enzymic Creatinine Assay: A New Colorimetric Method Based on the Hydrogen Peroxide Measurement," *Clin. Chem.* 29:1494-1496 (1983).

Fry et al., "A New Approach to Template Purification for Sequencing Applications using Paramagnetic Particles" *BioTechniques* 13:127 (1992).

Garey et al., "Time to Initiation of Fluconazole Therapy Impacts Mortality in Patients with Candidemia: A Multi-Institutional Study," *Clin. Infect. Dis.* 43:25-31 (2006).

Garrigue et al., "Whole Blood Real-Time Quantitative PCR for Cytomegalovirus Infection Follow-Up in Transplant Recipients," *J. Clin. Virol.* 36:72-75 (2006).

Gijs, "Manetic Bead Handling On-chip: New Opportunities for Analytical Applications" *Microfluid Nanofluidics* 1:22-40 (2004).

Gonschior et al., "Tacrolimus (FK506) Metabolite Patterns in Blood from Liver and Kidney Transplant Patients," *Clin. Chem.* 42:1426-1432 (1996).

Griffiths et al., "Comparison of DNA Extraction Methods for *Aspergillus fumigates* Using Real-Time PCR," *J. Med. Microbiol.* 55:1187-1191 (2006).

Grimm et al., "Novel Nanosensors for Rapid Analysis of Telomerase Activity" *Cancer Res.* 64: 639-643 (2004).

Harris et al., "Proteolytic Actuation of Nanoparticle Self-assembly" *Angew. Chem. Int. Ed.* 45:3161-3165 (2006).

Hatch and Stelter, "Magnetic Design Considerations for Devices and Particles Used for Biological High-Gradient Magnetic Separation (HGMS) Systems," *J. Magnet. Mag. Mat.* 225:262-276 (2001).

Hirose et al., "Simultaneous Cultivation and Disruption of Escherichia coli Using Glass Beads to Release Recombinant α-Amylase and Other Enzymes," *Biotechnol. Techniques* 13:571-575 (1999).

Hong et al.,. "Magnetic Microparticle Aggregation for Viscosity Determination by MR," *Mag. Reson. in Med.* 59:515-520 (2008).

Hoorfar et al., "Practical Considerations in Design of Internal Amplification Controls for Diagnostic PCR Assays" *J. Clin. Microbiol.* 42:1863-1868 (2004).

Horn et al., "Epidemiology and Outcomes of Candidemia in 2019 Patients: Date From Prospective Antifungal Therapy Alliance Registry," *Clin. Infect. Dis.* 48:1695-1703 (2009).

Horvath et al., "Detection of Simulated Candidemia by the BACTEC 9240 System with Plus Aerobic/F and Anaerobic/F Blood Culture Bottles," *J. Clin. Microbiol.* 41:4714-4717 (2003).

Inglis et al., "Microfluidic High Gradient Magnetic Cell Separation," *J. Appl. Physics* 99:08K101 (2006) (3 pages).

Josephson et al., "Magnetic Nanosensors for the Detection of Oligonucleotide Sequences," *Angew. Chem. Int. Ed.* 40:3204-3206 (2001).

Josephson et al., "High-efficiency Intracellular Magnetic labeling with Novel Superparamagnetic-Tat Peptide Conjugates" *Bioconjugate Chem.* 10:186-191 (1999).

Kaittanis et al., "One-step Nanoparticle-mediated Bacterial Detection with Magnetic Relaxation" *Nano Lett.* 7:380-383 (2007).

Keeney et al., "A Whole Blood, Multiplex PCR Detection Method for Factor V Leiden and the Prothrombin G20210A Variant," *Thromb. Haemost* 81:464-465 (1999).

Keevil et al., "Simultaneous and Rapid Analysis of Cyclosporine A and Creatinine in Finger Prick Blood Samples Using Liquid Chromatography Tandem Mass Spectrometry and its Application in C2 Monitoring," *Ther. Drug Monit.* 24:757-767 (2002).

Kermekchiev et al., "Mutants of Taq DNA Polymerase Resistant to PCR Inhibitors Allow DNA Amplification from Whole Blood and Crude Soil Samples," *Nucleic Acids Res.* 37:e40 (2009) (14 pages).

Kermekchiev et al., "Cold-sensitive Mutants of Taq DNA Polymerase Provide a Hot Start for PCR" *Nucleic Acids Res.* 31:6139-6147 (2003).

Khot et al., "Sequencing and Analysis of Fungal rRNA Operons for Development of Broad-range Fungal PCR Assays" *Appl. Environ. Microbiol.* 75:1559-1565 (2009).

Kim et al., "Magnetic Relaxation Switch Detection of Human Chorionic Gonadotrophin," *Bioconjug. Chem.* 18:2024-2028 (2007).

Klungthong et al., "Dengue Virus Detection Using Whole Blood for Reverse Transcriptase PCR and Virus Isolation," *J. Clin. Microbiol.* 45:2480-2485 (2007).

Koh et al., "Sensitive NMR Sensors Detect Antibodies to Influenza," *Angew. Chem. Int. Ed.* 47:4119-4121 (2008) (4 pages).

Koh et al., "Nanoparticle-Target Interactions Parallel Antibody-Protein Interactions," *Anal. Chem.* 81:3618-3622 (2009).

Koh and Josephson, "Magnetic Nanoparticle Sensors," *Sensors* 9:8130-8145 (2009).

Kost et al., "Multicenter Study of Whole-Blood Creatinine, Total Carbon Dioxide, Content, and Chemistry Profiling for Laboratory and Point-of-Care Testing in Critical Care in the United States," *Crit. Care Med.* 28:2379-2389 (2000).

Kötitz et al., "Determination of the Binding Reaction between Avidin and Biotin by Relaxation Measurements of Magnetic Nanoparticles" *J. Magn. Magn. Mater.* 194:62-68 (1999).

Kriz et al., "Magentic Permeability Measurements in Bioanalysis and Biosensors" *Anal. Chem.* 68:1966-1970 (1996).

Kriz et al., "Advancements Toward Magneto Immunoassays" *Biosens Bioelectron.* 13:817-823 (1998).

Kroll et al., "Mechanism of Interference with the Jaffe Reaction for Creatinine," *Clin. Chem.* 33:1129-1132 (1987).

Kula and Schutte, "Purification of Proteins and the Disruption of Microbial Cells," *Biotechnol. Progress* 3:31-42 (1987).

Kulkarni et al., "Detection of Carbohydrate Binding Proteins Using Magnetic Relaxation Switches," *Anal. Chem.* 82:7430-7435 (2010) (6 pages).

Kumar et al., "Initiation of Inappropriate Antimicrobial Therapy Results in a Fivefold Reduction of Survival in Human Septic Shock," *Chest* 136:1237-1248 (2009).

Kumari et al., "Surface Oxidation of Nickel Thin Films," *J. Mater. Sci. Letters* 11:761-762 (1992).

Lacharme et al., "Full On-Chip Nanoliter Immunoassay by Geometrical Magnetic Trapping of Nanoparticle Chains," *Anal. Chem.* 80:2905-2910 (2008).

Lamanna and Mallette, "Use of Glass Beads for the Mechanical Rupture of Microorganisms in Concentrated Suspensions," *J. Bacteriol.* 67:503-504 (1954).

Lee et al., "Ligand-Receptor Interactions in Chains of Colloids: When Reactions are Limited by Rotational Diffusion," *Langmuir* 24:1296-1307 (2008).

Lee et al., "Microelectromagnets for the Control of Magnetic Nanoparticles," *Appl. Phys. Letters* 79:3308-3310 (2001).

Lee et al., "Exclude Routes-Extension to RSVP-TE" Internet Engineering Task Force, IETF, CH, vol. Ccamp, No. 1 (2003).

Lee et al., "Ultrasensitive Detection of Bacteria using Core-shell Nanoparticles and a NMR Filter System" *Angew. Chem. Int. Ed. Engl.* 48:5657-5660 (2009).

Lehmann et al., "A Multiplex Real-Time PCR Assay for Rapid Detection and Differentiation of 25 Bacterial and Fungal Pathogens from Whole Blood Samples," *Med. Microbiol. Immunol.* 197:313-324 (2008).

Levey et al., "Using Standardized Serum Creatinine Values in the Modification of Diet in Renal Disease Study Equation for Estimating Glomerular Filtration Rate," *Ann. Intern. Med.* 145:247-254 (2006).

Lewin et al., "Tat Peptide-derivatized Magnetic Nanoparticles Allow in vivo Tracking and Recovery of Progenitor Cells" *Nat Biotechnol.* 18:410-414 (2000).

Li et al., "Rapid Identification of Yeasts Commonly Found in Positive Blood Cultures by Amplification of the Internal Transcribed Spacer Regions 1 and 2," *Eur. J. Clin. Microbiol. Infect. Dis.* 22:693-696 (2003).

Liao and Tang, "High-Throughput Miniaturized lmmnoassay for Human Interleukin-6 Using Electrochemical Sandwich-Type Enzyme Immunosensors," *Curr. Pharm. Analysis* 5:164-170 (2009).

Liu, "CMOS Magnetic Cell Manipulator and CMOS NMR Biomolecular Sensor" Ph.D. dissertation, Nov. 5, 2007, Harvard University.

(56) References Cited

OTHER PUBLICATIONS

Liu et al., "Rapid Distribution of a Liquid col. Into a Matrix of Nanoliter Wells for Parallel Real-Time Quantitative PCR," *Sens. Actuat. B* 135:671-677 (2009).

Lowery, "Nanomaterials-Based Magnetic Relaxation Biosensors," in Kumar, CSSR, ed. *Nanomaterials for the Life Sciences* vol. 4: Magnetic Nanomaterials. Weinheum: Wiley-VCH Verlan GmbH & Co., KgaA, pp. 1-53 (2009).

Lowery et al., "Application of Magnetics in Point of Care Testing," in Point-of-Care Testing: Needs, Opportunity and Innovation 3rd Edition, AACC Press, pp. 85-95 (2010).

Luck et al., "Analysis of Plasma Protein Adsorption on Polymeric Nanoparticles with Different Surface Characteristics," *J. Biomed. Mater. Res.* 39:478-485 (1998).

Lundqvist et al., "Nanoparticle Size and Surface Properties Determine the Protein Corona with Possible Implications for Biological Impacts," *Proc. Natl. Acad. Sci.* 105:14265-14270 (2008).

Lustgarten and Wenk, "Simple, Rapid, Kinetic Method for Serum Measurement," *Clin. Chem.* 18:1419-1422 (1972).

Ma et al., "Rapid and Sensitive Detection of Microcystin by Immmunosensor Based on Nuclear Magnetic Resonance" *Biosens Bioelectron.* 25:240-243 (2009).

Maaroufi et al., "Early Detection and Identification of Commonly Encountered *Candida* Species from Simulated Blood Cultures by Using a Real-Time PCR-Based Assay," *J. Mol. Diagn.* 6:108-114 (2004).

Magin et al., "Miniature Magnetic Resonance Machines" *IEEE Spectrum* 34:51-61 (1997).

Mäkiranta et al., "Modeling and Simulation of Magnetic Nanoparticle Sensor" Conf. Proc. IEEE Eng. Med. Biol. Soc., Shanghai, China, Sep. 1-4, 2005, pp. 1256-1259 (2005).

Malba et al., "Laser-Lathe Lithography—A novel Method for Manufacturing Nuclear Magnetic Resonance Microcoils," *Biomed. Microdevices* 5:21-27 (2003).

Martin et al., "Strong Intrinsic Mixing in Vortex Magnetic Fields," *Phys. Rev. E* 80:016312 (2009) (6 pages).

Martin, "Theory of Strong Intrinsic Mixing of Particle Suspensions in Vortex Magnetic Fields," *Phys. Rev. E* 79:011503 (2009) (12 pages).

Martin et al., "The Epidemiology of Sepsis in the United States from 1979 Through 2000," *NEJM* 348:1546-1554 (2003).

Massin et al., "Planar Microcoil-Based Microfluidic NMR Probes," *J. Magn. Reson.* 164:242-255 (2003).

Massin et al., "Planar Microcoil-based Magnetic Resonance Imaging of Cells" Transducers, Solid-state Sensors, Actuators and Microsystems 12th Int'l conference vol. 2: 967-970 (2003).

Masson et al., "Combined Enzymic-Jaffe Method for Determination of Creatinine in Serum," *Clin. Chem.* 27:18-21 (1981).

McCusker et al., "Improved Method for Direct PCR Amplification from Whole Blood," *Nucleic Acids Res.* 20:6747 (1992) (1 page).

McDowell et al., "Operating Nanoliter Scale NMR Microcoils in a 1 Tesla Field" *J. Magn. Reson.* 188:74-82 (2007).

Mercier et al., "Direct PCR from Whole Blood, Without Dna Extraction," *Nucleic Acids Res.* 18:5908 (1990) (1 page).

Metwally et al., "Improving Molecular Detection of Candida DNA in Whole Blood: Comparison of Seven Fungal DNA Extraction Protocols Using Real-Time PCR," *J. Med. Microbiol.* 57:296-303 (2008).

Morrell et al., "Delaying the Empiric Treatment of *Candida* Bloodstream Infection Until Positive Blood Culture Results are Obtained: A Potential Risk Factor for Hospital Mortality," *Antimicrob. Agents Chemother.* 49:3640-3645 (2005).

Niemeyer et al., "Self-Assembly of DNA-Streptavidin Nanostructures and Their Use as Reagents in Immuno-PCR" *Nucleic Acids Res.* 27:4553-4561 (1999).

Panaccio et al., "FoLT PCR: A Simple PCR Protocol for Amplifying DNA Directly from Whole Blood," *BioTechniques* 14:238-240, 242, 243 (1993).

Pappas and Wong, "Cellular Separations: a Review of New Challenges in Analytical Chemistry" *Anal Chim. Acta.* 601:26-35 (2007).

Park et al., "Determination of Nanoparticle Vehicle Unpackaging by MR Imaging of a $T_2$ Magnetic Relaxation Switch" *Biomaterials* 29:724-732 (2008).

Peake and Whiting, "Measurement of Serum Creatinine—Current Status and Future Goals," *Clin. Biochem. Rev.* 27:173-184 (2006).

Peck et al., "RF Microcoils Patterned Using Microlithographic Techniques for Use as Microsensors in NMR" Engineering in Medicine and Biology Scoiety, Proceedings of the 15th annual international conference of the IEEE, pp. 174-175 (Oct. 28-31, 1993).

Perez et al., "DNA-based Magnetic Nanoparticle Assembly Acts as a Magnetic Relaxation Nanoswitch Allowing Screening of DNA-cleaving Agents" *J. Am. Chem. Soc.* 124:2856-2857 (2002).

Perez et al., "Peroxidase Substrate Nanosensors for MR Imaging", *Nano Lett* 4:119-122 (2004).

Perez et al., "Integrated Nanosensors to Determine Levels and Functional Activity of Human Telomerase" *Neoplasia* 10:1066-1072 (2008).

Perez et al., "Magnetic Relaxation Switches Capable of Sensing Molecular Interactions," *Nat. Biotechnol.* 20:816-820 (2002).

Perez et al., "Viral-Induced Self Assembly of Magnetic Nanoparticles Allows the Detection of Viral Particles in Biological Media," *J. Am. Chem. Soc.* 125:10192-10193 (2003).

Perez et al., "Use of Magnetic Nanoparticles as Nanosensors to Probe for Molecular Interactions," *ChemBioChem.* 5:261-264 (2004).

Pryce et al., "Real-Time Automated Polymerase Chain Reaction (PCR) to Detect *Candida albicans* and *Aspergillus fumigatus* DNA in Whole Blood from High-Risk Patients," *Diagn. Microbiol. Infect. Dis.* 47:487-496 (2003).

Ramadan et al., "On-Chip Micro-electromagnets for Magnetic-based Bio-molecules Separation" *J. Magn. Magn. Mater.* 281:150-172 (2004).

Renaud et al., "Implantable Planar rF Microcoils for NMR Microspectroscopy" *Sens Actuators, A Phys.* 99:244- 248 (2002).

Rida et al., "Long-Range Transport of Magnetic Microbeads Using Simple Planar Coils Placed in a Uniform Magnetostatic Field" *Appl. Phys. Lett.* 83:2396-2398 (2003).

Rosenstraus et al., "An Internal Control for Routine Diagnostic PCR: Design, Properties and Effect on Clinical Performance" *J. Clin. Microbiol.* 36:191-197 (1998).

Routley et al., "The Halo System—A Light Weight Portable Imaging System" *Magn Reson Imaging.* 22:1145-1151 (2004).

Rüttimann et al., "DNA Polymerases from the Extremely Thermophilic Bacterium *Thermus thermophllis* HB-8," *Eur. J. Biochem.* 149:41-46 (1985).

Seeber et al., "Triaxial Magnetic Field Gradient System for Microcoil Magnetic Resonance Imaging" *Rev. Sci. Instrum.* 71:4263-4272 (2000).

Shapiro et al., "Dynamic Imaging with MRI Contrast Agents: Quantitative Considerations" *Magn Reson Imaging* 24:449-462 (2006).

Siegel et al., "Affinity Maturation of Tacrolimus Antibody for Improved Immunoassay Performance," *Clin. Chem.* 54:1008-1017 (2008).

Sillerud et al., "$^1$H NMR Detection of Superparamagnetic Nanoparticles at 1 T Using a Microcoil and Novel Tuning Circuit," *J. Magn. Reson.* 181:181-190 (2006).

Skurup et al., "New Creatinine Sensor for Point-of-Care Testing of Creatinine Meets the National Kidney Disease Education Program Guidelines," *Clin. Chem. Lab Med.* 46:3-8 (2008).

Stöcklein et al., "Enzyme Kinetic Assays with Surface Plasmon Resonance (BlAcore) Based on Competition Between Enzyme and Creatinine Antibody," *Biosen. Bioelectron.* 15:377-382 (2000).

Sullivan and Irreverre, "A Highly Specific Test for Creatinine," *J. Biol. Chem.* 233:530-534 (1958).

Sun et al., "Experimental Study on $T_2$ Relaxation Time of Protons in Water Suspensions of Iron-Oxide Nanoparticles: Waiting Time Dependence" 321:2971-2975 (2009).

(56) References Cited

OTHER PUBLICATIONS

Syms et al., "MEMS Helmholtz Coils for Magnetic Resonance Imaging" *J. Micromech. Microeng.* 15:S1-S9 (2005).
Taktak et al., "Multiparameter Magnetic Relaxation Switch Assays" *Anal. Chem.* 79:8863-8869 (2007).
Taktak et al., "Electrode Chemistry Yields a Nanoparticle-based NMR Sensor for Calcium" *Langmuir* 24:7596-7598 (2008).
Tanaka et al., "Properties of Superparamagnetic Iron Oxide Nanoparticles Assembled on Nucleic Acids" *Nucleic Acid Symposium Series*, 52:693-694 (2008).
Taur et al., "Effect of Antifungal Therapy Timing on Mortality in Cancer Patients with Candidemia," *Antimicrob. Agents Chemother.* 54:184-190 (2010).
Thorne et al., "Analytic Validation of a Quantitative Real-Time PCR Assay to Measure CMV Viral Load in Whole Blood," *Diagn. Mol. Pathol.* 16:73-80 (2007).
Tong et al., "Coating Optimization of Superparamagnetic Iron Oxide Nanoparticles for High $T_2$ Relaxivity," *Nano Letters* 10:4607-4613 (2010) (7 pages).
Tsourkas et al., "Magnetic Relaxation Switch Immunosensors Detect Enantiomeric Impurities," *Angew. Chem. Int. Ed.* 43:2395-2399 (2004).
Ulvik and Ueland, "Single Nucleotide Polymorphism (SNP) Genotyping in Unprocessed Whole Blood and Serum by Real-Time PCR: Application to SNPs Affecting Homocysteine and Folate Metabolism," *Clin. Chem.* 47:2050-2053 (2001).
van Bentum et al., "Towards Nuclear Magnetic Resonance µ-spectrocopy and µ-imaging" *Analyst* 129:793-803 (2004).
Vasseur and Ayyangar, "Inter-area and Inter-AS MPLS Traffic Engineering" IETF Standard-working draft, internet Engineering Task Force, IETF, CH, Feb. 2004.
Vollenhofer-Schrumpf et al., "A Simple Nucleic Acid Hybridization/Latex Agglutination Assay for the Rapid Detection of Polymerase Chain Reaction Amplicons" *J. Microbiol Methods*. 68:568-576 (2007).
von Lilienfeld-Toal et al., "Utility of a Commercially Available Multiplex Real-Time PCR Assay to Detect Bacterial and Fungal Pathogens in Febrile Neutropenia," *J. Clin. Microbiol.* 47:2405-2410 (2009).
Wallemacq et al., "Improvement and Assessment of Enzyme-Linked Immunosorbent Assay to Detect Low FK506 Concentrations in Plasma or Whole Blood Within 6 Hours," *Clin. Chem.* 39:1045-1049 (1993).
Wang et al., "A Novel Strategy to Engineer DNA Polymerases for Enhanced Processivity and Improved Performance in vitro" *Nucleic Acids Res.* 32:1197-1207 (2004).
Weetall, "Preparation of Immobilized Proteins Covalently Coupled Through Silane Coupling Agents to Inorganic Supports," *App. Biochem. Biotechnol.* 41:157-188 (1993).
Weetall and Lee "Antibodies Immobilized on Inorganic Supports," *App. Biochem. Biotechnol.* 22:311-330 (1989).
Weissleder et al., "Cell-Specific Targeting of Nanoparticles by Multivalent Attachment of Small Molecules," *Nat. Biotechnol.* 23:1418-1423 (2005).
Wensink et al., "High Signal to Noise Ratio in Low Field NMR on chip Simulations and Experimental Results" Micro Electro Mechanical Systems 17th IEEE International Conference, Netherlands, pp. 407-410 (2004).
Wildgruber et al., "Monocyte Subset Dynamics in Human Atherosclerosis can be Profiled with Magentic Nano-Sensors" *Plos One* 4(5):e5663 (2009) (9 pages).
Wilson and Plass, "Creatine and Creatinine in Whole Blood and Plasma," *J. Biol. Chem.* 29:413-423 (1917).
Wu et al., "$^1$H-NMR Spectroscopy on the Nanoliter Scale for Static and On-Line Measurements," *Anal. Chem.* 66:3849-3857 (1994).
Xing et al., "Immobilization of Biomolecules on the Surface of Inorganic Nanoparticles for Biomedical Applications," *Sci. Technol. Adv. Mater.* 11:014101 (17pages) (2010).
Yigit et al., "Smart "Turn-On" Magnetic Resonance Contrast Agents Based on Aptamer-Functionalized Superparamagnetic Iron Oxide Nanoparticles," *ChemBioChem* 8:1675-1678 (2007).
Zhang et al., "A Probe Design for the Acquisition of Homonuclear, Heteronuclear, and Inverse Detected NMR Spectra from Multiple Samples" *J. Magn. Reson.* 153:254-258 (2001).
Zhao et al., "Magnetic Sensors for Protease Assays" *Angew. Chem. Int. Ed.* 42:1375-1378 (2003).
Examination Report for Australian Application No. 2011317073, dated Jun. 16, 2014 (4 pages).
Office Action for Chinese Application No. 201180061890.1, dated Nov. 4, 2014 (20 pages).
Morgenthaler et al., "Sensitive immunoluminometric assay for the detection of procalcitonin," Clin Chem. 48(5):788-90 (2002).
Ito et al., "Treatment of Candida infections with amphotericin B lipid complex," Clin Infect Dis. 40 Suppl 6:S384-91 (2005).
Cleary et al., "Amphotericin B enzyme-linked immunosorbent assay," Antimicrob Agents Chemother. 40(3):637-41 (1996).
Notice of Reasons for Rejection for Japanese Patent Application No. 2013-535053, dated Sep. 2, 2015 (6 pages).
Emery, "Investigation of CMV disease in immunocompromised patients," J Clin Pathol. 54(2):84-8 (2001).
Naber, "*Staphylococcus aureus* bacteremia: epidemiology, pathophysiology, and management strategies," Clin Infect Dis. 48 (Suppl 4):S231-7 (2009).
Extended European Search Report for European Application No. 15002772.0, dated Feb. 22, 2016 (12 pages).
Partial European Search Report for European Application No. 15002772.0, dated Nov. 4, 2015 (7 pages).
Partial Supplementary European Search Report for European Application No. 13779063.0, dated Feb. 17, 2016 (8 pages).
Office Action for Russian Patent Application No. 2013112118, dated Mar. 1, 2016 (13 pages).
Extended European Search Report for European Patent Application No. 13779063.0, dated Jun. 7, 2016 (17 pages).
Notice of Reasons for Rejection for Japanese Patent Application No. 2016-113224, dated Apr. 26, 2017 (12 pages).

\* cited by examiner

Figure 4
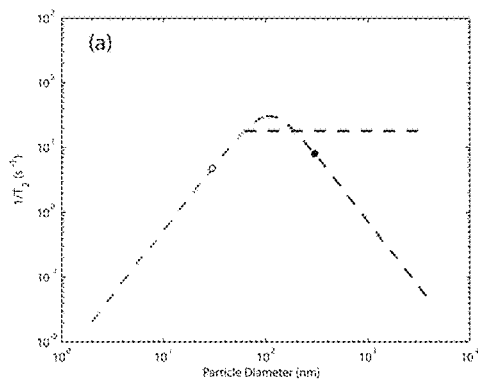
Figure 4A
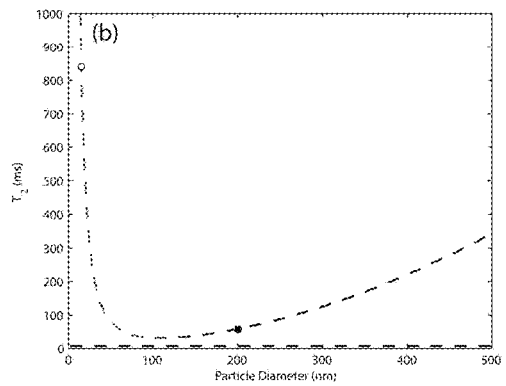
Figure 4B
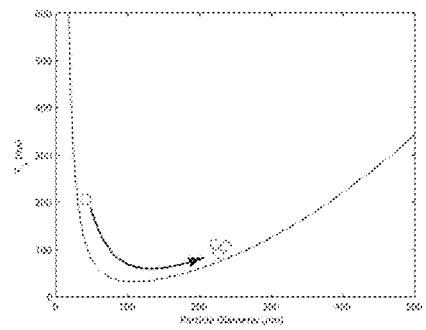
Figure 4C
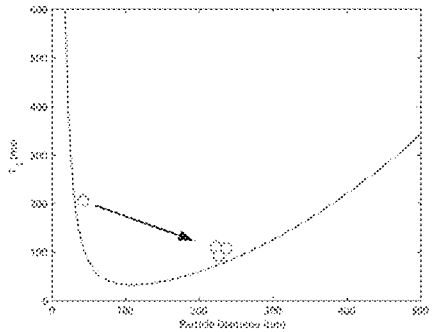
Figure 4D
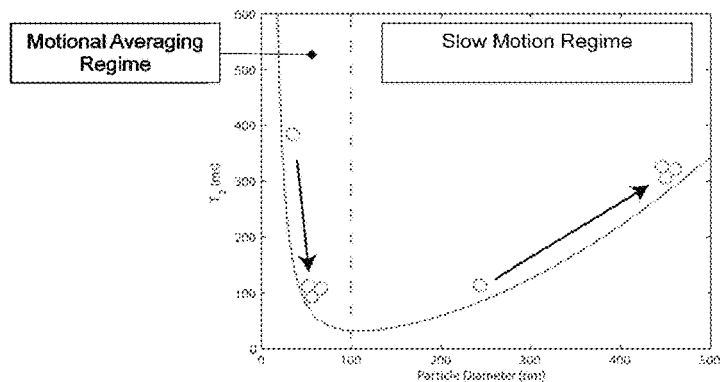
Figure 4E Figure 5
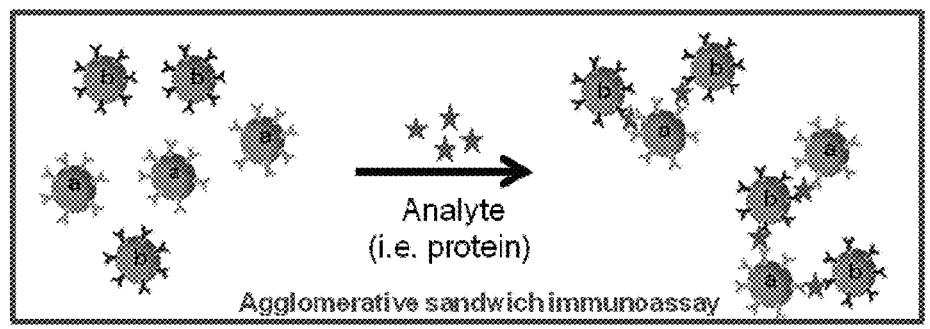
Figure 5A
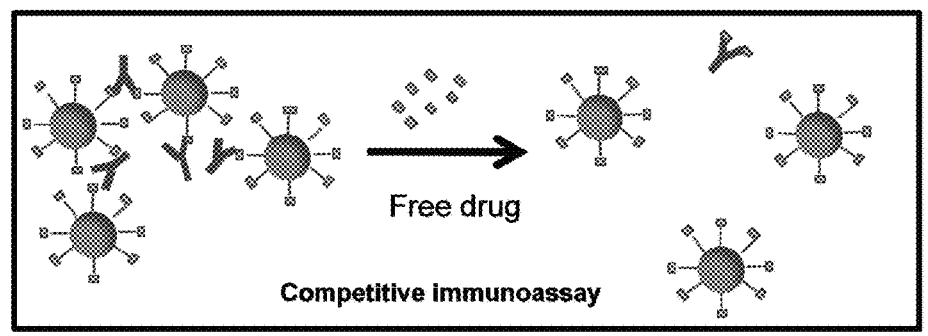
Figure 5B
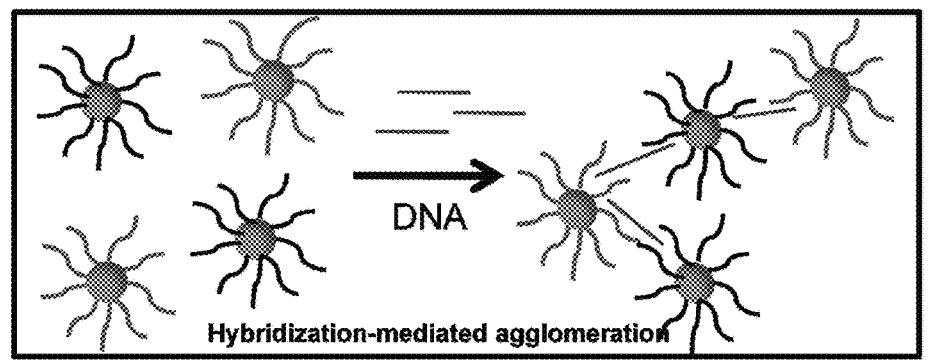
Figure 5C (L)6.56"x(W)2.23"x(H)2.24" (Including Tube Holder Assembly)

Figure 22
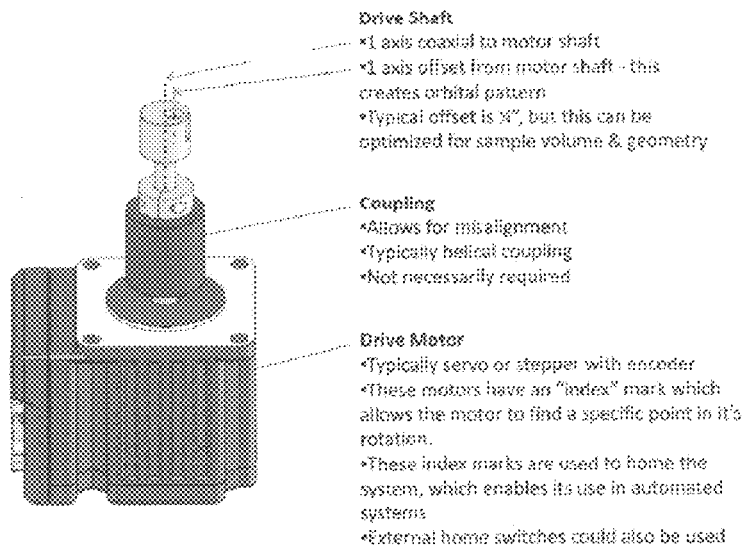
Figure 22A
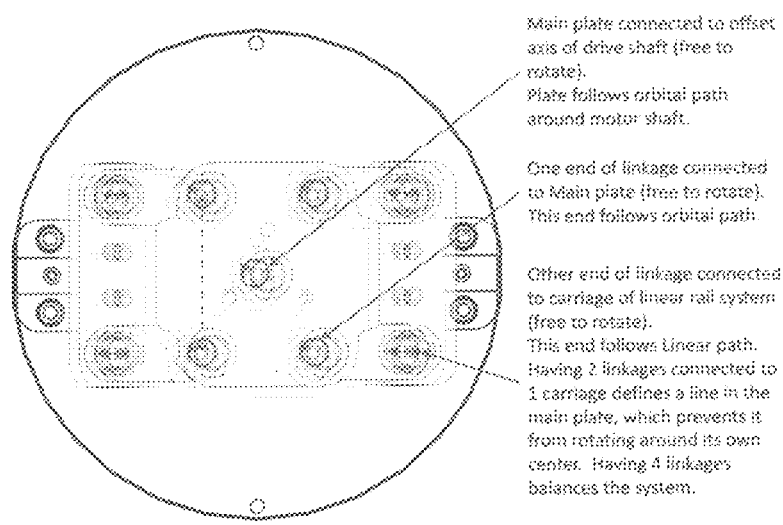
Figure 22B

Particle Surface before protein block

Particle Surface after protein block

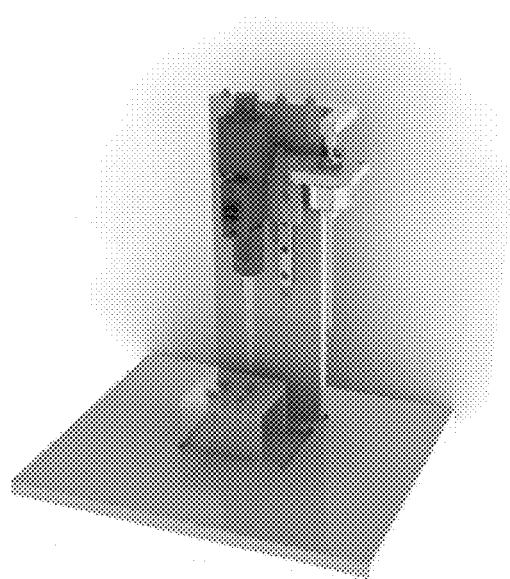
Figure 43A
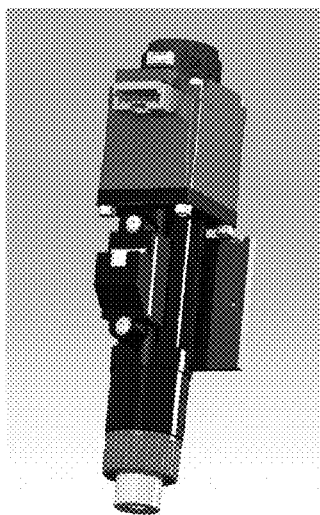 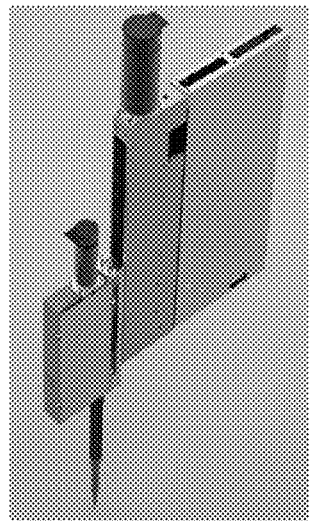 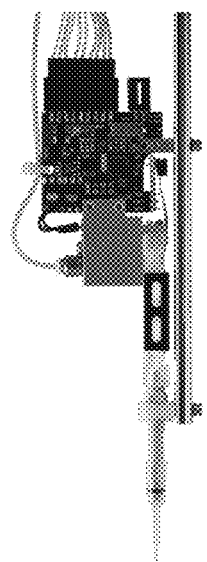
Figure 43B          Figure 43C          Figure 43D

| CFU/mL | day 1 | | day 2 | | day 3 | | day 4 | | day 5 | | day 6 | | day 7 | | day 8 | |
|---|---|---|---|---|---|---|---|---|---|---|---|---|---|---|---|---|
| | mean | %CV | mean | %CV | mean | %CV | mean | %CV | mean | %CV | mean | %CV | mean | %CV | mean | %CV |
| 100000 | 1143 | 5.2 | 1082 | 7.0 | 1031 | 8.5 | 1078 | 6.6 | 976 | 4.0 | 952 | 5.3 | 1040 | 2.2 | 1017 | 4.7 |
| 10000 | 1133 | 4.4 | 1160 | 1.4 | 1135 | 5.3 | 1078 | 7.5 | 931 | 6.7 | 975 | 9.4 | 1036 | 4.5 | 956 | 4.8 |
| 1000 | 1114 | 7.6 | 1056 | 3.0 | 1127 | 3.3 | 1049 | 3.7 | 972 | 7.4 | 952 | 5.0 | 1017 | 5.7 | 1025 | 6.0 |
| 100 | 936 | 5.4 | 871 | 2.1 | 891 | 8.1 | 831 | 11.9 | 750 | 3.3 | 895 | 10.1 | 807 | 3.6 | 760 | 9.5 |
| 10 | 383 | 1.0 | 440 | 6.4 | 379 | 7.0 | 371 | 5.0 | 365 | 11.7 | 374 | 4.3 | 417 | 8.4 | 361 | 11.1 |
| 0 | 107 | 2.2 | 108 | 1.0 | 100 | 0.6 | 101 | 0.9 | 95 | 0.8 | 94 | 2.1 | 93 | 2.6 | 91 | 0.5 |

NMR SYSTEMS AND METHODS FOR THE RAPID DETECTION OF ANALYTES

CROSS-REFERENCE TO RELATED APPLICATIONS

This application is the U.S. national stage filing under 35 U.S.C. §371 of international application PCT/US2011/056936, filed Oct. 19, 2011, which is a continuation-in-part claiming priority to U.S. application Ser. No. 12/910,594, filed Oct. 22, 2010, now U.S. Pat. No. 8,563,298, and also claims benefit of U.S. Provisional Patent Application No. 61/414,141, filed Nov. 16, 2010, U.S. Provisional Patent Application No. 61/418,465, filed Dec. 1, 2010, and U.S. Provisional Patent Application No. 61/497,374, filed Jun. 15, 2011, each of which is incorporated herein by reference.

BACKGROUND OF THE INVENTION

This invention features assays and devices for the detection of analytes, and their use in the treatment and diagnosis of disease.

Magnetic sensors have been designed to detect molecular interactions in a variety of media, including biofluids, food products, and soil samples, among other media. Upon target binding, these sensors cause changes in properties of neighboring water molecules (or any solvent molecule with free hydrogens) of a sample, which can be detected by magnetic resonance (NMR/MRI) techniques. Thus, by using these sensors in a liquid sample, it is possible to detect the presence, and potentially quantify the amount, of an analyte at very low concentration. For example, small molecules, DNA, RNA, proteins, carbohydrates, organisms, metabolites, and pathogens (e.g., viruses) can be detected using magnetic sensors.

In general, magnetic sensors are magnetic particles that bind or otherwise link to their intended molecular target to form clusters (aggregates). It is believed that when magnetic particles assemble into clusters and the effective cross sectional area becomes larger (and the cluster number density is smaller), the interactions with the water or other solvent molecules are altered, leading to a change in the measured relaxation rates (e.g., $T_2$, $T_1$, $T_2^*$), susceptibility, frequency of precession, among other physical changes. Additionally, cluster formation can be designed to be reversible (e.g., by temperature shift, chemical cleavage, pH shift, etc.) so that "forward" or "reverse" (competitive and inhibition) assays can be developed for detection of specific analytes. Forward (clustering) and reverse (declustering) types of assays can be used to detect a wide variety of biologically relevant materials. The MRS (magnetic resonance switch) phenomenon was previously described (see U.S. Patent Publication No. 20090029392).

Many diagnostic assays require sensitivity in the picomolar or subpicomolar range. In such assays an equally low concentration of paramagnetic particles is employed. As a result, the binding events leading to cluster formation can become a rate-limiting step in the completion of the assay as the collision frequency of antigens, paramagnetic particles, and partially formed clusters is low in this concentration range (see Baudry et al., Proc Natl Acad Sci USA, 103:16076 (2006)). The current detection of infectious agents, nucleic acids, small molecules, biowarfare agents and organisms, and molecular targets (biomarkers) or the combination of molecular and immunoassay targets usually requires up-front sample preparation, time to analyze the sample, and single tests for each of the individual analytes. There is a need for a rapid, commercially-realizable NMR-based analyte detection device suitable for use with magnetic nanosensors having four unique features and qualities: 1) little to no sample preparation, 2) multiplex detection across multiple molecular types, 3) rapid acquisition of diagnostic information, and 4) accurate information for point-of-care clinical decision making.

SUMMARY OF THE INVENTION

The invention features systems and methods for the detection of analytes.

The invention features a method for detecting the presence of an analyte in a liquid sample, the method including: (a) contacting a solution with magnetic particles to produce a liquid sample including from $1\times10^6$ to $1\times10^{13}$ magnetic particles per milliliter of the liquid sample (e.g., from $1\times10^6$ to $1\times10^8$, $1\times10^7$ to $1\times10^8$, $1\times10^7$ to $1\times10^9$, $1\times10^8$ to $1\times10^{10}$, $1\times10^9$ to $1\times10^{11}$, or $1\times10^{10}$ to $1\times10^{13}$ magnetic particles per milliliter), wherein the magnetic particles have a mean diameter of from 150 nm to 699 nm (e.g., from 150 to 250, 200 to 350, 250 to 450, 300 to 500, 450 to 650, or from 500 to 699 nm), a $T_2$ relaxivity per particle of from $1\times10^8$ to $1\times10^{12}$ mM$^{-1}$s$^{-1}$ (e.g., from $1\times10^8$ to $1\times10^9$, $1\times10^8$ to $1\times10^{10}$, $1\times10^9$ to $1\times10^{10}$, $1\times10^9$ to $1\times10^{11}$, or from $1\times10^{10}$ to $1\times10^{12}$ mM$^{-1}$s$^{-1}$), and binding moieties on their surface, the binding moieties operative to alter aggregation of the magnetic particles in the presence of the analyte or a multivalent binding agent; (b) placing the liquid sample in a device, the device including a support defining a well holding the liquid sample including the magnetic particles, the multivalent binding agent, and the analyte, and having an RF coil disposed about the well, the RF coil configured to detect a signal produced by exposing the liquid sample to a bias magnetic field created using one or more magnets and an RF pulse sequence; (c) exposing the sample to a bias magnetic field and an RF pulse sequence; (d) following step (c), measuring the signal; and (e) on the basis of the result of step (d), detecting the analyte. In certain embodiments, the magnetic particles are substantially monodisperse; exhibit nonspecific reversibility in the absence of the analyte and multivalent binding agent; and/or the magnetic particles further include a surface decorated with a blocking agent selected from albumin, fish skin gelatin, gamma globulin, lysozyme, casein, peptidase, and an amine-bearing moiety (e.g., amino polyethyleneglycol, glycine, ethylenediamine, or amino dextran). In particular embodiments, the liquid sample further includes a buffer, from 0.1% to 3% (w/w) albumin (e.g., from 0.1% to 0.5%, 0.3% to 0.7%, 0.5% to 1%, 0.8% to 2%, or from 1.5% to 3% (w/w) albumin), from 0.01% to 0.5% nonionic surfactant (e.g., from 0.01% to 0.05%, 0.05% to 0.1%, 0.05% to 0.2%, 0.1% to 0.3%, 0.2% to 0.4%, or from 0.3% to 0.5% nonionic surfactant), or a combination thereof. In still other embodiments, the magnetic particles include a surface decorated with 40 μg to 100 μg (e.g., 40 μg to 60 μg, 50 μg to 70 μg, 60 μg to 80 μg, or 80 μg to 100 μg,) of one or more proteins per milligram of the magnetic particles. The liquid sample can include a multivalent binding agent bearing a plurality of analytes conjugated to a polymeric scaffold. For example, the analyte can be creatinine, the liquid sample can include a multivalent binding agent bearing a plurality of creatinine conjugates, and the magnetic particles can include a surface decorated with creatinine antibodies. In another embodiment, the analyte can be tacrolimus, the liquid sample can include a multivalent binding agent bearing a plurality of tacrolimus conjugates, and the magnetic particles can include a surface decorated with tacrolimus antibodies. In particular embodiments of the method, step (d) includes measuring the $T_2$ relaxation response of the liquid sample, and wherein increasing agglomeration in the liquid sample produces an increase in the observed $T_2$ relaxation rate of the sample. In certain embodiments, the analyte is a target nucleic acid (e.g., a target nucleic acid extracted from a leukocyte, or a pathogen).

The invention features a method for detecting the presence of an analyte in a liquid sample, the method including (a) contacting a solution with magnetic particles to produce a liquid sample including from $1\times10^6$ to $1\times10^{13}$ magnetic particles per milliliter of the liquid sample (e.g., from $1\times10^6$ to $1\times10^8$, $1\times10^7$ to $1\times10^8$, to $1\times10^9$, $1\times10^8$ to $1\times10^{10}$, $1\times10^9$ to $1\times10^{11}$, or $1\times10^{19}$ to $1\times10^{13}$ magnetic particles per milliliter), wherein the magnetic particles have a mean diameter of from 700 nm to 1200 nm (e.g., from 700 to 850, 800 to 950, 900 to 1050, or from 1000 to 1200 nm), a $T_2$ relaxivity per particle of from $1\times10^9$ to $1\times10^{12}$ mM$^{-1}$s$^{-1}$ (e.g., from $1\times10^9$ to $1\times10^{10}$, $1\times10^9$ to $1\times10^{11}$, or from $1\times10^{10}$ to $1\times10^{12}$ mM$^{-1}$s$^{-1}$), and have binding moieties on their surface, the binding moieties operative to alter an aggregation of the magnetic particles in the presence of the analyte; (b) placing the liquid sample in a device, the device including a support defining a well holding the liquid sample including the magnetic particles, the multivalent binding agent, and the analyte, and having an RF coil disposed about the well, the RF coil configured to detect a signal produced by exposing the liquid sample to a bias magnetic field created using one or more magnets and an RF pulse sequence; (c) exposing the sample to a bias magnetic field and an RF pulse sequence; (d) following step (c), measuring the signal; and (e) on the basis of the result of step (d), detecting the presence or concentration of an analyte. In certain embodiments, the magnetic particles are substantially monodisperse; exhibit nonspecific reversibility in the absence of the analyte and multivalent binding agent; and/or the magnetic particles further include a surface decorated with a blocking agent selected from albumin, fish skin gelatin, gamma globulin, lysozyme, casein, peptidase, and an amine-bearing moiety (e.g., amino polyethyleneglycol, glycine, ethylenediamine, or amino dextran). In particular embodiments, the liquid sample further includes a buffer, from 0.1% to 3% (w/w) albumin (e.g., from 0.1% to 0.5%, 0.3% to 0.7%, 0.5% to 1%, 0.8% to 2%, or from 1.5% to 3% (w/w) albumin), from 0.01% to 0.5% nonionic surfactant (e.g., from 0.01% to 0.05%, 0.05% to 0.1%, 0.05% to 0.2%, 0.1% to 0.3%, 0.2% to 0.4%, or from 0.3% to 0.5% nonionic surfactant), or a combination thereof. In still other embodiments, the magnetic particles include a surface decorated with 40 µg to 100 µg (e.g., 40 µg to 60 µg, 50 µg to 70 µg, 60 µg to 80 µg, or 80 µg to 100 µg) of one or more proteins per milligram of the magnetic particles. The liquid sample can include a multivalent binding agent bearing a plurality of analytes conjugated to a polymeric scaffold. For example, the analyte can be creatinine, the liquid sample can include a multivalent binding agent bearing a plurality of creatinine conjugates, and the magnetic particles can include a surface decorated with creatinine antibodies. In another embodiment, the analyte can be tacrolimus, the liquid sample can include a multivalent binding agent bearing a plurality of tacrolimus conjugates, and the magnetic particles can include a surface decorated with tacrolimus antibodies. In particular embodiments of the method, step (d) includes measuring the $T_2$ relaxation response of the liquid sample, and wherein increasing agglomeration in the liquid sample produces an increase in the observed $T_2$ relaxation rate of the sample. In certain embodiments, the analyte is a target nucleic acid (e.g., a target nucleic acid extracted from a leukocyte, or a pathogen).

The invention further features a method for detecting the presence of a pathogen in a whole blood sample, the method including: (a) providing a whole blood sample from a subject; (b) mixing the whole blood sample with an erythrocyte lysis agent solution to produce disrupted red blood cells; (c) following step (b), centrifuging the sample to form a supernatant and a pellet, discarding some or all of the supernatant, and resuspending the pellet to form an extract, optionally washing the pellet (e.g., with TE buffer) prior to resuspending the pellet and optionally repeating step (c); (d) lysing cells of the extract to form a lysate; (e) placing the lysate of step (d) in a detection tube and amplifying a target nucleic acid in the lysate to form an amplified lysate solution including the target nucleic acid, wherein the target nucleic acid is characteristic of the pathogen to be detected; (f) following step (e), adding to the detection tube from $1\times10^6$ to $1\times10^{13}$ magnetic particles per milliliter of the amplified lysate solution (e.g., from $1\times10^6$ to $1\times10^8$, $1\times10^7$ to $1\times10^8$, $1\times10^7$ to $1\times10^9$, $1\times10^8$ to $1\times10^{10}$, $1\times10^9$ to $1\times10^{11}$, or $1\times10^{10}$ to $1\times10^{13}$ magnetic particles per milliliter), wherein the magnetic particles have a mean diameter of from 700 nm to 1200 nm (e.g., from 700 to 850, 800 to 950, 900 to 1050, or from 1000 to 1200 nm), and binding moieties on their surface, the binding moieties operative to alter aggregation of the magnetic particles in the presence of the target nucleic acid or a multivalent binding agent; (g) placing the detection tube in a device, the device including a support defining a well for holding the detection tube including the magnetic particles and the target nucleic acid, and having an RF coil disposed about the well, the RF coil configured to detect a signal produced by exposing the liquid sample to a bias magnetic field created using one or more magnets and an RF pulse sequence; (h) exposing the sample to a bias magnetic field and an RF pulse sequence; (i) following step (h), measuring the signal from the detection tube; and (j) on the basis of the result of step (i), detecting the pathogen. In certain embodiments, steps (a) through (i) are completed within 4 hours (e.g., within 3.5 hours, 3.0 hours, 2.5 hours, 2 hours, 1.5 hours, or 1 hour). In another embodiment, step (i) is carried out without any prior purification of the amplified lysate solution (i.e., the lysate solution is unfractionated after it is formed). In particular embodiments, step c includes washing the pellet prior to resuspending the pellet to form the extract. In particular embodiments step (d) includes combining the extract with beads to form a mixture and agitating the mixture to form a lysate. The magnetic particles can include one or more populations having a first probe and a second probe conjugated to their surface, the first probe operative to bind to a first segment of the target nucleic acid and the second probe operative to bind to a second segment of the target nucleic acid, wherein the magnetic particles form aggregates in the presence of the target nucleic acid. Alternatively, the assay can be a disaggregation assay in which the magnetic particles include a first population having a first binding moiety on their surface and a second population having a second binding moiety on their surface, and the multivalent binding moiety including a first probe and a second probe, the first probe operative to bind to the first binding moiety and the second probe operative to bind to a second binding moiety, the binding moieties and multivalent binding moiety operative to alter an aggregation of the magnetic particles in the presence of the target nucleic acid. In certain embodiments, the magnetic particles are substantially monodisperse; exhibit nonspecific reversibility in the absence of the analyte and multivalent binding agent; and/or the magnetic particles further include a surface decorated with a blocking agent selected from albumin, fish skin gelatin, gamma globulin, lysozyme, casein, peptidase, and an amine-bearing moiety (e.g., amino polyethyleneglycol, glycine, ethylenediamine, or amino dextran). In particular embodiments, the lysate further includes a buffer, from 0.1% to 3% (w/w) albumin (e.g., from 0.1% to 0.5%, 0.3% to 0.7%, 0.5% to 1%, 0.8% to 2%, or from 1.5% to 3% (w/w) albumin), from 0.01% to 0.5% nonionic surfactant (e.g., from 0.01% to 0.05%, 0.05% to 0.1%, 0.05% to 0.2%, 0.1% to 0.3%, 0.2% to 0.4%, or from 0.3% to 0.5% nonionic surfactant), or a combination thereof. In still other embodiments, the magnetic particles include a surface decorated with 40 µg to 100 µg (e.g., 40 µg to 60 µg, 50 µg to 70 µg, 60 µg to 80 µg, or 80 µg to 100 µg,) of one or more proteins per milligram of the magnetic particles. The lysate can include a multivalent binding agent bearing a plurality of analytes conjugated to a polymeric scaffold.

The invention features a method for detecting the presence of a target nucleic acid in a whole blood sample, the method including: (a) providing one or more cells from a whole blood sample from a subject; (b) lysing the cells to form a lysate; (c) amplifying a target nucleic acid in the lysate to form an amplified lysate solution comprising the target nucleic acid; (d) following step (c), adding to a detection tube the amplified lysate solution and from $1\times10^6$ to $1\times10^{13}$ magnetic particles per milliliter of the amplified lysate solution, wherein the magnetic particles have a mean diameter of from 700 nm to 1200 nm and binding moieties on their surface, the binding moieties operative to alter aggregation of the magnetic particles in the presence of the target nucleic acid or a multivalent binding agent; (e) placing the detection tube in a device, the device including a support defining a well for holding the detection tube including the magnetic particles and the target nucleic acid, and having an RF coil disposed about the well, the RF coil configured to detect a signal produced by exposing the liquid sample to a bias magnetic field created using one or more magnets and an RF pulse sequence; (f) exposing the sample to a bias magnetic field and an RF pulse sequence; (b) following step (f), measuring the signal from the detection tube; and (i) on the basis of the result of step (h), detecting the target nucleic acid. In particular embodiments, the target nucleic acid is purified prior to step (d). In particular embodiments, step (b) includes combining the extract with beads to form a mixture and agitating the mixture to form a lysate. The magnetic particles can include one or more populations having a first probe and a second probe conjugated to their surface, the first probe operative to bind to a first segment of the target nucleic acid and the second probe operative to bind to a second segment of the target nucleic acid, wherein the magnetic particles form aggregates in the presence of the target nucleic acid. Alternatively, the assay can be a disaggregation assay in which the magnetic particles include a first population having a first binding moiety on their surface and a second population having a second binding moiety on their surface, and the multivalent binding moiety including a first probe and a second probe, the first probe operative to bind to the first binding moiety and the second probe operative to bind to a second binding moiety, the binding moieties and multivalent binding moiety operative to alter an aggregation of the magnetic particles in the presence of the target nucleic acid. In certain embodiments, the magnetic particles are substantially monodisperse; exhibit nonspecific reversibility in the absence of the analyte and multivalent binding agent; and/or the magnetic particles further include a surface decorated with a blocking agent selected from albumin, fish skin gelatin, gamma globulin, lysozyme, casein, peptidase, and an amine-bearing moiety (e.g., amino polyethyleneglycol, glycine, ethylenediamine, or amino dextran). In particular embodiments, the lysate further includes a buffer, from 0.1% to 3% (w/w) albumin (e.g., from 0.1% to 0.5%, 0.3% to 0.7%, 0.5% to 1%, 0.8% to 2%, or from 1.5% to 3% (w/w) albumin), from 0.01% to 0.5% nonionic surfactant (e.g., from 0.01% to 0.05%, 0.05% to 0.1%, 0.05% to 0.2%, 0.1% to 0.3%, 0.2% to 0.4%, or from 0.3% to 0.5% nonionic surfactant), or a combination thereof. In still other embodiments, the magnetic particles optionally include a surface decorated with 40 µg to 100 µg (e.g., 40 µg to 60 µg, 50 µg to 70 µg, 60 µg to 80 µg, or 80 µg to 100 µg,) of one or more proteins per milligram of the magnetic particles. The lysate can include a multivalent binding agent bearing a plurality of analytes conjugated to a polymeric scaffold.

The invention further features a method for detecting the presence of a target nucleic acid in a whole blood sample, the method including: (a) providing an extract produced by lysing the red blood cells in a whole blood sample from a subject, centrifuging the sample to form a supernatant and a pellet, discarding some or all of the supernatant, and resuspending the pellet to form an extract, optionally washing the pellet (e.g., with TE buffer) prior to resuspending the pellet and optionally repeating the centrifuging, discarding, and washing of step (a); (b) lysing cells in the extract to form a lysate; (c) placing the lysate of step (b) in a detection tube and amplifying nucleic acids therein to form an amplified lysate solution including from 40% (w/w) to 95% (w/w) the target nucleic acid (e.g., from 40 to 60%, from 60 to 80%, or from 85 to 95% (w/w) target nucleic acid) and from 5% (w/w) to 60% (w/w) nontarget nucleic acid (e.g., from 5 to 20%, from 20 to 40%, or from 40 to 60% (w/w) nontarget nucleic acid); (d) following step (c), adding to the detection tube from $1\times10^6$ to $1\times10^{13}$ magnetic particles per milliliter of the amplified lysate solution, wherein the magnetic particles have a mean diameter of from 700 nm to 1200 nm and binding moieties on their surface, the binding moieties operative to alter aggregation of the magnetic particles in the presence of the target nucleic acid or a multivalent binding agent; (e) placing the detection tube in a device, the device including a support defining a well for holding the detection tube including the magnetic particles and the target nucleic acid, and having an RF coil disposed about the well, the RF coil configured to detect a signal produced by exposing the liquid sample to a bias magnetic field created using one or more magnets and an RF pulse sequence; (f) exposing the sample to a bias magnetic field and an RF pulse sequence; (g) following step (f), measuring the signal from the detection tube; and (h) on the basis of the result of step (g), detecting the target nucleic acid, wherein step (g) is carried out without any prior purification of the amplified lysate solution. In particular embodiments, step (b) includes combining the extract with beads to form a mixture and agitating the mixture to form a lysate. The magnetic particles can include one or more populations having a first probe and a second probe conjugated to their surface, the first probe operative to bind to a first segment of the target nucleic acid and the second probe operative to bind to a second segment of the target nucleic acid, wherein the magnetic particles form aggregates in the presence of the target nucleic acid. Alternatively, the assay can be a disaggregation assay in which the magnetic particles include a first population having a first binding moiety on their surface and a second population having a second binding moiety on their surface, and the multivalent binding moiety including a first probe and a second probe, the first probe operative to bind to the first binding moiety and the second probe operative to bind to a second binding moiety, the binding moieties and multivalent binding moiety operative to alter an aggregation of the magnetic particles in the presence of the target nucleic acid. In certain embodiments, the magnetic particles are substantially monodisperse; exhibit nonspecific reversibility in the absence of the analyte and multivalent binding agent; and/or the magnetic particles further include a surface decorated with a blocking agent selected from albumin, fish skin gelatin, gamma globulin, lysozyme, casein, peptidase, and an amine-bearing moiety (e.g., amino polyethyleneglycol, glycine, ethylenediamine, or amino dextran). In particular embodiments, the lysate further includes a buffer, from 0.1% to 3% (w/w) albumin (e.g., from 0.1% to 0.5%, 0.3% to 0.7%, 0.5% to 1%, 0.8% to 2%, or from 1.5% to 3% (w/w) albumin), from 0.01% to 0.5% nonionic surfactant (e.g., from 0.01% to 0.05%, 0.05% to 0.1%, 0.05% to 0.2%, 0.1% to 0.3%, 0.2% to 0.4%, or from 0.3% to 0.5% nonionic surfactant), or a combination thereof. In still other embodiments, the magnetic particles include a surface decorated with 40 μg to 100 μg (e.g., 40 μg to 60 μg, 50 μg to 70 μg, 60 μg to 80 μg, or 80 μg to 100 μg,) of one or more proteins per milligram of the magnetic particles. The lysate can include a multivalent binding agent bearing a plurality of analytes conjugated to a polymeric scaffold.

The invention features a method for detecting the presence of a *Candida* species in a liquid sample, the method including: (a) lysing the *Candida* cells in the liquid sample; (b) amplifying a nucleic acid to be detected in the presence of a forward primer and a reverse primer, each of which is universal to multiple *Candida* species to form a solution including a *Candida* amplicon; (c) contacting the solution with magnetic particles to produce a liquid sample including from $1\times10^6$ to $1\times10^{13}$ magnetic particles per milliliter of the liquid sample (e.g., from $1\times10^6$ to $1\times10^8$, $1\times10^7$ to $1\times10^8$, $1\times10^7$ to $1\times10^9$, $1\times10^8$ to $1\times10^{10}$, $1\times10^9$ to $1\times10^{11}$, or $1\times10^{10}$ to $1\times10^{13}$ magnetic particles per milliliter), wherein the magnetic particles have a mean diameter of from 700 nm to 1200 nm (e.g., from 700 to 850, 800 to 950, 900 to 1050, or from 1000 to 1200 nm), a $T_2$ relaxivity per particle of from $1\times10^9$ to $1\times10^{12}$ mM$^{-1}$s$^{-1}$ (e.g., from $1\times10^8$ to $1\times10^9$, $1\times10^8$ to $1\times10^{10}$, $1\times10^9$ to $1\times10^{11}$, or from $1\times10^{10}$ to $1\times10^{12}$ mM$^{-1}$s$^{-1}$), and binding moieties on their surface, the binding moieties operative to alter aggregation of the magnetic particles in the presence of the *Candida* amplicon or a multivalent binding agent; (d) placing the liquid sample in a device, the device including a support defining a well for holding the liquid sample including the magnetic particles and the *Candida* amplicon, and having an RF coil disposed about the well, the RF coil configured to detect a signal produced by exposing the liquid sample to a bias magnetic field created using one or more magnets and an RF pulse sequence; (e) exposing the sample to a bias magnetic field and an RF pulse sequence; (f) following step (e), measuring the signal; and (g) on the basis of the result of step (f), determining whether the *Candida* species was present in the sample. In certain embodiments, the magnetic particles are substantially monodisperse; exhibit nonspecific reversibility in the absence of the analyte and multivalent binding agent; and/or the magnetic particles further include a surface decorated with a blocking agent selected from albumin, fish skin gelatin, gamma globulin, lysozyme, casein, peptidase, and an amine-bearing moiety (e.g., amino polyethyleneglycol, glycine, ethylenediamine, or amino dextran). In particular embodiments, the liquid sample further includes a buffer, from 0.1% to 3% (w/w) albumin (e.g., from 0.1% to 0.5%, 0.3% to 0.7%, 0.5% to 1%, 0.8% to 2%, or from 1.5% to 3% (w/w) albumin), from 0.01% to 0.5% nonionic surfactant (e.g., from 0.01% to 0.05%, 0.05% to 0.1%, 0.05% to 0.2%, 0.1% to 0.3%, 0.2% to 0.4%, or from 0.3% to 0.5% nonionic surfactant), or a combination thereof. In still other embodiments, the magnetic particles include a surface decorated with 40 μg to 100 μg (e.g., 40 μg to 60 μg, 50 μg to 70 μg, 60 μg to 80 μg, or 80 μg to 100 μg,) of one or more proteins per milligram of the magnetic particles. The liquid sample can include a multivalent binding agent bearing a plurality of analytes conjugated to a polymeric scaffold. The forward primer can include, for example, the sequence 5'-GGC ATG CCT GTT TGA GCG TC-3' (SEQ ID NO. 1). The reverse primer can include, for example, the sequence 5'-GCT TAT TGA TAT GCT TAA GTT CAG CGG GT-3' (SEQ ID NO. 2). In certain embodiments, (i) the *Candida* species is *Candida albicans*, the first probe includes the oligonucleotide sequence 5'-ACC CAG CGG TTT GAG GGA GAA AC-3' (SEQ ID NO. 3), and the second probe includes the oligonucleotide sequence 5'-AAA GTT TGA AGA TAT ACG TGG TGG ACG TTA-3' (SEQ ID NO. 4); (ii) the *Candida* species is *Candida krusei* and the first probe and the second probe include an oligonucleotide sequence selected from: 5'-CGC ACG CGC AAG ATG GAA ACG-3' (SEQ ID NO. 5), 5'-AAG TTC AGC GGG TAT TCC TAC CT-3' (SEQ ID NO. 6), and 5'-AGC TTT TTG TTG TCT CGC AAC ACT CGC-3' (SEQ ID NO. 32); (iii) the *Candida* species is *Candida glabrata*, the first probe includes the oligonucleotide sequence: 5'-CTA CCA AAC ACA ATG TGT TTG AGA AG-3' (SEQ ID NO. 7), and the second probe includes the oligonucleotide sequence: 5'-CCT GAT TTG AGG TCA AAC TTA AAG ACG TCT G-3' (SEQ ID NO. 8); and (iv) the *Candida* species is *Candida parapsilosis* or *Candida tropicalis* and the first probe and the second probe include an oligonucleotide sequence selected from: 5'-AGT CCT ACC TGA TTT GAG GTCNitIndAA-3' (SEQ ID NO. 9), 5'-CCG NitIndGG GTT TGA GGG AGA AAT-3' (SEQ ID NO. 10), AAA GTT ATG AAATAA ATT GTG GTG GCC ACT AGC (SEQ ID NO. 33), ACC CGG GGGTTT GAG GGA GAA A (SEQ ID NO. 34), AGT CCT ACC TGA TTT GAG GTC GAA (SEQ ID NO. 35), and CCG AGG GTT TGA GGG AGA AAT (SEQ ID NO. 36). In certain embodiments, steps (a) through (h) are completed within 4 hours (e.g., within 3.5 hours, 3.0 hours, 2.5 hours, 2 hours, 1.5 hours, or 1 hour or less). In particular embodiments, the magnetic particles include two populations, a first population bearing the first probe on its surface, and the second population bearing the second probe on its surface. In another embodiment, the magnetic particles are a single population bearing both the first probe and the second probe on the surface of the magnetic particles. The magnetic particles can include one or more populations having a first probe and a second probe conjugated to their surface, the first probe operative to bind to a first segment of the *Candida* amplicon and the second probe operative to bind to a second segment of the *Candida* amplicon, wherein the magnetic particles form aggregates in the presence of the target nucleic acid. Alternatively, the assay can be a disaggregation assay in which the magnetic particles include a first population having a first binding moiety on their surface and a second population having a second binding moiety on their surface, and the multivalent binding moiety including a first probe and a second probe, the first probe operative to bind to the first binding moiety and the second probe operative to bind to a second binding moiety, the binding moieties and multivalent binding moiety operative to alter an aggregation of the magnetic particles in the presence of the *Candida* amplicon. In particular embodiments, the method can produce (i) a coefficient of variation in the T2 value of less than 20% on *Candida* positive samples; (ii) at least 95% correct detection at less than or equal to 5 cells/mL in samples spiked into 50 individual healthy patient blood samples; (iii) at least 95% correct detection less than or equal to 5 cells/mL in samples spiked into 50 individual unhealthy patient blood samples; and/or (iv) greater than or equal to 80% correct detection in clinically positive patient samples (i.e., *Candida* positive by another technique, such as by cell culture) starting with 2 mL of blood.

The invention features a method for detecting the presence of a *Candida* species in a whole blood sample sample, the method including: (a) providing an extract produced by lysing the red blood cells in a whole blood sample from a subject; (b) centrifuging the sample to form a supernatant and a pellet, discarding some or all of the supernatant; (c) washing the pellet (e.g., with TE buffer) by mixing the pellet with a buffer, agitating the sample (e.g., by vortexing), centrifuging the sample to form a supernatant and a pellet, discarding some or all of the supernatant; (d) optionally repeating steps (b) and (c); (e) bead beating the pellet to form a lysate in the presence of a buffer (e.g., TE buffer); (f) centrifuging the sample to form a supernatant containing the lysate; (g) amplifying nucleic acids in the lysate of step (f) to form a *Candida* amplicon; and (h) detecting the presence of the *Candida* amplicon, wherein, the method can produce (i) at least 95% correct detection at less than or equal to 5 cells/mL in samples spiked into 50 individual healthy patient blood samples; (ii) at least 95% correct detection less than or equal to 5 cells/mL in samples spiked into 50 individual unhealthy patient blood samples; and/or (iii) greater than or equal to 80% correct detection in clinically positive patient samples (i.e., *Candida* positive by cell culture) starting with 2 mL of blood at step (a).

The invention features a method for detecting the presence of a pathogen in a whole blood sample, the method including the steps of: (a) providing from 0.05 to 4.0 mL of the whole blood sample (e.g., from 0.05 to 0.25, 0.25 to 0.5, 0.25 to 0.75, 0.4 to 0.8, 0.5 to 0.75, 0.6 to 0.9, 0.65 to 1.25, 1.25 to 2.5, 2.5 to 3.5, or 3.0 to 4.0 mL of whole blood); (b) placing an aliquot of the sample of step (a) in a container and amplifying a target nucleic acid in the sample to form an amplified solution including the target nucleic acid, wherein the target nucleic acid is characteristic of the pathogen to be detected; (c) placing the amplified liquid sample in a detecting device; (d) on the basis of the result of step (c), detecting the pathogen, wherein the pathogen is selected from bacteria and fungi, and wherein the method is capable of detecting a pathogen concentration of 10 cells/mL (e.g., 1, 2, 3, 4, 5, 6, 7, 8, 9, 10, 15, 20, 25, 30, 35, 40, 45, or 50 cells/mL) in the whole blood sample. The detecting device can detect the pathogen via an optical, fluorescent, mass, density, magnetic, chromatographic, and/or electrochemical measurement of the amplified liquid sample. In certain embodiments, steps (a) through (d) are completed within 3 hours (e.g., within 3.2, 2.9, 2.7, 2.5, 2.3, 2.2, 2.1, 2.0, 1.9, 1.8, 1.7, 1.6, or 1.5 hours or 1 hour). In still other embodiments, step (c) is carried out without any prior purification of the amplified solution, and/or the liquid sample of step (c) includes whole blood proteins and non-target oligonucleotides. In certain embodiments, the pathogen is selected from bacteria and fungi. The pathogen can be any bacterial or fungal pathogen described herein.

The invention also features a method for detecting the presence of a pathogen in a whole blood sample, the method including the steps of: (a) providing a whole blood sample from a subject; (b) mixing from 0.05 to 4.0 mL of the whole blood sample (e.g., from 0.05 to 0.25, 0.25 to 0.5, 0.25 to 0.75, 0.4 to 0.8, 0.5 to 0.75, 0.6 to 0.9, 0.65 to 1.25, 1.25 to 2.5, 2.5 to 3.5, or 3.0 to 4.0 mL of whole blood) with an erythrocyte lysis agent solution to produce disrupted red blood cells; (c) following step (b), centrifuging the sample to form a supernatant and a pellet, discarding some or all of the supernatant, and resuspending the pellet to form an extract, optionally washing the pellet (e.g., with TE buffer) prior to resuspending the pellet and optionally repeating step (c); (d) lysing cells of the extract to form a lysate; (e) placing the lysate of step (d) in a container and amplifying a target nucleic acid in the lysate to form an amplified lysate solution including the target nucleic acid, wherein the target nucleic acid is characteristic of the pathogen to be detected; (f) following step (e), mixing the amplified lysate solution with from $1\times10^6$ to $1\times10^{13}$ magnetic particles per milliliter of the amplified lysate solution to form a liquid sample (e.g., from $1\times10^6$ to $1\times10^8$, $1\times10^7$ to $1\times10^8$, $1\times10^7$ to $1\times10^9$, $1\times10^8$ to $1\times10^{10}$, $1\times10^9$ to $1\times10^{11}$, or $1\times10^{10}$ to $1\times10^{13}$, magnetic particles per milliliter), wherein the magnetic particles have a mean diameter of from 150 nm to 1200 nm (e.g., from 150 to 250, 200 to 350, 250 to 450, 300 to 500, 450 to 650, 500 to 700 nm, 700 to 850, 800 to 950, 900 to 1050, or from 1000 to 1200 nm), a $T_2$ relaxivity per particle of from $1\times10^8$ to $1\times10^{12}$ mM$^{-1}$s$^{-1}$ (e.g., from $1\times10^8$ to $1\times10^9$, $1\times10^8$ to $1\times10^{10}$, $1\times10^9$ to $1\times10^{10}$, $1\times10^9$ to $1\times10^{11}$, or from $1\times10^{10}$ to $1\times10^{12}$ mM$^{-1}$s$^{-1}$), and binding moieties on their surface, the binding moieties operative to alter aggregation of the magnetic particles in the presence of the target nucleic acid or a multivalent binding agent; (g) placing the liquid sample in a device, the device including a support defining a well for holding the detection tube including the magnetic particles and the target nucleic acid, and having an RF coil disposed about the well, the RF coil configured to detect a signal produced by exposing the liquid sample to a bias magnetic field created using one or more magnets and an RF pulse sequence; (h) exposing the sample to a bias magnetic field and an RF pulse sequence; (i) following step (h), measuring the signal from the liquid sample; and (j) on the basis of the result of step (i), detecting the pathogen, wherein the pathogen is selected from bacteria and fungi, and wherein the method is capable of detecting a pathogen concentration of 10 cells/mL (e.g., 1, 2, 3, 4, 5, 6, 7, 8, 9, 10, 15, 20, 25, 30, 35, 40, 45, or 50 cells/mL) in the whole blood sample. In certain embodiments, steps (a) through (i) are completed within 3 hours (e.g., within 3.2, 2.9, 2.7, 2.5, 2.3, 2.2, 2.1, 2.0, 1.9, 1.8, 1.7, 1.6, 1.5, or for less hours). In still other embodiments, step (i) is carried out without any prior purification of the amplified lysate solution, and/or the liquid sample of step (i) includes whole blood proteins and non-target oligonucleotides. In certain embodiments, the pathogen is selected from bacteria and fungi. The pathogen can be any bacterial or fungal pathogen described herein. In particular embodiments the method is capable of measuring a pathogen concentration of 10 cells/mL in the whole blood sample with a coefficient of variation of less than 15% (e.g., 10 cells/mL with a coefficient of variation of less than 15%, 10%, 7.5%, or 5%; or 25 cells/mL with a coefficient of variation of less than 15%, 10%, 7.5%, or 5%; or 50 cells/mL with a coefficient of variation of less than 15%, 10%, 7.5%, or 5%; or 100 cells/mL with a coefficient of variation of less than 15%, 10%, 7.5%, or 5%). In certain embodiments, the magnetic particles are substantially monodisperse; exhibit nonspecific reversibility in the absence of the analyte and multivalent binding agent; and/or the magnetic particles further include a surface decorated with a blocking agent selected from albumin, fish skin gelatin, gamma globulin, lysozyme, casein, peptidase, and an amine-bearing moiety (e.g., amino polyethyleneglycol, glycine, ethylenediamine, or amino dextran). In particular embodiments, the liquid sample further includes a buffer, from 0.1% to 3% (w/w) albumin (e.g., from 0.1% to 0.5%, 0.3% to 0.7%, 0.5% to 1%, 0.8% to 2%, or from 1.5% to 3% (w/w) albumin), from 0.01% to 0.5% nonionic surfactant (e.g., from 0.01% to 0.05%, 0.05% to 0.1%, 0.05% to 0.2%, 0.1% to 0.3%, 0.2% to 0.4%, or from 0.3% to 0.5% nonionic surfactant), or a combination thereof. In still other embodiments, the magnetic particles include a surface decorated with 40 μg to 100 μg (e.g., 40 μg to 60 μg, 50 μg to 70 μg, 60 μg to 80 μg, or 80 μg to 100 μg,) of one or more proteins per milligram of the magnetic particles. The liquid sample can include a multivalent binding agent bearing a plurality of analytes conjugated to a polymeric scaffold. The method for monitoring can include any of the magnetic assisted agglomeration methods described herein. The magnetic particles can include one or more populations having a first probe and a second probe conjugated to their surface, the first probe operative to bind to a first segment of the target nucleic acid and the second probe operative to bind to a second segment of the target nucleic acid, wherein the magnetic particles form aggregates in the presence of the target nucleic acid. Alternatively, the assay can be a disaggregation assay in which the magnetic particles include a first population having a first binding moiety on their surface and a second population having a second binding moiety on their surface, and the multivalent binding moiety including a first probe and a second probe, the first probe operative to bind to the first binding moiety and the second probe operative to bind to a second binding moiety, the binding moieties and multivalent binding moiety operative to alter an aggregation of the magnetic particles in the presence of the target nucleic acid.

The invention further features a method for detecting the presence of a virus in a whole blood sample, the method including the steps of: (a) providing a plasma sample from a subject; (b) mixing from 0.05 to 4.0 mL of the plasma sample (e.g., from 0.05 to 0.25, 0.25 to 0.5, 0.25 to 0.75, 0.4 to 0.8, 0.5 to 0.75, 0.6 to 0.9, 0.65 to 1.25, 1.25 to 2.5, 2.5 to 3.5, or 3.0 to 4.0 mL of whole blood) with a lysis agent to produce a mixture comprising disrupted viruses; (c) placing the mixture of step (b) in a container and amplifying a target nucleic acid in the filtrate to form an amplified filtrate solution including the target nucleic acid, wherein the target nucleic acid is characteristic of the virus to be detected; (d) following step (c), mixing the amplified filtrate solution with from $1\times10^6$ to $1\times10^{13}$ magnetic particles per milliliter of the amplified filtrate solution to form a liquid sample (e.g., from $1\times10^6$ to $1\times10^8$, $1\times10^7$ to $1\times10^8$, $1\times10^7$ to $1\times10^9$, $1\times10^8$ to $1\times10^{10}$, $1\times10^9$ to $1\times10^{11}$, or $1\times10^{10}$ to $1\times10^{13}$ magnetic particles per milliliter), wherein the magnetic particles have a mean diameter of from 150 nm to 1200 nm (e.g., from 150 to 250, 200 to 350, 250 to 450, 300 to 500, 450 to 650, 500 to 700 nm, 700 to 850, 800 to 950, 900 to 1050, or from 1000 to 1200 nm), a $T_2$ relaxivity per particle of from $1\times10^8$ to $1\times10^{12}$ mM$^{-1}$s$^{-1}$ (e.g., from $1\times10^8$ to $1\times10^9$, $1\times10^8$ to $1\times10^{10}$, $1\times10^9$ to $1\times10^{16}$, $1\times10^9$ to $1\times10^{11}$, or from $1\times10^{16}$ to $1\times10^{12}$ mM$^{-1}$s$^{-1}$), and binding moieties on their surface, the binding moieties operative to alter aggregation of the magnetic particles in the presence of the target nucleic acid or a multivalent binding agent; (e) placing the liquid sample in a device, the device including a support defining a well for holding the detection tube including the magnetic particles and the target nucleic acid, and having an RF coil disposed about the well, the RF coil configured to detect a signal produced by exposing the liquid sample to a bias magnetic field created using one or more magnets and an RF pulse sequence; (f) exposing the liquid sample to a bias magnetic field and an RF pulse sequence; (g) following step (f), measuring the signal from the liquid sample; and (h) on the basis of the result of step (g), detecting the virus, wherein the method is capable of detecting fewer than 100 virus copies (e.g., fewer than 80, 70, 60, 50, 40, 30, 20, or 10 copies) in the whole blood sample. In certain embodiments, steps (a) through (g) are completed within 3 hours (e.g., within 3.2, 2.9, 2.7, 2.5, 2.3, 2.2, 2.1, 2.0, 1.9, 1.8, 1.7, 1.6, 1.5 hours, or 1 hour or less). The virus can be any viral pathogen described herein. In certain embodiments, the magnetic particles are substantially monodisperse; exhibit nonspecific reversibility in the absence of the analyte and multivalent binding agent; and/or the magnetic particles further include a surface decorated with a blocking agent selected from albumin, fish skin gelatin, gamma globulin, lysozyme, casein, peptidase, and an amine-bearing moiety (e.g., amino polyethyleneglycol, glycine, ethylenediamine, or amino dextran). In particular embodiments, the liquid sample further includes a buffer, from 0.1% to 3% (w/w) albumin (e.g., from 0.1% to 0.5%, 0.3% to 0.7%, 0.5% to 1%, 0.8% to 2%, or from 1.5% to 3% (w/w) albumin), from 0.01% to 0.5% nonionic surfactant (e.g., from 0.01% to 0.05%, 0.05% to 0.1%, 0.05% to 0.2%, 0.1% to 0.3%, 0.2% to 0.4%, or from 0.3% to 0.5% nonionic surfactant), or a combination thereof. In still other embodiments, the magnetic particles include a surface decorated with 40 μg to 100 μg (e.g., 40 μg to 60 μg, 50 μg to 70 μg, 60 μg to 80 μg, or 80 μg to 100 μg,) of one or more proteins per milligram of the magnetic particles. The liquid sample can include a multivalent binding agent bearing a plurality of analytes conjugated to a polymeric scaffold. The method for monitoring can include any of the magnetic assisted agglomeration methods described herein. The magnetic particles can include one or more populations having a first probe and a second probe conjugated to their surface, the first probe operative to bind to a first segment of the target nucleic acid and the second probe operative to bind to a second segment of the target nucleic acid, wherein the magnetic particles form aggregates in the presence of the target nucleic acid. Alternatively, the assay can be a disaggregation assay in which the magnetic particles include a first population having a first binding moiety on their surface and a second population having a second binding moiety on their surface, and the multivalent binding moiety including a first probe and a second probe, the first probe operative to bind to the first binding moiety and the second probe operative to bind to a second binding moiety, the binding moieties and multivalent binding moiety operative to alter an aggregation of the magnetic particles in the presence of the target nucleic acid.

In any of the systems and methods of the invention in which a PCR amplification is performed, the PCR method can be real time PCR for quantifying the amount of a target nucleic acid present in a sample.

The invention features a method of quantifying a target nucleic acid molecule in a sample by amplifying the target nucleic acid molecule (e.g., using PCR or isothermal amplification) in an amplification reaction mixture in a detection tube resulting in the production of amplicons corresponding to the target nucleic acid molecule, wherein the amplification reaction mixture includes (1) a target nucleic acid molecule, (2) biotin labeled amplification primers specific for the target nucleic acid molecule, and (3) avidin labeled superparamagnetic particles. In this method, the amplification is performed in a device including a support defining a well for holding the detection tube including the superparamagnetic particles and the target nucleic acid molecule, and having an RF coil disposed about the well, the RF coil configured to detect a signal produced by exposing the sample to a bias magnetic field created using one or more magnets and an RF pulse sequence. In this method, the amplification includes the following steps:
(a) performing one or more cycles of amplification;
(b) exposing the amplification reaction mixture to conditions permitting the aggregation or disaggregation of the avidin labeled superparamagnetic particles,
(c) exposing the sample to a bias magnetic field and an RF pulse sequence;
(d) following step (c), measuring the signal from the detection tube;
(e) repeating steps (a)-(d) until a desired amount of amplification is obtained; and
(f) on the basis of the result of step (d), quantifying the amplicons present at the corresponding cycle of amplification.

In this method, the initial quantity of target nucleic acid molecule in the sample is determined based on the quantity of amplicons determined at each cycle of the PCR.

The invention further features a method of quantifying a target nucleic acid molecule in a sample by amplifying the target nucleic acid molecule (e.g., using PCR or isothermal amplification) in an amplification reaction mixture in a detection tube resulting in the production of amplicons corresponding to the target nucleic acid molecule. In this method, the amplification reaction mixture includes (1) a target nucleic acid molecule, (2) amplification primers including a 5' overhang, wherein the amplification primers are specific for the target nucleic acid molecule, and (3) oligonucleotide labeled superparamagnetic particles, wherein the oligonucleotide label is substantially complementary to the 5' overhang of the amplification primers. In this method, the amplification is performed in a device including a support defining a well for holding the detection tube including the superparamagnetic particles and the target nucleic acid molecule, and having an RF coil disposed about the well, the RF coil configured to detect a signal produced by exposing the sample to a bias magnetic field created using one or more magnets and an RF pulse sequence. In this method, the amplification includes the following steps:
(a) performing one or more cycles of amplification;
(b) exposing the amplification reaction mixture to conditions permitting the hybridization of the oligonucleotide labeled superparamagnetic particles with the 5' overhang;
(c) exposing the sample to a bias magnetic field and an RF pulse sequence;
(d) following step (c), measuring the signal from the detection tube;
(e) repeating steps (a)-(d) until a desired amount of amplification is obtained; and
(f) on the basis of the result of step (d), quantifying the amplicons present at the corresponding cycle of amplification.

In this method, the initial quantity of target nucleic acid molecule in the sample is determined based on the quantity of amplicons determined at each cycle of the amplification.

The invention further features a method of quantifying a target nucleic acid molecule in a sample by amplifying the target nucleic acid molecule (e.g., using PCR or isothermal amplification) in an amplification reaction mixture in a detection tube resulting in the production of amplicons corresponding to the target nucleic acid molecule. In this method the amplification reaction mixture includes (1) a target nucleic acid molecule, (2) amplification primers specific for the target nucleic acid molecule, and (3) oligonucleotide labeled superparamagnetic particles, wherein the oligonucleotide label contains a hairpin structure and a portion of the hairpin structure is substantially complementary to a portion of the nucleic acid sequence of the amplicons. In this method, the amplification is performed in a device including a support defining a well for holding the detection tube including the superparamagnetic particles and the target nucleic acid molecule, and having an RF coil disposed about the well, the RF coil configured to detect a signal produced by exposing the sample to a bias magnetic field created using one or more magnets and an RF pulse sequence. This amplification of this method includes the following steps:
(a) performing one or more cycles of amplification;
(b) exposing the amplification reaction mixture to conditions permitting the hybridization of the portion of the hairpin structure of (3) with the amplicons;
(c) exposing the sample to a bias magnetic field and an RF pulse sequence;
(d) following step (c), measuring the signal from the detection tube;
(e) repeating steps (a)-(d) until a desired amount of amplification is obtained; and
(f) on the basis of the result of step (d), quantifying the amplicons present at the corresponding cycle of amplification.

In this method, the initial quantity of target nucleic acid molecule in the sample is determined based on the quantity of amplicons determined at each cycle of the amplification.

The invention also features a method of quantifying a target nucleic acid molecule in a sample by amplifying the target nucleic acid molecule using PCR in an amplification reaction mixture in a detection tube resulting in the production of amplicons corresponding to the target nucleic acid molecule. In this method, the amplification reaction mixture includes (1) a target nucleic acid molecule, (2) a polymerase with 5' exonuclease activity, (3) amplification primers specific for the target nucleic acid molecule, and (4) oligonucleotide tethered superparamagnetic particles, wherein the oligonucleotide tether connects at least two superparamagnetic particles and the oligonucleotide tether is substantially complementary to a portion of the nucleic acid sequence of the amplicons. In this method, the amplification is performed in a device including a support defining a well for holding the detection tube including the superparamagnetic particles and the target nucleic acid molecule, and having an RF coil disposed about the well, the RF coil configured to detect a signal produced by exposing the sample to a bias magnetic field created using one or more magnets and an RF pulse sequence. The amplification of this method includes the following steps:
(a) performing one or more cycles of PCR under conditions permitting the hybridization of the oligonucleotide tether to an amplicon during the extension phase of the PCR, wherein during the extension phase of the PCR, the 5' exonuclease activity of the polymerase untethers the at least two superparamagnetic particles permitting a decrease in superparamagnetic particle aggregation;
(b) exposing the sample to a bias magnetic field and an RF pulse sequence;

(c) following step (b), measuring the signal from the detection tube;
(d) repeating steps (a)-(c) until the PCR is complete; and
(e) on the basis of the result of step (c), quantifying the amplicons present at the corresponding cycle of PCR.

In this method, the initial quantity of target nucleic acid molecule in the sample is determined based on the quantity of amplicons determined at each cycle of the PCR.

The invention also features a method of quantifying a target nucleic acid molecule in a sample by amplifying the target nucleic acid molecule (e.g., using PCR or isothermal amplification) in an amplification reaction mixture in a detection tube resulting in the production of amplicons corresponding to the target nucleic acid molecule. In this method, the amplification reaction mixture includes (1) a target nucleic acid molecule, (2) amplification primers specific for the target nucleic acid molecule, and (3) superparamagnetic particles labeled with a plurality of oligonucleotides, wherein a first group of the plurality of oligonucleotides are substantially complementary to a portion of the nucleic acid sequence of the amplicons and substantially complementary to a second group of the plurality of oligonucleotides, wherein the first group of the plurality of oligonucleotides has a lesser hybridization affinity for the second group of the plurality of oligonucleotides than for the amplicons. In this method, the amplification is performed in a device including a support defining a well for holding the detection tube including the superparamagnetic particles and the target nucleic acid molecule, and having an RF coil disposed about the well, the RF coil configured to detect a signal produced by exposing the sample to a bias magnetic field created using one or more magnets and an RF pulse sequence. The amplification of this method includes the following steps:

(a) performing one or more cycles of amplification;
(b) exposing the amplification reaction mixture to conditions permitting the preferential hybridization of the first group of the plurality of oligonucleotides with the amplicons thereby permitting disaggregation of the superparamagnetic particles;
(c) exposing the sample to a bias magnetic field and an RF pulse sequence;
(d) following step (c), measuring the signal from the detection tube;
(e) repeating steps (a)-(d) until a desired amount of amplification is obtained; and
(f) on the basis of the result of step (d); quantifying the amplicons present at the corresponding cycle of amplification.

In this method, the initial quantity of target nucleic acid molecule in the sample is determined based on the quantity of amplicons determined at each cycle of the amplification.

The invention further features a method of quantifying a target nucleic acid molecule in a sample by amplifying the target nucleic acid molecule (e.g., using PCR or isothermal amplification) in an amplification reaction mixture in a detection tube resulting in the production of amplicons corresponding to the target nucleic acid molecule. In this method, the amplification reaction mixture includes (1) a target nucleic acid molecule, (2) amplification primers specific for the target nucleic acid molecule, and (3) superparamagnetic particles. In this method, the amplification is performed in a device including a support defining a well for holding the detection tube including the superparamagnetic particles and the target nucleic acid molecule, and having an RF coil disposed about the well, the RF coil configured to detect a signal produced by exposing the sample to a bias magnetic field created using one or more magnets and an RF pulse sequence. The amplification of this method including the following steps:

(a) performing one or more cycles of amplification;
(b) exposing the amplification reaction mixture to conditions permitting the aggregation or disaggregation of the superparamagnetic particles,
(c) exposing the sample to a bias magnetic field and an RF pulse sequence;
(d) following step (c), measuring the signal from the detection tube;
(e) repeating steps (a)-(d) until a desired amount of amplification is obtained; and
(f) on the basis of the result of step (d), quantifying the amplicons present at the corresponding cycle of amplification.

In this method, the initial quantity of target nucleic acid molecule in the sample is determined based on the quantity of amplicons determined at each cycle of the amplification.

In any of the foregoing methods of quantifying a target nucleic acid molecule, the detection tube can remained sealed throughout the amplification reaction. The superparamagnetic particles of these methods can be greater or less than 100 nm in diameter (e.g., 30 nm in diameter).

Also, in any of the foregoing methods of quantifying a target nucleic acid molecule, the methods can further include applying a magnetic field to the detection tube following the measuring the signal from the detection tube, resulting in the sequestration of the superparamagnetic particles to the side of the detection tube, and releasing the magnetic field subsequent to the completion of one or more additional cycles of amplification.

Also, in any of the foregoing methods of quantifying a target nucleic acid molecule, the sample can, e.g., not include isolated nucleic acid molecules prior to step (a) (e.g., the sample can be whole blood or not contain a target nucleic acid molecule prior to step (a)).

The invention features a method of monitoring one or more analytes in a liquid sample derived from a patient for the diagnosis, management, or treatment of a medical condition in a patient, the method including (a) combining with the liquid sample from $1 \times 10^6$ to $1 \times 10^{13}$ magnetic particles per milliliter of the liquid sample (e.g., from $1 \times 10^6$ to $1 \times 10^8$, $1 \times 10^7$ to $1 \times 10^8$, $1 \times 10^7$ to $1 \times 10^9$, $1 \times 10^8$ to $1 \times 10^{10}$, $1 \times 10^9$ to $1 \times 10^{11}$, or $1 \times 10^{10}$ to $1 \times 10^{13}$ magnetic particles per milliliter), wherein the magnetic particles have a mean diameter of from 150 nm to 1200 nm (e.g., from 150 to 250, 200 to 350, 250 to 450, 300 to 500, 450 to 650, 500 to 700 nm, 700 to 850, 800 to 950, 900 to 1050, or from 1000 to 1200 nm), and a $T_2$ relaxivity per particle of from $1 \times 10^8$ to $1 \times 10^{12}$ mM$^{-1}$s$^{-1}$ (e.g., from $1 \times 10^8$ to $1 \times 10^9$, $1 \times 10^8$ to $1 \times 10^{10}$, $1 \times 10^9$ to $1 \times 10^{10}$, $1 \times 10^9$ to $1 \times 10^{11}$, or from $1 \times 10^{10}$ to $1 \times 10^{12}$ mM$^{-1}$s$^{-1}$), and wherein the magnetic particles have binding moieties on their surfaces, the binding moieties operative to alter the specific aggregation of the magnetic particles in the presence of the one or more analytes or a multivalent binding agent; (b) placing the liquid sample in a device, the device including a support defining a well for holding the liquid sample including the magnetic particles and the one or more analytes, and having an RF coil disposed about the well, the RF coil configured to detect a signal produced by exposing the liquid sample to a bias magnetic field created using one or more magnets and an RF pulse sequence; (c) exposing the sample to the bias magnetic field and the RF pulse sequence; (d) following step (c), measuring the signal; (e) on the basis of the result of step (d), monitoring the one or more analytes; and (f) using the result of step (e) to diagnose, manage, or treat the medical condition. In one embodiment, the one or more analytes include creatinine. In another embodiment, the patient is immunocompromised, and the one or more analytes include an analyte selected from pathogen-associated analytes, antibiotic agents, antifungal agents, and antiviral agents (e.g., the one or more analytes can include *Candida* spp., tacrolimus, fluconazole, and/or creatinine). In still another embodiment, the patient has cancer, and the one or more analytes are selected from anticancer agents, and genetic markers present in a cancer cell. The patient can have, or be at risk of, an infection, and the one or more analytes include an analyte selected from pathogen-associated analytes, antibiotic agents, antifungal agents, and antiviral agents. The patient can have an immunoinflammatory condition, and the one or more analytes include an analyte selected from anti inflammatory agents and TNF-alpha. The patient can have heart disease, and the one or more analytes can include a cardiac marker. The patient can have HIV/AIDS, and the one or more analytes can include CD3, viral load, and AZT. In certain embodiments, the method is used to monitor the liver function of the patient, and wherein the one or more analytes are selected from albumin, aspartate transaminase, alanine transaminase, alkaline phosphatase, gamma glutamyl transpeptidase, bilirubin, alpha fetoprotein, lactase dehydrogenase, mitochondrial antibodies, and cytochrome P450. For example, the one or more analytes include cytochrome P450 polymorphisms, and the ability of the patient to metabolize a drug is evaluated. The method can include identifying the patient as a poor metabolizer, a normal metabolizer, an intermediate metabolizer, or an ultra rapid metabolizer. The method can be used to determine an appropriate dose of a therapeutic agent in a patient by (i) administering the therapeutic agent to the patient; (ii) following step (i), obtaining a sample including the therapeutic agent or metabolite thereof from the patient; (iii) contacting the sample with the magnetic particles and exposing the sample to the bias magnetic field and the RF pulse sequence and detecting a signal produced by the sample; and (iv) on the basis of the result of step (iii), determining the concentration of the therapeutic agent or metabolite thereof. The therapeutic agent can be an anticancer agent, antibiotic agent, antifungal agent, or any therapeutic agent described herein. In any of the above methods of monitoring, the monitoring can be intermittent (e.g., periodic), or continuous. In certain embodiments, the magnetic particles are substantially monodisperse; exhibit non-specific reversibility in the absence of the analyte and multivalent binding agent; and/or the magnetic particles further include a surface decorated with a blocking agent selected from albumin, fish skin gelatin, gamma globulin, lysozyme, casein, peptidase, and an amine-bearing moiety (e.g., amino polyethyleneglycol, glycine, ethylenediamine, or amino dextran). In particular embodiments, the liquid sample further includes a buffer, from 0.1% to 3% (w/w) albumin (e.g., from 0.1% to 0.5%, 0.3% to 0.7%, 0.5% to 1%, 0.8% to 2%, or from 1.5% to 3% (w/w) albumin), from 0.01% to 0.5% nonionic surfactant (e.g., from 0.01% to 0.05%, 0.05% to 0.1%, 0.05% to 0.2%, 0.1% to 0.3%, 0.2% to 0.4%, or from 0.3% to 0.5% nonionic surfactant), or a combination thereof. In still other embodiments, the magnetic particles include a surface decorated with 40 µg to 100 µg (e.g., 40 µg to 60 µg, 50 µg to 70 µg, 60 µg to 80 µg, or 80 µg to 100 µg,) of one or more proteins per milligram of the magnetic particles. The liquid sample can include a multivalent binding agent bearing a plurality of analytes conjugated to a polymeric scaffold. The method for monitoring can include any of the magnetic assisted agglomeration methods described herein.

The invention features a method of diagnosing sepsis in a subject, the method including (a) obtaining a liquid sample derived from the blood of a patient; (b) preparing a first assay sample by combining with a portion of the liquid sample from $1\times10^6$ to $1\times10^{13}$ magnetic particles per milliliter of the liquid sample (e.g., from $1\times10^6$ to $1\times10^8$, $1\times10^7$ to $1\times10^8$, $1\times10^7$ to $1\times10^9$, $1\times10^8$ to $1\times10^{10}$, $1\times10^9$ to $1\times10^1$ or $1\times10^{10}$ to $1\times10^{13}$ magnetic particles per milliliter), wherein the magnetic particles have a mean diameter of from 150 nm to 1200 nm (e.g., from 150 to 250, 200 to 350, 250 to 450, 300 to 500, 450 to 650, 500 to 700 nm, 700 to 850, 800 to 950, 900 to 1050, or from 1000 to 1200 nm), and a $T_2$ relaxivity per particle of from $1\times10^8$ to $1\times10^{12}$ mM$^{-1}$s$^{-1}$ (e.g., from $1\times10^8$ to $1\times10^9$, $1\times10^8$ to $1\times10^{10}$, $1\times10^9$ to $1\times10^{10}$, $1\times10^9$ to $1\times10^{11}$, or from $1\times10^{10}$ to $1\times10^{12}$ mM$^{-1}$s$^{-1}$), and wherein the magnetic particles have binding moieties on their surfaces, the binding moieties operative to alter the specific aggregation of the magnetic particles in the presence of one or more pathogen-associated analytes or a multivalent binding agent; (c) preparing a second assay sample by combining with a portion of the liquid sample from $1\times10^6$ to $1\times10^{13}$ magnetic particles per milliliter of the liquid sample (e.g., from $1\times10^6$ to $1\times10^8$, $1\times10^7$ to $1\times10^8$, $1\times10^7$ to $1\times10^9$, $1\times10^8$ to $1\times10^{10}$, $1\times10^9$ to $1\times10^{11}$, or $1\times10^{10}$ to $1\times10^{13}$ magnetic particles per milliliter), wherein the magnetic particles have a mean diameter of from 150 nm to 1200 nm (e.g., from 150 to 250, 200 to 350, 250 to 450, 300 to 500, 450 to 650, 500 to 700 nm, 700 to 850, 800 to 950, 900 to 1050, or from 1000 to 1200 nm), and a $T_2$ relaxivity per particle of from $1\times10^8$ to $1\times10^{12}$ mM$^{-1}$s$^{-1}$ (e.g., from $1\times10^8$ to $1\times10^9$, $1\times10^8$ to $1\times10^{10}$, $1\times10^9$ to $1\times10^{10}$, $1\times10^9$ to $1\times10^{11}$, or from $1\times10^{10}$ to $1\times10^{12}$ mM$^{-1}$s$^{-1}$), and wherein the magnetic particles have binding moieties on their surfaces, the binding moieties operative to alter the specific aggregation of the magnetic particles in the presence of one or more analytes characteristic of sepsis selected from GRO-alpha, High mobility group-box 1 protein (HMBG-1), IL-1 receptor, IL-1 receptor antagonist, IL-1b, IL-2, IL-4, IL-6, IL-8, IL-10, IL-12, IL-13, IL-18, macrophage inflammatory protein (MIP-1), macrophage migration inhibitory factor (MIF), osteopontin, RANTES (regulated on activation, normal T-cell expressed and secreted; or CCL5), TNF-α, C-reactive protein (CRP), CD64, monocyte chemotactic protein 1 (MCP-1), adenosine deaminase binding protein (ABP-26), inducible nitric oxide synthetase (iNOS), lipopolysaccharide binding protein, and procalcitonin; (d) placing each assay sample in a device, the device including a support defining a well for holding the liquid sample including the magnetic particles and the one or more analytes, and having an RF coil disposed about the well, the RF coil configured to detect a signal produced by exposing the liquid sample to a bias magnetic field created using one or more magnets and an RF pulse sequence; (e) exposing each assay sample to the bias magnetic field and the RF pulse sequence; (f) following step (e), measuring the signal produced by the first assay sample and the signal produced by the second assay sample; (g) on the basis of the result of step (f), monitoring the one or more analytes of the first assay sample and monitoring the one or more analytes of the second assay sample; and (h) using the results of step (g) to diagnose the subject. In one embodiment, the one or more pathogen-associated analytes of the first assay sample are derived from a pathogen associated with sepsis selected from *Acinetobacter baumannii, Aspergillus fumigatis, Bacteroides fragilis, B. fragilis,* blaSHV, *Burkholderia cepacia, Campylobacter jejuni/coli,*

*Candida guilliermondii, C. albicans, C. glabrata, C. krusei, C. lusitaniae, C. parapsilosis, C. tropicalis, Clostridium pefringens*, Coagulase negative *Staph, Enterobacter aeraogenes, E. cloacae*, Enterobacteriaceae, *Enterococcus faecalis, E. faecium, Escherichia coli, Haemophilus influenzae, Kingella Kingae, Klebsiella oxytoca, K. pneumoniae, Listeria monocytogenes*, Mec A gene (MRSA), *Morganella morgana, Neisseria meningitidis, Neisseria* spp. non-*meningitidis, Prevotella buccae, P. intermedia, P. melaminogenica, Propionibacterium acnes, Proteus mirabilis, P. vulgaris, Pseudomonas aeruginosa, Salmonella enterica, Serratia marcescens, Staphylococcus aureus, S. haemolyticus, S. maltophilia, S. saprophyticus, Stenotrophomonas maltophilia, S. maltophilia, Streptococcus agalactie, S. bovis, S. dysgalactie, S. mitis, S. mutans, S. pneumoniae, S. pyogenes*, and *S. sanguinis*. The one or more pathogen-associated analytes can be derived from treatment resistant strains of bacteria, such as penicillin-resistant, methicillin-resistant, quinolone-resistant, macrolide-resistant, and/or vancomycin-resistant bacterial strains (e.g., methicillin resistant *Staphylococcus aureus* or vancomycin-resistant enterococci). In certain embodiments, the one or more analytes of the second assay sample are selected from GRO-alpha, High mobility group-box 1 protein (HMBG-1), IL-1 receptor, IL-1 receptor antagonist, IL-1b, IL-2, IL-4, IL-6, IL-8, IL-10, IL-12, IL-13, IL-18, macrophage inflammatory protein (MIP-1), macrophage migration inhibitory factor (MIF), osteopontin, RANTES (regulated on activation, normal T-cell expressed and secreted; or CCL5), TNF-α, C-reactive protein (CRP), CD64, and monocyte chemotactic protein 1 (MCP-1). In a particular embodiment, the method further includes preparing a third assay sample to monitor the concentration of an antiviral agent, antibiotic agent, or antifungal agent circulating in the blood stream of the subject. In certain embodiments, the subject can be an immunocompromised subject, or a subject at risk of becoming immunocompromised. In any of the above methods of monitoring, the monitoring can be intermittent (e.g., periodic), or continuous. In certain embodiments, the magnetic particles are substantially monodisperse; exhibit nonspecific reversibility in the absence of the analyte and multivalent binding agent; and/or the magnetic particles further include a surface decorated with a blocking agent selected from albumin, fish skin gelatin, gamma globulin, lysozyme, casein, peptidase, and an amine-bearing moiety (e.g., amino polyethyleneglycol, glycine, ethylenediamine, or amino dextran). In particular embodiments, the liquid sample further includes a buffer, from 0.1% to 3% (w/w) albumin (e.g., from 0.1% to 0.5%, 0.3% to 0.7%, 0.5% to 1%, 0.8% to 2%, or from 1.5% to 3% (w/w) albumin), from 0.01% to 0.5% nonionic surfactant (e.g., from 0.01% to 0.05%, 0.05% to 0.1%, 0.05% to 0.2%, 0.1% to 0.3%, 0.2% to 0.4%, or from 0.3% to 0.5% nonionic surfactant), or a combination thereof. In still other embodiments, the magnetic particles include a surface decorated with 40 μg to 100 μg (e.g., 40 μg to 60 μg, 50 μg to 70 μg, 60 μg to 80 μg, or 80 μg to 100 μg,) of one or more proteins per milligram of the magnetic particles. The liquid sample can include a multivalent binding agent bearing a plurality of analytes conjugated to a polymeric scaffold. The method for monitoring can include any of the magnetic assisted agglomeration methods described herein.

The invention further features a method of monitoring one or more analytes in a liquid sample derived from a patient for the diagnosis, management, or treatment of sepsis or SIRS in a patient, the method including: (a) combining with the liquid sample from $1\times10^6$ to $1\times10^{13}$ magnetic particles per milliliter of the liquid sample (e.g., from $1\times10^6$ to $1\times10^8$, $1\times10^7$ to $1\times10^8$, $1\times10^7$ to $1\times10^9$, $1\times10^8$ to $1\times10^{10}$, $1\times10^9$ to $1\times10^{11}$, or $1\times10^{10}$ to $1\times10^{13}$ magnetic particles per milliliter), wherein the magnetic particles have a mean diameter of from 150 nm to 1200 nm (e.g., from 150 to 250, 200 to 350, 250 to 450, 300 to 500, 450 to 650, 500 to 700 nm, 700 to 850, 800 to 950, 900 to 1050, or from 1000 to 1200 nm), and a $T_2$ relaxivity per particle of from $1\times10^8$ to $1\times10^{12}$ mM$^{-1}$s$^{-1}$ (e.g., from $1\times10^8$ to $1\times10^9$, $1\times10^8$ to $1\times10^{10}$, $1\times10^9$ to $1\times10^{10}$, $1\times10^9$ to $1\times10^{11}$, or from $1\times10^{10}$ to $1\times10^{12}$ mM$^{-1}$s$^{-1}$), and wherein the magnetic particles have binding moieties on their surfaces, the binding moieties operative to alter the specific aggregation of the magnetic particles in the presence of the one or more analytes or a multivalent binding agent; (b) placing the liquid sample in a device, the device including a support defining a well for holding the liquid sample including the magnetic particles and the one or more analytes, and having an RF coil disposed about the well, the RF coil configured to detect a signal produced by exposing the liquid sample to a bias magnetic field created using one or more magnets and an RF pulse sequence; (c) exposing the sample to the bias magnetic field and the RF pulse sequence; (d) following step (c), measuring the signal; (e) on the basis of the result of step (d), monitoring the one or more analytes; and (f) using the result of step (e) to diagnose, manage, or treat the sepsis or SIRS. The method can include (i) monitoring a pathogen-associated analyte, and (ii) monitoring a second analyte characteristic of sepsis selected from GRO-alpha, High mobility group-box 1 protein (HMBG-1), IL-1 receptor, IL-1 receptor antagonist, IL-1b, IL-2, IL-4, IL-6, IL-8, IL-10, IL-12, IL-13, IL-18, macrophage inflammatory protein (MIP-1), macrophage migration inhibitory factor (MIF), osteopontin, RANTES (regulated on activation, normal T-cell expressed and secreted; or CCL5), TNF-α, C-reactive protein (CRP), CD64, monocyte chemotactic protein 1 (MCP-1), adenosine deaminase binding protein (ABP-26), inducible nitric oxide synthetase (iNOS), lipopolysaccharide binding protein, and procalcitonin. In certain embodiments, the pathogen-associated analyte is derived from a pathogen associated with sepsis selected from *Acinetobacter baumannii, Aspergillus fumigatis, Bacteroides fragilis, B. fragilis*, blaSHV, *Burkholderia cepacia, Campylobacter jejuni/coli, Candida guilliermondii, C. albicans, C. glabrata, C. krusei, C. Lusitaniae, C. parapsilosis, C. tropicalis, Clostridium pefringens*, Coagulase negative *Staph, Enterobacter aeraogenes*, E. cloacae, Enterobacteriaceae, *Enterococcus faecalis, E. faecium, Escherichia coli, Haemophilus influenzae, Kingella Kingae, Klebsiella oxytoca, K. pneumoniae, Listeria monocytogenes*, Mec A gene (MRSA), *Morganella morgana, Neisseria meningitidis, Neisseria* spp. non-*meningitidis, Prevotella buccae, P. intermedia, P. melaminogenica, Propionibacterium acnes, Proteus mirabilis, P. vulgaris, Pseudomonas aeruginosa, Salmonella enterica, Serratia marcescens, Staphylococcus aureus, S. haemolyticus, S. maltophilia, S. saprophyticus, Stenotrophomonas maltophilia, S. maltophilia, Streptococcus agalactie, S. bovis, S. dysgalactie, S. mitis, S. mutans, S. pneumoniae, S. pyogenes*, and *S. sanguinis*. The pathogen-associated analyte can be derived from a treatment resistant strain of bacteria, such as penicillin-resistant, methicillin-resistant, quinolone-resistant, macrolide-resistant, and/or vancomycin-resistant bacterial strains (e.g., methicillin resistant *Staphylococcus aureus* or vancomycin-resistant enterococci). In particular embodiments, the second analytes is selected from GRO-alpha, High mobility group-box 1 protein (HMBG-1), IL-1 receptor, IL-1 receptor antagonist, IL-1b, IL-2, IL-4, IL-6, IL-8, IL-10, IL-12, IL-13, IL-18, macrophage inflammatory protein (MIP-1), macrophage migration inhibitory factor (MIF), osteopontin, RANTES (regulated on activation, normal T-cell expressed and secreted; or CCL5), TNF-α, C-reactive protein (CRP), CD64, and monocyte chemotactic protein 1 (MCP-1). In a particular embodiment, the method further includes preparing a third assay sample to monitor the concentration of an antiviral agent, antibiotic agent, or antifungal agent circulating in the blood stream of the subject. In certain embodiments, the subject can be an immunocompromised subject, or a subject at risk of becoming immunocompromised. In any of the above methods of monitoring, the monitoring can be intermittent (e.g., periodic), or continuous. In certain embodiments, the magnetic particles are substantially monodisperse; exhibit nonspecific reversibility in the absence of the analyte and multivalent binding agent; and/or the magnetic particles further include a surface decorated with a blocking agent selected from albumin, fish skin gelatin, gamma globulin, lysozyme, casein, peptidase, and an amine-bearing moiety (e.g., amino polyethyleneglycol, glycine, ethylenediamine, or amino dextran). In particular embodiments, the liquid sample further includes a buffer, from 0.1% to 3% (w/w) albumin (e.g., from 0.1% to 0.5%, 0.3% to 0.7%, 0.5% to 1%, 0.8% to 2%, or from 1.5% to 3% (w/w) albumin), from 0.01% to 0.5% nonionic surfactant (e.g., from 0.01% to 0.05%, 0.05% to 0.1%, 0.05% to 0.2%, 0.1% to 0.3%, 0.2% to 0.4%, or from 0.3% to 0.5% nonionic surfactant), or a combination thereof. In still other embodiments, the magnetic particles include a surface decorated with 40 μg to 100 μg (e.g., 40 μg to 60 μg, 50 μg to 70 μg, 60 μg to 80 μg, or 80 μg to 100 μg,) of one or more proteins per milligram of the magnetic particles. The liquid sample can include a multivalent binding agent bearing a plurality of analytes conjugated to a polymeric scaffold. The method for monitoring can include any of the magnetic assisted agglomeration methods described herein.

In a related aspect, the invention features a method for assisting the specific agglomeration of magnetic particles in a liquid sample, the method including: (i) providing a liquid sample including one or more analytes and the magnetic particles, wherein the magnetic particles have binding moieties on their surfaces, the binding moieties operative to alter the specific aggregation of the magnetic particles in the presence of the one or more analytes or a multivalent binding agent; (ii) exposing the liquid sample to a magnetic field; (iii) removing the liquid sample from the magnetic field; and (iv) repeating step (ii).

The invention further features a method for assisting the specific agglomeration of magnetic particles in a liquid sample by (i) providing a liquid sample including one or more analytes and the magnetic particles, wherein the magnetic particles have binding moieties on their surfaces, the binding moieties operative to alter the specific aggregation of the magnetic particles in the presence of the one or more analytes or a multivalent binding agent; (ii) applying a magnetic field gradient to the liquid sample for a time sufficient to cause concentration of the magnetic particles in a first portion of the liquid sample, the magnetic field gradient being aligned in a first direction relative to the liquid sample; (iii) following step (ii), applying a magnetic field to the liquid sample for a time sufficient to cause concentration of the magnetic particles in a second portion of the liquid sample, the magnetic field being aligned in a second direction relative to the liquid sample; and (iv) optionally repeating steps (ii) and (iii). In certain embodiments, the angle between the first direction and the second direction relative to the liquid sample is between 0° and 180° (e.g., from 0° to 10°, 5° to 120°, 20° to 60°, 30° to 80°, 45° to 90°, 60° to 120°, 80° to 135°, or from 120° to 180°).

The invention features a method for assisting the specific agglomeration of magnetic particles in a liquid sample by (i) providing a liquid sample including one or more analytes and the magnetic particles, wherein the magnetic particles have binding moieties on their surfaces, the binding moieties operative to alter the specific aggregation of the magnetic particles in the presence of the one or more analytes or a multivalent binding agent; (ii) applying a magnetic field gradient to the liquid sample for a time sufficient to cause concentration of the magnetic particles in a first portion of the liquid sample; (iii) following step (ii), agitating the liquid sample; and (iv) repeating step (ii). In certain embodiments, step (iii) includes vortexing the liquid sample, or mixing the sample using any method described herein.

The invention also features a method for assisting the specific agglomeration of magnetic particles in a liquid sample by (i) providing a liquid sample including one or more analytes and the magnetic particles, wherein the magnetic particles have binding moieties on their surfaces, the binding moieties operative to alter the specific aggregation of the magnetic particles in the presence of the one or more analytes or a multivalent binding agent; and (ii) exposing the liquid sample to a gradient magnetic field and rotating the gradient magnetic field about the sample, or rotating the sample within the gradient magnetic field. The sample can be rotated slowly. In certain embodiments, the sample is rotated at a rate of 0.0333 Hz, or less (e.g., from 0.000833 Hz to 0.0333 Hz, from 0.00166 Hz to 0.0333 Hz, or from 0.00333 Hz to 0.0333 Hz). In other embodiments, the method further includes (iii) following step (ii), agitating the liquid sample; and (iv) repeating step (ii).

In any of the above methods for assisting specific agglomeration step (ii) can be repeated from 1 to 100 times (e.g., repeated 1, 2, 3, 4, 5, 6, 7, 8, 9, or 10 times, from 10 to 20 times, or from 80 to 100 times). In particular embodiments, the one or more magnets providing the magnetic field gradient within the liquid sample have a maximum field strength of from 0.01 T to 10 T (e.g., from 0.01 T to 0.05 T, 0.05 T to 0.1 T, 0.1 T to 0.5 T, 0.5 T to 1 T, 1 T to 3 T, or from 3 T to 10 T) and wherein the gradient magnetic field varies from 0.1 mT/mm to 10 T/mm across the liquid sample (e.g., from 0.1 mT/mm to 0.5 mT/mm, 0.3 mT/mm to 1 mT/mm, 0.5 mT/mm to 5 mT/mm, 5 mT/mm to 20 mT/mm, 10 mT/mm to 100 mT/mm, 100 mT/mm to 500 mT/mm, 500 mT/mm to 1 T/mm, or from 1 T/mm to 10 T/mm). In certain embodiments of any of the above methods for assisting specific agglomeration, step (ii) includes applying the magnetic field gradient to the liquid sample for a period of from 1 second to 5 minutes (e.g., from 1 to 20 seconds, from 20 to 60 seconds, from 30 seconds to 2 minutes, from 1 minutes to 3 minutes, or from 2 minutes to 5 minutes). In particular embodiments, (i) the liquid sample includes from $1\times10^5$ to $1\times10^{15}$ of the one or more analytes per milliliter of the liquid sample (e.g., from $1\times10^5$ to $1\times10^6$, $1\times10^6$ to $1\times10^8$, $1\times10^7$ to $1\times10^9$, $1\times10^8$ to $1\times10^{10}$, $1\times10^9$ to $1\times10^{12}$, or $1\times10^{11}$ to $1\times10^{15}$ analytes per milliliter); (ii) the liquid sample includes from $1\times10^6$ to $1\times10^{13}$ of the magnetic particles per milliliter of the liquid sample (e.g., from $1\times10^6$ to $1\times10^8$, $1\times10^7$ to $1\times10^8$, $1\times10^7$ to $1\times10^9$, $1\times10^8$ to $1\times10^{10}$, $1\times10^9$ to $1\times10^{11}$, or $1\times10^{10}$ to $1\times10^{13}$ magnetic particles per milliliter); (iii) the magnetic particles have a $T_2$ relaxivity per particle of from $1\times10^4$ to $1\times10^{12}$ mM$^{-1}$s$^{-1}$ (e.g., from $1\times10^4$ to $1\times10^7$, $1\times10^6$ to $1\times10^{10}$, $1\times10^7$ to $1\times10^9$, $1\times10^8$ to $1\times10^9$, $1\times10^8$ to $1\times10^{10}$, $1\times10^9$ to $1\times10^{10}$, $1\times10^9$ to $1\times10^{11}$, or from $1\times10^{10}$ to $1\times10^{12}$ mM$^{-1}$s$^{-1}$); (iv) the magnetic particles have an average diameter of from 150 nm to 1200 nm (e.g., from 150 to 250, 200 to 350, 250 to 450, 300 to 500, 450 to 650, 500 to 700 nm, 700 to 850, 800 to 950, 900 to 1050, or from 1000 to 1200 nm); (v) the magnetic particles are substantially monodisperse; (vi) the magnetic particles in the liquid sample exhibit nonspecific reversibility in the absence of the one or more analytes and multivalent binding agent; (vii) the magnetic particles further include a surface decorated with a blocking agent selected from albumin, fish skin gelatin, gamma globulin, lysozyme, casein, peptidase, and an amine-bearing moiety (e.g., amino polyethyleneglycol, glycine, ethylenediamine, or amino dextran); (viii) the liquid sample further includes a buffer, from 0.1% to 3% (w/w) albumin (e.g., from 0.1% to 0.5%, 0.3% to 0.7%, 0.5% to 1%, 0.8% to 2%, or from 1.5% to 3% (w/w) albumin), from 0.01% to 0.5% nonionic surfactant (e.g., from 0.01% to 0.05%, 0.05% to 0.1%, 0.05% to 0.2%, 0.1% to 0.3%, 0.2% to 0.4%, or from 0.3% to 0.5% nonionic surfactant), or a combination thereof; and/or (ix) the magnetic particles include a surface decorated with 40 µg to 100 µg (e.g., 40 µg to 60 µg, 50 µg to 70 µg, 60 µg to 80 µg, or 80 µg to 100 µg,) of one or more proteins per milligram of the magnetic particles.

The invention features a system for the detection of one or more analytes, the system including: (a) a first unit including (a1) a permanent magnet defining a magnetic field; (a2) a support defining a well for holding a liquid sample including magnetic particles and the one or more analytes and having an RF coil disposed about the well, the RF coil configured to detect a signal by exposing the liquid sample to a bias homogenous magnetic field created using the permanent magnet and an RF pulse sequence; and (a3) one or more electrical elements in communication with the RF coil, the electrical elements configured to amplify, rectify, transmit, and/or digitize the signal; and (b) one or more second units including (b1) a permanent magnet adjacent a first sample position for holding a liquid sample and configured to apply a first gradient magnetic field to the liquid sample. The one or more second units can further include a second permanent magnet adjacent a second sample position for holding a liquid sample and configured to apply a second gradient magnetic field to the liquid sample, the second magnetic field aligned to apply a gradient magnetic field to the sample from a direction different from the direction of the first field gradient, and a means for moving a liquid sample from the first sample position to the second sample position. In certain embodiments, the one or more second units is incapable of measuring a signal (e.g., incapable of measuring an NMR relaxation rate), and/or lacks an RF coil, or a means for producing an RF pulse. In certain embodiments, the angle between the first direction and the second direction relative to the liquid sample is between 0° and 180° (e.g., from 0° to 10°, 5° to 120°, 20° to 60°, 30° to 80°, 45° to 90°, 60° to 120°, 80° to 135°, or from 120° to 180°). The system can further include a sample holder for holding the liquid sample and configured to move the liquid sample from the first position to the second position. In particular embodiments, the system includes an array of the one or more second units for assisting the agglomeration of an array of samples simultaneously. For example, the array can be configured to rotate one or more liquid from a first position in which a magnetic field is applied to the side of a sample to a second position in which a magnetic field is applied to the bottom of a sample. The system can include a cartridge unit, an agitation unit, a centrifuge, or any other system component described herein. For example, the system can further include (c) a third unit including a removable cartridge sized to facilitate insertion into and removal from the system and having a compartment including one or more populations of magnetic particles having binding moieties on their surfaces, wherein the binding moieties are operative to alter an aggregation of the magnetic particles in the presence of the one or more analytes. In particular embodiments, the removable cartridge is a modular cartridge including (i) a reagent module for holding one or more assay reagents; and (ii) a detection module including a detection chamber for holding a liquid sample including magnetic particles and one or more analytes, wherein the reagent module and the detection module can be assembled into the modular cartridge prior to use, and wherein the detection chamber is removable from the modular cartridge. The modular cartridge can further include an inlet module, wherein the inlet module, the reagent module, and the detection module can be assembled into the modular cartridge prior to use, and wherein the inlet module is sterilizable. In another embodiment, the system can further include a system computer with processor for implementing an assay protocol and storing assay data, and wherein the removable cartridge further includes (i) a readable label indicating the analyte to be detected, (ii) a readable label indicating the assay protocol to be implemented, (iii) a readable label indicating a patient identification number, (iv) a readable label indicating the position of assay reagents contained in the cartridge, or (v) a readable label including instructions for the programmable processor.

The invention further features a system for the detection of one or more analytes, the system including: (a) a first unit including (a1) a permanent magnet defining a magnetic field; (a2) a support defining a well for holding a liquid sample including magnetic particles and the one or more analytes and having an RF coil disposed about the well, the RF coil configured to detect a signal produced by exposing the liquid sample to a bias magnetic field created using the permanent magnet and an RF pulse sequence; and (a3) one or more electrical elements in communication with the RF coil, the electrical elements configured to amplify, rectify, transmit, and/or digitize the signal; and (b) a second unit including a removable cartridge sized to facilitate insertion into and removal from the system, wherein the removable cartridge is a modular cartridge including (i) a reagent module for holding one or more assay reagents; and (ii) a detection module including a detection chamber for holding a liquid sample including the magnetic particles and the one or more analytes, wherein the reagent module and the detection module can be assembled into the modular cartridge prior to use, and wherein the detection chamber is removable from the modular cartridge. The modular cartridge can further include an inlet module, wherein the inlet module, the reagent module, and the detection module can be assembled into the modular cartridge prior to use, and wherein the inlet module is sterilizable. In certain embodiments, the system further includes a system computer with processor for implementing an assay protocol and storing assay data, and wherein the removable cartridge further includes (i) a readable label indicating the analyte to be detected, (ii) a readable label indicating the assay protocol to be implemented, (iii) a readable label indicating a patient identification number, (iv) a readable label indicating the position of assay reagents contained in the cartridge, or (v) a readable label including instructions for the programmable processor. The system can include a cartridge unit, an agitation unit, a centrifuge, or any other system component described herein.

The invention features an agitation unit for the automated mixing of a liquid sample in a sample chamber, including a motor for providing a rotational driving force to a motor shaft coupled to a drive shaft, the driveshaft having a first end coupled to the motor shaft and a second end coupled to a plate bearing a sample holder for holding the sample chamber, the draft shaft including a first axis coaxial to the motor shaft, and a second axis that is offset and parallel to the motor shaft, such that the second axis of the driveshaft, the plate, and the sample holder are driven in an orbital path, wherein the motor includes an index mark and/or other position sensing means such as an optical, magnetic or resistive position encoder for positioning the sample chamber in a predetermined position following the mixing or a sensor which tracks the sample's position throughout its path.

The invention features a system for the detection of one or more analytes, the system including: (a) a first unit including (a1) a permanent magnet defining a magnetic field; (a2) a support defining a well for holding a liquid sample including magnetic particles and the one or more analytes and having an RF coil disposed about the well, the RF coil configured to detect a signal produced by exposing the liquid sample to a bias magnetic field created using the permanent magnet and an RF pulse sequence; and (a3) one or more electrical elements in communication with the RF coil, the electrical elements configured to amplify, rectify, transmit, and/or digitize the signal; and (b) a second unit for the automated mixing of a liquid sample in a sample chamber, including a motor for providing a rotational driving force to a motor shaft coupled to a drive shaft, the driveshaft having a first end coupled to the motor shaft and a second end coupled to a plate bearing a sample holder for holding the sample chamber, the draft shaft including a first axis coaxial to the motor shaft, and a second axis that is offset and parallel to the motor shaft, such that the second axis of the driveshaft, the plate, and the sample holder are driven in an orbital path, wherein the motor includes an index mark and/or other position sensing means such as an optical, magnetic or resistive position encoder for positioning the sample chamber in a predetermined position following the mixing or a sensor which tracks the sample's position throughout its path.

In certain embodiments, the system further includes a robotic arm for placing the sample chamber in, and removing the sample chamber from, the agitation unit.

The invention further features a system for the detection of one or more analytes, the system including: (a) a first unit including (a1) a permanent magnet defining a magnetic field; (a2) a support defining a well for holding a liquid sample including magnetic particles and the one or more analytes and having an RF coil disposed about the well, the RF coil configured to detect a signal produced by exposing the liquid sample to a bias magnetic field created using the permanent magnet and an RF pulse sequence; and (a3) one or more electrical elements in communication with the RF coil, the electrical elements configured to amplify, rectify, transmit, and/or digitize the signal; and (b) a centrifuge including a motor for providing a rotational driving force to a drive shaft, the drive shaft having a first end coupled to the motor and a second end coupled to a centrifuge rotor bearing a sample holder for holding the sample chamber, wherein the motor includes an index mark and/or other position sensing means such as an optical, magnetic or resistive position encoder for positioning the sample chamber in a predetermined position following the centrifuging of the sample or a sensor which tracks the sample's position throughout its path.

The invention further features a system for the detection of one or more analytes, the system including: (a) a disposable sample holder defining a well for holding a liquid sample and having an RF coil contained within the disposable sample holder and disposed about the well, the RF coil configured to detect a signal produced by exposing the liquid sample to a bias magnetic field created using the permanent magnet and an RF pulse sequence, wherein the disposable sample holder includes one or more fusable links; and (b) an MR reader including (b1) a permanent magnet defining a magnetic field; (b2) an RF pulse sequence and detection coil; (b3) one or more electrical elements in communication with the RF coil, the electrical elements configured to amplify, rectify, transmit, and/or digitize the signal; and (b4) one or more electrical elements in communication with the fusable link and configured to apply excess current to the fusable link, causing the link to break and rendering the coil inoperable following a predetermined working lifetime. In certain embodiments, the electrical element in communication with the RF coil is inductively coupled to the RF coil.

The invention features a system for the detection of creatinine, tacrolimus, and *Candida*, the system including: (a) a first unit including (a1) a permanent magnet defining a magnetic field; (a2) a support defining a well for holding a liquid sample including magnetic particles and the creatinine, tacrolimus, and *Candida* and having an RF coil disposed about the well, the RF coil configured to detect signal produced by exposing the liquid sample to a bias magnetic field created using the permanent magnet and an RF pulse sequence; and (a3) an electrical element in communication with the RF coil, the electrical element configured to amplify, rectify, transmit, and/or digitize the signal; and (b) a second unit including a removable cartridge sized to facilitate insertion into and removal from the system, wherein the removable cartridge is a modular cartridge including (i) a plurality of reagent modules for holding one or more assay reagents; and (ii) a plurality of detection module including a detection chamber for holding a liquid sample including the magnetic particles and the creatinine, tacrolimus, and *Candida*, wherein the plurality of reagent modules includes (i) a first population of magnetic particles having a mean diameter of from 150 nm to 699 nm (e.g., from 150 to 250, 200 to 350, 250 to 450, 300 to 500, 450 to 650, or from 500 to 699 nm), a $T_2$ relaxivity per particle of from $1\times10^8$ to $1\times10^{12}$ mM$^{-1}$s$^{-1}$ (e.g., from $1\times10^8$ to $1\times10^9$, $1\times10^8$ to $1\times10^{10}$, $1\times10^9$ to $1\times10^{10}$, $1\times10^9$ to $1\times10^{11}$, or from $1\times10^{10}$ to $1\times10^{12}$ mM$^{-1}$s$^{-1}$), and creatinine antibodies conjugated to their surface; (ii) a multivalent binding agent bearing a plurality of creatinine conjugates designed to form aggregates with the first population of magnetic particles in the absence of creatinine; (iii) a second population of magnetic particles having a mean diameter of from 150 nm to 699 nm (e.g., from 150 to 250, 200 to 350, 250 to 450, 300 to 500, 450 to 650, or from 500 to 699 nm), a $T_2$ relaxivity per particle of from $1\times10^8$ to $1\times10^{12}$ mM$^{-1}$s$^{-1}$ (e.g., from $1\times10^8$ to $1\times10^9$, $1\times10^8$ to $1\times10^{10}$, $1\times10^9$ to $1\times10^{10}$, $1\times10^9$ to $1\times10^{11}$, or from $1\times10^{10}$ to $1\times10^{12}$ mM$^{-1}$s$^{-1}$), and tacrolimus antibodies conjugated to their surface; (iv) a multivalent binding agent bearing a plurality of tacrolimus conjugates designed to form aggregates with the second population of magnetic particles in the absence of tacrolimus; (v) a third population of magnetic particles have a mean diameter of from 700 nm to 1200 nm (e.g., from 700 to 850, 800 to 950, 900 to 1050, or from 1000 to 1200 nm), a $T_2$ relaxivity per particle of from $1\times10^9$ to $1\times10^{12}$ mM$^{-1}$s$^{-1}$ (e.g., from $1\times10^8$ to $1\times10^9$, $1\times10^8$ to $1\times10^{10}$, $1\times10^9$ to $1\times10^{10}$, $1\times10^9$ to $1\times10^{11}$, or from $1\times10^{10}$ to $1\times10^{12}$ mM$^{-1}$s$^{-1}$), and having a first probe and a second probe conjugated to their surface selected to form aggregates in the presence of a *Candida* nucleic acid, the first probe operative to bind to a first segment of the *Candida* nucleic acid and the second probe operative to bind to a second segment of the *Candida* nucleic acid. In certain embodiments, the magnetic particles are substantially monodisperse; exhibit nonspecific reversibility in the absence of the analyte and multivalent binding agent; and/or the magnetic particles further include a surface decorated with a blocking agent selected from albumin, fish skin gelatin, gamma globulin, lysozyme, casein, peptidase, and an amine-bearing moiety (e.g., amino polyethyleneglycol, glycine, ethylenediamine, or amino dextran). In particular embodiments, the liquid sample further includes a buffer, from 0.1% to 3% (w/w) albumin (e.g., from 0.1% to 0.5%, 0.3% to 0.7%, 0.5% to 1%, 0.8% to 2%, or from 1.5% to 3% (w/w) albumin), from 0.01% to 0.5% nonionic surfactant (e.g., from 0.01% to 0.05%, 0.05% to 0.1%, 0.05% to 0.2%, 0.1% to 0.3%, 0.2% to 0.4%, or from 0.3% to 0.5% nonionic surfactant), or a combination thereof. In still other embodiments, the magnetic particles include a surface decorated with 40 μg to 100 μg (e.g., 40 μg to 60 μg, 50 μg to 70 μg, 60 μg to 80 or 80 μg to 100 μg) of one or more proteins per milligram of the magnetic particles. The liquid sample can include a multivalent binding agent bearing a plurality of analytes conjugated to a polymeric scaffold. In another embodiment, the liquid sample includes from $1\times10^6$ to $1\times10^{13}$ of the magnetic particles per milliliter of the liquid sample (e.g., from $1\times10^6$ to $1\times10^8$, $1\times10^7$ to $1\times10^8$, $1\times10^7$ to $1\times10^9$, $1\times10^8$ to $1\times10^{10}$, $1\times10^9$ to $1\times10^{11}$, or $1\times10^{10}$ to $1\times10^{13}$ magnetic particles per milliliter).

The invention features a method for measuring the concentration of creatinine in a liquid sample, the method including: (a) contacting a solution with (i) magnetic particles to produce a liquid sample including from $1\times10^6$ to $1\times10^{13}$ magnetic particles per milliliter of the liquid sample (e.g., from $1\times10^6$ to $1\times10^8$, $1\times10^7$ to $1\times10^8$, $1\times10^7$ to $1\times10^9$, $1\times10^8$ to $1\times10^{10}$, $1\times10^9$ to $1\times10^{11}$, or $1\times10^{10}$ to $1\times10^{13}$ magnetic particles per milliliter), wherein the magnetic particles have a mean diameter of from 150 nm to 1200 nm (e.g., from 150 to 250, 200 to 350, 250 to 450, 300 to 500, 450 to 650, 500 to 700 nm, 700 to 850, 800 to 950, 900 to 1050, or from 1000 to 1200 nm), a $T_2$ relaxivity per particle of from $1\times10^8$ to $1\times10^{12}$ mM$^{-1}$s$^{-1}$ (e.g., from $1\times10^8$ to $1\times10^9$, $1\times10^8$ to $1\times10^{10}$, $1\times10^9$ to $1\times10^{10}$, $1\times10^9$ to $1\times10^{11}$, or from $1\times10^{10}$ to $1\times10^{12}$ mM$^{-1}$s$^{-1}$), and creatinine antibodies conjugated to their surface, and (ii) a multivalent binding agent bearing a plurality of creatinine conjugates designed to form aggregates with the magnetic particles in the absence of creatinine; (b) placing the liquid sample in a device, the device including a support defining a well for holding the liquid sample including the magnetic particles, the multivalent binding agent, and the creatinine, and having an RF coil disposed about the well, the RF coil configured to detect a signal produced by exposing the liquid sample to a bias magnetic field created using one or more magnets and an RF pulse sequence; (c) exposing the sample to a bias magnetic field and an RF pulse sequence; (d) following step (c), measuring the signal; and (e) on the basis of the result of step (d), determining the concentration of creatinine in the liquid sample. In certain embodiments, the magnetic particles are substantially monodisperse; exhibit nonspecific reversibility in the absence of the analyte and multivalent binding agent; and/or the magnetic particles further include a surface decorated with a blocking agent selected from albumin, fish skin gelatin, gamma globulin, lysozyme, casein, peptidase, and an amine-bearing moiety (e.g., amino polyethyleneglycol, glycine, ethylenediamine, or amino dextran). In particular embodiments, the liquid sample further includes a buffer, from 0.1% to 3% (w/w) albumin (e.g., from 0.1% to 0.5%, 0.3% to 0.7%, 0.5% to 1%, 0.8% to 2%, or from 1.5% to 3% (w/w) albumin), from 0.01% to 0.5% nonionic surfactant (e.g., from 0.01% to 0.05%, 0.05% to 0.1%, 0.05% to 0.2%, 0.1% to 0.3%, 0.2% to 0.4%, or from 0.3% to 0.5% nonionic surfactant), or a combination thereof. In still other embodiments, the magnetic particles include a surface decorated with 40 μg to 100 μg (e.g., 40 μg to 60 μg, 50 μg to 70 μg, 60 μg to 80 μg, or 80 μg to 100 μg,) of one or more proteins per milligram of the magnetic particles. The liquid sample can include a multivalent binding agent bearing a plurality of analytes conjugated to a polymeric scaffold.

The invention features a multivalent binding agent including two or more creatinine moieties covalently linked to a scaffold. In certain embodiments, the multivalent binding agent is a compound of formula (I):

$$(A)_n\text{-}(B) \qquad (I)$$

wherein (A) is

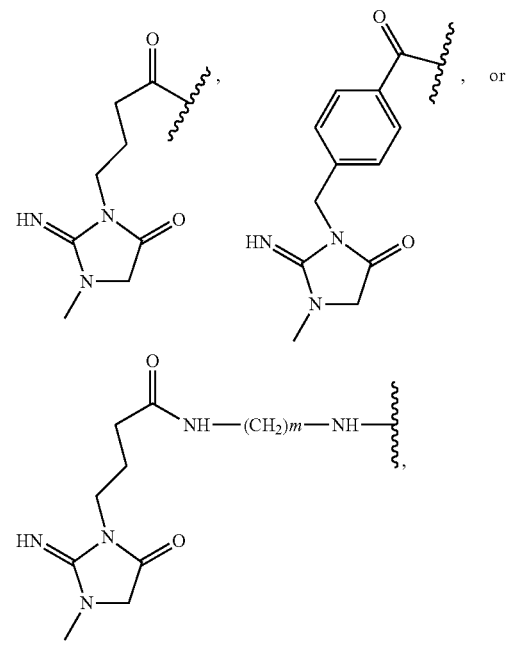

(B) is a polymeric scaffold covalently attached to each (A), m is an integer from 2 to 10, and n is an integer from 2 to 50.

The invention features a solution including from $1\times10^6$ to $1\times10^{13}$ magnetic particles per milliliter of the solution (e.g., from $1\times10^6$ to $1\times10^8$, $1\times10^7$ to $1\times10^8$, $1\times10^7$ to $1\times10^9$, $1\times10^8$ to $1\times10^{10}$, $1\times10^9$ to $1\times10^{11}$, or $1\times10^{10}$ to $1\times10^{13}$ magnetic particles per milliliter), wherein the magnetic particles have a mean diameter of from 150 nm to 600 nm (e.g., from 150 to 250, 200 to 350, 250 to 450, 300 to 500, 450 to 650, or from 500 to 600 nm), a $T_2$ relaxivity per particle of from $1\times10^8$ to $1\times10^{12}$ mM$^{-1}$s$^{-1}$ (e.g., from $1\times10^8$ to $1\times10^9$, $1\times10^8$ to $1\times10^{10}$, $1\times10^9$ to $1\times10^{10}$, $1\times10^9$ to $1\times10^{11}$, or from $1\times10^{10}$ to $1\times10^{12}$ and a surface bearing creatinine conjugate (A), wherein (A) is selected from:

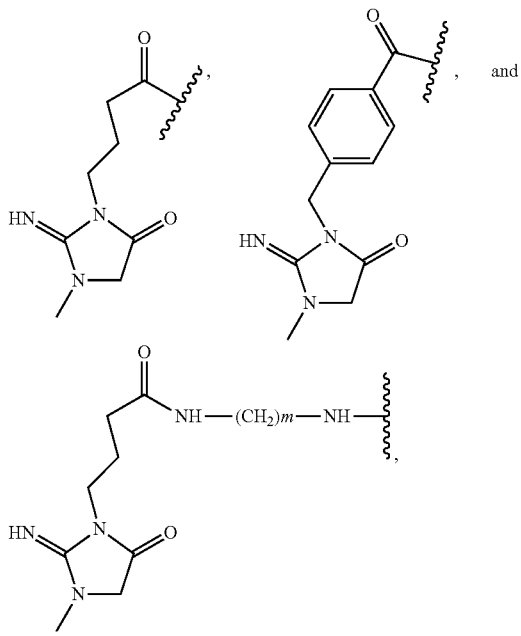

and m is an integer from 2 to 10.

The invention further features solution including from $1\times10^6$ to $1\times10^{13}$ magnetic particles per milliliter of the solution (e.g., from $1\times10^6$ to $1\times10^8$, $1\times10^7$ to $1\times10^8$, $1\times10^7$ to $1\times10^9$, $1\times10^8$ to $1\times10^{10}$, $1\times10^9$ to $1\times10^{11}$, or $1\times10^{10}$ to $1\times10^{13}$ magnetic particles per milliliter), wherein the magnetic particles have a mean diameter of from 150 nm to 600 nm (e.g., from 150 to 250, 200 to 350, 250 to 450, 300 to 500, 450 to 650, or from 500 to 600 nm), a $T_2$ relaxivity per particle of from $1\times10^8$ to $1\times10^{12}$ mM$^{-1}$s$^{-1}$ (e.g., from $1\times10^8$ to $1\times10^9$, $1\times10^8$ to $1\times10^{10}$, $1\times10^9$ to $1\times10^{10}$, $1\times10^9$ to $1\times10^{11}$, or from $1\times10^{10}$ to $1\times10^{12}$ mM$^{-1}$s$^{-1}$), and a surface bearing antibodies having affinity for the creatinine conjugate:

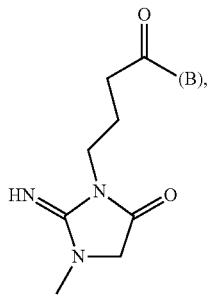

(B), wherein (B) is a polymeric scaffold.

The invention further features a method for measuring the concentration of tacrolimus in a liquid sample, the method including: (a) contacting a solution with (i) magnetic particles to produce a liquid sample including from $1\times10^6$ to $1\times10^{13}$ magnetic particles per milliliter of the liquid sample (e.g., from $1\times10^6$ to $1\times10^8$, $1\times10^7$ to $1\times10^8$, $1\times10^7$ to $1\times10^9$, $1\times10^8$ to $1\times10^{10}$, $1\times10^9$ to $1\times10^{11}$, or $1\times10^{10}$ to $1\times10^{13}$ magnetic particles per milliliter), wherein the magnetic particles have a mean diameter of from 150 nm to 1200 nm (e.g., from 150 to 250, 200 to 350, 250 to 450, 300 to 500, 450 to 650, 500 to 700 nm, 700 to 850, 800 to 950, 900 to 1050, or from 1000 to 1200 nm), a $T_2$ relaxivity per particle of from $1\times10^8$ to $1\times10^{12}$ mM$^{-1}$s$^{-1}$ (e.g., from $1\times10^8$ to $1\times10^9$, $1\times10^8$ to $1\times10^{10}$, $1\times10^9$ to $1\times10^{10}$, $1\times10^9$ to $1\times10^{11}$, or from $1\times10^{10}$ to $1\times10^{12}$ mM$^{-1}$s$^{-1}$), and tacrolimus antibodies conjugated to their surface, and (ii) a multivalent binding agent bearing a plurality of tacrolimus conjugates designed to form aggregates with the magnetic particles in the absence of tacrolimus; (b) placing the liquid sample in a device, the device including a support defining a well for holding the liquid sample including the magnetic particles, the multivalent binding agent, and the tacrolimus, and having an RF coil disposed about the well, the RF coil configured to detect a signal produced by exposing the liquid sample to a bias magnetic field created using one or more magnets and an RF pulse sequence; (c) exposing the sample to a bias magnetic field and an RF pulse sequence; (d) following step (c), measuring the signal; and (e) on the basis of the result of step (d), determining the concentration of tacrolimus in the liquid sample. In certain embodiments, the magnetic particles are substantially monodisperse; exhibit nonspecific reversibility in the absence of the analyte and multivalent binding agent; and/or the magnetic particles further include a surface decorated with a blocking agent selected from albumin, fish skin gelatin, gamma globulin, lysozyme, casein, peptidase, and an amine-bearing moiety (e.g., amino polyethyleneglycol, glycine, ethylenediamine, or amino dextran). In particular embodiments, the liquid sample further includes a buffer, from 0.1% to 3% (w/w) albumin (e.g., from 0.1% to 0.5%, 0.3% to 0.7%, 0.5% to 1%, 0.8% to 2%, or from 1.5% to 3% (w/w) albumin), from 0.01% to 0.5% nonionic surfactant (e.g., from 0.01% to 0.05%, 0.05% to 0.1%, 0.05% to 0.2%, 0.1% to 0.3%, 0.2% to 0.4%, or from 0.3% to 0.5% nonionic surfactant), or a combination thereof. In still other embodiments, the magnetic particles include a surface decorated with 40 μg to 100 μg (e.g., 40 μg to 60 μg, 50 μg to 70 μg, 60 μg to 80 μg, or 80 μg to 100 μg,) of one or more proteins per milligram of the magnetic particles. The liquid sample can include a multivalent binding agent bearing a plurality of analytes conjugated to a polymeric scaffold.

The invention features a multivalent binding agent including two or more tacrolimus moieties, including tacrolimus metabolites described herein or structurally similar compounds for which the antibody has affinity covalently linked to a scaffold. In certain embodiments, the multivalent binding agent is a compound of formula (II):

$$(A)_n\text{-}(B) \qquad (II)$$

wherein (A) is

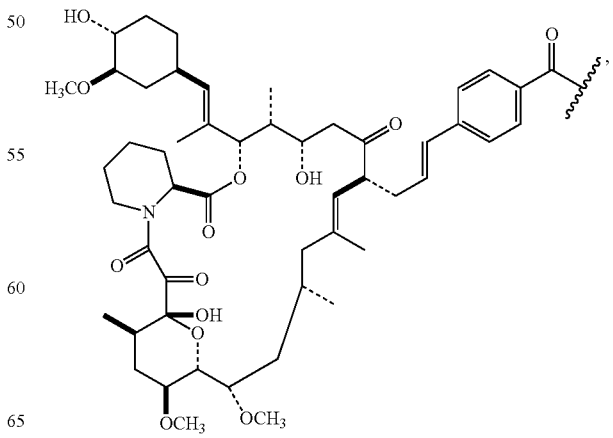

(B) is a polymeric scaffold covalently attached to each (A), and n is an integer from 2 to 50.

The invention features a solution including from $1\times10^6$ to $1\times10^{13}$ magnetic particles per milliliter of the solution (e.g., from $1\times10^6$ to $1\times10^8$, $1\times10^7$ to $1\times10^8$, $1\times10^7$ to $1\times10^9$, $1\times10^8$ to $1\times10^{10}$, $1\times10^9$ to $1\times10^{11}$, or $1\times10^{10}$ to $1\times10^{13}$ magnetic particles per milliliter), wherein the magnetic particles have a mean diameter of from 150 nm to 600 nm (e.g., from 150 to 250, 200 to 350, 250 to 450, 300 to 500, 450 to 650, or from 500 to 600 nm), a $T_2$ relaxivity per particle of from $1\times10^8$ to $1\times10^{12}$ $mM^{-1}s^{-1}$ (e.g., from $1\times10^8$ to $1\times10^9$, $1\times10^8$ to $1\times10^{10}$, $1\times10^9$ to $1\times10^{10}$, $1\times10^9$ to $1\times10^{11}$, or from $1\times10^{10}$ to $1\times10^{12}$ $mM^{-1}s^{-1}$), and a surface bearing antibodies having affinity for the tacrolimus conjugate:

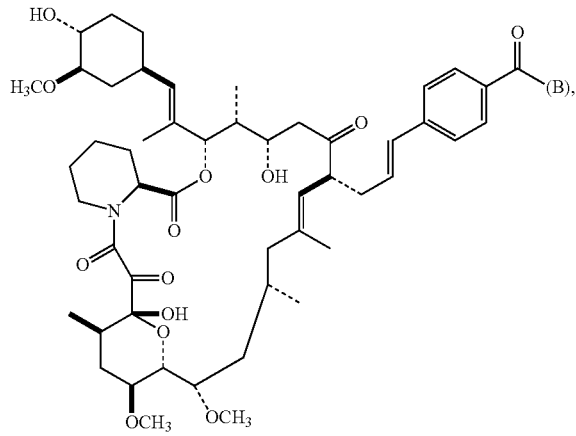

wherein (B) is a polymeric scaffold.

In an embodiment of any of the above solutions, (i) the magnetic particles are substantially monodisperse; (ii) the magnetic particles exhibit nonspecific reversibility in plasma; (iii) the magnetic particles further include a surface decorated with a blocking agent selected from albumin, fish skin gelatin, gamma globulin, lysozyme, casein, peptidase, and an amine-bearing moiety (e.g., amino polyethyleneglycol, glycine, ethylenediamine, or amino dextran); (iv) the liquid sample further includes a buffer, from 0.1% to 3% (w/w) albumin (e.g., from 0.1% to 0.5%, 0.3% to 0.7%, 0.5% to 1%, 0.8% to 2%, or from 1.5% to 3% (w/w) albumin), from 0.01% to 0.5% nonionic surfactant (e.g., from 0.01% to 0.05%, 0.05% to 0.1%, 0.05% to 0.2%, 0.1% to 0.3%, 0.2% to 0.4%, or from 0.3% to 0.5% nonionic surfactant), or a combination thereof; and/or (iv) the magnetic particles include a surface decorated with 40 µg to 100 µg (e.g., 40 µg to 60 µg, 50 µg to 70 µg, 60 µg to 80 µg, or 80 µg to 100 µg,) of one or more proteins per milligram of the magnetic particles. The solutions can be used in any of the systems or methods described herein.

The invention features a removable cartridge sized to facilitate insertion into and removal from a system of the invention, wherein the removable cartridge includes one or more chambers for holding a plurality of reagent modules for holding one or more assay reagents, wherein the reagent modules include (i) a chamber for holding from $1\times10^6$ to $1\times10^{13}$ magnetic particles (e.g., from $1\times10^6$ to $1\times10^8$, $1\times10^7$ to $1\times10^8$, $1\times10^7$ to $1\times10^9$, $1\times10^8$ to $1\times10^{10}$, $1\times10^9$ to $1\times10^{11}$, or $1\times10^{10}$ to $1\times10^{13}$ magnetic particles) having a mean diameter of from 100 nm to 699 nm (e.g., from 150 to 250, 200 to 350, 250 to 450, 300 to 500, 450 to 650, or from 500 to 699 nm), a $T_2$ relaxivity per particle of from $1\times10^8$ to $1\times10^{12}$ $mM^{-1}s^{-1}$ (e.g., from $1\times10^8$ to $1\times10^9$, $1\times10^8$ to $1\times10^{10}$, $1\times10^9$ to $1\times10^{10}$, $1\times10^9$ to $1\times10^{11}$, or from $1\times10^{10}$ to $1\times10^{12}$ $mM^{-1}s^{-1}$), and binding moieties on their surfaces, the binding moieties operative to alter the specific aggregation of the magnetic particles in the presence of the one or more analytes or a multivalent binding agent; and (ii) a chamber for holding a buffer. In a related aspect, the invention features a removable cartridge sized to facilitate insertion into and removal from a system of the invention, wherein the removable cartridge comprises one or more chambers for holding a plurality of reagent modules for holding one or more assay reagents, wherein the reagent modules include (i) a chamber for holding from $1\times10^6$ to $1\times10^{13}$ magnetic particles (e.g., from $1\times10^6$ to $1\times10^8$, $1\times10^7$ to $1\times10^8$, $1\times10^7$ to $1\times10^9$, $1\times10^8$ to $1\times10^{10}$, $1\times10^9$ to $1\times10^{11}$, or $1\times10^{10}$ to $1\times10^{13}$ magnetic particles) having a mean diameter of from 700 nm to 1200 nm (e.g., from 700 to 850, 800 to 950, 900 to 1050, or from 1000 to 1200 nm), a $T_2$ relaxivity per particle of from $1\times10^9$ to $1\times10^{12}$ $mM^{-1}s^{-1}$ (e.g., from $1\times10^9$ to $1\times10^{10}$, $1\times10^9$ to $1\times10^{11}$, or from $1\times10^{10}$ to $1\times10^{12}$ $mM^{-1}s^{-1}$), and oligonucleotide binding moieties on their surfaces, the oligonucleotide binding moieties operative to alter the specific aggregation of the magnetic particles in the presence of the one or more analytes; and (ii) a chamber for holding a buffer. The magnetic particles can be any described herein, decorated with any binding moieties described herein, for detecting any analyte described herein. In particular embodiments of the removable cartridges, the magnetic particles and buffer are together in a single chamber withing the cartridge. In still other embodiments, the buffer includes from 0.1% to 3% (w/w) albumin, from 0.01% to 0.5% nonionic surfactant, a lysis agent, or a combination thereof. The removable cartridge can further include a chamber including beads for lysing cells; a chamber including a polymerase; and/or a chamber including a primer.

The invention features a removable cartridge sized to facilitate insertion into and removal from a system of the invention, wherein the removable cartridge includes one ore more chambers for holding a plurality of reagent modules for holding one or more assay reagents, wherein the reagent modules include (i) a chamber for holding from $1\times10^8$ to $1\times10^{10}$ magnetic particles having a mean diameter of from 100 nm to 350 nm, a $T_2$ relaxivity per particle of from $5\times10^8$ to $1\times10^{10}$ and binding moieties on their surfaces (e.g., antibodies, conjugated analyte), the binding moieties operative to alter the specific aggregation of the magnetic particles in the presence of the one or more analytes or a multivalent binding agent; and (ii) a chamber for holding a buffer including from 0.1% to 3% (w/w) albumin (e.g., from 0.1% to 0.5%, 0.3% to 0.7%, 0.5% to 1%, 0.8% to 2%, or from 1.5% to 3% (w/w) albumin), from 0.01% to 0.5% nonionic surfactant (e.g., from 0.01% to 0.05%, 0.05% to 0.1%, 0.05% to 0.2%, 0.1% to 0.3%, 0.2% to 0.4%, or from 0.3% to 0.5% nonionic surfactant), or a combination thereof. In one embodiment, the magnetic particles and buffer are together in a single chamber withing the cartridge.

In any of the systems, kits, cartridges, and methods of the invention, the liquid sample can include from $1\times10^8$ to $1\times10^{10}$ magnetic particles having a mean diameter of from 100 nm to 350 nm, a $T_2$ relaxivity per particle of from $5\times10^8$ to $1\times10^{10}$ $mM^{-1}s^{-1}$, and binding moieties on their surfaces (e.g., antibodies, conjugated analyte), the binding moieties operative to alter the specific aggregation of the magnetic particles in the presence of the one or more analytes or a multivalent binding agent.

In any of the systems, kits, cartridges, and methods of the invention for detection of any analyte in a whole blood sample, the disruption of the red blood cells can be carried out using an erythrocyte lysis agent (i.e., a lysis buffer, or a nonionic detergent). Erythrocyte lysis buffers which can be used in the methods of the invention include, without limitation, isotonic solutions of ammonium chloride (optionally including carbonate buffer and/or EDTA), and hypotonic solutions. Alternatively, the erythrocyte lysis agent can be an aqueous solutions of nonionic detergents (e.g., nonyl phenoxypolyethoxylethanol (NP-40), 4-octylphenol polyethoxylate (Triton-X100), Brij-58, or related nonionic surfactants, and mixtures thereof). The erythrocyte lysis agent disrupts at least some of the red blood cells, allowing a large fraction of certain components of whole blood (e.g., certain whole blood proteins) to be separated (e.g., as supernatant following centrifugation) from the white blood cells, yeast cells, and/or bacteria cells present in the whole blood sample. Following Erythrocyte lysis and centrifugation, the resulting pellet is reconstituted to form an extract.

The methods, kits, cartridges, and systems of the invention can be configured to detect a predetermined panel of pathogen-associated analytes. For example, the panel can be a *candida* fungal panel configured to individually detect three or more of *Candida guilliermondii, C. albicans, C. glabrata, C. krusei, C. Lusitaniae, C. parapsilosis*, and *C. tropicalis*. In another embodiment, the panel can be a bacterial panel configured to individually detect three or more of coagulase negative *Staphylococcus, Enterococcus faecalis, E. faecium, Pseudomonas aeruginosa, Staphylococcus aureus*, and *Escherichia coli*. In a particular embodiment, the panel can be a viral panel configured to individually detect three or more of Cytomegalovirus (CMV), Epstein Barr Virus, BK Virus, Hepatitis B virus, Hepatitis C virus, Herpes simplex virus (HSV), HSV1, HSV2, Respiratory syncytial virus (RSV), Influenza; Influenza A, Influenza A subtype H1, Influenza A subtype H3, Influenza B, Human Herpes Virus 6, Human Herpes Virus 8, Human Metapneumovirus (hMPV), Rhinovirus, Parainfluenza 1, Parainfluenza 2, Parainfluenza 3, and Adenovirus. The panel can be a bacterial panel configured to individually detect three or more of *E. coli*, CoNS (coagulase negative staph), *Pseudomonas aeruginosa, S. aureus, E. faecium, E. faecalis*, and *Klebsiella pneumonia*. The panel can be a bacterial panel configured to individually detect three or more of *A. fumigates*, and *A. flavum*. The panel can be a bacterial panel configured to individually detect three or more of *Acinetobacter baumannii, Enterobacter aerogenes, Enterobacter cloacae, Klebsiella oxytoca, Proteus mirabilis, Serratia marcescens, Staphylococcus haemolyticus, Stenotro-phomonas maltophilia, Streptococcus agalactie, Streptococcus mitis, Streptococcus pneumonia*, and *Streptococcus pyogenes*. The panel can be a meningitis panel configured to individually detect three or more of *Streptococcus pneumonia, H. influenza, Neisseria Meningitis*, HSV1, HSV2, Enterovirus, *Listeria, E. coli*, Group B *Streptococcus*. The panel can be configured to individually detect three or more of *N. gonnorrhoeae, S. aureus, S. pyogenes*, CoNS, and *Borrelia burgdorferi*. The panel can be configured to individually detect three or more of *C. Difficile*, Toxin A, and Toxin B. The panel can be a pneumonia panel configured to individually detect three or more of *Streptococcus pneumonia*, MRSA, *Legionella, C. pneumonia*, and *Mycoplasma Pneumonia*. The panel can be configured to individually detect three or more of treatment resistant mutations selected from mecA, vanA, vanB, NDM-1, KPC, and VIM. The panel can be configured to individually detect three or more of *H. influenza, N. gonnorrhoeae, H. pylori, Campylobacter, Brucella, Legionella*, and *Stenotrophomonas maltophilia*. The panel can be configured to detect total viral load caused by CMV, EBV, BK Virus, HIV, HBV, and HCV. The panel can be configured to detect fungal load and/or bacterial load. Viral load determination can be using a standard curve and measuring the sample against this standard curve or some other method of quantitation of the pathogen in a sample. The quantitative measuring method may include real-time PCR, competitive PCR (ratio of two cometiting signals) or other methods mentioned here. The panel can be configured to detect immune response in a subject by monitoring PCT, MCP-1, CRP, GRO-alpha, High mobility group-box 1 protein (HMBG-1), IL-1 receptor, IL-1 receptor antagonist, IL-1b, IL-2, IL-4, IL-6, IL-8, IL-10, IL-12, IL-13, IL-18, macrophage inflammatory protein (MIP-1), macrophage migration inhibitory factor (MIF), osteopontin, RANTES (regulated on activation, normal T-cell expressed and secreted; or CCL5), Th1, Th17, and/or TNF-α. The panel can be configured to individually detect three or more of Ehrlichea, *Mycobacterium, Syphillis, Borrelia burgdorferi, Cryptococcus, Histoplasma*, and *Blastomyces*. The panel can be an influenza panel configured to individually detect three or more of Influenza A, Influenza B, RSV, Parainfluenza, Meta-pneumovirus, Rhinovirus, and Adenovirus.

The methods, kits, cartridges, and systems of the invention can be configured to reduce sample to sample variablility by determining a magnetic resonance signal prior to and after hybridization. The addition of derivatized nanoparticles to the sample prior to methods to enhance clustering may provide a baseline, internal $T_2$ signal that can either be subtracted or used to modify the $T_2$ signal after analyte-derivatized particle binding and clustering. This method may also be used to determine or manage cartridge to cartridge variability.

The terms "aggregation," "agglomeration," and "clustering" are used interchangeably in the context of the magnetic particles described herein and mean the binding of two or more magnetic particles to one another, e.g., via a multivalent analyte, multimeric form of analyte, antibody, nucleic acid molecule, or other binding molecule or entity. In some instances, magnetic particle agglomeration is reversible.

By "analyte" is meant a substance or a constituent of a sample to be analyzed. Exemplary analytes include one or more species of one or more of the following: a protein, a peptide, a polypeptide, an amino acid, a nucleic acid, an oligonucleotide, RNA, DNA, an antibody, a carbohydrate, a polysaccharide, glucose, a lipid, a gas (e.g., oxygen or carbon dioxide), an electrolyte (e.g., sodium, potassium, chloride, bicarbonate, BUN, magnesium, phosphate, calcium, ammonia, lactate), a lipoprotein, cholesterol, a fatty acid, a glycoprotein, a proteoglycan, a lipopolysaccharide, a cell surface marker (e.g., CD3, CD4, CD8, IL2R, or CD35), a cytoplasmic marker (e.g., CD4/CD8 or CD4/viral load), a therapeutic agent, a metabolite of a therapeutic agent, a marker for the detection of a weapon (e.g., a chemical or biological weapon), an organism, a pathogen, a pathogen byproduct, a parasite (e.g., a protozoan or a helminth), a protist, a fungus (e.g., yeast or mold), a bacterium, an actinomycete, a cell (e.g., a whole cell, a tumor cell, a stem cell, a white blood cell, a T cell (e.g., displaying CD3, CD4, CD8, IL2R, CD35, or other surface markers), or another cell identified with one or more specific markers), a virus, a prion, a plant component, a plant by-product, algae, an algae by-product, plant growth hormone, an insecticide, a man-made toxin, an environmental toxin, an oil component, and components derived therefrom. As used herein, the term "small molecule" refers to a drug, medication, medicament, or other chemically synthesized compound that is contemplated for human therapeutic use. As used herein, the term "biologic" refers to a substance derived from a biological source, not synthesized and that is contemplated for human therapeutic use. A "biomarker" is a biological substance that can be used as an indicator of a particular disease state or particular physiological state of an organism, generally a biomarker is a protein or other native compound measured in bodily fluid whose concentration reflects the presence or severity or staging of a disease state or dysfunction, can be used to monitor therapeutic progress of treatment of a disease or disorder or dysfunction, or can be used as a surrogate measure of clinical outcome or progression. As used herein, the term "metabolic biomarker" refers to a substance, molecule, or compound that is synthesized or biologically derived that is used to determine the status of a patient or subject's liver or kidney function. As used herein, the term "genotyping" refers to the ability to determine genetic differences in specific genes that may or may not affect the phenotype of the specific gene. As used herein, the term "phenotype" refers to the resultant biological expression, (metabolic or physiological) of the protein set by the genotype. As used herein, the term "gene expression profiling" refers to the ability to determine the rate or amount of the production of a gene product or the activity of gene transcription in a specific tissue, in a temporal or spatial manner. As used herein, the term "proteomic analysis" refers to a protein pattern or array to identify key differences in proteins or peptides in normal and diseased tissues. Additional exemplary analytes are described herein. The term analyte further includes components of a sample that are a direct product of a biochemical means of amplification of the initial target analyte, such as the product of a nucleic acid amplification reaction.

By an "isolated" nucleic acid molecule is meant a nucleic acid molecule that is removed from the environment in which it naturally occurs. For example, a naturally-occurring nucleic acid molecule present in the genome of cell or as part of a gene bank is not isolated, but the same molecule, separated from the remaining part of the genome, as a result of, e.g., a cloning event, amplification, or enrichment, is "isolated." Typically, an isolated nucleic acid molecule is free from nucleic acid regions (e.g., coding regions) with which it is immediately contiguous, at the 5' or 3' ends, in the naturally occurring genome. Such isolated nucleic acid molecules can be part of a vector or a composition and still be isolated, as such a vector or composition is not part of its natural environment.

As used herein, "linked" means attached or bound by covalent bonds, non-covalent bonds, and/or linked via Van der Waals forces, hydrogen bonds, and/or other intermolecular forces.

The term "magnetic particle" refers to particles including materials of high positive magnetic susceptibility such as paramagnetic compounds, superparamagnetic compounds, and magnetite, gamma ferric oxide, or metallic iron.

As used herein, "nonspecific reversibility" refers to the colloidal stability and robustness of magnetic particles against non-specific aggregation in a liquid sample and can be determined by subjecting the particles to the intended assay conditions in the absence of a specific clustering moiety (i.e., an analyte or an agglomerator). For example, nonspecific reversibility can be determined by measuring the $T_2$ values of a solution of magnetic particles before and after incubation in a uniform magnetic field (defined as <5000 ppm) at 0.45 T for 3 minutes at 37° C. Magnetic particles are deemed to have nonspecific reversibility if the difference in $T_2$ values before and after subjecting the magnetic particles to the intended assay conditions vary by less than 10% (e.g., vary by less than 9%, 8%, 6%, 4%, 3%, 2%, or 1%). If the difference is greater than 10%, then the particles exhibit irreversibility in the buffer, diluents, and matrix tested, and manipulation of particle and matrix properties (e.g., coating and buffer formulation) may be required to produce a system in which the particles have nonspecific reversibility. In another example, the test can be applied by measuring the $T_2$ values of a solution of magnetic particles before and after incubation in a gradient magnetic field 1 Gauss/mm-10000 Gauss/mm.

As used herein, the term "NMR relaxation rate" refers to a measuring any of the following in a sample $T_1$, $T_2$, $T_1/T_2$ hybrid, $T_{1rho}$, $T_{2rho}$, and $T_2^*$. The systems and methods of the invention are designed to produce an NMR relaxation rate characteristic of whether an analyte is present in the liquid sample. In some instances the NMR relaxation rate is characteristic of the quantity of analyte present in the liquid sample.

As used herein, the term "$T_1/T_2$ hybrid" refers to any detection method that combines a $T_1$ and a $T_2$ measurement. For example, the value of a $T_1/T_2$ hybrid can be a composite signal obtained through the combination of, ratio, or difference between two or more different $T_1$ and $T_2$ measurements. The $T_1/T_2$ hybrid can be obtained, for example, by using a pulse sequence in which $T_1$ and $T_2$ are alternatively measured or acquired in an interleaved fashion. Additionally, the $T_1/T_2$ hybrid signal can be acquired with a pulse sequence that measures a relaxation rate that is comprised of both $T_1$ and $T_2$ relaxation rates or mechanisms.

A "pathogen" means an agent causing disease or illness to its host, such as an organism or infectious particle, capable of producing a disease in another organism, and includes but is not limited to bacteria, viruses, protozoa, prions, yeast and fungi or pathogen by-products. "Pathogen by-products" are those biological substances arising from the pathogen that can be deleterious to the host or stimulate an excessive host immune response, for example pathogen antigen/s, metabolic substances, enzymes, biological substances, or toxins.

By "pathogen-associated analyte" is meant an analyte characteristic of the presence of a pathogen (e.g., a bacterium, fungus, or virus) in a sample. The pathogen-associated analyte can be a particular substance derived from a pathogen (e.g., a protein, nucleic acid, lipid, polysaccharide, or any other material produced by a pathogen) or a mixture derived from a pathogen (e.g., whole cells, or whole viruses). In certain instances, the pathogen-associated analyte is selected to be characteristic of the genus, species, or specific strain of pathogen being detected. Alternatively, the pathogen-associated analyte is selected to ascertain a property of the pathogen, such as resistance to a particular therapy. For example, the pathogen-associated analyte can be a gene, such as a Van A gene or Van B gene, characteristic of vancomycin resistance in a number of different bacterial species.

By "pulse sequence" or "RF pulse sequence" is meant one or more radio frequency pulses to be applied to a sample and designed to measure, e.g., certain NMR relaxation rates, such as spin echo sequences. A pulse sequence may also include the acquisition of a signal following one or more pulses to minimize noise and improve accuracy in the resulting signal value.

As used herein, the term "signal" refers to an NMR relaxation rate, frequency shift, susceptibility measurement, diffusion measurement, or correlation measurements.

As used herein, reference to the "size" of a magnetic particle refers to the average diameter for a mixture of the magnetic particles as determined by microscopy, light scattering, or other methods.

As used herein, the term "substantially monodisperse" refers to a mixture of magnetic particles having a polydispersity in size distribution as determined by the shape of the distribution curve of particle size in light scattering measurements. The FWHM (full width half max) of the particle distribution curve less than 25% of the peak position is considered substantially monodisperse. In addition, only one peak should be observed in the light scattering experiments and the peak position should be within one standard deviation of a population of known monodisperse particles.

By "$T_2$ relaxivity per particle" is meant the average $T_2$ relaxivity per particle in a population of magnetic particles.

As used herein, "unfractionated" refers to an assay in which none of the components of the sample being tested are removed following the addition of magnetic particles to the sample and prior to the NMR relaxation measurement.

It is contemplated that units, systems, methods, and processes of the claimed invention encompass variations and adaptations developed using information from the embodiments described herein. Throughout the description, where units and systems are described as having, including, or including specific components, or where processes and methods are described as having, including, or including specific steps, it is contemplated that, additionally, there are units and systems of the present invention that consist essentially of, or consist of, the recited components, and that there are processes and methods according to the present invention that consist essentially of, or consist of, the recited processing steps. It should be understood that the order of steps or order for performing certain actions is immaterial, unless otherwise specified, so long as the invention remains operable. Moreover, in many instances two or more steps or actions may be conducted simultaneously.

Other features and advantages of the invention will be apparent from the following detailed description, the drawings, and the claims.

BRIEF DESCRIPTION OF THE DRAWINGS

FIGS. 4A-4E are a series of graphs depicting the dependence of transverse relaxivity ($R_2$) (FIG. 4A) or T2 (FIGS. 4B-4E) on particle diameter and particle aggregation. FIG. 4A is a graph depicting the motional averaging regime (light line, left side); the $R_2$ ($1/T_2$) measured by a CPMG sequence increases as particle size increases because the refocusing pulses are ineffective to counteract the dephasing effects of the particles. As the system transitions to the visit limited regime (dark line, right side) the refocusing pulses begin to become effective and the $R_2$ decreases as particle size increases. For homogeneous magnetic fields, the $R_2^*$ in the motional averaging regime matches the $R_2$ and the $R_2^*$ reaches a constant value in the visit limited regime. In a homogenous field, when the $R_2^*$ is less than the $R_2$ of either the motional averaging regime or visit limited regime the system is in the static dephasing regime. The empty circle represents the $R_2$ of a solution of 100% dispersed particles (diameter=15 nm) and the solid circle represents a solution of 100% clustered particles (diameter=200 nm). This is an example of how to interpret these curves for clustering reactions. The conditions for this curve are 0.1 mM Fe, $\Delta\omega=8.85\times10^6$, $D=2.5\times10^{-5}$ m²/s, and $\tau_{CP}=0.25$ ms. FIG. 4B is a graph depicting the same light and dark curves plotted in terms of $T_2$ and diameter, on a linear scale. In this figure the black dashed line represents the $T_2^*$ measured in a non-uniform magnetic field where $T_2^*$ is always lower than $T_2$ and doesn't reflect the particle size. The data points are the same as well. FIG. 4C is a graph depicting the monodisperse clustering model and showing that $T_2$ will follow the curve as analyte is added because the average diameter of the population particles will cover all intermediate diameters between the initial and final states. FIG. 4D is a graph depicting the polydisperse model and showing that the $T_2$ will transition between the two points on this curve when particles form clusters of specific sizes. The response curve will be linear with regard to analyte addition, but non-linear with regard to volume fraction of clusters, because particles transition between state 1 and state 2. The slope of the response curve is directly proportional to the sensitivity of the assay. FIG. 4E is a graph showing the two regimes for particle aggregation and $T_2$ affects based on particle size and how clustering assays in the different regimes map onto the $T_2$ versus diameter curves (i) for the motional averaging regime $T_2$ decreases when particles cluster; and (ii) for the slow motion regime $T_2$ increases when particles cluster. Under the conditions shown in these models, the boundary between the two regimes is ca. 100 nm diameter particles. When small magnetic particles form aggregates under 100 nm in diameter, the result is a decrease in $T_2$ upon aggregate formation. When magnetic particles at or above 100 nm in diameter form larger aggregates, the result is an increase in $T_2$ upon aggregate formation.

FIGS. 5A-5C are drawings depicting different assay formats for the assays of the invention. FIG. 5A depicts an agglomerative sandwich immunoassay in which two populations of magnetic particles are designed to bind to two different epitopes of an analyte. FIG. 5B depicts a competitive immunoassay in which analyte in a liquid sample binds to a multivalent binding agent (a multivalent antibody), thereby inhibiting aggregation. FIG. 5C depicts a hybridization-mediated agglomerative assay in which two populations of particles are designed to bind to the first and second portions of a nucleic acid target, respectively.

FIG. 7A shows it in the inverted position after the user has removed the closure from the Vacutainer tube and placed the cartridge onto it. FIG. 7B shows the molded in path that the blood will follow out of the Vacutainer and into the sample loading region once the cartridge is turned right side up. The foil seal can be the bottom side of the channels, forming an inexpensively molded part with closed channels. FIG. 7C is a cutaway view showing the vent tube which allows air to enter into the vial as the blood leaves and fills the sample region. FIGS. 7D-7F depict an inlet module for sample aliquoting designed to interface with uncapped vacutainer tubes, and to aliquot two a sample volume that can be used to perform, for example, a *candida* assay. The inlet module has two hard plastic parts, that get ultrasonically welded together and foil sealed to form a network of channels to allow a flow path to form into the first well overflow to the second sample well. A soft vacutainer seal part is used to for a seal with the vacutainer. It has a port for sample flow, and a venting port, to allow the flow to occur.

FIG. 9A depicts the module of the cartridge that is intended to hold reagents and consumables for use during the assay. On the left are sealed pre-dispensed aliquots of reagents. On the right is a 2.8 ml conical bottomed centrifuge tube that is used for initial centrifugation of the blood. The other holes can be filled as need with vials, microcentrifuge tubes, and pipette tips. FIG. 9B is a cutaway view of the reagent module showing the holders for the pre-aliquoted reagent tips, including the feature at the bottom into which the tips are pressed to provide a seal. FIG. 9C depicts three representative pipette tips into which reagents can be pre-dispensed, and then the backs sealed. The tips are pressed into the sample holder to provide a seal.

FIG. 13A is a view of the detection tube. The tube itself could be an off the shelf 200 microliter PCR tube, while the cap is a custom molded elastomer part that provides a pressure resistant duckbill seal on the inside and a first seal to the pipette tip from the top. The seal is thus a make-break type of seal, where one seal is made before the other is broken. FIG. 13B depicts the custom molded seal component. Note the circular hole into which the pipette tip is inserted and the duckbill seal below, which provides a second seal that resists pressure developed in the tube. FIG. 13C depicts the seal showing the duckbill at bottom and the hole at top.

FIG. 14A shows a reagent strip for the cartridge. The oval holes are the supports for the detection modules, and these are constructed separately and then placed into the holes. The detection wells could be custom designed or commercially available. FIG. 14B shows the detection module for the cartridge depicted in FIG. 14A. In this example, the detection module contains two detection chambers, but could contain any number of chambers as required by the assay and as the detection system (the MR reader) is designed to accept. FIG. 14C depicts an alternate footprint for the modular multiplexed cartridge. This cartridge includes 3 detection modules that are molded as part of the reagent strip, and these portions are popped out of the frame and individually processed at other units (i.e., the NMR unit and/or magnetic assisted agglomeration (MAA) unit) within the assay system.

FIG. 18A depicts the gMAA unit array of 32 bottom magnets and 40 side magnets (32 functional, 8 used to balance the stray magnetic fields seen by all sample), each with a field strength of about 0.5 T, used for assisting agglomeration in an array of samples simultaneously. FIGS. 18B-18C depict a top view (FIG. 18B) and side view (FIG. 18C) of a setup for the automation of the an automated gMAA unit wherein a plate gMAA along with a configuration for containing an array of samples is cycled between the bottom and side magnet positions by a robotic systems, within a temperature controlled array. The magnets are stationary, while the plate holding the sample tubes moves through a preset trajectory. An exemplary field strength on the surface of individual magnets is 0.4-0.5 T, with a gradient in the order of 0.1 T/mm.

FIGS. 22A and 22B depict portions of a vortexer. FIG. 22A is a drawing depicting the bottom portion (i.e., the drive motor, coupling, and drive shaft) of a vortexer of the invention. The motor includes an index mark and/or other position sensing means such as an optical, magnetic or resistive position encoder that allows the motor to find a specific point in its rotation. These index marks are used to home the system, and ensure that the sample can be returned to a known position after mixing and allows the vortexer to be easily accessed by robotic actuators, and thus integrated into an automated system. In lieu of index marks, external home switches or position tracking sensors could be employed. FIG. 22B is a drawing depicting the guide mechanism of a vortexer of the invention. The main plate is connected to the offset axis of the drive shaft and is free to rotate. The plate follows the orbital path around and dictated by the motor shaft.

FIG. 23A is an overall view showing the vortexer configured for one large tube. FIG. 23B is a section view showing two tube holders for small tubes. FIG. 23C is an overall view of vortexer showing four tubes and a close up of planetary belt drive mechanism.

FIG. 25A is a graph showing a standard curve for the creatinine competitive assay of Example 6 correlating the observed $T_2$ relaxation rate with the concentration of creatinine in the liquid sample. FIG. 25B shows the $T_2$ response of a creatinine-decorated particle with 2 different preparations of antibody. Preparation 1 is pre-production (with aggregated antibody) and Preparation 2 is production purified (no aggregated antibody present). FIG. 25C shows the $T_2$ response of a creatinine-decorated particle with unaggregated antibody, biotinylated antibody and deliberately multimerized antibody, and confirms the increased clustering ability of multi-valent agglomerating agents.

In FIG. 26 (i) "control" is gMAA (magnet exposure+vortex, repeat) in which the relative position of the sample and the magnetic field direction are unchanged with each cycle; (ii) "twist" is gMAA (magnet exposure+rotation within magnet, repeat) with rotating tube ca. 90° relative to the gradient magnet with each cycle; (iii) "180° turn" is gMAA (magnet exposure+remove tube from magnet, rotate, place back in magnet, repeat) with rotating tube ca. 180° relative to the gradient magnet with each cycle; and "remove 5 s" is removal of tube from magnet, 5 seconds rest (no rotation), repeat. The results show that the rate at which a steady state degree of agglomeration, and stable $T_2$ reading, is achieved is expedited by cycling between the two or more positions over a number of gMAA treatments. Further, field gradient combinations, cycling field (side or bottom) to null or side field to bottom, field (side or bottom) to vortex are also iterations that can be used for gMAA. Exposure or dwell times (either on the field or away), and number of cycles can be varied to optimize assisted aggregation for a specific assay (not shown).

FIG. 30A is a graph showing that the degree of aggregation as determined by measuring the $T_2$ response of the sample is increased with increasing dwell time at room temperature. FIG. 30B is a graph showing that the degree of aggregation as determined by measuring the $T_2$ response of the sample is increased with increasing gMAA dwell time at 37° C. As shown in FIGS. 30A and 30B, increasing temperature and increasing dwell time enhance the extent of gMAA assisted aggregation as observed by changes in the observed $T_2$.

FIG. 41A depicts experimental results in buffer; while FIG. 41B depicts experimental results in lysed blood.

FIGS. 43A-43D are images depicting various fluid transfer units which can be used in the systems of the invention.

FIG. 48A is a graph depicting the results obtained from 16 experiments designed to assess the assay's performance in 6 different donor blood samples spiked with a range of *C. albicans* cells (see Example 17). Each data point is the mean+/-the 95% confidence interval (n=48). At the lowest test concentration (10 cells/mL), we failed to detect *Candida albicans* 37% of the time (6 out of 16 experiments); however at 100 cells/mL *Candida albicans* was detected 100% of the time. This suggests the assay can robustly detect at *C. albicans* concentrations greater than or equal to 100 cells/mL with no major inhibition of performance introduced through the donor blood samples. FIG. 48B is a graph depicting the results obtained from 7 experiments designed to assess the assay's performance in 6 different donor blood samples spiked with a range of *C. krusei* cells (see Example 17). Each data point is the mean+/-the 95% confidence interval (n=21). We do not detect at 10 cells/mL in any of the experimental runs but detect at 100 cells/mL for all experimental runs. This suggests the LOD between 10 and 100 cells/mL.

DETAILED DESCRIPTION

Figure 1A:
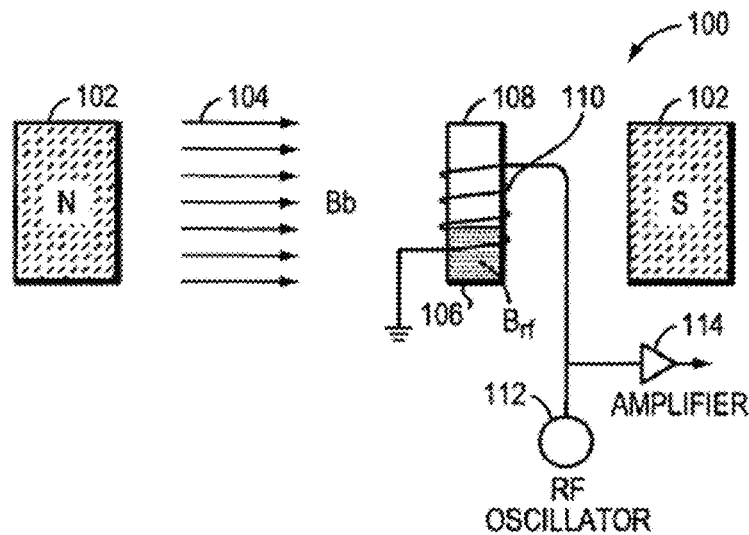
FIG. 1A is a schematic diagram of an NMR unit for detection of a signal response of a sample to an RF pulse sequence, according to an illustrative embodiment of the invention.
Figure 1A:
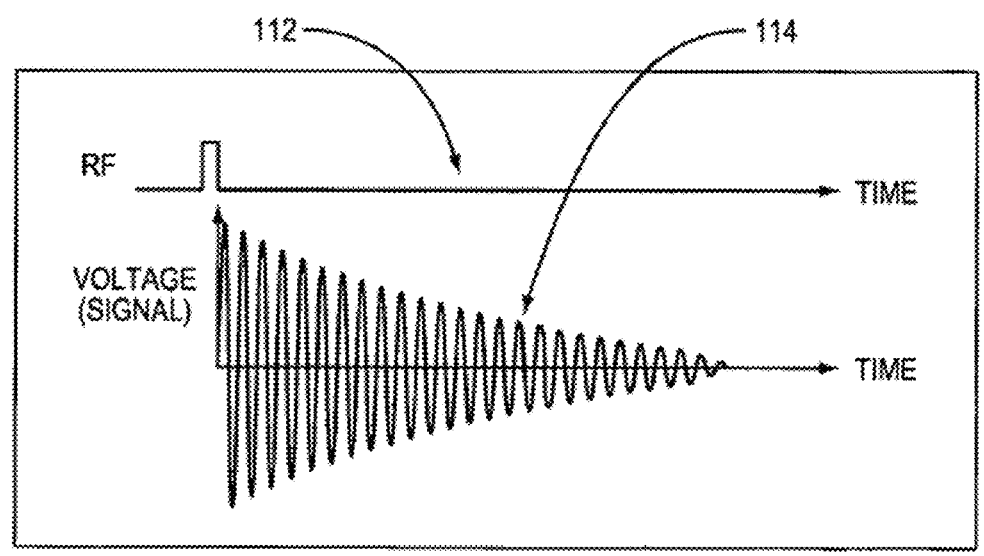

The invention features systems, devices, and methods for the rapid detection of analytes or determination of analyte concentration in a sample. The systems and methods of the invention employ magnetic particles, an NMR unit, optionally one or more MAA units, optionally one or more incubation stations at different temperatures, optionally one or more vortexer, optionally one or more centrifuges, optionally a fluidic manipulation station, optionally a robotic system, and optionally one or more modular cartridges. The systems, devices, and methods of the invention can be used to assay a biological sample (e.g., blood, sweat, tears, urine, saliva, semen, serum, plasma, cerebrospinal fluid (CSF), feces, vaginal fluid or tissue, sputum, nasopharyngeal aspirate or swab, lacrimal fluid, mucous, or epithelial swab (buccal swab), tissues, organs, bones, teeth, or tumors, among others). Alternatively, the systems, devices, and methods of the invention are used to monitor an environmental condition (e.g., plant growth hormone, insecticides, man-made or environmental toxins, nucleic acid sequences that are important for insect resistance/susceptibility, algae and algae by-products), as part of a bioremediation program, for use in farming plants or animals, or to identify environmental hazards. Similarly, the systems, devices, and methods of the invention are used to detect and monitor biowarfare or biological warfare agents, such as ricin, *Salmonella typhimurium*, botulinum toxin, aflatoxin, mycotoxins, *Francisella tularesis*, small pox, anthrax, or others.

The magnetic particles can be coated with a binding moiety (i.e., antibody, oligo, etc.) such that in the presence of analyte, or multivalent binding agent, aggregates are formed. Aggregation depletes portions of the sample from the microscopic magnetic non-uniformities that disrupt the solvent's $T_2$ signal, leading to an increase in $T_2$ relaxation (see FIG. 3).

The $T_2$ measurement is a single measure of all spins in the ensemble, measurements lasting typically 1-10 seconds, which allows the solvent to travel hundreds of microns, a long distance relative to the microscopic non-uniformities in the liquid sample. Each solvent molecule samples a volume in the liquid sample and the $T_2$ signal is an average (net total signal) of all (nuclear spins) on solvent molecules in the sample; in other words, the $T_2$ measurement is a net measurement of the entire environment experienced by a solvent molecule, and is an average measurement of all microscopic non-uniformities in the sample.

The observed $T_2$ relaxation rate for the solvent molecules in the liquid sample is dominated by the magnetic particles, which in the presence of a magnetic field form high magnetic dipole moments. In the absence of magnetic particles, the observed $T_2$ relaxation rates for a liquid sample are typically long (i.e., $T_2$ (water)=~2000 ms, $T_2$ (blood)=~1500 ms). As particle concentration increases, the microscopic non-uniformities in the sample increase and the diffusion of solvent through these microscopic non-uniformities leads to an increase in spin decoherence and a decrease in the $T_2$ value. The observed $T_2$ value depends upon the particle concentration in a non-linear fashion, and on the relaxivity per particle parameter.

In the aggregation assays of the invention, the number of magnetic particles, and if present the number of agglomerant particles, remain constant during the assay. The spatial distribution of the particles change when the particles cluster. Aggregation changes the average "experience" of a solvent molecule because particle localization into clusters is promoted rather than more even particle distributions. At a high degree of aggregation, many solvent molecules do not experience microscopic non-uniformities created by magnetic particles and the $T_2$ approaches that of solvent. As the fraction of aggregated magnetic particles increases in a liquid sample, the observed $T_2$ is the average of the non-uniform suspension of aggregated and single (unaggregated) magnetic particles. The assays of the invention are designed to maximize the change in $T_2$ with aggregation to increase the sensitivity of the assay to the presence of analytes, and to differences in analyte concentration.

In designing magnetic relaxation switch (MRSw) biosensors, it is important to consider the relaxation mechanisms of the magnetic particles. First, in the case of superparamagnetic particles the solvent longitudinal and transverse relaxivities (defined as $R_1=1/T_1$ and $R_2=1/T_2$, respectively) are a function of particle size. Furthermore, $R_2$ and $R_2^*$ (where $R_2^*=1/T_2^*$, $R_2^*=R_2+\Delta\omega_F$, where $\Delta\omega_F$ is dephasing due to field inhomgeneities) increase with particle diameter until about 100 nm, and then $R_2$ decreases with increasing particle size and the $R_2^*$ reaches a plateau for uniform fields (see FIG. 4A). Superparamagnetic particles are typically divided into categories of strongly magnetized and weakly magnetized particles, based on the relative magnitude of the precession frequency difference between nuclei at the surface of the particle and nuclei distant from the particle, $\Delta\omega$, and the inter-echo delay of the CPMG detection sequence, $\tau_{CP}$. $\Delta\omega$ is essentially a relative measure of the effect of the dipolar magnetic field generated by a superparamagnetic particle on the resonant frequency of hydrogen nuclei in adjacent water molecules. When the product $\Delta\omega\tau_{CP}>1$ then the particles are classified as strongly magnetized and when $\Delta\omega\tau_{CP}<1$ then the particles are classified as weakly magnetized. For typical relaxometers, $\tau_{CP}$ is no shorter than tens of microseconds, so $\Delta\omega$ must be less than $10^5$ for the particles to be within the weakly magnetized regime. Most superparamagnetic particles used for MRSw assays have a surface dephasing $\Delta\omega$ of approximately $1\times10^7$, therefore they are classified as strongly magnetized. This means that the inter-echo delay is always longer than the amount of dephasing that occurs at the surface of a particle.

Another characteristic of superparamagnetic particle solutions that is used to differentiate physical behavior is the diffusion time, or travel time, of water ($\tau_D$) relative to the inter-echo time of the pulse sequence, $\tau_{CP}$. Particle solutions are in the long echo limit when the m is significantly less than that $\tau_{CP}$. $\tau_D$ can be determined by the relationship:

$$\tau_D = \frac{R^2}{D}, \quad (1)$$

where $\tau_D$ is the time it takes a water molecule to diffuse the distance of a particle radius, R, and D the diffusion constant of water, $10^{-9}$ m$^2$/s. $\tau_D$ can be thought of as the time it takes a water molecule to pass a hemisphere of a particle, or a flyby time. When $\tau_D$ is much larger than $\tau_{CP}$, then the particle system is within the "short echo limit". Typical CPMG sequences have echo times on the order of hundreds of microseconds to several milliseconds. Therefore, the "short echo limit" cannot be approached unless the particle diameter approaches 1000 nm. The most common MRSw biosensors are within the "long echo limit" because the length of the inter-echo delays ($\tau_{CP}>0.25$ ms) is longer than the time it takes a water molecule to diffuse past the hemisphere of a particle (0.2-100 microseconds).

As the particle size of a solution of superparamagnetic particles at fixed iron concentration is increased there is an initial increase in $R_2$, then a plateau and later decrease (FIG. 4A). The regime on the left hand side of the curve is been termed the motional averaging regime, the regime in the middle is been termed the static dephasing regime, and the regime on the right is been termed the visit limited, or slow motion regime. The boundaries between the motional averaging and visit limited regimes can be determined by generating plots such as that shown in FIG. 4A, or they can be determined by the relationship between $\Delta\omega$ and $\tau_D$. If $\Delta\omega\tau_D<1$, then the system is in the motional averaging regime; if $\Delta\omega\tau_D>1$, then the system is in the visit limited regime (also termed the slow motion regime). As the diameter of the particles increases in the motional averaging regime the refocusing echos in the CPMG pulse sequence cannot efficiently refocus the magnetization that has been dephased by the particles, hence the increase in $R_2$ (or decrease in $T_2$). In other words, the refocusing pulses cannot compensate for increased dephasing by larger particles. The flat region of the static dephasing regime is due to the $R_2$ being limited by $R_2^*$. The decreasing $R_2$ with increasing diameter in the visit limited regime results in the refocusing pulses being able to refocus the dephasing caused by the particles. Also apparent in FIG. 4A is that the $R_2$ in the slow motion regime exhibits a dependence on the inter-echo delay of the spin echo sequence.

In a homogenous magnetic field, one can determine which regime applies to a sample by comparing the $R_2$ to the $R_2^*$; the two values are identical in the motional averaging or static dephasing regime and they are different in the visit limited regime. However, in cases of inhomogeneous fields, such as those present on benchtop and portable MR devices, the $T_2^*$ is dominated by the field gradient. In fact, the measured $T_2^*$ value is not indicative of the particle or particle cluster size state (FIG. 4B). The shape of the $R_2$ response as particles agglomerated generally matches the expected trend for the increase in average particle size. The similarity between the $R_2$ of particle agglomerates and that of spherical particles suggests that one can equate particle aggregates and spherical shapes. Even though this assumption may seem to be in contradiction with the fractal nature of particle agglomerates, the shape of the particle aggregates observed by the magnetic resonance measurement is determined by the ensemble of diffusing water molecules in solution, which can be approximated by the radius of hydration measured by light scattering.

The analytical models for $R_2$ can be applied to magnetic relaxation biosensors to aid in the design of biosensor assays. Conveniently, these models accurately predict the dependence of $R_2$ on parameters that a biosensor designer can control—iron concentration, temperature, magnetic susceptibility, and particle size. Additionally, these analytical models allow for predictive modeling of the dependence of $T_2$ relaxation on these parameters. Results are not entirely quantitative, but the general trends and response curves predicted by these models can be instructive. One useful model is the chemical exchange model for strongly magnetized spheres:

$$1/T_2 = \frac{(4/9)V\tau_D(\Delta\omega_r)^2}{1+(4/9)^2(\tau_D/\tau_{CP})^2\alpha^5} \quad (2)$$

$$\alpha = \left[\frac{\Delta\omega\tau_{CP}}{a + b\Delta\omega\tau_{CP}V}\right]^{1/3} \quad (3)$$

where $1/T_2$ is the transverse relaxivity, V the volume fraction of iron in solution, $\tau_D$ the diffusion, or flyby time, $\Delta\omega_r$ the frequency shift at the surface of a particle relative to bulk solution, $\tau_{CP}$ one half the inter-echo delay in a CPMG sequence, and a and b are derived constants (a=1.34 and b=0.99). Equations (2) and (3) can be used to generate a curve that describes the dependence of $R_2$ on particle sizes, as shown by the light and dark lines in FIGS. 4A and 4B (dark line on right side of the curve; light line on left side of the curve).

Figure 2:
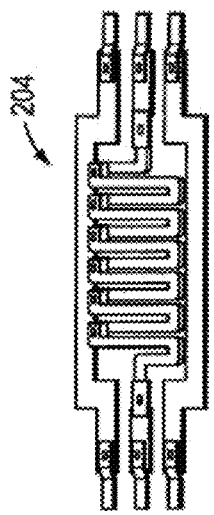
FIGS. 2A-2E illustrate micro coil geometries which can be used in NMR (for excitation and/or detection); designs include, but are not limited to a wound solenoid coil (FIG. 2A), a planar coil (FIG. 2B), a MEMS solenoid coil (FIG. 2C), a MEMS Helmholz coil (FIG. 2D), and a saddle coil (FIG. 2E), according to an illustrative embodiment of the invention. Three dimensional lithographic coil fabrication of well characterized coils used in MR detection is also established and can be used for these applications, Demas et al. "Electronic characterization of lithographically patterned microcoils for high sensitivity NMR detection" J Magn Reson 200:56 (2009).
Figure 2:
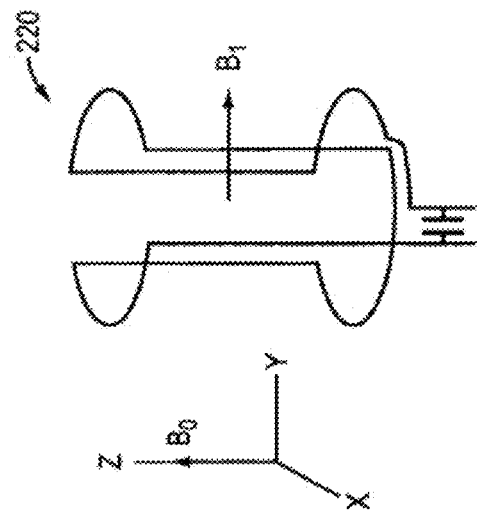
Figure 2:
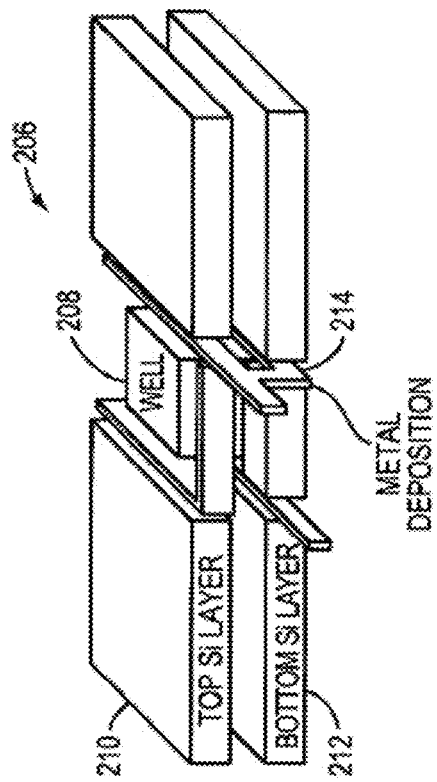

A modification of Equation 2 can be used to generate a plot that is more intuitive to an assay developer. This plot is in terms of $T_2$ and particle diameter with linear units rather than logarithmic units (FIG. 2). As discussed above, magnetic relaxation biosensor assays function due to a transition between dispersed and clustered states. For a given agglomerative assay, the measured $T_2$ can follow one of two pathways over the course of an analyte titration. The population of dispersed particles can cluster in a uniform manner leading to an increase in average particle size that is proportional to the amount of analyte that has been added. This type of agglomeration is termed the monodisperse model because it would lead to a monodisperse intermediate population of particles. In this case, $T_2$ would be expected to decrease as particle size increases as long as the system is within the motional averaging regime. As the system approaches and enters the visit limited regime the $T_2$ would increase with particle size (FIG. 4C).

A different type of agglomeration that may occur is one in which the addition of analyte seeds the self-assembly of clusters, a process with energetics similar to crystal formation or fractal aggregation. For this model one would expect a preferred size for particle clusters that depended on the conditions of the solution. Systems that followed this model would exhibit polydisperse intermediate populations; one would find a mixture of particles with discrete sizes. Given two discrete populations, dispersed particles and clustered particles, the system would transition between the $T_2$ value of the starting monodisperse population of unclustered particles and the final $T_2$ value of the fully clustered particles. For both models, full titration may lead to a monodisperse solution of clustered particles. Although the exact energetics, kinetics, and thermodynamics of particle agglomeration will depend on characteristics of the assay system such as valency and binding affinities, these two models are instructive in understanding the dependencies and possible scenarios one may encounter during MRSw biosensor design.

There are two regimes for particle clustering and $T_2$ affects based on particle size (see FIG. 4D, the boundary is typically ca. 100 nm diameter particles). For any given assay of a liquid sample the particle count for 250 nm sized magnetic particles can be ca. $1\times10^7$ particles, whereas for 30 nm sized magnetic particles can be ca. $1\times10^{13}$. This is because the smaller particles have a lower relaxivity per particle (for the same type of material), resulting in an inherent sensitivity disadvantage. In a typical assay of the invention, the magnetic particles are selected such that $T_2$ increases with an increase in the fraction of aggregated particles.

The assay of the invention can be designed to change the direction of $T_2$ in the presence of analyte (see FIGS. 5A-5C). For example, the assay can be an agglomerative sandwich immunoassay in which two populations of magnetic particles bind to different epitopes of an analyte (see FIG. 5A); a competitive assay in which analyte competes with a multivalent binding agents to inhibit the aggregation of magnetic particles (see FIG. 5B); or a hybridization-mediated agglomeration in which two populations of magnetic particles bind to a first and second portion of an oligonucleotide (see FIG. 5C). Additional competitive format might include when two particles binding moieties bind without agglomerator (e.g. the DNA oligonucleotides are designed so that two nanoparticles have two different oligos and they can anneal together and when heated the analyte or amplicon or target DNA competes or disrupts the np annealing).

Other formats for carrying out the assays of the invention can be used, such as: (i) a target sample can be incubated in the presence of a magnetic particle that has been decorated with binding moieties specific to a target analyte and a multivalent binding agent, in an inhibition assay the binding of the analyte to the magnetic particles blocks agglomeration of the magnetic particles with the multivalent binding agent; (ii) a target sample can be incubated in the presence of a magnetic particle that has been decorated with binding moieties specific to a target analyte and a multivalent binding agent, in a disaggregation assay the analyte is exposed to a pre-formed aggregate of the multivalent binding agent and the magnetic particle and the analyte displaces the multivalent binding agent to reduce aggregation in the liquid sample; or (iii) a target sample can be incubated in the presence of a magnetic particle that has been decorated with binding moieties specific to a target analyte and the target analyte itself to form a self-assembling single population of magnetic particles, in an inhibition assay or disaggregation assay the presence the binding of the analyte to the magnetic particles blocks the self agglomeration of the magnetic particles; or (iv) a target sample can be incubated in the presence of a soluble agglomerating agent and a magnetic particle decorated with the analyte or analog of the analyte, in an inhibition assay the presence of the analyte binds the soluble agglomerating agent blocking the agglomeration of the particles.

Where a multivalent binding agent (agglomerant) is employed, multiple analytes are linked to a carrier (e.g., a simple synthetic scaffold, or a larger carrier protein or polysaccharide, such as BSA, transferrin, or dextran).

Magnetic Particles

The magnetic particles described herein include those described, e.g., in U.S. Pat. No. 7,564,245 and U.S. Patent Application Publication No. 2003-0092029, each of which is incorporated herein by reference. The magnetic particles are generally in the form of conjugates, that is, a magnetic particle with one or more binding moieties (e.g., an oligonucleotide, nucleic acid, polypeptide, or polysaccharide) linked thereto. The binding moiety causes a specific interaction with a target analyte. The binding moiety specifically binds to a selected target analyte, for example, a nucleic acid, polypeptide, or polysaccharide. In some instances, binding causes aggregation of the conjugates, resulting in a change, e.g., a decrease (e.g., in the case of smaller magnetic particles) or an increase (e.g., in the case of larger magnetic particles) in the spin-spin relaxation time (T2) of adjacent water protons in an aqueous solution (or protons in a non-aqueous solvent). Alternatively, the analyte binds to a preformed aggregate in a competitive disaggregation assay (e.g., an aggregate formed from a multivalent binding agent and magnetic particles), or competes with a multivalent binding agent for binding moieties on the magnetic particles in an inhibition assay (i.e., the formation of aggregates is inhibited in the presence of the analyte).

The conjugates have high relaxivity owing to the superparamagnetism of their iron, metal oxide, or other ferro or ferrimagnetic nanomaterials. Iron, cobalt, and nickel compounds and their alloys, rare earth elements such as gadolinium, and certain intermetallics such as gold and vanadium are ferromagnets can be used to produce superparamagnetic particles. The magnetic particles can be monodisperse (a single crystal of a magnetic material, e.g., metal oxide, such as superparamagnetic iron oxide, per magnetic particle) or polydisperse (e.g., a plurality of crystals per magnetic particle). The magnetic metal oxide can also include cobalt, magnesium, zinc, or mixtures of these metals with iron. Important features and elements of magnetic particles that are useful to produce conjugates include: (i) a high relaxivity, i.e., strong effect on water (or other solvent) relaxation, (ii) a functional group to which the binding moiety can be covalently attached, (iii) a low non-specific binding of interactive moieties to the magnetic particle, and/or (iv) stability in solution, i.e., the magnetic particles remain suspended in solution, not precipitated and/or the nps retain their ability to be employed in the described method (i.e. the nps have a shelf life).

The magnetic particles may be linked to the binding moieties via functional groups. In some embodiments, the magnetic particles can be associated with a polymer that includes functional groups selected, in part, to enhance the magnetic particles nonspecific reversibility. The polymer can be a synthetic polymer, such as, but not limited to, polyethylene glycol or silane, natural polymers, or derivatives of either synthetic or natural polymers or a combination of these. The polymer may be hydrophilic. In some embodiments, the polymer "coating" is not a continuous film around the magnetic metal oxide, but is a "mesh" or "cloud" of extended polymer chains attached to and surrounding the metal oxide. The polymer can include polysaccharides and derivatives, including dextran, pullanan, carboxydextran, carboxmethyl dextran, and/or reduced carboxymethyl dextran. The metal oxide can be a collection of one or more crystals that contact each other, or that are individually entrapped or surrounded by the polymer.

Alternatively, the magnetic particles can be associated with non-polymeric functional group compositions. Methods of synthesizing stabilized, functionalized magnetic particles without associated polymers are described, for example, in Halbreich et al., Biochimie, 80:379 (1998).

The magnetic particles typically include metal oxide mono and polycrystals of about 1-25 nm, e.g., about 3-10 nm, or about 5 nm in diameter per crystal. The magnetic particles can also include a polymer component in the form of a core and/or coating, e.g., about 5 to 20 nm thick or more. The overall size of the magnetic particles can be, e.g., from 20 to 50 nm, from 50 to 200 nm, from 100 to 300 nm, from 250 to 500 nm, from 400 to 600 nm, from 500 to 750 nm, from 700 to 1,200 nm, from 1,000 to 1,500 nm, or from 1,500 to 2,000 nm.

The magnetic particles may be prepared in a variety of ways. It is preferred that the magnetic particle have functional groups that link the magnetic particle to the binding moiety. Carboxy functionalized magnetic particles can be made, for example, according to the method of Gorman (see PCT Publication No. WO00/61191). In this method, reduced carboxymethyl (CM) dextran is synthesized from commercial dextran. The CM-dextran and iron salts are mixed together and are then neutralized with ammonium hydroxide. The resulting carboxy functionalized magnetic particles can be used for coupling amino functionalized oligonucleotides. Carboxy-functionalized magnetic particles can also be made from polysaccharide coated magnetic particles by reaction with bromo or chloroacetic acid in strong base to attach carboxyl groups. In addition, carboxy-functionalized particles can be made from amino-functionalized magnetic particles by converting amino to carboxy groups by the use of reagents such as succinic anhydride or maleic anhydride.

Magnetic particle size can be controlled by adjusting reaction conditions, for example, by using low temperature during the neutralization of iron salts with a base as described in U.S. Pat. No. 5,262,176. Uniform particle size materials can also be made by fractionating the particles using centrifugation, ultrafiltration, or gel filtration, as described, for example in U.S. Pat. No. 5,492,814.

Magnetic particles can also be synthesized according to the method of Molday (Molday, R. S, and D. MacKenzie, "Immunospecific ferromagnetic iron-dextran reagents for the labeling and magnetic separation of cells," J. Immunol. Methods, 52:353 (1982)), and treated with periodate to form aldehyde groups. The aldehyde-containing magnetic particles can then be reacted with a diamine (e.g., ethylene diamine or hexanediamine), which will form a Schiff base, followed by reduction with sodium borohydride or sodium cyanoborohydride.

Dextran-coated magnetic particles can be made and cross-linked with epichlorohydrin. The addition of ammonia reacts with epoxy groups to generate amine groups, see Hogemann, D., et al., Improvement of MRI probes to allow efficient detection of gene expression Bioconjug. Chem., 11:941 (2000), and Josephson et al., "High-efficiency intracellular magnetic labeling with novel superparamagnetic-Tat peptide conjugates," Bioconjug. Chem., 10:186 (1999). This material is known as cross-linked iron oxide or "CLIO" and when functionalized with amine is referred to as amine-CLIO or $NH_2$—CLIO. Carboxy-functionalized magnetic particles can be converted to amino-functionalized magnetic particles by the use of water-soluble carbodiimides and diamines such as ethylene diamine or hexane diamine.

The magnetic particles can be formed from a ferrofluid (i.e., a stable colloidal suspension of magnetic particles). For example, the magnetic particle can be a composite of including multiple metal oxide crystals of the order of a few tens of nanometers in size and dispersed in a fluid containing a surfactant, which adsorbs onto the particles and stabilizes them, or by precipitation, in a basic medium, of a solution of metal ions. Suitable ferrofluids are sold by the company Liquids Research Ltd. under the references: WHKS1S9 (A, B or C), which is a water-based ferrofluid including magnetite ($Fe_3O_4$), having particles 10 nm in diameter; WHJS1 (A, B or C), which is an isoparaffin-based ferrofluid including particles of magnetite ($Fe_3O_4$) 10 nm in diameter; and BKS25 dextran, which is a water-based ferrofluid stabilized with dextran, including particles of magnetite ($Fe_3O_4$) 9 nm in diameter. Other suitable ferrofluids for use in the systems and methods of the invention are oleic acid-stabilized ferrofluids available from Ademtech, which include ca. 70% weight $\alpha$-$Fe_2O_3$ particles (ca. 10 nm in diameter), 15% weight octane, and 15% weight oleic acid.

The magnetic particles are typically a composite including multiple metal oxide crystals and an organic matrix, and having a surface decorated with functional groups (i.e., amine groups or carboxy groups) for the linking binding moieties to the surface of the magnetic particle. For example, the magnetic particles useful in the methods of the invention include those commercially available from Dynal, Seradyn, Kisker, Miltenyi Biotec, Chemicell, Anvil, Biopal, Estapor, Genovis, Thermo Fisher Scientific, JSR micro, Invitrogen, and Ademtech, as well as those described in U.S. Pat. Nos. 4,101,435; 4,452,773; 5,204,457; 5,262,176; 5,424,419; 6,165,378; 6,866,838; 7,001,589; and 7,217,457, each of which is incorporated herein by reference.

Avidin or streptavidin can be attached to magnetic particles for use with a biotinylated binding moiety, such as an oligonucleotide or polypeptide (see, e.g., Shen et al., "Magnetically labeled secretin retains receptor affinity to pancreas acinar cells," Bioconjug. Chem., 7:311 (1996)). Similarly, biotin can be attached to a magnetic particle for use with an avidin-labeled binding moiety. Alternatively, the binding moiety is covalently linked to the surface of the magnetic particle; the particles may be decorated with IgG molecules; the particles may be decorated with anti his antibodies; or the particles may be decorated with his-tagged FAbs.

Low molecular weight materials can be separated from the magnetic particles by ultra-filtration, dialysis, magnetic separation, or other means prior to use. For example, unreacted binding moieties and linking agents can be separated from the magnetic particle conjugates by magnetic separation or size exclusion chromatography. In certain instances the magnetic particles can be fractionated by size to produce mixtures of particles of a particular size range and average diameter.

For certain assays requiring high sensitivity, analyte detection using $T_2$ relaxation assays can require selecting a proper particle to enable sufficiently sensitive analyte-induced agglomeration. Higher sensitivities can be achieved using particles that contain multiple superparamagnetic iron oxide cores (5-15 nm diameter) within a single larger polymer matrix or ferrofluid assembly (100 nm-1200 nm total diameter, such as particles having an average diameter of 100 nm, 200 nm, 250 nm, 300 nm, 500 nm, 800 nm, or 1000 nm), or by using a higher magnetic moment materials or particles with higher density, and/or particles with higher iron content. Without being limited by theory, it is postulated these types of particles provided a sensitivity gain of over 100× due to a much higher number of iron atoms per particle, which is believed to lead to an increase in sensitivity due to the decreased number of particles present in the assay solution and possibly a higher amount of superparamagnetic iron affected by each clustering event.

Relaxivity per particle and particle size is one useful term for selecting an optimal particle for high sensitivity assays. Ideally, this term will be as large as possible. Relaxivity per particle is a measure of the effect of each particle on the measured $T_2$ value. The larger this number, the fewer the number of particles needed to elicit a given $T_2$ response. Furthermore, lowering the concentration of particles in the reactive solution can improve the analytical sensitivity of the assay. Relaxivity per particle can be a more useful parameter in that the iron density and relaxivity can vary from magnetic particle to magnetic particle, depending upon the components used to make the particles (see Table 1). Relaxivity per particle is proportional to the saturation magnetization of a superparamagnetic material.

TABLE 1

| Hydroynamic Diameter (nm) | # Metal Atoms per Particle | Relaxivity per Particle (mM$^{-1}$ s$^{-1}$) |
|---|---|---|
| 10-30 | 1.0E+03-1.0E+06 | 1.0E+6-1.0E+11 |
| 10-50 | 8.0E+02-4.0E+04 | 1.0E+04-4.0E+06 |
| 10-50 | 1.0E+04-5.0E+05 | 1.0E+06-1.0E+08 |
| 50-100 | 1.0E+04-1.0E+07 | 1.0E+06-1.0E+09 |
| 100-200 | 5.0E+06-5.0E+07 | 5.0E+08-8.0E+09 |
| 200-300 | 1.0E+07-1.0E+08 | 3.0E+09-1.0E+10 |
| 300-500 | 5.0E+07-1.0E+09 | 7.0E+09-5.0E+10 |

TABLE 1-continued

| Hydroynamic Diameter (nm) | # Metal Atoms per Particle | Relaxivity per Particle (mM$^{-1}$ s$^{-1}$) |
|---|---|---|
| 500-800 | 1.0E+08-4.1E+09 | 1.0E+10-5.0E+11 |
| 800-1000 | 5.0E+08-5.0E+09 | 5.0E+10-5.0E+11 |
| 1000-1200 | 1.0E+09-7.0E+09 | 1.0E+11-1.0E+12 |

The base particle for use in the systems and methods of the invention can be any of the commercially available particles identified in Table 2.

TABLE 2

| Catalogue No. | Source/Description | Diameter (μm) |
|---|---|---|
| Kisker | | |
| MAv-1 | Polystyrene, Magnet Particles Avidin coated | 1.0-1.9 |
| PMSt-0.6 | Polystyrene, Magnet Particles Streptavidin coated | 0.5-0.69 |
| PMSt-0.7 | Polystyrene, Magnet Particles Streptavidin coated | 0.7-0.9 |
| PMSt-1.0 | Polystyrene, Magnet Particles Streptavidin coated | 1.0-1.4 |
| PMB-1 | Polystyrene, Magnet Particles Biotin covalently coupled to BSA coating | 1.0-1.9 |
| PMP-200 | Dextran based, No coating, plain | 0.2 |
| PMP-1000 | Dextran based, No coating, plain | 0.10 |
| PMP-1300 | Dextran based, No coating, plain | 0.13 |
| PMP-2500 | Dextran based, No coating, plain | 0.25 |
| PMN-1300 | Dextran based, NH2— coated | 0.13 |
| PMN-2500 | Dextran based, NH2— coated | 0.25 |
| PMC-1000 | Dextran based, COOH— coated | 0.10 |
| PMC-1300 | Dextran based, COOH— coated | 0.13 |
| PMC-2500 | Dextran based, COOH— coated | 0.25 |
| PMAV-1300 | Dextran based, Avidin coated | 0.13 |
| PMAV-2500 | Dextran based, Avidin coated | 0.25 |
| PMSA-1000 | Dextran based, Streptavidin coated | 0.1 |
| PMSA-1300 | Dextran based, Streptavidin coated | 0.13 |
| PMSA-2500 | Dextran based, Streptavidin coated | 0.25 |
| PMB-1000 | Dextran based, Biotin coated | 0.1 |
| PMB-1300 | Dextran based, Biotin coated | 0.13 |
| PMB-2500 | Dextran based, Biotin coated | 0.25 |
| PMPA-1000 | Dextran based, Protein A coated | 0.1 |
| PMPA-1300 | Dextran based, Protein A coated | 0.13 |
| PMPA-2500 | Dextran based, Protein A coated | 0.25 |
| PMC-0.1 | Dextran based, COOH functionalized | 0.1-0.4 |
| PMC-0.4 | Dextran based, COOH functionalized | 0.4-0.7 |
| PMC-0.7 | Dextran based, COOH functionalized | 0.7-0.9 |
| PMC-1.0 | Dextran based, COOH functionalized | 1.0-1.4 |
| PMN-1.0 | Dextran based, NH2 functionalized | 1.0-1.4 |
| PMC-0.1 | Dextran based, COOH functionalized | 0.1-0.4 |
| Accurate Chemical | | |
| ADM01020 | Carboxyl-functionality | 0.2 |
| ADM01030 | Carboxyl-functionality | 0.3 |
| ADM02020 | Carboxyl-functionality | 0.2 |
| ADM02133 | high Carboxyl-functionality | 0.3 |
| ADM02150 | Carboxyl-functionality | 0.5 |
| ADM02220 | very high Amino-functionality | 0.2 |
| ADM02230 | very high Amino-functionality | 0.3 |
| ADM02250 | Carboxyl-functionality | 0.5 |
| ADM02030 | high Carboxyl-functionality | 0.3 |
| ADM02110 | high Carboxyl-functionality | 0.1 |
| ADM02120 | very high Carboxyl-functionality | 0.2 |
| ADM02130 | very high Carboxyl-functionality | 0.3 |
| ADM02252 | Carboxyl-functionality | 0.5 |
| ADM03120 | Streptavidin-functionality | 0.2 |
| ADM03121 | Streptavidin-functionality | 0.2 |
| chemicell | | |
| 1201-5 1 | Si—(CH$_2$)$_3$—COOH | 0.5 |
| 1201-5 1 | Si—(CH$_2$)$_3$—COOH | 0.75 |
| 1201-5 1 | Si—(CH$_2$)$_3$—COOH | 1.0 |

TABLE 2-continued

| Catalogue No. | Source/Description | Diameter (μm) |
|---|---|---|
| 1202-5 1 | Si—(CH$_2$)$_3$—SO$_3$H | 0.5 |
| 1202-5 1 | Si—(CH$_2$)$_3$—SO$_3$H | 0.75 |
| 1202-5 1 | Si—(CH$_2$)$_3$—SO$_3$H | 1.0 |
| 1205-1 | Si—(CH$_2$)$_3$—PO$_3$H$_2$ | 0.5 |
| 1205-1 | Si—(CH$_2$)$_3$—PO$_3$H$_2$ | 0.75 |
| 1205-1 | Si—(CH$_2$)$_3$—PO$_3$H$_2$ Estapor | 1.0 |
| M1-130/12 | Carboxylated Polystyrene | 0.7-1.3 |
| M1-180/12 | Carboxylated Polystyrene | 0.9-1.3 |
| M1-180/20 | Carboxylated Divinylbenzene | 0.8-1.2 |
| M1-050/20 | Carboxylated Polystyrene | 0.5-0.7 |
| M1-070/40 | Carboxylated Polystyrene | 0.7-1.3 |
| M1-070/60 | Carboxylated Polystyrene | 0.7-1.3 |
| M1-020/50 | Carboxylated Polystyrene | 0.16-0.24 |
| M1-030/40 | Carboxylated Polystyrene Genovis | 0.3-0.5 |
| AMI-25 | Dextran Thermo Fisher | 80-150 |
| 4515-2105 | Carboxylate-Modified (MG-CM) | 1.0 |
| 7815-2104 | NeutrAvidin (MG-NA) | 1.0 |
| 5915-2104 | Streptavidin (MG-SA) | 1.0 |
| 2415-2105 | Carboxylate-Modified (MG-CM) | 1.0 |
| 4415-2105 | Carboxylate-Modified (MG-CM) JSR micro | 1.0 |
| MB100 | Carboxylated Invitrogen | 1.1 |
| 354-01 | Carboxylated | 1 |
| 355-00 | Tosylactivated | 1 |
| 650-11 | Carboxylated | 1 |
| 655-11 | Tosylactivated Biopal | 1 |
| M02Q05 | Amino activated | 1.5 |
| M02Q05 | Biotin activated | 1.5 |
| M02Q05 | Strepavidin activated | 1.5 |

The magnetic particles for use in the systems and methods of the invention can have a hydrodynamic diameter from 10 nm to 1200 nm, and containing on average from $8\times10^2$-$1\times10^{10}$ metal atoms per particle, and having a relaxivity per particle of from $1\times10^4$-$1\times10^{13}$ mM$^{-1}$ s$^{-1}$. The magnetic particles used in the systems and methods of the invention can be any of the designs, composites, or sources described above, and can be further modified has described herein for use as a magnetic resonance switch.

In addition to relaxivity per particle, several other practical issues must be address in the selection and design of magnetic particles for high analytical sensitivity assays.

For example, the use of large particles (i.e., 1000 nm or greater) may be desired to maximize iron content and the relaxivity per particle. However, we have observed that particles of this size tend to settle rapidly out of solution. We have observed that particle settling does not typically interfere with the assay if magnetic particle sizes are kept below 500 nm. When use of a particle above 500 nm in the described assays or smaller particles with high density are employed, settling is monitored and effect on $T_2$ measurement is determined. We have found a magnetic particle size of about 100-300 nm particle to be ideal for stability in terms of settling, even after functionalization (increasing the hydrodynamic diameter to 300 nm by approximately 50 nm), and to afford the high sensitivity enabled by a high relaxivity per particle. Particle density certainly plays a role in buoyancy. As such, the relative density of the solution and particles plays an important role in settling of the particle.

Accordingly, a possible solution to this problem is the use of buoyant magnetic particles (i.e., a hollow particle, or particle containing both a low density matrix and high density metal oxide). Settling may affect the $T_2$ detection, thus, solution additives may be employed to change the ratio of the particle to solution density. $T_2$ detection can be impacted by settling if there is a significant portioning of the superparamagentic material from the measured volume of liquid. Settling can be assessed by diluting the particles to a concentration such that UV-Vis absorbance at 410 nm is between 0.6-0.8 absorbance units and then monitoring the absorbance for 90 minutes. If settling occurs, the difference between the initial and final absorbances divided by the initial absorbance will be greater than 5%. If % settling is above 5% then the particle is typically not suitable for use in assays requiring high analytical sensitivity. The magnetic particles used in the assays of the invention can be, but are not limited to, nonsettling magnetic particles. High settling represents handling difficulties and may lead to reproducibility issues.

For magnetic particles on the order of 100 nm or larger, the multiple superparamagnetic iron oxide crystals that typically include the particle core results in a net dipole moment when in the presence of external magnetic fields, i.e. the dipole monment is a sufficient force to overcome Brownian motion. Nonspecific reversibility is a measure of the colloidal stability and robustness against non-specific aggregation. Nonspecific reversibility is assessed by measuring the $T_2$ values of a solution of particles before and after incubation in a uniform magnetic field (defined as <5000 ppm). Starting $T_2$ values are typically 200 ms for a particle with an iron concentration of 0.01 mM Fe. If the difference in $T_2$ values before and after incubation in the uniform magnetic field is less than 20 ms, the samples are deemed reversible. Further, 10% is a threshold allowing starting $T_2$ measurements to reflect assay particle concentration. If the difference is greater than 10%, then the particles exhibit irreversibility in the buffer, diluents, and matrix tested. The MAA reversibility of the magnetic particles can be altered as described herein. For example, colloidal stability and robustness against non-specific aggregation can be influenced by the surface characteristics of the particles, the binding moieties, the assay buffer, the matrix and the assay processing conditions. Maintenance of colloidal stability and resistance to non-specific biding can be altered by conjugation chemistry, blocking methods, buffer modifications, and/or changes in assay processing conditions.

We have observed that a very important attribute for robust and reproducible assays is the monodispersity in the size distribution of the magnetic particles used, a distinction observed in polydisperse particles post-coating versus monodisperse particle pre-coating. Polydisperse batches of magnetic particles can lack reproducibility and compromise sensitivity. Polydisperse samples can also present problems in terms of achieving uniform coatings. For certain highly sensitive assays it is desirable that the magnetic particles be substantially monodisperse in size distribution (i.e., having a polydispersity index of less than about 0.8-0.9). Alternatively, the assays of the invention can be designed to accommodate the use of polydisperse magnetic particles.

Given that the assays of the invention require monitoring a shift in the clustering states of the agglomeration assays and that measuring a change in clustering likely requires a significant fraction of clustered particles (e.g., thought to be >1-10%), the total number of particles in an assay should be minimized to enable the highest sensitivity. However, sufficient number of particles must be present to allow utilization of the $T_2$ detection dynamic range. We have found that the highest sensitivity is observed when the number of magnetic particles (or molar equivalent) is approximately on the same order of magnitude of the number (or molar equivalent) of the analyte being detected, and the magnitude of the number (or molar equivalent) multivalent binding agents employed (i.e., in an inhibition assay).

For proteinaceous samples it may also be required to modify the magnetic particle surface to reduce non-specific binding of background proteins to the magnetic particles. Non-specific binding of background proteins to particles can induce or impede particle clustering, resulting in false signals and/or false lack of signals. For example, in some instances the surface of the magnetic particle can include blocking agents covalently linked to the surface of the magnetic particle which reduce non-specific binding of background proteins. There are a variety of agents that one could use to achieve the desired effect, and in some cases, it is a combination of agents that is optimal (see Table 3; exemplary particles, coatings, and binding moieties).

TABLE 3

| Base Particle | Coating | Binding Moiety |
|---|---|---|
| NP-COOH: | amino Dextran | Small molecule |
| | Transferrin | |
| | Lysozyme | |
| | BSA | |
| | FSG | |
| | BGG | |
| | Ovalbumin | |
| | amino PEG | |
| | Human albumin | |
| | none | Antibody |
| | amino PEG | |
| | BSA | |
| | amino Dextran | |
| NP-amino: | none | Small molecule |
| | PEG | |
| NP-SA: | none | biotinylated Ab |
| | biotinylated amino PEG | Antibody |
| NP-SA: | biotinylated amino PEG | small molecule |
| NP-anti-species: | none | Antibody |
| NP-Ni: | none | his-tagged antibody |

Thus, we have found a protein block may be required to achieve assay activity and sensitivity, particularly in proteinaceous samples (e.g., plasma samples or whole blood samples), that is comparable to results in nonproteinaceous buffer samples. Some commonly used protein blockers which may be used in provided preparations include, e.g., bovine serum albumin (BSA), fish skin gelatin (FSG), bovine gamma globulin (BGG), lysozyme, casein, peptidase, or non-fat dry milk. In certain embodiments a magnetic particle coating includes BSA or FSG. In other embodiments, a combination of coatings are combinations of those exemplary coatings listed in Table 3.

Furthermore, nonspecific binding can be due to lipids or other non-proteinaceous molecules in the biological sample. For non-proteinaceous mediated non-specific binding, changes in pH and buffer ionic strength maybe selected to enhance the particle repulsive forces, but not enough to limit the results of the intended interactions.

Assay Reagents

The assays of the invention can include reagents for reducing the non-specific binding to the magnetic particles. For example, the assay can include one or more proteins (e.g., albumin, fish skin gelatin, lysozyme, or transferrin); low molecular weight (<500 Daltons) amines (e.g., amino acids, glycine, ethylamine, or mercaptoethanol amine); and/or water soluble non-ionic surface active agents (e.g., polyethyleneglycol, Tween® 20, Tween® 80, Pluronic®, or Igepal®) (see Table 4).

TABLE 4

| Blocking Agents |
|---|
| PEG |
| BSA—Bovine serum albumin |
| HSA—Human serum albumin |
| FSG—Fish skin gelatin |
| Lysozyme |
| Transferrin |
| Glycine or other small amine containing molecules |
| Ethylamine |
| Mercaptoethanol amine |
| Tween 20 |
| Tween 80 |
| Pluronic |
| Igepal |
| Triton X-100 |
| Other surfactants/detergents |

The surfactant may be selected from a wide variety of soluble non-ionic surface active agents including surfactants that are generally commercially available under the IGEPAL trade name from GAF Company. The IGEPAL liquid non-ionic surfactants are polyethylene glycol p-isooctylphenyl ether compounds and are available in various molecular weight designations, for example, IGEPAL CA720, IGEPAL CA630, and IGEPAL CA890. Other suitable non-ionic surfactants include those available under the trade name TETRONIC 909 from BASF Wyandotte Corporation. This material is a tetra-functional block copolymer surfactant terminating in primary hydroxyl groups. Suitable non-ionic surfactants are also available under the VISTA ALPHONIC trade name from Vista Chemical Company and such materials are ethoxylates that are non-ionic biodegradables derived from linear primary alcohol blends of various molecular weights. The surfactant may also be selected from poloxamers, such as polyoxyethylene-polyoxypropylene block copolymers, such as those available under the trade names Synperonic PE series (ICI), Pluronic® series (BASF), Supronic, Monolan, Pluracare, and Plurodac, polysorbate surfactants, such as Tween® 20 (PEG-20 sorbitan monolaurate), and glycols such as ethylene glycol and propylene glycol.

Such non-ionic surfactants may be selected to provide an appropriate amount of detergency for an assay without having a deleterious effect on assay reactions. In particular, surfactants may be included in a reaction mixture for the purpose of suppressing non-specific interactions among various ingredients of the aggregation assays of the invention. The non-ionic surfactants are typically added to the liquid sample prior in an amount from 0.01% (w/w) to 5% (w/w).

The non-ionic surfactants may be used in combination with one or more proteins (e.g., albumin, fish skin gelatin, lysozyme, or transferrin) also added to the liquid sample prior in an amount from 0.01% (w/w) to 5% (w/w).

Furthermore, the assays, methods, and cartridge units of the invention can include additional suitable buffer components (e.g., Tris base, selected to provide a pH of about 7.8 to 8.2 in the reaction milieu); and chelating agents to scavenge cations (e.g., EDTA disodium, ethylene diamine tetraacetic acid (EDTA), citric acid, tartaric acid, glucuronic acid, saccharic acid or suitable salts thereof).

Binding Moieties

In general, a binding moiety is a molecule, synthetic or natural, that specifically binds or otherwise links to, e.g., covalently or non-covalently binds to or hybridizes with, a target molecule, or with another binding moiety (or, in certain embodiments, with an aggregation inducing molecule). For example, the binding moiety can be an antibody directed toward an antigen or any protein-protein interaction. Alternatively, the binding moiety can be a polysaccharide that binds to a corresponding target or a synthetic oligonucleotide that hybridizes to a specific complementary nucleic acid target. In certain embodiments, the binding moieties can be designed or selected to serve, when bound to another binding moiety, as substrates for a target molecule such as enzyme in solution.

Binding moieties include, for example, oligonucleotide binding moieties (DNA, RNA, or substituted or derivatized nucleotide substitutes), polypeptide binding moieties, antibody binding moieties, aptamers, and polysaccharide binding moieties.

Oligonucleotide Binding Moieties

In certain embodiments, the binding moieties are oligonucleotides, attached/linked to the magnetic particles using any of a variety of chemistries, by a single, e.g., covalent, bond, e.g., at the 3' or 5' end to a functional group on the magnetic particle. Such binding moieties can be used in the systems, devices, and methods of the invention to detect mutations (e.g., SNPs, translocations, large deletions, small deletions, insertions, substitutions) or to monitor gene expression (e.g., the presence of expression, or changes in the level of gene expression, monitoring RNA transcription), or CHP analysis characteristic of the presence of a pathogen, disease state, or the progression of disease.

An oligonucleotide binding moiety can be constructed using chemical synthesis. A double-stranded DNA binding moiety can be constructed by enzymatic ligation reactions using procedures known in the art. For example, a nucleic acid (e.g., an oligonucleotide) can be chemically synthesized using naturally occurring nucleotides or variously modified nucleotides designed to increase the biological stability of the molecules or to increase the physical stability of the duplex formed between the complementary strands, e.g., phosphorothioate derivatives and acridine substituted nucleotides can be used. The nucleic acid also can be produced biologically using an expression vector into which a nucleic acid has been subcloned.

One method uses at least two populations of oligonucleotide magnetic particles, each with strong effects on water (or other solvent) relaxation. As the oligonucleotide-magnetic particle conjugates react with a target oligonucleotide, they form aggregates (e.g., clusters of magnetic particles). Upon prolonged standing, e.g., overnight at room temperature, the aggregates form large clusters (micron-sized clusters). Using the methods of the invention, the formation of large clusters can be accomplished more quickly by employing multiple cycles of magnetic assisted agglomeration. Magnetic resonance is used to determine the relaxation properties of the solvent, which are altered when the mixture of magnetic oligonucleotide magnetic particles reacts with a target nucleic acid to form aggregates.

Certain embodiments employ a mixture of at least two types of magnetic metal oxide magnetic particles, each with a specific sequence of oligonucleotide, and each with more than one copy of the oligonucleotide attached, e.g., covalently, per magnetic particle. For example, the assay protocol may involve preparing a mixture of populations of oligonucleotide-magnetic particle conjugates and reacting the mixture with a target nucleic acid. Alternatively, oligonucleotide-magnetic particle conjugates can be reacted with the target in a sequential fashion. Certain embodiments feature the use of magnetic resonance to detect the reaction of the oligonucleotide-magnetic particle conjugates with the target nucleic acid. When a target is present, the dispersed conjugates self-assemble to form small aggregates.

For example, oligonucleotide binding moieties can be linked to the metal oxide through covalent attachment to a functionalized polymer or to non-polymeric surface-functionalized metal oxides. In the latter method, the magnetic particles can be synthesized according to the method of Albrecht et al., Biochimie, 80:379 (1998). Dimercaptosuccinic acid is coupled to the iron oxide and provides a carboxyl functional group.

In certain embodiments, oligonucleotides are attached to magnetic particles via a functionalized polymer associated with the metal oxide. In some embodiments, the polymer is hydrophilic. In certain embodiments, the conjugates are made using oligonucleotides that have terminal amino, sulfhydryl, or phosphate groups, and superparamagnetic iron oxide magnetic particles bearing amino or carboxy groups on a hydrophilic polymer. There are several methods for synthesizing carboxy and amino derivatized-magnetic particles.

In one embodiment, oligonucleotides are attached to a particle via ligand-protein binding interaction, such as biotin-streptavidin, where the ligand is covalently attached to the oligonucleotide and the protein to the particle, or vice versa. This approach can allow for more rapid reagent preparation.

Other forms of oligonucleotides may be used. For example, aptamers are single-stranded RNA or DNA oligonucleotides 15 to 60 base in length that in solution form intramolecular interactions that fold the linear nucleic acid molecule into a three dimensional complex that then can bind with high affinity to specific molecular targets; often with equilibrium constants in the range of 1 pM to 1 nM which is similar to some monoclonal antibodies-antigen interactions. Aptamers can specifically bind to other nucleic acid molecules, proteins, small organic compounds, small molecules, and cells (organisms or pathogens).

Polypeptide Binding Moieties

In certain embodiments, the binding moiety is a polypeptide (i.e., a protein, polypeptide, or peptide), attached, using any of a variety of chemistries, by a single covalent bond in such a manner so as to not affect the biological activity of the polypeptide. In one embodiment, attachment is done through the thiol group of single reactive cysteine residue so placed that its modification does not affect the biological activity of the polypeptide. In this regard the use of linear polypeptides, with cysteine at the C-terminal or N-terminal end, provides a single thiol in a manner similar to which alkanethiol supplies a thiol group at the 3' or 5' end of an oligonucleotide. Similar bifunctional conjugation reagents, such as SPDP and reacting with the amino group of the magnetic particle and thiol group of the polypeptide, can be used with any thiol bearing binding moiety. The types of polypeptides used as binding moieties can be antibodies, antibody fragments, and natural and synthetic polypeptide sequences. The peptide binding moieties have a binding partner, that is, a molecule to which they selectively bind.

Use of peptides as binding moieties offers several advantages. For example, polypeptides can be engineered to have uniquely reactive residues, distal from the residues required for biological activity, for attachment to the magnetic particle. The reactive residue can be a cysteine thiol, an N-terminal amino group, a C-terminal carboxyl group or a carboxyl group of aspartate or glutamate, etc. A single reactive residue on the peptide is used to insure a unique site of attachment. These design principles can be followed with chemically synthesized peptides or biologically produced polypeptides.

The binding moieties can also contain amino acid sequences from naturally occurring (wild-type) polypeptides or proteins. For example, the natural polypeptide may be a hormone, (e.g., a cytokine, a growth factor), a serum protein, a viral protein (e.g., hemagglutinin), an extracellular matrix protein, a lectin, or an ectodomain of a cell surface protein. Another example is a ligand binding protein, such as streptavidin or avidin that bind biotin. In general, the resulting binding moiety-magnetic particle is used to measure the presence of analytes in a test media reacting with the binding moiety.

Additionally, a polypeptide binding moiety can be used in a universal reagent configuration, where the target of the binding moiety (e.g., small molecule, ligand, or binding partner) is pre-attached to the target analyte to create a labeled analyte that, in the presence of the polypeptide decorated particles, induces clustering.

Examples of protein hormones which can be utilized as binding moieties include, without limitation, platelet-derived growth factor (PDGF), which binds the PDGF receptor; insulin-like growth factor-I and -II (Igf), which binds the Igf receptor; nerve growth factor (NGF), which binds the NGF receptor; fibroblast growth factor (FGF), which binds the FGF receptor (e.g., aFGF and bFGF); epidermal growth factor (EGF), which binds the EGF receptor; transforming growth factor (TGF, e.g., TGFα and TGF-β), which bind the TGF receptor; erythropoietin, which binds the erythropoitin receptor; growth hormone (e.g., human growth hormone), which binds the growth hormone receptor; and proinsulin, insulin, A-chain insulin, and B-chain insulin, which all bind to the insulin receptor.

Receptor binding moieties are useful for detecting and imaging receptor clustering on the surface of a cell. Useful ectodomains include those of the Notch protein, Delta protein, integrins, cadherins, and other cell adhesion molecules.

Antibody Binding Moieties

Other polypeptide binding moieties include immunoglobulin binding moieties that include at least one immunoglobulin domain, and typically at least two such domains. An "immunoglobulin domain" refers to a domain of an antibody molecule, e.g., a variable or constant domain. An "immunoglobulin superfamily domain" refers to a domain that has a three-dimensional structure related to an immunoglobulin domain, but is from a non-immunoglobulin molecule. Immunoglobulin domains and immunoglobulin superfamily domains typically include two β-sheets formed of about seven β-strands, and a conserved disulfide bond (see, e.g., Williams and Barclay Ann. Rev Immunol., 6:381 (1988)). Proteins that include domains of the Ig superfamily domains include T cell receptors, CD4, platelet derived growth factor receptor (PDGFR), and intercellular adhesion molecule (ICAM).

One type of immunoglobulin binding moiety is an antibody. The term "antibody," as used herein, refers to a full-length, two-chain immunoglobulin molecule and an antigen-binding portion and fragments thereof, including synthetic variants. A typical antibody includes two heavy (H) chain variable regions (abbreviated herein as VH), and two light (L) chain variable regions (abbreviated herein as VL). The VH and VL regions can be further subdivided into regions of hypervariability, termed "complementarity determining regions" (CDR), interspersed with regions that are more conserved, termed "framework regions" (FR). The extent of the framework region and CDR's has been precisely defined (see, Kabat, E. A., et al. (1991) Sequences of Proteins of Immunological Interest, Fifth Edition, U.S. Department of Health and Human Services, NIH Publication No. 91-3242, and Chothia et al., J. Mol. Biol., 196:901 (1987)). Each VH and VL is composed of three CDR's and four FRs, arranged from amino-terminus to carboxy-terminus in the following order: FR1, CDR1, FR2, CDR2, FR3, CDR3, and FR4.

An antibody can also include a constant region as part of a light or heavy chain. Light chains can include a kappa or lambda constant region gene at the COOH-terminus (termed CL). Heavy chains can include, for example, a gamma constant region (IgG1, IgG2, IgG3, IgG4; encoding about 330 amino acids). A gamma constant region can include, e.g., CH1, CH2, and CH3. The term "full-length antibody" refers to a protein that includes one polypeptide that includes VL and CL, and a second polypeptide that includes VH, CH1, CH2, and CH3.

The term "antigen-binding fragment" of an antibody, as used herein, refers to one or more fragments of a full-length antibody that retain the ability to specifically bind to a target. Examples of antigen-binding fragments include, but are not limited to: (i) an Fab fragment, a monovalent fragment consisting of the VL, VH, CL and CH1 domains; (ii) an F(ab')$_2$ fragment, a bivalent fragment including two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., Nature 341:544 (1989)), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al., Science 242:423 (1988); and Huston et al., Proc. Natl. Acad. Sci. USA, 85:5879 (1988)). Such single chain antibodies are also encompassed within the term "antigen-binding fragment."

A single domain antibody (sdAb, nanobody) is an antibody fragment consisting of a single monomeric variable antibody domain, and may also be used in the systems and methods of the invention. Like a whole antibody, sdAbs are able to bind selectively to a specific antigen. With a molecular weight of only 12-15 kDa, single domain antibodies are much smaller than common antibodies (150-160 kDa) which are composed of two heavy protein chains and two light chains, and even smaller than Fab fragments (~50 kDa, one light chain and half a heavy chain) and single-chain variable fragments (~25 kDa, two variable domains, one from a light and one from a heavy chain).

Polysaccharide Binding Moieties

In certain embodiments, the binding moiety is a polysaccharide, linked, for example, using any of a variety of chemistries, by a single bond, e.g., a covalent bond, at one of the two ends, to a functional group on the magnetic particle. The polysaccharides can be synthetic or natural. Mono-, di-, tri- and polysaccharides can be used as the binding moiety. These include, e.g., glycosides, N-glycosylamines, O-acyl derivatives, O-methyl derivatives, osazones, sugar alcohols, sugar acids, sugar phosphates when used with appropriate attachment chemistry to the magnetic particle.

A method of accomplishing linking is to couple avidin to a magnetic particle and react the avidin-magnetic particle with commercially available biotinylated polysaccharides, to yield polysaccharide-magnetic particle conjugates. For example, sialyl Lewis based polysaccharides are commercially available as biotinylated reagents and will react with avidin-CLIO (see Syntesome, Gesellschaft fur medizinische Biochemie mbH.). The sialyl Lewis×tetrasaccharide (Sle$^x$) is recognized by proteins known as Selectins, which are present on the surfaces of leukocytes and function as part of the inflammatory cascade for the recruitment of leukocytes.

Still other targeting moieties include a non-proteinaceous element, e.g., a glycosyl modification (such as a Lewis antigen) or another non-proteinaceous organic molecule. Another method is covalent coupling of the protein to the magnetic particle.

Another feature of the methods includes identification of specific cell types, for hematological or histopatholgical investigations for example CD4/CD3 cell counts and circulating tumor cells using any of the binding moieties described above.

Multivalent Binding Agents

The assays of the invention can include a multivalent binding agent (i) bearing multiple analytes are linked to a carrier (e.g., a simple synthetic scaffold, or a larger carrier protein or polysaccharide, such as BSA, transferrin, or dextran), or bearing multiple epitopes for binding to, for example, two or more populations of magnetic particles to form an aggregate.

Where a multivalent binding agent is employed, multiple analytes can be linked to a carrier (e.g., a simple synthetic scaffold, or a larger carrier protein or polysaccharide, such as BSA, transferrin, or dextran). Alternatively, the multivalent binding agent can be a nucleic acid designed to bind to two or more populations of magnetic particles. Such multivalent binding agents act as agglomerants and the assay architecture is characterized by a competition between the analyte being detected and the multivalent binding agent (e.g., in an inhibition assay, competition assay, or disaggregation assay).

The functional group, present in the analyte can be used to form a covalent bond with the carrier. Alternatively, the analyte can be derivatized to provide a linker (i.e., a spacer separating the analyte from the carrier in the conjugate) terminating in a functional group (i.e., an alcohol, an amine, a carboxyl group, a sulfhydryl group, or a phosphate group), which is used to form the covalent linkage with the carrier.

The covalent linking of an analyte and a carrier may be effected using a linker which contains reactive moieties capable of reaction with such functional groups present in the analyte and the carrier. For example, a hydroxyl group of the analyte may react with a carboxyl group of the linker, or an activated derivative thereof, resulting in the formation of an ester linking the two.

Examples of moieties capable of reaction with sulfhydryl groups include α-haloacetyl compounds of the type $XCH_2CO-$ (where X=Br, Cl or I), which show particular reactivity for sulfhydryl groups, but which can also be used to modify imidazolyl, thioether, phenol, and amino groups as described by Gurd, Methods Enzymol. 11:532 (1967). N-Maleimide derivatives are also considered selective towards sulfhydryl groups, but may additionally be useful in coupling to amino groups under certain conditions. Reagents such as 2-iminothiolane (Traut et al., Biochemistry 12:3266 (1973)), which introduce a thiol group through conversion of an amino group, may be considered as sulfhydryl reagents if linking occurs through the formation of disulphide bridges.

Examples of reactive moieties capable of reaction with amino groups include, for example, alkylating and acylating agents. Representative alkylating agents include:
(i) α-haloacetyl compounds, which show specificity towards amino groups in the absence of reactive thiol groups and are of the type $XCH_2CO-$ (where X=Cl, Br or I), for example, as described by Wong, Biochemistry 24:5337 (1979); (ii) N-maleimide derivatives, which may react with amino groups either through a Michael type reaction or through acylation by addition to the ring carbonyl group, for example, as described by Smyth et al., J. Am. Chem. Soc. 82:4600 (1960) and Biochem. J. 91:589 (1964); (iii) aryl halides such as reactive nitrohaloaromatic compounds; (iv) alkyl halides, as described, for example, by McKenzie et al., J. Protein Chem. 7:581 (1988); (v) aldehydes and ketones capable of Schiff's base formation with amino groups, the adducts formed usually being stabilized through reduction to give a stable amine; (vi) epoxide derivatives such as epichlorohydrin and bisoxiranes, which may react with amino, sulfhydryl, or phenolic hydroxyl groups; (vii) chlorine-containing derivatives of s-triazines, which are very reactive towards nucleophiles such as amino, sufhydryl, and hydroxyl groups; (viii) aziridines based on s-triazine compounds detailed above, e.g., as described by Ross, J. Adv. Cancer Res. 2:1 (1954), which react with nucleophiles such as amino groups by ring opening; (ix) squaric acid diethyl esters as described by Tietze, Chem. Ber. 124:1215 (1991); and (x) α-haloalkyl ethers, which are more reactive alkylating agents than normal alkyl halides because of the activation caused by the ether oxygen atom, as described by Benneche et al., Eur. J. Med. Chem. 28:463 (1993).

Representative amino-reactive acylating agents include:
(i) isocyanates and isothiocyanates, particularly aromatic derivatives, which form stable urea and thiourea derivatives respectively; (ii) sulfonyl chlorides, which have been described by Herzig et al., Biopolymers 2:349 (1964); (iii) acid halides; (iv) active esters such as nitrophenylesters or N-hydroxysuccinimidyl esters; (v) acid anhydrides such as mixed, symmetrical, or N-carboxyanhydrides; (vi) other useful reagents for amide bond formation, for example, as described by M. Bodansky, Principles of Peptide Synthesis, Springer-Verlag, 1984; (vii) acylazides, e.g. wherein the azide group is generated from a preformed hydrazide derivative using sodium nitrite, as described by Wetz et al., Anal. Biochem. 58:347 (1974); and (viii) imidoesters, which form stable amidines on reaction with amino groups, for example, as described by Hunter and Ludwig, J. Am. Chem. Soc. 84:3491 (1962). Aldehydes and ketones may be reacted with amines to form Schiff's bases, which may advantageously be stabilized through reductive amination. Alkoxylamino moieties readily react with ketones and aldehydes to produce stable alkoxamines, for example, as described by Webb et al., Bioconjugate Chem. 1:96 (1990).

Examples of reactive moieties capable of reaction with carboxyl groups include diazo compounds such as diazoacetate esters and diazoacetamides, which react with high specificity to generate ester groups, for example, as described by Herriot, Adv. Protein Chem. 3:169 (1947). Carboxyl modifying reagents such as carbodiimides, which react through O-acylurea formation followed by amide bond formation, may also be employed.

It will be appreciated that functional groups in the analyte and/or the carrier may, if desired, be converted to other functional groups prior to reaction, for example, to confer additional reactivity or selectivity. Examples of methods useful for this purpose include conversion of amines to carboxyls using reagents such as dicarboxylic anhydrides; conversion of amines to thiols using reagents such as N-acetylhomocysteine thiolactone, S-acetylmercaptosuccinic anhydride, 2-iminothiolane, or thiol-containing succinimidyl derivatives; conversion of thiols to carboxyls using reagents such as α-haloacetates; conversion of thiols to amines using reagents such as ethylenimine or 2-bromoethylamine; conversion of carboxyls to amines using reagents such as carbodiimides followed by diamines; and conversion of alcohols to thiols using reagents such as tosyl chloride followed by transesterification with thioacetate and hydrolysis to the thiol with sodium acetate.

So-called zero-length linkers, involving direct covalent joining of a reactive chemical group of the analyte with a reactive chemical group of the carrier without introducing additional linking material may, if desired, be used in accordance with the invention. Most commonly, however, the linker will include two or more reactive moieties, as described above, connected by a spacer element. The presence of such a spacer permits bifunctional linkers to react with specific functional groups within the analyte and the carrier, resulting in a covalent linkage between the two. The reactive moieties in a linker may be the same (homobifunctional linker) or different (heterobifunctional linker, or, where several dissimilar reactive moieties are present, heteromultifunctional linker), providing a diversity of potential reagents that may bring about covalent attachment between the analyte and the carrier.

Spacer elements in the linker typically consist of linear or branched chains and may include a $C_{1-10}$ alkyl, a heteroalkyl of 1 to 10 atoms, a $C_{2-10}$ alkene, a $C_{2-10}$ alkyne, $C_{5-10}$ aryl, a cyclic system of 3 to 10 atoms, or —$(CH_2CH_2O)_nCH_2CH_2$—, in which n is 1 to 4.

Typically, a multivalent binding agent will include 2, 3, 4, 5, 6, 7, 8, 15, 50, or 100 (e.g., from 3 to 100, from 3 to 30, from 4 to 25, or from 6 to 20) conjugated analytes. The multivalent binding agents are typically from 10 kDa to 200 kDa in size and can be prepared as described in the Examples.

Analytes

Embodiments of the invention include devices, systems, and/or methods for detecting and/or measuring the concentration of one or more analytes in a sample (e.g., a protein, a peptide, an enzyme, a polypeptide, an amino acid, a nucleic acid, an oligonucleotide, a therapeutic agent, a metabolite of a therapeutic agent, RNA, DNA, circulating DNA (e.g., from a cell, tumor, pathogen, or fetus), an antibody, an organism, a virus, bacteria, a carbohydrate, a polysaccharide, glucose, a lipid, a gas (e.g., oxygen and/or carbon dioxide), an electrolyte (e.g., sodium, potassium, chloride, bicarbonate, BUN, magnesium, phosphate, calcium, ammonia, and/or lactate), general chemistry molecules (creatinine, glucose), a lipoprotein, cholesterol, a fatty acid, a glycoprotein, a proteoglycan, and/or a lipopolysaccharide). The analytes may include identification of cells or specific cell types. The analyte(s) may include one or more biologically active substances and/or metabolite(s), marker(s), and/or other indicator(s) of biologically active substances. A biologically active substance may be described as a single entity or a combination of entities. The term "biologically active substance" includes without limitation, medications; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment; or biologically toxic agents such as those used in biowarfare including organisms such as anthrax, ebola, *Salmonella typhimurium, Marburg virus, plague, cholera, Francisella tulariesis* (tularemia), brucellosis, Q fever, Bolivian hemorrhagic fever, *Coccidioides mycosis*, glanders, Melioidosis, *Shigella*, Rocky Mountain spotted fever, typhus, Psittacosis, yellow fever, Japanese B encephalitis, Rift Valley fever, and smallpox; naturally-occurring toxins that can be used as weapons include ricin, aflatoxin, SEB, botulinum toxin, saxitoxin, and many mycotoxins. Analytes may also include organisms such as *Candida albicans, Candida glabrata, Candida krusei, Candida parapsilosis, Candida tropicalis,* Coagulase negative *Staphalococcus, Enterococcus faecalis, Enterococcus faecium, Escherichia coli, Klebsiella pneumonia, Pseudomonas aeruginosa, Staphylococcus aureus, Acinetobacter baumannii, Aspergillus fumigates, Bacteroides fragilis, Bacteroides fragilis,* blaSHV, *Burkholderia cepacia, Campylobacter jejuni/coli, Candida guilliermondii, Candida lusitaniae, Clostridium pefringens, Enterobacter aeraogenesl, Enterobacter cloacae,* Enterobacteriaceae spp., *Haemophilus influenza, Kingella kingae, Klebsiella oxytoca, Listeria monocytogenes,* Mec A gene-bearing bacteria (MRSA), *Morganella morgana, Neisseria meningitides, Neisseria* spp., non-*meningitidis, Prevotella buccae, Prevotella intermedia, Prevotella melaminogenica, Propionibacterium acnes, Proteus mirabilis, Proteus vulgaris, Salmonella enteric, Serratia marcescens, Staphylococcus haemolyticus, Staphylococcus maltophilia, Staphylococcus saprophyticus, Stenotrophomonas maltophilia, Stenotrophomonas maltophilia, Streptococcus agalactie, Streptococcus bovis, Streptococcus dysgalactie, Streptococcus mitis, Streptococcus mutans, Streptococcus pneumonia, Streptococcus pyogenes, Streptococcus sanguinis,* Van A gene, Van B gene. Analytes may also include viral organisms such as dsDNA viruses (e.g., adenoviruses, herpes viruses, poxviruses); ssDNA viruses (+)sense DNA (e.g., parvoviruses); dsRNA viruses (e.g., reoviruses); (+)ssRNA viruses (+)sense RNA (e.g., picornaviruses, togaviruses); (−)ssRNA viruses (−)sense RNA (e.g., orthomyxoviruses, rhabdoviruses); ssRNA-RT viruses (+)sense RNA with DNA intermediate in life-cycle (e.g., retroviruses); and dsDNA-RT viruses (e.g., hepadnaviruses).

Opportunistic infections which can be detected using the systems and methods of the invention include, without limitation, fungal, viral, bacterial, protozoan infections, such as: 1) fungal infections, such as those by *Candida* spp. (drug resistant and non-resistant strains), *C. albicans, C. krusei, C. glabrata,* and *Aspergillus* fumigates; 2) gram negative infections, such as those by *E. coli, Stenotrophomonas maltophilia, Klebsiella pneumonia/oxytoca,* and *Pseudomonas aeruginosa;* and 3) gram positive infections, such as those by *Staphylococcus* spp., *S. aureus, S. pneumonia, Enterococcus* ssp. (*E. faecalis* and *E. faecium*). The infection can be by coagulase negative *staphylococcus, Corynebacterium* spp., *Fusobacterium* spp., *Morganella morganii, Pneumocystis jirovecii* (previously known as *Pneumocystis carinii*), *F. hominis, S. pyogenes, Pseudomonas aeruginosa,* polyomavirus JC polyomavirus (the virus that causes progressive multifocal leukoencephalopathy), *Acinetobacter baumanni, Toxoplasma gondii,* cytomegalovirus, *Aspergillus* spp., Kaposi's Sarcoma, *Cryptosporidium* spp., *Cryptococcus neoformans,* and *Histoplasma capsulatum.*

Non-limiting examples of broad categories of analytes which can be detected using the devices, systems, and methods of the invention include, without limitation, the following therapeutic categories: anabolic agents, antacids, anti-asthmatic agents, anti-cholesterolemic and anti-lipid agents, anti-coagulants, anti-convulsants, anti-diarrheals, anti-emetics, anti-infective agents, anti-inflammatory agents, anti-manic agents, anti-nauseants, anti-neoplastic agents, anti-obesity agents, anti-pyretic and analgesic agents, anti-spasmodic agents, anti-thrombotic agents, anti-uricemic agents, anti-anginal agents, antihistamines, anti-tussives, appetite suppressants, biologicals, cerebral dilators, coronary dilators, decongestants, diuretics, diagnostic agents, erythropoietic agents, expectorants, gastrointestinal sedatives, hyperglycemic agents, hypnotics, hypoglycemic agents, ion exchange resins, laxatives, mineral supplements, mucolytic agents, neuromuscular drugs, peripheral vasodilators, psychotropics, sedatives, stimulants, thyroid and antithyroid agents, uterine relaxants, vitamins, and prodrugs.

More specifically, non-limiting examples of analytes which can be detected using the devices, systems, and methods of the invention include, without limitation, the following therapeutic categories: analgesics, such as non-steroidal anti-inflammatory drugs, opiate agonists and salicylates; antihistamines, such as $H_1$-blockers and $H_2$-blockers; anti-infective agents, such as anthelmintics, antianaerobics, antibiotics, aminoglycoside antibiotics, antifungal antibiotics, cephalosporin antibiotics, macrolide antibiotics, miscellaneous β-lactam antibiotics, penicillin antibiotics, quinolone antibiotics, sulfonamide antibiotics, tetracycline antibiotics, antimycobacterials, antituberculosis antimycobacterials, antiprotozoals, antimalarial antiprotozoals, antiviral agents, antiretroviral agents, scabicides, and urinary anti-infectives; antineoplastic agents, such as alkylating agents, nitrogen mustard alkylating agents, nitrosourea alkylating agents, antimetabolites, purine analog antimetabolites, pyrimidine analog antimetabolites, hormonal antineoplastics, natural antineoplastics, antibiotic natural antineoplastics, and vinca alkaloid natural antineoplastics; autonomic agents, such as anticholinergics, antimuscarinic anticholinergics, ergot alkaloids, parasympathomimetics, cholinergic agonist parasympathomimetics, cholinesterase inhibitor parasympathomimetics, sympatholytics, alpha-blocker sympatholytics, beta-blocker sympatholytics, sympathomimetics, and adrenergic agonist sympathomimetics; cardiovascular agents, such as antianginals, beta-blocker antianginals, calcium-channel blocker antianginals, nitrate antianginals, antiarrhythmics, cardiac glycoside antiarrhythmics, class I antiarrhythmics, class II antiarrhythmics, class III antiarrhythmics, class IV antiarrhythmics, antihypertensive agents, alpha-blocker antihypertensives, angiotensin-converting enzyme inhibitor (ACE inhibitor) antihypertensives, beta-blocker antihypertensives, calcium-channel blocker antihypertensives, central-acting adrenergic antihypertensives, diuretic antihypertensive agents, peripheral vasodilator antihypertensives, antilipemics, bile acid sequestrant antilipemics, HMG-COA reductase inhibitor antilipemics, inotropes, cardiac glycoside inotropes, and thrombolytic agents; dermatological agents, such as antihistamines, anti-inflammatory agents, corticosteroid anti-inflammatory agents, antipruritics/local anesthetics, topical anti-infectives, antifungal topical anti-infectives, antiviral topical anti-infectives, and topical antineoplastics; electrolytic and renal agents, such as acidifying agents, alkalinizing agents, diuretics, carbonic anhydrase inhibitor diuretics, loop diuretics, osmotic diuretics, potassium-sparing diuretics, thiazide diuretics, electrolyte replacements, and uricosuric agents; enzymes, such as pancreatic enzymes and thrombolytic enzymes; gastrointestinal agents, such as antidiarrheals, antiemetics, gastrointestinal anti-inflammatory agents, salicylate gastrointestinal anti-inflammatory agents, antacid anti-ulcer agents, gastric acid-pump inhibitor anti-ulcer agents, gastric mucosal anti-ulcer agents, $H_2$-blocker anti-ulcer agents, cholelitholytic agents, digestants, emetics, laxatives and stool softeners, and prokinetic agents; general anesthetics, such as inhalation anesthetics, halogenated inhalation anesthetics, intravenous anesthetics, barbiturate intravenous anesthetics, benzodiazepine intravenous anesthetics, and opiate agonist intravenous anesthetics; hematological agents, such as antianemia agents, hematopoietic antianemia agents, coagulation agents, anticoagulants, hemostatic coagulation agents, platelet inhibitor coagulation agents, thrombolytic enzyme coagulation agents, and plasma volume expanders; hormones and hormone modifiers, such as abortifacients, adrenal agents, corticosteroid adrenal agents, androgens, anti-androgens, antidiabetic agents, sulfonylurea antidiabetic agents, antihypoglycemic agents, oral contraceptives, progestin contraceptives, estrogens, fertility agents, oxytocics, parathyroid agents, pituitary hormones, progestins, antithyroid agents, thyroid hormones, and tocolytics; immunobiologic agents, such as immunoglobulins, immunosuppressives, toxoids, and vaccines; local anesthetics, such as amide local anesthetics and ester local anesthetics; musculoskeletal agents, such as anti-gout anti-inflammatory agents, corticosteroid anti-inflammatory agents, gold compound anti-inflammatory agents, immuno-suppressive anti-inflammatory agents, nonsteroidal anti-inflammatory drugs (NSAIDs), salicylate anti-inflammatory agents, skeletal muscle relaxants, neuromuscular blocker skeletal muscle relaxants, and reverse neuromuscular blocker skeletal muscle relaxants; neurological agents, such as anticonvulsants, barbiturate anticonvulsants, benzodiazepine anticonvulsants, anti-migraine agents, anti-parkinsonian agents, anti-vertigo agents, opiate agonists, and opiate antagonists; ophthalmic agents, such as anti-glaucoma agents, beta-blocker anti-gluacoma agents, miotic anti-glaucoma agents, mydriatics, adrenergic agonist mydriatics, antimuscarinic mydriatics, ophthalmic anesthetics, ophthalmic anti-infectives, ophthalmic aminoglycoside anti-infectives, ophthalmic macrolide anti-infectives, ophthalmic quinolone anti-infectives, ophthalmic sulfonamide anti-infectives, ophthalmic tetracycline anti-infectives, ophthalmic anti-inflammatory agents, ophthalmic corticosteroid anti-inflammatory agents, and ophthalmic nonsteroidal anti-inflammatory drugs (NSAIDs); psychotropic agents, such as antidepressants, heterocyclic antidepressants, monoamine oxidase inhibitors (MAOIs), selective serotonin re-uptake inhibitors (SSRIs), tricyclic antidepressants, antimanics, antipsychotics, phenothiazine antipsychotics, anxiolytics, sedatives, and hypnotics, barbiturate sedatives and hypnotics, benzodiazepine anxiolytics, sedatives, and hypnotics, and psychostimulants; respiratory agents, such as antitussives, bronchodilators, adrenergic agonist bronchodilators, antimuscarinic bronchodilators, expectorants, mucolytic agents, respiratory anti-inflammatory agents, and respiratory corticosteroid anti-inflammatory agents; toxicology agents, such as antidotes, heavy metal antagonists/chelating agents, substance abuse agents, deterrent substance abuse agents, and withdrawal substance abuse agents; minerals; and vitamins, such as vitamin A, vitamin B, vitamin C, vitamin D, vitamin E, and vitamin K.

Examples of classes of biologically active substances from the above categories which can be detected using the devices, systems, and methods of the invention include, without limitation, nonsteroidal anti-inflammatory drugs (NSAIDs) analgesics, such as diclofenac, ibuprofen, ketoprofen, and naproxen; opiate agonist analgesics, such as codeine, fentanyl, hydromorphone, and morphine; salicylate analgesics, such as aspirin (ASA) (enteric coated ASA); $H_1$-blocker antihistamines, such as clemastine and terfenadine; $H_2$-blocker antihistamines, such as cimetidine, famotidine, nizadine, and ranitidine; anti-infective agents, such as mupirocin; antianaerobic anti-infectives, such as chloramphenicol and clindamycin; antifungal antibiotic anti-infectives, such as amphotericin b, clotrimazole, fluconazole, and ketoconazole; macrolide antibiotic anti-infectives, such as azithromycin and erythromycin; miscellaneous beta-lactam antibiotic anti-infectives, such as aztreonam and imipenem; penicillin antibiotic anti-infectives, such as nafcillin, oxacillin, penicillin G, and penicillin V; quinolone antibiotic anti-infectives, such as ciprofloxacin and norfloxacin; tetracycline antibiotic anti-infectives, such as doxycycline, minocycline, and tetracycline; antituberculosis antimycobacterial anti-infectives such as isoniazid (INH), and rifampin; antiprotozoal anti-infectives, such as atovaquone and dapsone; antimalarial antiprotozoal anti-infectives, such as chloroquine and pyrimethamine; anti-retroviral anti-infectives, such as ritonavir and zidovudine; antiviral anti-infective agents, such as acyclovir, ganciclovir, interferon alfa, and rimantadine; alkylating antineoplastic agents, such as carboplatin and cisplatin; nitrosourea alkylating antineoplastic agents, such as carmustine (BCNU); antimetabolite antineoplastic agents, such as methotrexate; pyrimidine analog antimetabolite antineoplastic agents, such as fluorouracil (5-FU) and gemcitabine; hormonal antineoplastics, such as goserelin, leuprolide, and tamoxifen; natural antineoplastics, such as aldesleukin, interleukin-2, docetaxel, etoposide (VP-16), interferon alfa, paclitaxel, and tretinoin (ATRA); antibiotic natural antineoplastics, such as bleomycin, dactinomycin, daunorubicin, doxorubicin, and mitomycin; vinca alkaloid natural antineoplastics, such as vinblastine and vincristine; autonomic agents, such as nicotine; anticholinergic autonomic agents, such as benztropine and trihexyphenidyl; antimuscarinic anticholinergic autonomic agents, such as atropine and oxybutynin; ergot alkaloid autonomic agents, such as bromocriptine; cholinergic agonist parasympathomimetics, such as pilocarpine; cholinesterase inhibitor parasympathomimetics, such as pyridostigmine; alpha-blocker sympatholytics, such as prazosin; 9-blocker sympatholytics, such as atenolol; adrenergic agonist sympathomimetics, such as albuterol and dobutamine; cardiovascular agents, such as aspirin (ASA) (enteric coated ASA); i-blocker antianginals, such as atenolol and propranolol; calcium-channel blocker antianginals, such as nifedipine and verapamil; nitrate antianginals, such as isosorbide dinitrate (ISDN); cardiac glycoside antiarrhythmics, such as digoxin; class I antiarrhythmics, such as lidocaine, mexiletine, phenyloin, procainamide, and quinidine; class II antiarrhythmics, such as atenolol, metoprolol, propranolol, and timolol; class III antiarrhythmics, such as amiodarone; class IV antiarrhythmics, such as diltiazem and verapamil; alpha-blocker antihypertensives, such as prazosin; angiotensin-converting enzyme inhibitor (ACE inhibitor) antihypertensives, such as captopril and enalapril; beta-blocker antihypertensives, such as atenolol, metoprolol, nadolol, and propanolol; calcium-channel blocker antihypertensive agents, such as diltiazem and nifedipine; central-acting adrenergic antihypertensives, such as clonidine and methyldopa; diurectic antihypertensive agents, such as amiloride, furosemide, hydrochlorothiazide (HCTZ), and spironolactone; peripheral vasodilator antihypertensives, such as hydralazine and minoxidil; antilipemics, such as gemfibrozil and probucol; bile acid sequestrant antilipemics, such as cholestyramine; HMG-CoA reductase inhibitor antilipemics, such as lovastatin and pravastatin; inotropes, such as aminone, dobutamine, and dopamine; cardiac glycoside inotropes, such as digoxin; thrombolytic agents, such as alteplase (TPA), anistreplase, streptokinase, and urokinase; dermatological agents, such as colchicine, isotretinoin, methotrexate, minoxidil, tretinoin (ATRA); dermatological corticosteroid anti-inflammatory agents, such as betamethasone and dexamethasone; antifungal topical anti-infectives, such as amphotericin B, clotrimazole, miconazole, and nystatin; antiviral topical anti-infectives, such as acyclovir; topical antineoplastics, such as fluorouracil (5-FU); electrolytic and renal agents, such as lactulose; loop diuretics, such as furosemide; potassium-sparing diuretics, such as triamterene; thiazide diuretics, such as hydrochlorothiazide (HCTZ); uricosuric agents, such as probenecid; enzymes such as RNase and DNase; thrombolytic enzymes, such as alteplase, anistreplase, streptokinase and urokinase; antiemetics, such as prochlorperazine; salicylate gastrointestinal anti-inflammatory agents, such as sulfasalazine; gastric acid-pump inhibitor anti-ulcer agents, such as omeprazole; $H_2$-blocker anti-ulcer agents, such as cimetidine, famotidine, nizatidine, and ranitidine; digestants, such as pancrelipase; prokinetic agents, such as erythromycin; opiate agonist intravenous anesthetics such as fentanyl; hematopoietic anti-anemia agents, such as erythropoietin, filgrastim (G-CSF), and sargramostim (GM-CSF); coagulation agents, such as antihemophilic factors 1-10 (AHF 1-10); anticoagulants, such as warfarin; thrombolytic enzyme coagulation agents, such as alteplase, anistreplase, streptokinase and urokinase; hormones and hormone modifiers, such as bromocriptine; abortifacients, such as methotrexate; antidiabetic agents, such as insulin; oral contraceptives, such as estrogen and progestin; progestin contraceptives, such as levonorgestrel and norgestrel; estrogens such as conjugated estrogens, diethylstilbestrol (DES), estrogen (estradiol, estrone, and estropipate); fertility agents, such as clomiphene, human chorionic gonadatropin (HCG), and menotropins; parathyroid agents such as calcitonin; pituitary hormones, such as desmopressin, goserelin, oxytocin, and vasopressin (ADH); progestins, such as medroxyprogesterone, norethindrone, and progesterone; thyroid hormones, such as levothyroxine; immunobiologic agents, such as interferon beta-1b and interferon gamma-1b; immunoglobulins, such as immune globulin IM, IMIG, IGIM and immune globulin IV, IVIG, IGIV; amide local anesthetics, such as lidocaine; ester local anesthetics, such as benzocaine and procaine; musculoskeletal corticosteroid anti-inflammatory agents, such as beclomethasone, betamethasone, cortisone, dexamethasone, hydrocortisone, and prednisone; musculoskeletal anti-inflammatory immunosuppressives, such as azathioprine, cyclophosphamide, and methotrexate; musculoskeletal non-steroidal anti-inflammatory drugs (NSAIDs), such as diclofenac, ibuprofen, ketoprofen, ketorlac, and naproxen; skeletal muscle relaxants, such as baclofen, cyclobenzaprine, and diazepam; reverse neuromuscular blocker skeletal muscle relaxants, such as pyridostigmine; neurological agents, such as nimodipine, riluzole, tacrine and ticlopidine; anticonvulsants, such as carbamazepine, gabapentin, lamotrigine, phenyloin, and valproic acid; barbiturate anticonvulsants, such as phenobarbital and primidone; benzodiazepine anticonvulsants, such as clonazepam, diazepam, and lorazepam; anti-parkisonian agents, such as bromocriptine, levodopa, carbidopa, and pergolide; anti-vertigo agents, such as meclizine; opiate agonists, such as codeine, fentanyl, hydromorphone, methadone, and morphine; opiate antagonists, such as naloxone; beta-blocker anti-glaucoma agents, such as timolol; miotic anti-glaucoma agents, such as pilocarpine; ophthalmic aminoglycoside antiinfectives, such as gentamicin, neomycin, and tobramycin; ophthalmic quinolone anti-infectives, such as ciprofloxacin, norfloxacin, and ofloxacin; ophthalmic corticosteroid anti-inflammatory agents, such as dexamethasone and prednisolone; ophthalmic nonsteroidal anti-inflammatory drugs (NSAIDs), such as diclofenac; antipsychotics, such as clozapine, haloperidol, and risperidone; benzodiazepine anxiolytics, sedatives and hypnotics, such as clonazepam, diazepam, lorazepam, oxazepam, and prazepam; psychostimulants, such as methylphenidate and pemoline; antitussives, such as codeine; bronchodilators, such as theophylline; adrenergic agonist bronchodilators, such as albuterol; respiratory corticosteroid anti-inflammatory agents, such as dexamethasone; antidotes, such as flumazenil and naloxone; heavy metal antagonists/chelating agents, such as penicillamine; deterrent substance abuse agents, such as disulfuram, naltrexone, and nicotine; withdrawal substance abuse agents, such as bromocriptine; minerals, such as iron, calcium, and magnesium; vitamin B compounds, such as cyanocobalamin (vitamin $B_{12}$) and niacin (vitamin $B_3$); vitamin C compounds, such as ascorbic acid; and vitamin D compounds, such as calcitriol; recombinant beta-glucan; bovine immunoglobulin concentrate; bovine superoxide dismutase; the formulation including fluorouracil, epinephrine, and bovine collagen; recombinant hirudin (r-Hir), HIV-1 immunogen; human anti-TAC antibody; recombinant human growth hormone (r-hGH); recombinant human hemoglobin (r-Hb); recombinant human mecasermin (r-IGF-1); recombinant interferon beta-1a; lenograstim (G-CSF); olanzapine; recombinant thyroid stimulating hormone (r-TSH); topotecan; acyclovir sodium; aldesleukin; atenolol; bleomycin sulfate, human calcitonin; salmon calcitonin; carboplatin; carmustine; dactinomycin, daunorubicin HCl; docetaxel; doxorubicin HCl; epoetin alfa; etoposide (VP-16); fluorouracil (5-FU); ganciclovir sodium; gentamicin sulfate; interferon alfa; leuprolide acetate; meperidine HCl; methadone HCl; methotrexate sodium; paclitaxel; ranitidine HCl; vinblastin sulfate; and zidovudine (AZT).

Further specific examples of biologically active substances from the above categories which can be detected using the devices, systems, and methods of the invention include, without limitation, antineoplastics such as androgen inhibitors, antimetabolites, cytotoxic agents, and immunomodulators; anti-tussives such as dextromethorphan, dextromethorphan hydrobromide, noscapine, carbetapentane citrate, and chlorphedianol hydrochloride; antihistamines such as chlorpheniramine maleate, phenindamine tartrate, pyrilamine maleate, doxylamine succinate, and phenyltoloxamine citrate; decongestants such as phenylephrine hydrochloride, phenylpropanolamine hydrochloride, pseudoephedrine hydrochloride, and ephedrine; various alkaloids such as codeine phosphate, codeine sulfate and morphine; mineral supplements such as potassium chloride, zinc chloride, calcium carbonates, magnesium oxide, and other alkali metal and alkaline earth metal salts; ion exchange resins such as cholestryramine; anti-arrhythmics such as N-acetylprocainamide; antipyretics and analgesics such as acetaminophen, aspirin and ibuprofen; appetite suppressants such as phenyl-propanolamine hydrochloride or caffeine; expectorants such as guaifenesin; antacids such as aluminum hydroxide and magnesium hydroxide; biologicals such as peptides, polypeptides, proteins and amino acids, hormones, interferons or cytokines, and other bioactive peptidic compounds, such as interleukins 1-18 including mutants and analogues, RNase, DNase, luteinizing hormone releasing hormone (LHRH) and analogues, gonadotropin releasing hormone (GnRH), transforming growth factor-beta (TGF-beta), fibroblast growth factor (FGF), tumor necrosis factor-alpha & beta (TNF-alpha & beta), nerve growth factor (NGF), growth hormone releasing factor (GHRF), epidermal growth factor (EGF), fibroblast growth factor homologous factor (FGFHF), hepatocyte growth factor (HGF), insulin growth factor (IGF), invasion inhibiting factor-2 (IIF-2), bone morphogenetic proteins 1-7 (BMP 1-7), somatostatin, thymosin-α-1, T-globulin, superoxide dismutase (SOD), complement factors, hGH, tPA, calcitonin, ANF, EPO and insulin; and anti-infective agents such as antifungals, anti-virals, antiseptics and antibiotics.

Biologically active substances which can be detected using the devices, systems, and methods of the invention also include radiosensitizers, such as metoclopramide, sensamide or neusensamide (manufactured by Oxigene); profiromycin (made by Vion); RSR13 (made by Allos); Thymitaq (made by Agouron), etanidazole or lobenguane (manufactured by Nycomed); gadolinium texaphrin (made by Pharmacyclics); BuDR/Broxine (made by NeoPharm); IPdR (made by Sparta); CR2412 (made by Cell Therapeutic); L1X (made by Terrapin); or the like.

Biologically active substances which can be detected using the devices, systems, and methods of the invention include, without limitation, medications for the gastrointestinal tract or digestive system, for example, antacids, reflux suppressants, antiflatulents, antidoopaminergics, proton pump inhibitors, $H_2$-receptor antagonists, cytoprotectants, prostaglandin analogues, laxatives, antispasmodics, antidiarrheals, bile acid sequestrants, and opioids; medications for the cardiovascular system, for example, beta-receptor blockers, calcium channel blockers, diuretics, cardiac glycosides, antiarrhythmics, nitrate, antianginals, vascoconstrictors, vasodilators, peripheral activators, ACE inhibitors, angiotensin receptor blockers, alpha blockers, anticoagulants, heparin, HSGAGs, antiplatelet drugs, fibrinolytics, antihemophilic factors, haemostatic drugs, hypolipaemic agents, and statins; medications for the central nervous system, for example, hypnotics, anaesthetics, antipsychotics, antidepressants, anti-emetics, anticonvulsants, antiepileptics, anxiolytics, barbiturates, movement disorder drugs, stimulants, benzodiazepine, cyclopyrrolone, dopamine antagonists, antihistamine, cholinergics, anticholinergics, emetics, cannabinoids, 5-HT antigonists; medications for pain and/or consciousness, for example, NSAIDs, opioids and orphans such as paracetamol, tricyclic antidepressants, and anticonvulsants; for musculo-skeletal disorders, for example, NSAIDs, muscle relaxants, and neuromuscular drug anticholinersterase; medications for the eye, for example, adrenergic neurone blockers, astringents, ocular lubricants, topical anesthetics, sympathomimetics, parasympatholytics, mydriatics, cycloplegics, antibiotics, topical antibiotics, sulfa drugs, aminoglycosides, fluoroquinolones, anti-virals, anti-fungals, imidazoles, polyenes, NSAIDs, corticosteroids, mast cell inhibitors, adrenergic agnoists, beta-blockers, carbonic anhydrase inhibitors/hyperosmotiics, cholinergics, miotics, parasympathomimetics, prostaglandin, agonists/prostaglandin inhibitors, nitroglycerin; medications for the ear, nose and oropharynx, for example, sympathomimetics, antihistamines, anticholinergics, NSAIDs, steroids, antiseptics, local anesthetics, antifungals, cerumenolytics; medications for the respiratory system, for example, bronchodilators, NSAIDs, anti-allergies, antitussives, mucolytics, decongestants, corticosteroids, beta-receptor antagonists, anticholinergics, steroids; medications for endocrine problems, for example, androgen, antiandrogen, gonadotropin, corticosteroids, growth hormone, insulin, antidiabetics, thyroid hormones, antithyroid drugs, calcitonin, diphosphonate, and vasopressin analogues; medications for the reproductive system or urinary system, for example, antifungals, alkalising agents, quinolones, antibiotics, cholinergics, anticholinergics, anticholinesterase, antispasmodics, 5-alpha reductase inhibitor, selective alpha-I blockers, and sildenafil; medications for contraception, for example, oral contraceptives, spermicides, and depot contraceptives; medications for obstetrics and gynacology, for example, NSAIDs, anticholinergics, haemostatic drugs, antifibrinolytics, hormone replacement therapy, bone regulator, beta-receptor agonists, follicle stimulating hormone, luteinising hormone, LHRH gamolenic acid, gonadotropin release inhibitor, progestogen, dopamine agonist, oestrogen, prostaglandin, gonadorelin, clomiphene, tammoxifen, and diethylstilbestrol; medications for the skin, for example, emollients, anti-pruritics, antifungals, disinfectants, scabicide, pediculicide, tar products, vitamin A derivatives, vitamin D analogue, keratolytics, abrasives, systemic antibiotics, topical antibiotics, hormones, desloughing agents, exudate absorbents, fibrinolytics, proteolytics, sunscreens, antiperspirants, and corticosteroids; medications for infections and infestations, for example, antibiotics, antifungals, antileprotics, antituberculous drugs, antimalarials, anthelmintics, amoebicide, antivirals, antiprotozoals, and antiserum; medications for the immune system, for example, vaccines, immunoglobulin, immunosuppressants, interferon, monoclonal antibodies; medications for allergic disorders, for example, anti-allergies, antihistamines, and NSAIDs; medications for nutrition, for example, tonics, iron preparations, electrolytes, vitamins, anti-obesity drugs, anabolic drugs, haematopoietic drugs, and food product drugs; medications for neoplastic disorders, for example, cytotoxic drugs, sex hormones, aromatase inhibitors, somatostatin inhibitors, recombinant interleukins, G-CSF, and erythropoietin; medications for diagnostics, for example, contrast agents; and medications for cancer (anticancer agents).

Examples of pain medications (e.g., analgesics) which can be detected using the devices, systems, and methods of the invention include opioids such as buprenorphine, butorphanol, dextropropoxyphene, dihydrocodeine, fentanyl, diamorphine (heroin), hydromorphone, morphine, nalbuphine, oxycodone, oxymorphone, pentazocine, pethidine (meperidine), and tramadol; salicylic acid and derivatives such as acetylsalicylic acid (aspirin), diflunisal, and ethenzamide; pyrazolones such as aminophenazone, metamizole, and phenazone; anilides such as paracetamol (acetaminophen), phenacetin; and others such as ziconotide and tetradyrocannabinol.

Examples of blood pressure medications (e.g., antihypertensives and diuretics) which can be detected using the devices, systems, and methods of the invention include antiadrenergic agents such as clonidine, doxazosin, guanethidine, guanfacine, mecamylamine, methyldopa, moxonidinie, prazosin, rescinnamine, and reserpine; vasodilators such as diazoxide, hydralazine, minoxidil, and nitroprusside; low ceiling diuretics such as bendroflumethiazide, chlorothiazide, chlortalidone, hydrochlorothiazide, indapamide, quinethazone, mersalyl, metolazone, and theobromine; high ceiling diuretics such as bumetanide, furosemide, and torasemide; potassium-sparing diuretics such as amiloride, eplerenone, spironolactone, and triamterene; and other antihypertensives such as bosentan and ketanserin.

Examples of anti-thrombotics (e.g., thrombolytics, anticoagulants, and antiplatelet drugs) which can be detected using the devices, systems, and methods of the invention include vitamin K antagonists such as acenocoumarol, clorindione, dicumarol, diphenadione, ethyl biscoumacetate, phenprocoumon, phenindione, tioclomarol, and warfarin; heparin group (platelet aggregation inhibitors) such as antithrombin III, bemiparin, dalteparin, danaparoid, enoxaparin, heparin, nadroparin, parnaparin, reviparin, sulodexide, and tinzaparin; other platelet aggregation inhibitors such as abciximab, acetylsalicylic acid (aspirin), aloxiprin, beraprost, ditazole, carbasalate calcium, cloricromen, clopidogrel, dipyridamole, epoprostenol, eptifibatide, indobufen, iloprost, picotamide, prasugrel, ticlopidine, tirofiban, treprostinil, and triflusal; enzymes such as alteplase, ancrod, anistreplase, brinase, drotrecogin alfa, fibrinolysin, protein C, reteplase, saruplase, streptokinase, tenecteplase, and urokinase; direct thrombin inhibitors such as argatroban, bivalirudin, desirudin, lepirudin, melagatran, and ximelagatran; other antithrombotics such as dabigatran, defibrotide, dermatan sulfate, fondaparinux, and rivaroxaban; and others such as citrate, EDTA, and oxalate.

Examples of anticonvulsants which can be detected using the devices, systems, and methods of the invention include barbiturates such as barbexaclone, metharbital, methylphenobarbital, phenobarbital, and primidone; hydantoins such as ethotoin, fosphenyloin, mephenyloin, and phenyloin; oxazolidinediones such as ethadione, paramethadione, and trimethadione; succinimides such as ethosuximide, mesuximide, and phensuximide; benzodiazepines such as clobazam, clonazepam, clorazepate, diazepam, lorazepam, midazolam, and nitrazepam; carboxamides such as carbamazepine, oxcarbazepine, rufinamide; fatty acid derivatives such as valpromide and valnoctamide; carboxylic acids such as valproic acid, tiagabine; GABA analogs such as gabapentin, pregabalin, progabide, and givabatrin; monosaccharides such as topiramate; aromatic allyllic alcohols such as stiripentol; ureas such as phenacemide and pheneturide; carbamates such as emylcamate, felbamate, and meprobamate; pyrrolidines such as brivaracetam, levetiracetam, nefiracetam, and seletracetam; sulfa drugs such as acetazolamide, ethoxolamide, sultiame, and zonisamide; propionates such as beclamide; aldehydes such as paraldehyde; and bromides such as potassium bromide.

Examples of anti-cancer agents which can be detected using the devices, systems, and methods of the invention include acivicin; aclarubicin; acodazole hydrochloride; acronine; adriamycin; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; topotecan hydrochloride; toremifene citrate; trestolone acetate; triciribine phosphate; trimetrexate; trimetrexate glucuronate; triptorelin; tubulozole hydrochloride; Uracil mustard; rredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other biologically active substances which can be detected using the devices, systems, and methods of the invention include those mentioned in Basic and Clinical Pharmacology (LANGE Basic Science), Katzung and Katzung, ISBN 0071410929, McGraw-Hill Medical, 9$^{th}$ edition (2003).

Medical Conditions

Embodiments of the invention may be used in the monitoring of one or more analytes in the diagnosis, management, and/or treatment of any of a wide range of medical conditions. Various categories of medical conditions include, for example, disorders of pain; of alterations in body temperature (e.g., fever); of nervous system dysfunction (e.g., syncope, myalgias, movement disorders, numbness, sensory loss, delirium, dementia, memory loss, or sleep disorders); of the eyes, ears, nose, and throat; of circulatory and/or respiratory functions (e.g., dyspinea, pulmonary edema, cough, hemoptysis, hypertension, myocardial infarctions, hypoxia, cyanosis, cardiovascular collapse, congestive heart failure, edema, or shock); of gastrointestinal function (e.g., dysphagia, diarrhea, constipation, GI bleeding, jaundice, ascites, indigestion, nasusea, vomiting); of renal and urinary tract function (e.g., acidosis, alkalosis, fluid and electrolyte imbalances, azotemia, or urinary abnormalities); of sexual function and reproduction (e.g., erectile dysfunction, menstrual disturbances, hirsutism, virilization, infertility, pregnancy associated disorders and standard measurements); of the skin (e.g., eczema, psoriasis, acne, rosacea, cutaneous infection, immunological skin diseases, or photosensitivity); of the blood (e.g., hematology); of genes (e.g., genetic disorders); of drug response (e.g., adverse drug responses); and of nutrition (e.g., obesity, eating disorders, or nutritional assessment). Other medical fields with which embodiments of the invention find utility include oncology (e.g., neoplasms, malignancies, angiogenesis, paraneoplasic syndromes, or oncologic emergencies); hematology (e.g., anemia, hemoglobinopathies, megalooblastic anemias, hemolytic anemias, aplastic anemia, myelodysplasia, bone marrow failure, polycythemia vera, myloproliferative diseases, acute myeloid leukemia, chronic myeloid leukemia, lymphoid malignancies, plasma cell disorders, transfusion biology, or transplants); hemostasis (e.g., disorders of coagulation and thrombosis, or disorders of the platelet and vessel wall); and infectious diseases (e.g., sepsis, septic shock, fever of unknown origin, endocardidtis, bites, burns, osteomyelitis, abscesses, food poisoning, pelvic inflammatory disease, bacterial (e.g., gram positive, gram negative, miscellaneous (nocardia, actimoyces, mixed), mycobacterial, spirochetal, *rickettsia*, or *mycoplasma*); chlamydia; viral (DNA, RNA), fungal and algal infections; protozoal and helminthic infections; endocrine diseases; nutritional diseases; and metabolic diseases.

Other medical conditions and/or fields with which embodiments of the invention find utility include those mentioned in Harrison's Principles of Internal Medicine, Kasper et al., ISBN 0071402357, McGraw-Hill Professional, 16$^{th}$ edition (2004), as well as those mentioned in Robbins Basic Pathology, Kumar, Cotran, and Robbins, eds., ISBN 1416025340, Elsevier, 7$^{th}$ edition (2005).

Medical tests (e.g., blood tests, urine tests, and/or other human or animal tissue tests) that may be performed using various embodiments of the invention described herein include, for example, general chemistry tests (e.g., analytes include albumin, blood urea nitrogen, calcium, creatinine, magnesium, phosphorus, total protein, and/or uric acid); electrolyte tests (e.g., analytes include sodium, potassium, chloride, and/or carbon dioxide); diabetes tests (e.g., analytes include glucose, hemoglobin A 1C, and/or microalbumin); lipids tests (e.g., analytes include apolipoprotein A1, apolipoprotein B, cholesterol, triglyceride, low density lipoprotein cholesteral, and/or high density lipoprotein cholesterol); nutritional assessment (e.g., analytes include albumin, prealbumin, transferrin, retinol binding protein, alpha1-acid glycoprotein, and/or ferritin); hepatic tests (e.g., analytes include alanine transaminase, albumin, alkaline phosphatase, aspartate transaminase, direct bilirubin, gamma glutamyl transaminase, lactate dehydrogenase, immunoglobulin A, immunoglobulin G, immunoglobulin M, prealbumin, total bilirubin, and/or total protein); cardiac tests (e.g., analytes include apolipoprotein A1, apolipoprotein B, cardiac troponin-1, creatine kinase, creatine kinase MB isoenzyme, high sensitivity CRP, mass creatine kinase MB isoenzyme myoglobin, and/or N-terminal pro-brain natriuretic peptide); tests for anemia (e.g., analytes include ferritin, folate, homocysteine, haptoglobin, iron, soluble transferrin receptor, total iron binding capacity, transferrin, and/or vitamin B12); pancreatic tests (e.g., analytes include amylase and/or lipase); nephropathies (e.g., analytes include albumin, alpha1-microglobulin, alpha2-macroglobulin, beta2-microglobulin, cystatin C, retinol binding protein, and/or transferrin); bone tests (e.g., analytes include alkaline phosphatase, calcium, and/or phosphorous); cancer marker monitoring (e.g., analytes include total PSA); thyroid tests (e.g., analytes include free thyroxine, free triiodothyronine, thyroxine, thyroid stimulating hormone, and/or triiodothyronine); fertility tests (e.g., analytes include beta-human chorionic gonadotropin); therapeutic drug monitoring (e.g., analytes include carbamazepine, digoxin, digitoxin, gentamicin, lidocaine, lithium, N-acetyl procainamide, phenobarbital, phenyloin, procainamide, theophylline, tobramycin, valproic acid, and/or vancomycin); immunosuppressive drugs (e.g., analytes include cyclosporine A, sirolimus, and/or tacrolimus); tests for complement activity and/or autoimmune disease (e.g., analytes include C3 complement, C4 complement, C1 inhibitor, C-reactive protein, and/or rheumatoid fator); polyclonal/monoclonal gammopathies (e.g., analytes include immunoglobulin A, immunoglobulin G, immunoglobulin M, 1 g light chains types kappa and/or lambda, immunoglobulin G subclasses 1, 2, 3, and/or 4); tests for infectious disease (e.g., analytes include antistreptolysin O); tests for inflammatory disorders (e.g., analytes include alpha1-acid glycoprotein, alpha1-antitrypsin, ceruloplasmin, C-reactive protein, and/or haptoglobin); allergy testing (e.g., analytes include immunoglobulin E); urine protein tests (e.g., analytes include alpha1-microglobulin, immunoglobulin G, 1 g light chains type kappa and/or lambda, microalbumin, and/or urinary/cerebrospinal fluid protein); tests for protein—CSF (e.g., analytes include immunoglobulin G and/or urinary/cerebrospinal fluid protein); toxicology tests (e.g., analytes include serum acetaminophen, serum barbiturates, serum benzodiazepines, serum salicylate, serum tricyclic antidepressants, and/or urine ethyl alcohol); and/or tests for drugs of abuse (e.g., analytes include amphetamine, cocaine, barbiturates, benzodiazepines, ecstasy, methadone, opiate, phencyclidine, tetrahydrocannabinoids, propoxyphene, and/or methaqualone). Specific cancer markers that can be detected using the methods, devices, cartridges, and kits of the invention include, without limitation, 17-beta-hydroxysteroid dehydrogenase type 1, Abl interactor 2, Actin-related protein 2/3 complex subunit 1A, Albumin, Aldolase A, Alkaline phosphatase, placental type, Alpha 1 antitrypsin, Alpha-1-acid glycoprotein 1, Alpha-2-HS-glycoprotein, Alpha lactalbumin, Alpha-2-macroglobulin, Alpha-fetoprotein (AFP), Angiogenin ribonuclease RNase A family 5, Angiopoietin 1, Angiopoietin 2, Antigen identified by monoclonal antibody Ki-67, Antileukoproteinase 1(SLPI), Apolipoprotein A1, ATP7B, $\beta$2-microglobulin, B-cell CLL/lymphoma 2, BCL2-associated X protein, BRCA1, BRCA2, BrMS1, Butyrate-induced transcript 1, CA15.3/CA27-29, Cancer antigen 125, Cancer antigen 15.3, Cancer antigen 19.9, Cancer antigen 602, Cancer antigen 72-4/TAG-72, Cancer associated galactotransferase antigen, Cancer associated serum antigen (CASA), Carcinoembryonic antigen (CEA), Catenin beta 1, Cathepsin D, Cathepsin member 8, CC chemokine 4 (HCC-4), CCL21 (small inducible cytokine A21), CCL5, CD15, CD24, CD34, CD44, Cell division protein kinase 5, ceruloplasmin, Cervical cancer 1 protooncogene protein p40, c-Ets1, Chaparonin containing TCP1, subunit 3, Chemokine (c-c motif) ligan 4 small inducible cytokine A4 (CCL4, MIP-1-beta), Chemokine ligand 5, Chitinase-3 like protein 1 (YKL-40), Chloride intracellular channel 4 (CLIC4), Choriogonadotropin beta chain, Claudin-3, Claudin-4, clusterin, Coagulation factor II (prothrombin), Coagulation factor III, Coagulation factor XIII a chain, Coagulation factor XIII b chain, Collagen I c-terminal peptide, Colony stimulating factor 2, Colony stimulating factor 3, Complement component 3, c-reactive protein, Creatinine kinase brain (CKB), CTD small phosphatase-like, CyclinDI, Cyclin dependent kinase 6 (CDK 6), Cyclin-dependent kinase inhibitor 1 (p21), Cyclooxygenase-1, Cytochrome c oxidase Va, Cytochrome c-1, Desmin, Dystroglycan 1, Endoglin, Endothelin 1, Epidermal growth factor receptor (EGFR), Epidermal growth factor (EGF), Erythropoietin, E-selectin, EST translocation variant 4 (EST 4), Extracellular matrix metalloproteinase inducer (EMMPRIN), Ferritin H, Ferritin L, Fibroblast growth factor 2, fibronectin, Flt-3 ligand, Fluorodeoxyglucose-PET (FDG-PET) with CA125, Fms-related tyrosine kinase 1 (VEGFR-1), GADD45A, Geminin, Glyphosate N-acetyltransferase, Granulin-epithelin precursor (GEP), Growth differentiation factor 15, Haptoglobin 1, Haptoglobulin-a-subunit, HE4 (human epidiymis protein), Her2, HER2-neu, hK10, hK11, hK13, hk6, hk7, hK8, HLA class II Do$\beta$, hLMH1, hLMH2, HNF-1$\beta$, Human chorionic gonadotropin-$\beta$ subunit, Human chorionic gonadotrpin (hCG), IGFBP-2, IL-2R alpha (soluble interleukin 2 receptor alpha), Immunoglobulins, Immunosuppressive acidic protein (IAP), Indoleamine 2,3-dioxygenase, Insulin-like growth factor binding protein 1, Insulin-like growth factor binding protein 2, Insulin-like growth factor binding protein 3, Integrin $\alpha$-V, Integrin $\alpha v \beta 6$, Intercellular adhesion molecule, Interfereon alpha 1, Interleukin 1 alpha, Interleukin 1 beta, Interleukin 10, Interleukin 12A, Interleukin 16, Inter-$\alpha$-trypsin inhibitor fragment, Kallikrein 8, Keratin, Keratin 18, Keratin, type I cytoskeletal 19 (cytokeratin 19), Kit ligand, KRAS, Lactotransferrin, Laminin-$\beta$3, Leptil-selectin, Luteinizing hormone releasing hormone receptor, Mac-2 binding protein 90 k, Macrophage colony stimulating factor, Macrophage migration inhibitory factor, Mammary serum antigen, Mammoglobin B, M-CAM, MIR21, Mesothelin, MMP3, Mucin-type glycoprotein antigen, Myosin X, Nerve growth factor beta, Netrin-1, Neuroendocrine secretory protein-55, Neutrophil defensin 1, Neutrophil defensin 3, Nm23-H1, Nonmetallic cells protein 2, Non-metastatic cells 1 protein (NM23A), O-acyltransferase domain containing 2, OVX1, OX40, P53, Paraoxonase 2, Pcaf, p-glycoprotein, Phopshribosylaminoimidazole carboxylase, Platelet derived growth factor receptor alpha, Platelet derived growth factor receptor beta, Platelet endothelial cell adhesion molecule (PECAM-1), Platelet factor 4, Pregnancy associated plasma protein-A, Pregnancy zone protein, Procol-lys 1,2 oxoglute 5-digixyg 3, Procol-lys 1,2 oxoglute 5-digoxyg 1, Progesterone receptor (PR), Prolactin, Prostate secretory protein PSP94, Prostate specific antigen (PSA), Prostatin, Protein kinase C binding protein 1, p-selectin, Pyrroline-5-carboxylate reductase 1, Regulator of G protein signaling 12, Reticulocalbin, S-100 alpha chain, s-adenosylhomocysteine hydrolase, Serum amyloid A protein, Seven transmembrance domain protein, Sex determining factor Y-box-4, Sialyl SSEA-1, Small inducible cytokine A18 (CCL18, M1P-4), Small inducible cytokine A2 (CCL2), Small inducible cytokine A3 (CCL3) (macrophage inflammatory protein 1-alpha, Small inducible cytokine B5 (CXCL5), Somatostatin, Somatotropin growth factor, growth factor, Squamous cell carcinoma antigen 1, Squamous cell carcinoma antigen 2, Steroid hormone receptors, Survivin, Syndecan-1, Synuclein gamma, Tetranectin, Tetraspanin 9, TGF-$\alpha$, Thymidine phosphorylase (TP), Thyroglobulin (Tg), Tissue inhibitor of metalloproteinase 2, Tissue-specific transplantation antigen P35B, Tissue-type plasminogen activator (tPA), Topoisomerase II, Transferring receptor p90 CD71, Transforming growth factor alpha, Transforming growth factor beta 1, Translocase of outer mitochondrial membrane, T ransthyretin, Transthyretin (realbumin) fragment, Trophoblast glycoprotein, Tropomyosin 1 alpha chain (alpha-tropomysoin), Trypsin, Tubulin 132, Tubulin (33, Tumor necrosis factor (ligand) superfamily member 5 (CD154), Tumor necrosis factor (ligand) superfamily member 6 (Fas ligand), Tumor necrosis factor alpha, Tumor necrosis factor receptor p75/p55, Tumor necrosis factor receptor super family member 6 (fas), Tumor necrosis factor receptor-associate protein 1, Tumor protein p53, Ubiquitin congujating enzyme E2C (Ubiquitin cong enz), Urinary angiostatin (uAS), Vascular endothelial growth factor (VEGF), Vascular smooth muscle growth-promoting factor (VSGPIF-Spondin), VEGF (165) b, V-erb-b2, Vitamin D binding protein, Vitamin K dependent protein C, Vitronectin, Von Willebrand factor, Wilms tumor 1 (WT-1), WW domain binding protein 11, X box binding protein-1, and YKL-40. See Polanski et al., Biomarker Insights, 1:1 (2006); Cherneva et al., Biotechnol. & Biotechnol. EQ. 21/2007/2:145 (2007); Alaoui-Jamali et al., J. Zhejiang Science B 7:411 (2006); Basil et al., Cancer Res. 66:2953 (2006); Suh et al., Expert Rev. Mol. Diagn. 10:1069 (2010); and Diamandis, E. P., Molecular and Cellular Proteomics 3:367 (2004).

Other analytes which can be detected using the devices, systems, and methods of the invention include those mentioned in the Tietz Textbook of Clinical Chemistry and Molecular Diagnostics, Burtis, Ashwood, and Bruns, ISBN 0721601898, Elsevier, $4^{th}$ edition (2006).

The methods, kits, cartridges, and systems of the invention can be configured to detect a predetermined combination panel of analytes that may be used to understand the medical condition of the subject. For example, a combination panel may include detection of pathogens, therapeutic agents used to treat the suspected pathogen/s, and a potential biomarker to monitor the therapeutic pharmacologic progress (efficacy or pharmacokinetic), or monitoring the presence of the pathogen or pathogen by-products. Further, one could envision a disease treatment panel configured for use to detect a disease or a disease biomarker, the level or concentration of a therapeutic drug for use in treating the suspected disease, a potential biomarker to monitor the therapeutic pharmacologic progress (efficacy or pharmacokinetic), and general chemistry biomarker or other physiological marker of the disease or effect of treatment. In this way, panels of analyte detection can be used to inform and lead to appropriate medical decision making.

For example, the systems and methods of the invention can be used to monitor immuno-compromised subjects following allogenic transplantation. In transplant subjects that receive solid organ, bone marrow, hematopoietic stem cell, or other allogeneic donations, there is a need to monitor the immune status, organ function, and if necessary, rapidly and accurately identify opportunistic infections. Tacrolimus (also FK-506, Prograf, or Fujimycin) is an immunosuppressive drug whose main use is after allogeneic organ transplant to reduce the activity of the subject's immune system and so lower the risk of organ rejection. It reduces interleukin-2 (IL-2) production by T-cells. It is also used in a topical preparation in the treatment of severe atopic dermatitis (eczema), severe refractory uveitis after bone marrow transplants, and the skin condition vitiligo. It is a 23-membered macrolide lactone discovered in 1984 from the fermentation broth of a Japanese soil sample that contained the bacteria *Streptomyces* tsukubaensis. It has similar immunosuppressive properties to cyclosporin, but is much more potent in equal volumes. Immunosuppression with tacrolimus was associated with a significantly lower rate of acute rejection compared with cyclosporin-based immunosuppression (30.7% vs. 46.4%) in one study. Long term outcome has not been improved to the same extent. Tacrolimus is normally prescribed as part of a post-transplant cocktail including steroids, mycophenolate and IL-2 receptor inhibitors. Dosages are titrated to target blood levels. Side effects can be severe and include infection, cardiac damage, hypertension, blurred vision, liver and kidney problems, seizures, tremors, hyperkalemia, hypomagnesaemia, hyperglycemia, diabetes mellitus, itching, insomnia, and neurological problems such as confusion, loss of appetite, weakness, depression, cramps, and neuropathy. In addition tacrolimus may potentially increase the severity of existing fungal or infectious conditions such as herpes zoster or polyoma viral infections, and certain antibiotics cross-react with tacrolimus.

Measuring serum creatinine is a simple test and it is the most commonly used indicator of renal function. A rise in blood creatinine levels is observed only with marked damage to functioning nephrons. Therefore, this test is not suitable for detecting early stage kidney disease. A better estimation of kidney function is given by the creatinine clearance test. Creatinine clearance can be accurately calculated using serum creatinine concentration and some or all of the following variables: sex, age, weight, and race as suggested by the American Diabetes Association without a 24 hour urine collection. Some laboratories will calculate the creatinine clearance if written on the pathology request form; and, the necessary age, sex, and weight are included in the subject information.

There is a need to monitor creatinine and tacrolimus levels from the same blood sample from a subject as the monitoring of the drug concentration and the renal function can assist and guide the physician to optimal therapy post-transplantation. Optimizing therapy is a tight balance of preventing rejection but also to ensure immune function to fight opportunistic infections and overall results in enhanced subject compliance to the immunosuppressive therapy. In large part, transplant recipients succumb to transplant rejection, graft versus host disease, or opportunistic infections. In the first two, immunosuppressive agents can ablate or inhibit the reactions. However, if the subject has an underlying infection, then clinical management is challenging. For a specific example, a heart, lung transplant subject presenting with fever of unknown origin enters a health care facility. The subject is started on broad spectrum antibiotics until the culture results are known. If the condition worsens, and the culture reveals a specific infection, for example *candida*, a specific antifungal, fluconazole, can be administered to the known subject. However, this antifungal may alter the levels of the immunosuppressive agent given to almost all allogenic transplant recipients, tacrolimus. Upon testing for both tacrolimus and creatinine levels, the physician halts the tacrolimus, believing that the fluconazole will defeat the infection, and in a rapid manner. Under this regimen, the subject may worsen if the *candida* species is resistant to fluconazole, and the subject is then started on an appropriate anti-fungal agent. However, since the tacrolimus may be halted, the immunosuppressive therapy is unmanaged and the subject may become unresponsive to any additional therapy and death may ensue. Thus, if there was a test to simultaneously monitor creatinine (kidney function), tacrolimus blood levels, and accurate identification of opportunistic infections, the above subject may have been saved.

The systems and methods of the invention can include a multiplexed, no sample preparation, single detection method, automated system to determine the drug level, the toxicity or adverse effect determinant, and the pathogen identification having a critical role in the immunocompromised subject setting. For example, a cartridge having portals or wells containing 1) magnetic particles having creatinine specific antibodies decorated on their surface, 2) magnetic particles having tacrolimus specific antibodies on their surface, and 3) magnetic particles having specific nucleic acid probes to identify pathogen species could be employed to rapidly determine and provide clinical management values for a given transplant subject. Opportunistic infections that can be monitored in such subjects, and any other patient populations at risk of infection, include, without limitation, fungal; *candida* (resistant and non-resistant strains); gram negative bacterial infections (e.g., *E. coli, stenotrophomonas maltophilia, Klebsiella pneumonia/oxytoca*, or *Pseudomonas aeruginosa*); and gram positive bacterial infections (e.g., *Staphylococcus* species: *S. aureus, S. pneumonia, E. faecalis*, and *E. faecium*). Other opportunistic infections that can be monitored include coaglulase negative *staphylococcus, Corynebacterium* spp., *Fusobacterium* spp., and *Morganella morganii*, and viral organisms, such as CMV, BKV, EBC, HIV, HCV, HBV, and HAV.

The systems and methods of the invention can also be used to monitor and diagnose cancer patients as part of a multiplexed diagnostic test. One specific form of cancer, colorectal cancer, has demonstrated positive promise for personalized medical treatment for a specific solid tumor. Pharmacogenetic markers can be used to optimize treatment of colorectal and other cancers. Significant individual genetic variation exists in drug metabolism of 5FU, capecitabine, irinotecan, and oxaliplatin that influences both the toxicity and efficacy of these agents. Examples of genetic markers include UGT1A1*28 leads to reduced conjugation of SN-38, the active metabolite of irinotecan, resulting in an increased rate of adverse effects, especially neutropenia. To a lesser extent, increased 5-FU toxicity is predicted by DPYD*2A. A variable number of tandem repeats polymorphism in the thymidylate synthase enhancer region, in combination with a single nucleotide polymorphism C>G, may predict poorer response to 5-FU. Efficacy of oxaliplatin is influenced by polymorphisms in components of DNA repair systems, such as ERCC1 and XRCC1. Polymorphic changes in the endothelial growth factor receptor probably predict cetuximab efficacy. Furthermore, the antibody-depended cell-mediated cytotoxic effect of cetuximab may be reduced by polymorphisms in the immunoglobin G fragment C receptors. Polymorphic changes in the VEGF gene and the hypoxia inducible factor 1 alpha gene are also believed to play a role in the variability of therapy outcome. Thus, identification of such polymorphisms in subjects can be used to assist physicians with treatment decisions. For example, PCR-based genetics tests have been developed to assist physicians with therapeutic treatment decisions for subjects with non-small cell lung cancer (NSCLC), colorectal cancer (CRC) and gastric cancer. Expression of ERCC1, TS, EGFR, RRM1, VEGFR2, HER2, and detection of mutations in KRAS, EGFR, and BRAF are available for physicians to order to identify the optimal therapeutic option. However, these PCR tests are not available on site, and thus the sample must be delivered to the off-site laboratory. These solid tumors are often biopsied and FFPE (Formalin-Fixed, Paraffin-Embedded (tissue)) samples are prepared. The systems and methods of the invention can be used without the 5-7 day turnaround to get the data and information and use of fixed samples required for existing methods. The systems and methods of the invention can provide a single platform to analyze samples, without sample prep, for multiple analyte types, as in cancer for chemotherapeutic drugs, genpotyping, toxicity and efficacy markers can revolutionize the practice of personalized medicine and provide rapid, accurate diagnostic testing.

The systems and methods of the invention can also be used to monitor and diagnose neurological disease, such as dementia (a loss of cognitive ability in a previously-unimpaired person) and other forms of cognitive impairment. Without careful assessment of history, the short-term syndrome of delirium (often lasting days to weeks) can easily be confused with dementia, because they have all symptoms in common, save duration, and the fact that delirium is often associated with over-activity of the sympathetic nervous system. Some mental illnesses, including depression and psychosis, may also produce symptoms that must be differentiated from both delirium and dementia. Routine blood tests are also usually performed to rule out treatable causes. These tests include vitamin B12, folic acid, thyroid-stimulating hormone (TSH), C-reactive protein, full blood count, electrolytes, calcium, renal function, and liver enzymes. Abnormalities may suggest vitamin deficiency, infection or other problems that commonly cause confusion or disorientation in the elderly. The problem is complicated by the fact that these cause confusion more often in persons who have early dementia, so that "reversal" of such problems may ultimately only be temporary. Testing for alcohol and other known dementia-inducing drugs may be indicated. Acetylcholinesterase inhibitors-Tacrine (Cognex), donepezil (Aricept), galantamine (Razadyne), and rivastigmine (Exelon) are approved by the United States Food and Drug Administration (FDA) for treatment of dementia induced by Alzheimer disease. They may be useful for other similar diseases causing dementia such as Parkinsons or vascular dementia. N-methyl-D-aspartate blockers include memantine (Namenda), which is a drug representative of this class. It can be used in combination with acetylcholinesterase inhibitors. Amyloid deposit inhibitors include minocycline and clioquinoline, which are antibiotics that may help reduce amyloid deposits in the brains of persons with Alzheimer disease. Depression is frequently associated with dementia and generally worsens the degree of cognitive and behavioral impairment. Antidepressants effectively treat the cognitive and behavioral symptoms of depression in subjects with Alzheimer's disease, but evidence for their use in other forms of dementia is weak. Many subjects with dementia experience anxiety symptoms. Although benzodiazepines like diazepam (Valium) have been used for treating anxiety in other situations, they are often avoided because they may increase agitation in persons with dementia and are likely to worsen cognitive problems or are too sedating. Buspirone (Buspar) is often initially tried for mild-to-moderate anxiety. There is little evidence for the effectiveness of benzodiazepines in dementia, whereas there is evidence for the effectiveness of antipsychotics (at low doses). Selegiline, a drug used primarily in the treatment of Parkinson's disease, appears to slow the development of dementia. Selegiline is thought to act as an antioxidant, preventing free radical damage. However, it also acts as a stimulant, making it difficult to determine whether the delay in onset of dementia symptoms is due to protection from free radicals or to the general elevation of brain activity from the stimulant effect. Both typical antipsychotics (such as haloperidol) and atypical antipsychotics such as (risperidone) increases the risk of death in dementia-associated psychosis. This means that any use of antipsychotic medication for dementia-associated psychosis is off-label and should only be considered after discussing the risks and benefits of treatment with these drugs, and after other treatment modalities have failed. In the UK around 144,000 dementia sufferers are unnecessarily prescribed antipsychotic drugs, around 2000 subjects die as a result of taking the drugs each year. Dementia can be broadly categorized into two groups: cortical dementias and subcortical dementias. Cortical dementias include: Alzheimer's disease, vascular dementia (also known as multi-infarct dementia), including Binswanger's disease, dementia with Lewy bodies (DLB), alcohol-induced persisting dementia, Korsakoff's syndrome, Wernicke's encephalopathy, frontotemporal lobar degenerations (FTLD), including Pick's disease, frontotemporal dementia (or frontal variant FTLD), semantic dementia (or temporal variant FTLD), progressive non-fluent aphasia, Creutzfeldt-Jakob disease, dementia pugilistica, Moyamoya disease, thebestia (often mistaken for a cancer), posterior cortical atrophy or Benson's syndrome. Subcortical dementias include dementia due to Huntington's disease, dementia due to hypothyroidism, dementia due to Parkinson's disease, dementia due to vitamin B1 deficiency, dementia due to vitamin B12 deficiency, dementia due to folate deficiency, dementia due to syphilis, dementia due to subdural hematoma, dementia due to hypercalcaemia, dementia due to hypoglycemia, AIDS dementia complex, pseudodementia (a major depressive episode with prominent cognitive symptoms), aubstance-induced persisting dementia (related to psychoactive use and formerly absinthism), dementia due to multiple etiologies, fementia due to other general medical conditions (i.e., end stage renal failure, cardiovascular disease etc.), or dementia not otherwise specified (used in cases where no specific criteria is met). Alzheimer's disease is a common form of dementia. There are three companies that a currently offer for research only diagnostic testing of proteins (Satoris), splice variants (Exonhit), or protein expression levels (Diagenic) in subjects suffering from dementia, Lewy Body disease, or mild cognitive impairment. Since dementia is fundamentally associated with many neurodegenerative diseases, the ability to test for these proteins, as biomarkers of the disease, along with drug or drug metabolite levels in a single platform will assist a physician to adjust the dosage, alter a regimen, or generally monitor the progression of the disease. These tests are currently run off-site at locations far from the subject and care giver. Thus, to have the ability to monitor the drug levels and the biomarker in the same detection system, on-site will provide a huge advantage to this debilitating and devastating disease. The method of the invention can be a multiplexed, no sample preparation, single detection method, automated system to determine the drug level, the toxicity or adverse effect determinant, and the potential biomarker of the progression of the disease. For example, a cartridge having portals or wells containing 1) magnetic particles having protein biomarker specific antibodies decorated on their surface, 2) magnetic particles having specific antibodies on their surface, and 3) magnetic particles having nucleic acid specific probes to identify protein expression levels could be employed to rapidly determine and provide clinical management values for a given dementia subject.

The systems and methods of the invention can also be used to monitor and diagnose infectious disease in a multiplexed, automated, no sample preparation system. Examples of pathogens that may be detected using the devices, systems, and methods of the invention include, e.g., *Candida* (resistant and non-resistant strains), e.g., *C. albicans, C. glabrata, C. krusei, C. tropicalis,* and *C. parapsilosis; A. fumigatus; E. coli, Stenotrophomonas maltophilia, Klebsiella pneumonia/oxytoca, P. aeruginosa; Staphylococcus* spp. (e.g., *S. aureus* or *S. pneumonia); E. faecalis, E. faecium, Coaglulase* negative *staphylococcus* spp., *Corynebacterium* spp., *Fusobacterium* spp., *Morganella morganii, Pneumocystis jirovecii*, previously known as *pneumocystis carinii, F. hominis, streptococcus pyogenes, Pseudomonas aeruginosa,* Polyomavirus JC polyomavirus (the virus that causes progressive multifocal leukoencephalopathy), *Acinetobacter baumanni, Toxoplasma gondii, Cytomegalovirus, Aspergillus* spp., Kaposi's Sarcoma, *cryptosporidium, Cryptococcus neoformans,* and *Histoplasma capsulatum,* among other bacteria, yeast, fungal, virus, prion, mold, actinomycetes, protozoal, parasitic, protist and helminthic infectious organisms.

The systems and methods of the invention can be used to identify and monitor the pathogenesis of disease in a subject, to select therapeutic interventions, and to monitor the effectiveness of the selected treatment. For example, for a patient having or at risk of a viral infection, the systems and methods of the invention can be used to identify the infectious virus, viral load, and to monitor white cell count and/or biomarkers indicative of the status of the infection. The identity of the virus can be used to select an appropriate therapy. The therapeutic intervention (e.g., a particular antiviral agent) can be monitored as well to correlate the treatment regiman to the circulating concentration of antiviral agent and viral load to ensure that the patient is responding to treatment.

The systems and methods of the invention can be used to monitor a viral infection in a subject, e.g., with a viral panel configured to detect Cytomegalovirus (CMV), Epstein Barr Virus, BK Virus, Hepatitis B virus, Hepatitis C virus, Herpes simplex virus (HSV), HSV1, HSV2, Respiratory syncytial virus (RSV), Influenza; Influenza A, Influenza A subtype H1, Influenza A subtype H3, Influenza B, Human Herpes Virus 6, Human Herpes Virus 8, Human Metapneumovirus (hMPV), Rhinovirus, Parainfluenza 1, Parainfluenza 2, Parainfluenza 3, and Adenovirus. The methods of the invention can be used to monitor a suitable therapy for the subject with a viral infection (e.g., Abacavir, Aciclovir, Acyclovir, Adefovir, Amantadine, Amprenavir, Ampligen, Arbidol, Atazanavir, Atripla, Boceprevir, Cidofovir, Combivir, Darunavir, Delavirdine, Didanosine, Docosanol, Edoxudine, Efavirenz, Emtricitabine, Enfuvirtide, Entecavir, Famciclovir, Fomivirsen, Fosamprenavir, Foscarnet, Fosfonet, Ganciclovir, Ibacitabine, Immunovir, Idoxuridine, Imiquimod, Indinavir, Inosine, Integrase inhibitor, Interferon type III, Interferon type II, Interferon type I, Interferon α, Interferon β, Lamivudine, Lopinavir, Loviride, Maraviroc, Moroxydine, Methisazone, Nelfinavir, Nevirapine, Nexavir, Nucleoside analogues, Oseltamivir (Tamiflu), Peginterferon alfa-2a, Penciclovir, Peramivir, Pleconaril, Podophyllotoxin, Raltegravir, Reverse transcriptase inhibitor, Ribavirin, Rimantadine, Ritonavir, Pyramidine, Saquinavir, Stavudine, Tea tree oil, Tenofovir, Tenofovir disoproxil, Tipranavir, Trifluridine, Trizivir, Tromantadine, Truvada, Valaciclovir (Valtrex), Valganciclovir, Vicriviroc, Vidarabine, Viramidine, Zalcitabine, Zanamivir (Relenza), or Zidovudine), and to monitor the circulating concentration of the therapeutic administered to the subject.

The systems and methods of the invention can also be used to monitor HIV/AIDS patients. When clinicians suspect acute infection (e.g., in a subject with a report of recent risk behavior in association with symptoms and signs of the acute retroviral syndrome), a test for HIV RNA is usually performed. High levels of HIV RNA detected in plasma through use of sensitive amplification assays (PCR, bDNA, or NASBA), in combination with a negative or indeterminate HIV antibody test, support the diagnosis of acute HIV infection. Low-level positive PCR results (<5000 copies/mL) are often not diagnostic of acute HIV infection and should be repeated to exclude a false-positive result. HIV RNA levels tend to be very high in acute infection; however, a low value may represent any point on the upward or downward slope of the viremia associated with acute infection. Plasma HIV RNA levels during seroconversion do not appear significantly different in subjects who have acute symptoms versus those who are asymptomatic. Viremia occurs approximately 2 weeks prior to the detection of a specific immune response. Subjects diagnosed with acute HIV infection by HIV RNA. Fever and flu- or mono-like symptoms are common in acute HIV infection but are nonspecific rash, mucocutaneous ulcers, or pharyngeal candidiasis and meningismus are more specific and should raise the index of suspicion testing still require antibody testing with confirmatory Western blot 3 to 6 weeks later.

Subjects undergoing HIV testing who are not suspected to be in the acute stages of infection should receive HIV antibody testing according to standard protocol. Antibody test results that are initially negative should be followed up with HIV antibody testing at 3 months to identify HIV infection in individuals who may not yet have seroconverted at the time of initial presentation. Plasma HIV RNA levels indicate the magnitude of HIV replication and its associated rate of CD4+ T cell destruction, while CD4+ T-cell counts indicate the extent of HIV-induced immune damage already suffered. Regular, periodic measurement of plasma HIV RNA levels and CD4+ T-cell counts is necessary to determine the risk of disease progression in an HIV-infected individual and to determine when to initiate or modify antiretroviral treatment regimens.

As rates of disease progression differ among individuals, treatment decisions should be individualized by level of risk indicated by plasma HIV RNA levels and CD4+ T-cell counts. Current WHO guidelines and recommendations for HIV therapy includes a combination of the following drugs, AZT (zidovudine), 3TC (lamivudine), ABC (abacavir), ATV (atazanavir), d4T (stavudine), ddI (didanosine), NVP (nevirapine), EFV (efavirenz), FTC (emtricitabine), LPV (lopinavir), RTV (ritonavir), TDF (tenofovir disoproxil fumarate) in established regimens. Drug therapy for HIV is to commence in subjects who have a CD4 count<350 cell/mm$^3$ irrespective of clinical symptoms. At least one of the four following regimens for antiretroviral naïve subjects is begun: I) AZT+3TC+EFV, 2) AZT+3TC+NVP, 3) TDF+3TC or FTC+EFV, or 4) TDF+3TC or FTC+NVP. These regimens avoid d4T (stavudine) to limit the disfiguring, unpleasant, and potentially life-threatening toxicities of this drug. Treatment failure is usually determined by viral load, a persistent value of 5,000 copies/ml confirms treatment failure. In cases whereby viral load measurement is not available, immunological criteria (CD4 cell count) can be used to determine therapeutic progress. In cases of treatment failure, a boosted protease inhibitor plus two nucleoside analogs are added to the regimen and is considered second line antiretroviral therapy. ATV plus low dose RTV, or LPV with low dose RTV is also considered second line therapy. Often the goal in treatment failure cases is simpler timed regimens and fixed doses.

For subjects failing the second line treatment regimens should be maintained on a tolerated regimen for the duration. The use of potent combination antiretroviral therapy to suppress HIV replication to below the levels of detection of sensitive plasma HIV RNA assays limits the potential for selection of antiretroviral-resistant HIV variants, the major factor limiting the ability of antiretroviral drugs to inhibit virus replication and delay disease progression. Therefore, maximum achievable suppression of HIV replication should be the goal of therapy. The most effective means to accomplish durable suppression of HIV replication is the simultaneous initiation of combinations of effective anti-HIV drugs with which the subject has not been previously treated and that are not cross-resistant with antiretroviral agents with which the subject has been treated previously. Each of the antiretroviral drugs used in combination therapy regimens should always be used according to optimum schedules and dosages. The available effective antiretroviral drugs are limited in number and mechanism of action, and cross-resistance between specific drugs has been documented. Therefore, any change in antiretroviral therapy increases future therapeutic constraints.

Monitoring HIV/AIDS subjects for viral load, drug levels, CD4 cell counts, and toxicity patterns in a single platform diagnostic method would provide distinct advantages to a subject. The systems and methods of the invention can be used in a multiplexed, no sample preparation, single detection method, automated system to determine the drug level, the toxicity or adverse effect determinants, and the potential biomarker of the progression of the disease. For example, a cartridge having portals or wells containing 1) magnetic particles having CD4 cell specific antibodies decorated on their surface, 2) magnetic particles having toxicity biomarker specific antibodies on their surface, and 3) magnetic particles having nucleic acid specific probes to identify viral load levels could be employed to rapidly determine and provide clinical management values for a given HIV/AIDS subject.

The systems and methods of the invention can also be used to monitor and diagnose immune disease in a subject (e.g., Crohn's disease, ileitis, enteritis, inflammatory bowel disease, irritable bowel syndrome, ulcerative colitis, as well as non-gastrointestinal immune disease). The relatively recent development of genetically engineered agents has the potential to alter the treatment of immune disease radically, and Remicade (also known as Infliximab, an anti-TNF antibody) was introduced as a new therapeutic class with high efficacy, rapid onset of action, prolonged effect, and improved tolerance. However these agents are expensive and at least one-third of the eligible patients fail to show any useful response. Finding a means to predict those who will respond, and to anticipate relapse is, therefore, of obvious importance. T helper-type 1 (Th1) lymphocytes orchestrate much of the inflammation in Crohn's disease mainly via production of TNF-alpha, which appears to play a pivotal role as a pro-inflammatory cytokine. It exerts its effects through its own family of receptors (TNFR1 and TNFR2), the end results of which include apoptosis, c-Jun N-terminal kinase/stress-activated protein kinase (JNK/SAPK) activation and NF-kappaB activation. Activated NF-kappaB enters the nucleus and induces transcription of genes associated with inflammation, host defense and cell survival. The promoter region of the TNF gene lies between nucleotides −1 and −1300, and encompasses numerous polymorphic sites associated with potential binding sites for various transcription factors. Carriers of the TNF allele 2 (TNF2) (which contains a single base-pair polymorphism at the −308 promoter position) produce slightly more TNF-alpha in their intestinal mucosa than non-TNF2 carriers. TNF polymorphisms also appear to influence the nature and frequency of extra-intestinal manifestations of inflammatory bowel disease (IBD). A number of routes of inhibition of TNF are being investigated. Most extensively evaluated is the use of remicade. Several large controlled trials indicate that remicade has a role in treating patients with moderate to severely active Crohn's disease and in fistulating Crohn's disease. Small studies have shown possible associations between poor response to remicade and increasing mucosal levels of activated NF-kappaB, homozygosity for the polymorphism in exon 6 of TNFR2 (genotype Arg196Arg), positivity for perinuclear antineutrophil cytoplasmic antibodies (ANCA), and with the presence of increased numbers of activated lamina propia mononuclear cells producing interferon-gamma and TNF-alpha. Thus, monitoring Crohn's disease patients for TNF-alpha and toxicity patterns in a single platform diagnostic method would have distinct advantages. The method of the invention can be a multiplexed, no sample preparation, single detection method, automated system to determine the drug level, the toxicity or adverse effect determinants, and the potential biomarker of the progression of the disease. For example, a cartridge having portals or wells containing 1) magnetic particles having anti-TNF-alpha specific antibodies decorated on their surface, 2) magnetic particles having toxicity biomarker specific antibodies on their surface, and 3) magnetic particles having specific probes to identify disease markers of progression could be employed to rapidly determine and provide clinical management values for a given Crohn's disease patient.

The systems and methods of the invention can also be used to monitor and diagnose infectious disease and inflammation in a multiplexed, automated, no sample preparation system. Such systems and methods could be used to monitor, for example, bacteremia, sepsis, and/or Systemic Inflammatory Response Syndrome (SIRS). Early diagnosis is clinically important as this type of infection, if left untreated, can lead to organ dysfunction, hypoperfusion, hypotension, refractory (septic) shock/SIRS shock, and/or Multiple Organ Dysfunction Syndrome (MODS). For a typical patient, many bacterial or fungal infections are the result of incubation at the time of admission to a healthcare setting and are termed healthcare-associated infections (HAI), also known as nosocomial, hospital-acquired or hospital-onset infections. Healthcare-associated infections are most commonly caused by viral, bacterial, and fungal pathogens and are commonly transmitted via wounds, invasive devices (catheters, tracheostomy, intubation, surgical drains) or ventilators and are found as urinary tract infections, surgical site infections, or a form of pneumonia. Within hours after admission, a patient's flora begins to acquire characteristics of the surrounding bacterial pool. Most infections that become clinically evident after 48 hours of hospitalization are considered hospital-acquired and the pathogens should be investigated in all febrile patients who are admitted for a nonfebrile illness or those who develop clinical deterioration unexplained by the initial diagnosis. More careful and selective use of antimicrobial agents, such as antibiotics, is also desirable to decrease the selection pressure for the emergence of resistant strains. Infections that occur after the patient is discharged from the hospital can be considered healthcare-associated if the organisms were acquired during the hospital stay. Patient-related risk factors for invasion of colonizing pathogen include severity of illness, underlying immunocompromised state and/or the length of in-patient stay. Risk factors for the development of catheter-associated bloodstream infections in neonates include catheter hub colonization, exit site colonization, catheter insertion after the first week of life, duration of parenteral nutrition, and extremely low birth weight (<1000 g) at the time of catheter insertion. In patients in the PICU risks, for catheter-associated bloodstream infections increase with neutropenia, prolonged catheter dwell time (>7 days), use of percutaneously placed CVL (higher than tunneled or implanted devices), and frequent manipulation of lines. Candida infections are increasingly important pathogens in the NICU. Risk factors for the development of candidemia in neonates include gestational age less than 32 weeks, 5-min Apgar scores of less than 5, shock, disseminated intravascular coagulopathy, prior use of intralipids, parenteral nutrition administration, CVL use, 1-12 blocker administration, intubation, or length of stay longer than 7 days. Risk factors for the development of ventilator-associated pneumonia (VAP) in pediatric patients include reintubation, genetic syndromes, immunodeficiency, and immunosuppression. In neonates, a prior episode of bloodstream infection is a risk factor for the development of VAP. Risk factors for the development of healthcare-associated urinary tract infection in pediatric patients include bladder catheterization, prior antibiotic therapy, and cerebral palsy. Among the categories of bacteria most known to infect immunocompromised patients are MRSA (Methicillin resistant *Staphylococcus aureus*), gram-positive bacteria and *Helicobacter*, which is gram-negative. While there are antibiotic drugs that can treat diseases caused by Gram-positive MRSA, there are currently few effective drugs for *Acinetobacter*. Common pathogens in bloodstream infections are coagulase-negative staphylococci, *Enterococcus*, and *Staphylococcus aureus*. In addition, *Candida albicans* and pathogens for pneumonia such as *Pseudomonas aeruginosa, Staphylococcus aureus, Klebsiella pneumoniae*, and *Haemophilus influenza* account for many infections. Pathogens for urinary tract infections include *Escherichia coli, Candida albicans*, and *Pseudomonnas aeruginosa*. Gram-negative enteric organisms are additionally common in urinary tract infections. Surgical site infections include *Staphylococcus aureus, Pseudomonas aeruginosa*, and coagulase-negative staphylococci. The infectious agent can be selected from, without limitation, pathogens associated with sepsis, such as *Acinetobacter baumannii, Aspergillus fumigatis, Bacteroides fragilis, B. fragilis*, blaSHV, *Burkholderia cepacia, Campylobacter jejuni/coli, Candida guilliermondii, C. albicans, C. glabrata, C. krusei, C. Lusitaniae, C. parapsilosis, C. tropicalis, Clostridium pefringens*, Coagulase negative *Staph, Enterobacter aeraogenes, E. cloacae,* Enterobacteriaceae, *Enterococcus faecalis, E. faecium, Escherichia coli, Haemophilus influenzae, Kingella Kingae, Klebsiella oxytoca, K. pneumoniae, Listeria monocytogenes,* Mec A gene (MRSA), *Morganella morgana, Neisseria meningitidis, Neisseria* spp. non-*meningitidis, Prevotella buccae, P. intermedia, P. melaminogenica, Propionibacterium acnes, Proteus mirabilis, P. vulgaris, Pseudomonas aeruginosa, Salmonella enterica, Serratia marcescens, Staphylococcus aureus, S. haemolyticus, S. maltophilia, S. saprophyticus, Stenotrophomonas maltophilia, S. maltophilia, Streptococcus agalactie, S. bovis, S. dysgalactie, S. mitis, S. mutans, S. pneumoniae, S. pyogenes*, and *S. sanguinis*; or any other infectious agent described herein. In certain instances, the method and system will be designed to ascertain whether the infectious agent bears a Van A gene or Van B gene characteristic of vancomycin resistance; mecA for methicillin resistance, NDM-1 and ESBL for more general resistance to beta-lactams.

Sepsis or septic shock are serious medical conditions that are characterized by a whole-body inflammatory state (systemic inflammatory response syndrome or SIRS) and the presence of a known or suspected infection. Sepsis is defined as SIRS in the presence of an infection, septic shock is defined as sepsis with refractory arterial hypotension or hypoperfusion abnormalities in spite of adequate fluid resuscitation, and severe sepsis is defined as sepsis with organ dysfunction, hypoperfusion, or hypotension. In addition to symptoms related to the provoking infection, sepsis is characterized by presence of acute inflammation present throughout the entire body, and is, therefore, frequently associated with fever and leukocytosis or low white blood cell count and lower-than-average temperature, and vomiting. It is currently believed that sepsis is the host's immune response to an infection and it is thought that this response causes most of the symptoms of sepsis, resulting in hemodynamic consequences and damage to organs. SIRS is characterized by hemodynamic compromise and resultant metabolic derangement. Outward physical symptoms of this response frequently include a high heart rate (above 90 beats per minute), high respiratory rate (above 20 breaths per minute), elevated WBC count (above 12,000) and elevated or lowered body temperature (under 36° C. (97° F.) or over 38° C. (100° F.)). Sepsis is differentiated from SIRS by the presence of a known pathogen. For example, SIRS and a positive blood culture for a pathogen indicates the presence of sepsis. Without a known infection, it's not possible to classify the above symptoms as sepsis, only SIRS. SIRS causes widespread activation of acute-phase proteins, affecting the complement system and the coagulation pathways, which then cause damage to the vasculature as well as to the organs. Various neuroendocrine counter-regulatory systems are then activated as well, often compounding the problem. Even with immediate and aggressive treatment, this may progress to multiple organ dysfunction syndrome and eventually death. The laboratory component of sepsis diagnosis can include several markers are considered at once and/or measured serially. A number of studies have examined the value of combining currently available markers like GRO-alpha, High mobility group-box 1 protein (HMBG-1), IL-1 receptor, IL-1 receptor antagonist, IL-1b, IL-2, IL-4, IL-6, IL-8, IL-10, IL-12, IL-13, IL-18, macrophage inflammatory protein (MIP-1), macrophage migration inhibitory factor (MIF), osteopontin, RANTES (regulated on activation, normal T-cell expressed and secreted; or CCL5), TNF-α, C-reactive protein (CRP), CD64, and monocyte chemotactic protein 1 (MCP-1). Additionally, the systems and methods can be designed to monitor certain proteins characteristic of sepsis, such as adenosine deaminase binding protein (ABP-26), inducible nitric oxide synthetase (iNOS), lipopolysaccharide binding protein (LBP), and procalcitonin (PCT). Sepsis is usually treated in the intensive care unit with intravenous fluids and antibiotics. If fluid replacement is insufficient to maintain blood pressure, specific vasopressor medications can be used. Mechanical ventilation and dialysis may be needed to support the function of the lungs and kidneys, respectively. To guide therapy, a central venous catheter and an arterial catheter may be placed. Sepsis patients may require preventive measures for deep vein thrombosis, stress ulcers and pressure ulcers, and some patients may benefit from tight control of blood sugar levels with insulin (targeting stress hyperglycemia), low-dose corticosteroids, or activated drotrecogin alfa (recombinant protein C). For an immunocompromised patient, or a patient with a suspected infection that may be experiencing sepsis or SIRS, such methods and systems of the invention provide a diagnostic platform for the rapid identification of one or more pathogens, and whether or not the pathogens are resistant to certain therapies (for the selection of an appropriate antimicrobial therapy). The platform as described allows for the simultaneous determination of the levels of the factors (e.g., GRO-alpha, High mobility group-box 1 protein (HMBG-1), IL-1 receptor, IL-1 receptor antagonist, IL-1b, IL-2, IL-4, IL-6, IL-8, IL-10, IL-12, IL-13, IL-18, macrophage inflammatory protein (MIP-1), macrophage migration inhibitory factor (MIF), osteopontin, RANTES (regulated on activation, normal T-cell expressed and secreted; or CCL5), TNF-α, C-reactive protein (CRP), CD64, and monocyte chemotactic protein 1 (MCP-1)) and/or proteins (e.g., adenosine deaminase binding protein (ABP-26), inducible nitric oxide synthetase (iNOS), lipopolysaccharide binding protein (LBP), and procalcitonin (PCT)) thought to be involved in SIRS, allowing for the optimization for the treatment of sepsis and SIRS. Thus, this platform reduces the empirical protocols and/or use of non-specific/general antimicrobials that may or may not be targeting the specific pathogen and/or the underlying system dysfunction for a given patient. This platform allows for rapid and accurate diagnoses, which can point to effective therapy, providing a key component to a physician's decision making and reducing morbidity and mortality.

To determine whether a patient has sepsis, it is necessary to identify the presence of a pathogen. To most effectively treat a patient, the earliest initiation of appropriate therapy is critical. Antimicrobial and other treatments for sepsis rely on the classification of pathogens at multiple levels, including the identification of an agent as 1) bacterial, viral, fungal, parasitic or otherwise; 2) gram positive, gram negative, yeast, or mold, 3) species, and 4) susceptibility.

Each of these levels of specificity improves the time to initiation of appropriate therapy, and each step further down the track will lead to a narrowing of therapeutic agents to the most specific set. Without absolute susceptibility data, empiric approaches to care rely on the information available about the pathogen (at whichever level) and the pattern of pathogen frequency and susceptibility trends in the hospital of another site of care. Thus, certain categories of pathogens are frequently presumed to be causative until there are more data to refine the pairing of pathogen and therapy. Specifically, these targets fall into the ESKAPE category (which is a series of resistant pathogens) and the SPACE category, which is a set of high virulence pathogens that require isolation of patients.

In addition to identifying these pathogens in multiple sample types (blood, tissue, urine, etc.), another method to distinguish symptomatic patients, for instance, patients with systemic inflammatory syndrome, or SIRS, from septic patients, is to use biomarkers that correlate either individually or via an index, to identify patients with infection. In cases where infections are not detected due to antimicrobial therapy interference with diagnostics, immune system control of the therapy, or otherwise, these biomarkers, which can be multiple types of analytes (cytokines, metabolites, DNA, RNA/gene expression, etc.) will indicate infection and thus sepsis.

To generate the diagnostic information required for both the presence of an infection and some level of species identification, one panel could be: (i) gram positiive clusters (e.g., S. aureus, and CoNS (coagulase negative staph)); (ii) gram positive chains/pairs (e.g., Strep spp., mitis, pneumonia spp., agalactiae spp., pyogenes spp., Enterococcus spp. (E. faecium, E. fetalis); (iii) gram negative rods (e.g., E. coli, Proteus spp., Klebsiella spp., Serratia spp., Acinetobacter spp., Stenotrophomonas spp.); (iv) SPACE (e.g., Serratia spp., Pseudomonas spp., Acinetobacter spp., Citrobacter spp., Enterobacter spp.); (v) Pseudomonas (e.g., Pseudomonas spp.); (vi) ESKAPE (E. faecium, Staphylococcus aureas, Klebsiella spp., Acinetobacter spp., Pseudomonas spp., Enterobacter spp.); and (vii) Pan-Bacterial (all bacterial species).

This panel should be used in conjunction with a fungal assay for full coverage. The categories represent the information required for an effective intervention with appropriate therapy, given that each site of care will have an empirically derived approach based on a positive response to gram +, gram −, etc. The species identified in each category represent those that would fit under each heading, but are not comprehensive. Further, a pan-bacterial marker is included to cover any species that is not covered by the diagnostic method employed for each category. Further, the combination of results will also give an indication of the species, although not fully, if included as described above. Cross-referencing positives and negatives by category allow a process of elimination approach to identify some of the species, probabilistically.

In addition to pathogen panels, a standalone or companion test could be performed for biomarkers that can indicate sepsis. Examples of these markers are below, and may be used individually or in combination: IL-1β, GRO-alpha, High mobility group-box 1 protein (HMBG-1), IL-1 receptor, IL-1 receptor antagonist, IL-1b, IL-2, IL-4, IL-6, IL-8, IL-10, IL-12, IL-13, IL-18, macrophage inflammatory protein (MIP-1), macrophage migration inhibitory factor (MIF), osteopontin, RANTES (regulated on activation, normal T-cell expressed and secreted; or CCL5), IL-10, GM-CSF, MCP-1, TNF-α, hsCRP, PCT, LFB, and lactate.

The systems and methods of the invention can also be used to monitor and diagnose heart disease in a subject, such as a myocardial infarction. Cardiac markers or cardiac enzymes are proteins that leak out of injured myocardial cells and are used to assess cardiac injury. Cardiac markers include, without limitation, the enzymes SGOT, LDH, the MB subtype of the enzyme creatine kinase, and cardiac troponins (T and I). The cardiac troponins T and I which are released within 4-6 hours of an attack of myocardial infarction (and remain elevated for up to 2 weeks) have nearly complete tissue specificity and are now the preferred markers for assessing myocardial damage. Elevated troponins in the setting of chest pain may accurately predict a high likelihood of a myocardial infarction in the near future. The diagnosis of myocardial infarction is typically based upon subject history, ECG, and cardiac markers. When damage to the heart occurs, levels of cardiac markers rise over time, which is why blood tests for them are taken over a 24-hour period. Because these enzyme levels are not elevated immediately following a heart attack, patients presenting with chest pain are generally treated with the assumption that a myocardial infarction has occurred and then evaluated for a more precise diagnosis. A MI is a medical emergency which requires immediate medical attention. Treatment attempts to salvage as much myocardium as possible and to prevent further complications, thus the phrase "time is muscle". Oxygen, aspirin, and nitroglycerin are usually administered as soon as possible. Thus, in the acute setting, monitoring Troponin I and T, as well as potential other biomarkers of cardiac ischemia, in addition to drug therapy and toxicity patterns in a single platform diagnostic method would have distinct advantages. The systems and methods of the invention can be used to provide a multiplexed, no sample preparation, single detection method, automated system to determine the drug level, the toxicity or adverse effect determinants, and the potential biomarker of the progression of the disease. For example, a cartridge having portals or wells containing 1) magnetic particles having anti-troponin I or troponin T specific antibodies decorated on their surface, 2) magnetic particles having toxicity biomarker specific antibodies on their surface, and 3) magnetic particles having specific probes to identify disease markers of progression could be employed to rapidly determine and provide clinical management values for a given myocardial infarction patient.

One or more multi-well cartridges can be configured for use in the systems and methods of the invention and prepared with at least one whole blood sample from the patient; magnetic particles for detecting each of the analytes to be detected (one or more small molecules; one or more metabolites of the one or more small molecules; metabolic biomarker such as described for the hepatic function panel); and dilution and wash buffers. Liver function tests are done on a patient's serum or plasma sample and clinical biochemistry laboratory blood analysis furnishes crucial data regarding the condition of the patient's liver. A "hepatic function panel" is a blood test wherein low or high levels of one or more enzymes may point to liver diseases or damage. For example, the hepatic function panel can include one or more of the following analyte detection assays: one or more small molecules; one or more metabolites of the one or more small molecules; a biologic, metabolic biomarkers; genotyping, gene expression profiling; and proteomic analysis.

A hepatic function panel can include analysis of one or more of the following proteins in a patient or subject biological sample: 1) albumin (the major constituent of the total protein in the liver; while the remnant is called globulin; albumin must be present as 3.9 to 5.0 g/dL, hypoalbuminaemia indicates poor nutrition, lower protein catabolism, cirrhosis or nephrotic syndrome); 2) aspartate transaminase (AST) (also known as serum glutamic oxaloacetic transaminase or aspartate aminotransferase, is an enzyme in liver parenchymal cells and is normally 10 to 34 IU/L; elevated levels are indicative of acute liver damage); 3) alanine transaminase (ALT) (also known as serum glutamic pyruvic transaminase or alanine aminotransferase, is an enzyme is present in hepatocytes at levels between 8 to 37 IU/L; elevated levels are indicative of acute liver damage in viral hepatitis or paracetamol overdose; the ratio of AST to ALT is used to differentiate between the reasons of liver damage); 4) alkaline phosphatase (ALP) (an enzyme that is present in the cells lining the biliary ducts of the liver; the normal range is 44 to 147 IU/L and the level rises in case of infiltrative diseases of the liver, intrahepatic cholestasis or large bile duct obstruction); 5) Gamma glutamyl transpeptidase (GGT) (a more sensitive marker for cholestatic damage than ALP, is very specific to the liver; the standard range is 0 to 51 IU/L; both acute and chronic alcohol toxicity raise GGT; the reason of an isolated elevation in ALP can be detected by GGT); 6) total bilirubin (TBIL) (an increase in the total bilirubin can lead to jaundice and can be attributed to cirrhosis, viral hepatitis, hemolytic anemias, or internal hemorrhage); 7) direct bilirubin; 8) prothrombin time (PTT) (hepatic cell damage and bile flow obstruction can cause changes to blood clotting time); 9) alpha-fetoprotein test (elevated levels indicate hepatitis or cancer); 10) lactate dehydrogenase; and 11) mitochondrial antibodies (if present may indicate chronic active hepatitis, primary biliary cirrhosis, or other autoimmune disorders). The proteins described above would be analyzed in the hepatic function panel using the systems and methods of the invention.

An additional hepatic function panel may include genotyping of cytochrome P450 enzymes. The cytochrome P450 superfamily (CYP) is a large and diverse group of enzymes. The function of most CYP enzymes is to catalyze the oxidation of organic substances. The substrates of CYP enzymes include metabolic intermediates such as lipids and steroidal hormones, as well as xenobiotic substances such as drugs and other toxic chemicals. CYPs are the major enzymes involved in drug metabolism and bioactivation, accounting for ca. 75% of the total metabolism. Most drugs undergo biotransformation and are eventually excreted from the body; and many require bioactivation to form the active compound. The CYP enzymes that metabolize many medications include CYP3A4/5 (36%), CYP2D6 (19%), CYP2C8/9 (16%), and CYP1A2 (11%).

Cytochrome P450 genotyping tests are used to determine how well a patient or subject metabolizes a drug. The results of cytochrome P450 tests can be used to divide individuals into four main types:

(i) Poor metabolizers. Certain drugs are metabolized more slowly than normal and the medication will have a longer half life and possibly increase the likelihood that it will cause side effects.

(ii) Normal metabolizers. Drugs will be metabolized at an average rate and thus is indicative that there is a benefit from treatment and points to fewer side effects than are other individuals who don't metabolize those particular medications as well.

(iii) Intermediate metabolizers. Drugs may or may not be metabolized at an average rate. At least one gene involved in drug metabolism is suspected to function abnormally. There then is a predisposition to metabolize certain drugs differently.

(iv) Ultra rapid metabolizers. Drugs are metabolized faster and more efficiently than the average. Since the metabolic rate is higher than average, some medications are inactivated sooner or are excreted sooner than normal and the medication may not have the desired efficacy.

Currently, genotyping the genes responsible for these enzymes across a population has been shown that polymorphic differences in these enzymes can lead to variation in efficacy and toxicity of some drugs. Assessing cytochrome P450 status in a patient sample can be accomplished by measuring the enzyme activity of the sample, or determining if a genetic difference occurs in one of the genes of this metabolic system in the genome. Genotyping requires a cell sample representative of the patient or subject's genome and the analysis is aimed at determining genetic differences in these clinically important genes. Alternatively, CYP450 enzyme phenotyping (identifying enzymatic metabolizer status) can be accomplished by administering a test enzyme substrate to a patient and monitoring parent substrate and metabolite concentrations over time (e.g., in urine). However, testing and interpretation are time-consuming and inconvenient; as a result, phenotyping is seldom performed.

Below is a listing of the possible hepatic metabolic enzymes that may be part of a hepatic function panel.

CYP2C19 metabolizes several important types of drugs, including proton-pump inhibitors, diazepam, propranolol, imipramine, and amitriptyline. FDA cleared the test "based on results of a study conducted by the manufacturers of hundreds of DNA samples as well as on a broad range of supporting peer-reviewed literature." According to FDA labeling, "Information about CYP2D6 genotype may be used as an aid to clinicians in determining therapeutic strategy and treatment doses for therapeutics that are metabolized by the CYP2D6 product." Thus, a hepatic function panel employing the methods of the invention, may be used to genotype patient or subject samples to assess the status of the cytochrome P450 enzyme system to then optimize therapeutic efficacy and safety.

CYP2D6 (cytochrome P450 2D6) is the best studied of the DMEs and acts on one-fourth of all prescription drugs, including the selective serotonin reuptake inhibitors (SSRI), tricylic antidepressants (TCA), beta-blockers such as Inderal and the Type 1A antiarrhythmics. Approximately 10% of the population has a slow acting form of this enzyme and 7% a super-fast acting form. Thirty-five percent are carriers of a non-functional 2D6 allele, especially elevating the risk of ADRs when these individuals are taking multiple drugs. Drugs that CYP2D6 metabolizes include Prozac, Zoloft, Paxil, Effexor, hydrocodone, amitriptyline, Claritin, cyclobenzaprine, Haldol, metoprolol, Rythmol, Tagamet, tamoxifen, dextromethorphan, beta-blockers, antiarrhythmics, antidepressants, and morphine derivatives, including many of the most prescribed drugs and the over-the-counter diphenylhydramine drugs (e.g., Allegra, Dytuss, and Tusstat). CYP2D6 is responsible for activating the pro-drug codeine into its active form and the drug is therefore inactive in CYP2D6 slow metabolizers.

CYP2C9 (cytochrome P450 2C9) is the primary route of metabolism for Coumadin (warfarin). Approximately 10% of the population are carriers of at least one allele for the slow-metabolizing form of CYP2C9 and may be treatable with 50% of the dose at which normal metabolizers are treated. Other drugs metabolized by CYP2C9 include Amaryl, isoniazid, ibuprofen, amitriptyline, Dilantin, Hyzaar, THC (tetrahydrocannabinol), naproxen, and Viagra.

CYP2C19 (cytochrome P450 2C19) is associated with the metabolism of carisoprodol, diazepam, Dilantin, and Prevacid.

CYP1A2 (cytochrome P450 1A2) is associated with the metabolism of amitriptyline, olanzapine, haloperidol, duloxetine, propranolol, theophylline, caffeine, diazepam, chlordiazepoxide, estrogens, tamoxifen, and cyclobenzaprine.

NAT2 (N-acetyltransferase 2) is a secondary drug metabolizing enzyme that acts on isoniazid, procainamide, and Azulfidine. The frequency of the NAT2 "slow acetylator" in various worldwide populations ranges from 10% to more than 90%.

DPD (Dihydropyrimidine dehydrogenase) is responsible for the metabolism of Fluorouracil (5-FU), one of the most successful and widely used chemotherapy drugs.

UGT1A1 (UDP-glucuronosyltransferase) variations can lead to severe even fatal reactions to the first dost of Camptosar (irinotecan).

5HTT (Serotonin Transporter) helps determine whether people are likely to respond to SSRIs, a class of medications that includes citalopram, fluoxetine, paroxetine, and sertraline, among others, and often is prescribed for depression or anxiety.

Diagnostic genotyping tests for certain CYP450 enzymes are now available. Some tests are offered as in house laboratory-developed test services, which do not require U.S. Food and Drug Administration (FDA) approval but which must meet CLIA quality standards for high complexity testing. The AmpliChip® (Roche Molecular Systems, Inc.) is the only FDA-cleared test for CYP450 genotyping. The AmpliChip® is a microarray consisting of many DNA sequences complementary to 2 CYP450 genes and applied in microscopic quantities at ordered locations on a solid surface (chip). The AmpliChip® tests the DNA from a patient's white blood cells collected in a standard anticoagulated blood sample for 29 polymorphisms and mutations for the CYP2D6 gene and 2 polymorphisms for the CYP2C19 gene.

Therefore, the invention features a multiplexed analysis of a single blood sample (e.g., a single blood draw, or any other type of patient sample described herein) from a patient to determine a) liver enzymatic status, as well as b) the genotype of key metabolic enzymes to then be able to design pharmacotherapy regimes for optimal therapeutic care using the systems and methods of the invention.

The systems and methods of the invention can include one or more multi-well cartridges prepared with at least one whole blood sample from the patient; magnetic particles for detecting each of the analytes to be detected; analyte antibodies; multivalent binding agents; and/or dilution and wash buffers for use in a multiplexed assay as described above.

Nephrotoxicity

Renal toxicity is a common side effect of use of xenobiotics and early, rapid detection of early stages of nephrotoxicity may assist in medical decision making. Early reports of detection of renal toxicity suggest that increased mRNA expression of certain genes can be monitored. However, others have suggested that markers of renal toxicity can be detected in urine. These markers include: kim-1, lipocalin-2, neutrophil gelatinase-associated lipocalin (NGAL), timp-1, clusterin, osteopontin, vimentin, and heme oxygenase 1 (HO-1). More broadly, detection of DNA, heavy metal ions or BUN levels in urine can be useful clinical information. Thus, the methods and utlity of the instant invention also includes the ability to detect these markers of renal toxicity. Optionally, a hepatic function panel may also include one or two hallmark biomarkers of nephrotoxicity, or visa versa.

Non-Agglomeration-Based Assays and Methods

In some embodiments, the magnetic particles described herein may be utilized in an assay that does not feature particle agglomeration. For example, the magnetic particles may be used to capture or concentrate an analyte, e.g., by passing a liquid sample containing the analyte over magnetic particles that include binding moieties specific for the analyte. Some advantages of this approach include a) no clusters need be formed (the clusters may be inherently unstable over a certain size, leading to increased CV's); b) no clustering may not require vortexing as flow shear forces may dislodge non-specific binding of magnetic particles, c) fluidic handling steps may be reduced, and d) miniaturization of the assay may favor these non-agglomerative methods. Broadly, two models for surface based detection include: (i) changes in T2 signal arising from the depletion of magnetic particles from a solution and (ii) changes in T2 signal arising from magnetic particle enrichment of a surface.

The magnetic particles derivatized with a binding moiety can be held in position by an external magnetic field while sample containing the corresponding analyte is circulated past the "trapped" magnetic particles allowing for capture and/or concentrate the analyte of interest. The particles may be pulled to the side or bottom of the assay vessel, or a magnetizable mesh or magnetizable metal foam with appropriate pore size can be present in the reaction vessel, creating very high local magnetic gradients. An advantage of having the mesh/metal foam in the reaction vessel is that the distance each magnetic particle needs to travel to be "trapped" or "captured" can be very short, improving assay kinetics.

Another non-agglomerative assay is to have surfaces derivitized with ligands complementary to the binding moiety present on the magnetic particle and using a capture/depletion/flow through format. Specific binding of magnetic particles to a surface depletes magnetic particles from the bulk particle suspension used in the assay, thus leading to a change in the $T_2$ value in the reaction volume interrogated by the MR reader. Pre-incubation of the particles with the sample containing analyte can reduce/inhibit the specific binding/capture/depletion of the magnetic particle by the derivitized surface in proportion to the concentration of analyte in the sample. One example of this type of assay approach has been demonstrated using PhyNexus affinity chromatography micropipette tips. The 200 ul PhyTips contain a 20 µl volume of resin bed trapped between 2 fits. The resin bed consists of 200 µm cross-linked agarose beads derivitized with avidin, protein A, protein G, or an analyte. A programmable electronic pipettor can aspirate and dispense various volumes at various flow rates. The magnetic particles flow through the pores created by the packed agarose bead resin bed. By repeatedly passing the appropriate magnetic particle suspension over the trapped resin bed to allow for productive interactions to occur between, say, an avidin-derivatized agarose bead resin bed and biotin-derivatized magnetic particles, some of the magnetic particles will specifically bind to and be depleted from the particles suspension. By measuring the $T_2$ of the particle suspension before and after exposure to the agarose resin bed, the amount of particle depletion can be quantified.

Another non-agglomerative assay format is similar to that described above, but uses derivatized magnetizable metal foam to replace the resin bed. The advantage of the metal foam as the solid phase substrate is that when placed in a magnetic field, the metal foam generates very high local magnetic field gradients over very short distances which can attract the derivatized magnetic particles and bring them in contact with the complementary binding partner on the metal foam and improve the chances of a specific productive interaction. By optimizing the pore size and surface area of the metal foam, the assay kinetics can be vastly improved because the particles need to travel much shorter distances to find a complementary surface to bind. The particle concentration in the flow-through reaction volume will be reduced inversely proportional to the analyte concentration in the sample and can be quantified using the MR reader. The metal foam can be nickel bearing directly bound his-tagged moieties, or can be nickel treated with aminosilane and covalently linkedbinding moieties. This process has been demonstrated using aminosilane-treated nickel metal foam with 400 µm pores decorated with anti-creatinine antibodies and shown to specifically bind creatinine-derivatized magnetic particles.

To prepare small circular pieces of nickel metal foam (NMF), NMF material is incubated with deionized water and then frozen. The frozen water in the NMF crevices support the foam so that it will not collapse or create differential edges. Next, a punch is used to create uniform-sized pieces of NMF; a hammer and punch (e.g., a circular tube having a circular cutting edge at one end) is used to cut out circular pieces, e.g., 2-3 mm in size, of the frozen foam. A wire is then used to poke out the pieces, which are dried in a glassware oven. To derivatize the NMF pieces and prepare them for use in the devices and methods described herein, the following steps are performed. First, NMF pieces are cleaned with 2M $H_2SO_4$ in a sonicator, and sulfuric acid solution is used to clean the NMF and to roughen the NMF surfaces in order to assist in subsequent attachment of the amino groups of aminosilane. The acid-washed NMF pieces are then rinsed with deionized water to remove any residual acid solution, and the NMF pieces are dried in a glassware oven. Next the NMF pieces are derivatized with aminosilane, and 70 kD aminodextran is covalently attached. The aminodextran is then optionally crosslinked with gluteraldehyde. Specific antibodies, oligonucleotides, and analytes can then be covalently attached to the amino groups on the aminodextran using various chemistries, and the derivatized NMF pieces are incubated to block non-specific binding. Common blockers include but are not limited to BSA, non-fat dried milk, detergents, salmon sperm DNA, among others.

Further, there are examples of assays that would be aimed at detecting a physical property change in a liquid sample. As described in pending cases, PCT/US2009/062537 (published as WO2010/051362) and PCT/US2008/073346 (published as WO2009/026164), coagulation of blood can be determined by the instant methods described therein. Further, other physical properties may be detected such as solidification, changes in density and may have uses in determining curing of materials (plastic compositions), changes in food and food products with time, contamination of products found in nature, and monitoring certain biological fluids such as urine as a function of kidney function.

The magnetic particles utilized in the non-agglomerative methods described herein can have an average diameter of from 10 nm to 1200 nm (e.g., from 10 to 50, 50 to 150, 150 to 250, 200 to 350, 250 to 450, 300 to 500, 450 to 650, 500 to 700 nm, 700 to 850, 800 to 950, 900 to 1050, or from 1000 to 1200 nm).

Amplification and Detection of Nucleic Acids from Complex Samples

Systems and methods of the invention can include amplification based nucleic acid detection assays conducted starting with complex samples (e.g., for diagnostic, forensic, and environmental analyses).

Sample preparation must also remove or provide resistance for common PCR inhibitors found in complex samples (e.g., body fluids, soil, or other complex milieu). Common inhibitors are listed in Table 5 (see also, Wilson, Appl. Environ. Microbiol., 63:3741 (1997)). Inhibitors typically act by either prevention of cell lysis, degradation or sequestering a target nucleic acid, and/or inhibition of a polymerase activity. The most commonly employed polymerase, Taq, is inhibited by the presence of 0.1% blood in a reaction. Very recently, mutant Taq polymerases have been engineered that are resistant to common inhibitors (e.g., hemoglobin and/or humic acid) found in blood and soil (Kermekchiev et al., Nucl. Acid. Res., 37(5): e40, (2009)). Manufacturer recommendations indicate these mutations enable direct amplification from up to 20% blood. Despite resistance afforded by the mutations, accurate real time PCR detection is complicated due to fluorescence quenching observed in the presence of blood sample (Kermekchiev et al., Nucl. Acid. Res., 37:e40 (2009)).

TABLE 5

PCR inhibitors and facilitators/methods for overcoming inhibition.

| Substrate | Target | Inhibitor | Facilitator |
|---|---|---|---|
| feces | Escherichia coli | >10^3 bacterial cells | ion-exchange column |
| CSF | Treponema pallidum | Cellular debris causing nonspecific amplification | nested primers |
| whole blood | mammalian tissue | >4 μl of blood/100-ml reaction mix (hemoglobin) | 1-2% blood per reaction |
| feces | Rotatvirus | unknown dilution | cellulose fiber |
| clinical specimens | Cytomegalovirus | unidentified components | glass bead extraction |
| human blood and tissue | human genes | DNA binding proteins | thermophilic protease from Thermus strain rt44A |
| mammalian tissue | Mammalian tissue genetics | thermal cycler variations | formamide |
| mammalian tissue | Mammalian tissue genetics | thermal cycler variations | DMSO, glycerol, PEG, organic solvents |
| clinical specimens | Treponema pallidum | unknown factors | Various substrate-specific physicochemical methods |
| forensic semen samples | Sperm | Genotyping errors; selective/total PCR inhibition by vaginal microorganisms | |
| feces | Salmonella enterica | various body fluids | immunomagnetic separation |
| feces | Various enteric viruses | unknown | size exclusion chromatography, physicochemical extraction |
| clinical specimens | Herpes simplex virus | endogenous inhibitors, random effects | repurification, coamplified positive control |
| feces | Escherichia coli | nonspecific inhibitors, urea, hemoglobin, heparin, phenol, SDS | additional primers and reaction cyclers, booster PCR |
| tissue culture suspensions, skin biopsies | Cytomegalovirus HIV Mycobacterium leprae | glove powder mercury-based fixatives, neutral buffered formaline | reduced fixation times, ethanol fixation |
| clinical specimens | Mycobacterium tuberculosis | unknown inhibitors in pus, tissue biopsies, sputum, pleural fluid | physicochemical extraction |
| mammalian tissue | mammalian tissue genetics | unknown contaminant of reverse transcriptase | additional DNA |
| formalin-fixed paraffin tissue | Hepatitus C virus | ribonucleotide vanadyl complexes | phenol/chloroform extraction |
| nasopharyngeal aspirates and swabs | Bordetella pertussis | unknown inhibitors | phenol/chloroform extraction |
| human mononuclear blood cells | HIV type I | detergents | mineral oil |
| bloodstain | human mitochondrial DNA | unidentified heme compound, hemin | BSA |

TABLE 5-continued

PCR inhibitors and facilitators/methods for overcoming inhibition.

| Substrate | Target | Inhibitor | Facilitator |
|---|---|---|---|
| blood | various | heparin | alternative polymerases and buffers, chelex, spermine, [Mg2+], glycerol, BSA, heparinase |
| sputa | Mycoplasma pneumonia | N-acetyl-L-cysteine, dithiothreitol, mucolytic agents | |
| human tissue | HLA-DRB1 genotyping | pollen, glove powder, impure DNA, heparin, hemoglobin | |
| clinical specimens | Mycobacterium tuberculosis | unknown | competitive internal control |
| dental plaque | many | unknown | diatomaceous earth, guanidium isothiocyante, ethanol, acetone |
| ancient mammalian tissues | Cytochrome b gene | unknown | ammonium acetate, ethidium bromide |

Polymerase chain reaction amplification of DNA or cDNA is a tried and trusted methodology; however, as discussed above, polymerases are inhibited by agents contained in crude samples, including but not limited to commonly used anticoagulants and hemoglobin. Recently mutant Taq polymerases have been engineered to harbor resistance to common inhibitors found in blood and soil. Currently available polymerases, e.g., HemoKlenTaq™ (New England BioLabs, Inc., Ipswich, Mass.) as well as OmniTaq™ and OmniKlenTaq™ (DNA Polymerase Technology, Inc., St. Louis, Mo.) are mutant (e.g., N-terminal truncation and/or point mutations) Taq polymerase that render them capable of amplifying DNA in the presence of up to 10%, 20% or 25% whole blood, depending on the product and reaction conditions (See, e.g., Kermekchiev et al. Nucl. Acids Res. 31:6139 (2003); and Kermekchiev et al., Nucl. Acid. Res., 37:e40 (2009); and see U.S. Pat. No. 7,462,475). Additionally, Phusion® Blood Direct PCR Kits (Finnzymes Oy, Espoo, Finland), include a unique fusion DNA polymerase enzyme engineered to incorporate a double-stranded DNA binding domain, which allows amplification under conditions which are typically inhibitory to conventional polymerases such as Taq or Pfu, and allow for amplification of DNA in the presence of up to about 40% whole blood under certain reaction conditions. See Wang et al., Nuc. Acids Res. 32:1197 (2004); and see U.S. Pat. Nos. 5,352,778 and 5,500,363. Furthermore, Kapa Blood PCR Mixes (Kapa Biosystems, Woburn, Mass.), provide a genetically engineered DNA polymerase enzyme which allows for direct amplification of whole blood at up to about 20% of the reaction volume under certain reaction conditions. Despite these breakthroughs, direct optical detection of generated amplicons is not possible with existing methods since fluorescence, absorbance, and other light based methods yield signals that are quenched by the presence of blood. See Kermekchiev et al., Nucl. Acid. Res., 37:e40 (2009).

We have found that complex samples such as whole blood can be directly amplified using about 5%, about 10%, about 20%, about 25%, about 30%, about 25%, about 40%, and about 45% or more whole blood in amplification reactions, and that the resulting amplicons can be directly detected from amplification reaction using magnetic resonance (MR) relaxation measurements upon the addition of conjugated magnetic particles bound to oligonucleotides complementary to the target nucleic acid sequence. Alternatively, the magnetic particles can be added to the sample prior to amplification. Thus, provided are methods for the use of nucleic acid amplification in a complex dirty sample, hybridization of the resulting amplicon to paramagnetic particles, followed by direct detection of hybridized magnetic particle conjugate and target amplicons using magnetic particle based detection systems. In particular embodiments, direct detection of hybridized magnetic particle conjugates and amplicons is via MR relaxation measurements (e.g., $T_2$, $T_1$, T1/T2 hybrid, $T_2$*, etc). Further provided are methods which are kinetic, in order to quantify the original nucleic acid copy number within the sample (e.g., sampling and nucleic acid detection at pre-defined cycle numbers, comparison of endogenous internal control nucleic acid, use of exogenous spiked homologous competitive control nucleic acid).

The terms "amplification" or "amplify" or derivatives thereof as used herein mean one or more methods known in the art for copying a target or template nucleic acid, thereby increasing the number of copies of a selected nucleic acid sequence. Amplification may be exponential or linear. A target or template nucleic acid may be either DNA or RNA. The sequences amplified in this manner form an "amplified region" or "amplicon." Primer probes can be readily designed by those skilled in the art to target a specific template nucleic acid sequence. In certain preferred embodiments, resulting amplicons are short to allow for rapid cycling and generation of copies. The size of the amplicon can vary as needed to provide the ability to discriminate target nucleic acids from non-target nucleic acids. For example, amplicons can be less than about 1,000 nucleotides in length. Desirably the amplicons are from 100 to 500 nucleotides in length (e.g., 100 to 200, 150 to 250, 300 to 400, 350 to 450, or 400 to 500 nucleotides in length).

While the exemplary methods described hereinafter relate to amplification using polymerase chain reaction ("PCR"), numerous other methods are known in the art for amplification of nucleic acids (e.g., isothermal methods, rolling circle methods, etc.). Those skilled in the art will understand that these other methods may be used either in place of, or together with, PCR methods. See, e.g., Saiki, "Amplification of Genomic DNA" in PCR Protocols, Innis et al., Eds., Academic Press, San Diego, Calif., pp 13-20 (1990); Wharam et al., Nucleic Acids Res. 29:E54 (2001); Hafner et al., Biotechniques, 30:852 (2001). Further amplification methods suitable for use with the present methods include, for example, polymerase chain reaction (PCR) method, reverse transcription PCR (RT-PCR), ligase chain reaction (LCR), transcription based amplification system (TAS), transcription mediated amplification (TMA), nucleic acid sequence based amplification (NASBA) method, the strand displacement amplification (SDA) method, the loop mediated isothermal amplification (LAMP) method, the isothermal and chimeric primer-initiated amplification of nucleic acid (ICAN) method, and the smart amplification system (SMAP) method. These methods, as well as others are well known in the art and can be adapted for use in conjunction with provided methods of detection of amplified nucleic acid. The PCR method is a technique for making many copies of a specific template DNA sequence.

The PCR process is disclosed in U.S. Pat. Nos. 4,683,195; 4,683,202; and 4,965,188, each of which is incorporated herein by reference. One set of primers complementary to a template DNA are designed, and a region flanked by the primers is amplified by DNA polymerase in a reaction including multiple amplification cycles. Each amplification cycle includes an initial denaturation, and up to 50 cycles of annealing, strand elongation (or extension) and strand separation (denaturation). In each cycle of the reaction, the DNA sequence between the primers is copied. Primers can bind to the copied DNA as well as the original template sequence, so the total number of copies increases exponentially with time. PCR can be performed as according to Whelan, et al, Journal of Clinical Microbiology, 33:556 (1995). Various modified PCR methods are available and well known in the art. Various modifications such as the "RT-PCR" method, in which DNA is synthesized from RNA using a reverse transcriptase before performing PCR; and the "TaqMan PCR" method, in which only a specific allele is amplified and detected using a fluorescently labeled TaqMan probe, and Taq DNA polymerase, are known to those skilled in the art. RT-PCR and variations thereof have been described, for example, in U.S. Pat. Nos. 5,804,383; 5,407,800; 5,322,770; and 5,310,652, and references described therein, which are hereby incorporated by reference; and TaqMan PCR and related reagents for use in the method have been described, for example, in U.S. Pat. Nos. 5,210,015; 5,876,930; 5,538, 848; 6,030,787; and 6,258,569, which are hereby incorporated by reference.

LCR is a method of DNA amplification similar to PCR, except that it uses four primers instead of two and uses the enzyme ligase to ligate or join two segments of DNA. Amplification can be performed in a thermal cycler (e.g., LCx of Abbott Labs, North Chicago, Ill.). LCR can be performed for example, as according to Moore et al., Journal of Clinical Microbiology 36:1028 (1998). LCR methods and variations have been described, for example, in European Patent Application Publication No. EP0320308, and U.S. Pat. No. 5,427,930, each of which is incorporated herein by reference.

The TAS method is a method for specifically amplifying a target RNA in which a transcript is obtained from a template RNA by a cDNA synthesis step and an RNA transcription step. In the cDNA synthesis step, a sequence recognized by a DNA-dependent RNA polymerase (i.e., a polymerase-binding sequence or PBS) is inserted into the cDNA copy downstream of the target or marker sequence to be amplified using a two-domain oligonucleotide primer. In the second step, an RNA polymerase is used to synthesize multiple copies of RNA from the cDNA template. Amplification using TAS requires only a few cycles because DNA-dependent RNA transcription can result in 10-1000 copies for each copy of cDNA template. TAS can be performed according to Kwoh et al., PNAS 86:1173 (1989). The TAS method has been described, for example, in International Patent Application Publication No. WO1988/ 010315, which is incorporated herein by reference.

Transcription mediated amplification (TMA) is a transcription-based isothermal amplification reaction that uses RNA transcription by RNA polymerase and DNA transcription by reverse transcriptase to produce an RNA amplicon from target nucleic acid. TMA methods are advantageous in that they can produce 100 to 1000 copies of amplicon per amplification cycle, as opposed to PCR or LCR methods that produce only 2 copies per cycle. TMA has been described, for example, in U.S. Pat. No. 5,399,491 which is incorporated herein by reference. NASBA is a transcription-based method which for specifically amplifying a target RNA from either an RNA or DNA template. NASBA is a method used for the continuous amplification of nucleic acids in a single mixture at one temperature. A transcript is obtained from a template RNA by a DNA-dependent RNA polymerase using a forward primer having a sequence identical to a target RNA and a reverse primer having a sequence complementary to the target RNA a on the 3' side and a promoter sequence that recognizes T7 RNA polymerase on the 5' side. A transcript is further synthesized using the obtained transcript as template. This method can be performed as according to Heim, et al., Nucleic Acids Res., 26:2250 (1998). The NASBA method has been described in U.S. Pat. No. 5,130, 238, which is incorporated herein by reference.

The SDA method is an isothermal nucleic acid amplification method in which target DNA is amplified using a DNA strand substituted with a strand synthesized by a strand substitution type DNA polymerase lacking 5'→3' exonuclease activity by a single stranded nick generated by a restriction enzyme as a template of the next replication. A primer containing a restriction site is annealed to template, and then amplification primers are annealed to 5' adjacent sequences (forming a nick). Amplification is initiated at a fixed temperature. Newly synthesized DNA strands are nicked by a restriction enzyme and the polymerase amplification begins again, displacing the newly synthesized strands. SDA can be performed according to Walker, et al., PNAS, 89:392 (1992). SDA methods have been described in U.S. Pat. Nos. 5,455,166 and 5,457,027, each of which are incorporated by reference.

The LAMP method is an isothermal amplification method in which a loop is always formed at the 3' end of a synthesized DNA, primers are annealed within the loop, and specific amplification of the target DNA is performed isothermally. LAMP can be performed according to Nagamine et al., Clinical Chemistry. 47:1742 (2001). LAMP methods have been described in U.S. Pat. Nos. 6,410,278; 6,974,670; and 7,175,985, each of which are incorporated by reference.

The ICAN method is anisothermal amplification method in which specific amplification of a target DNA is performed isothermally by a strand substitution reaction, a template exchange reaction, and a nick introduction reaction, using a chimeric primer including RNA-DNA and DNA polymerase having a strand substitution activity and RNase H. ICAN can be performed according to Mukai et al., J. Biochem. 142: 273 (2007). The ICAN method has been described in U.S. Pat. No. 6,951,722, which is incorporated herein by reference.

The SMAP (MITANI) method is a method in which a target nucleic acid is continuously synthesized under isothermal conditions using a primer set including two kinds of primers and DNA or RNA as a template. The first primer included in the primer set includes, in the 3' end region thereof, a sequence (Ac') hybridizable with a sequence (A)

in the 3' end region of a target nucleic acid sequence as well as, on the 5' side of the above-mentioned sequence (Ac'), a sequence (B') hybridizable with a sequence (Bc) complementary to a sequence (B) existing on the 5' side of the above-mentioned sequence (A) in the above-mentioned target nucleic acid sequence. The second primer includes, in the 3' end region thereof, a sequence (Cc') hybridizable with a sequence (C) in the 3' end region of a sequence complementary to the above-mentioned target nucleic acid sequence as well as a loopback sequence (D-Dc') including two nucleic acid sequences hybridizable with each other on an identical strand on the 5' side of the above-mentioned sequence (Cc'). SMAP can be performed according to Mitani et al., Nat. Methods, 4(3): 257 (2007). SMAP methods have been described in U.S. Patent Application Publication Nos. 2006/0160084, 2007/0190531 and 2009/0042197, each of which is incorporated herein by reference.

The amplification reaction can be designed to produce a specific type of amplified product, such as nucleic acids that are double stranded; single stranded; double stranded with 3' or 5' overhangs; or double stranded with chemical ligands on the 5' and 3' ends. The amplified PCR product can be detected by: (i) hybridization of the amplified product to magnetic particle bound complementary oligonucleotides, where two different oligonucleotides are used that hybridize to the amplified product such that the nucleic acid serves as an interparticle tether promoting particle agglomeration; (ii) hybridization mediated detection where the DNA of the amplified product must first be denatured; (iii) hybridization mediated detection where the particles hybridize to 5' and 3' overhangs of the amplified product; (iv) binding of the particles to the chemical or biochemical ligandson the termini of the amplified product, such as streptavidin functionalized particles binding to biotin functionalized amplified product.

Figure 52:
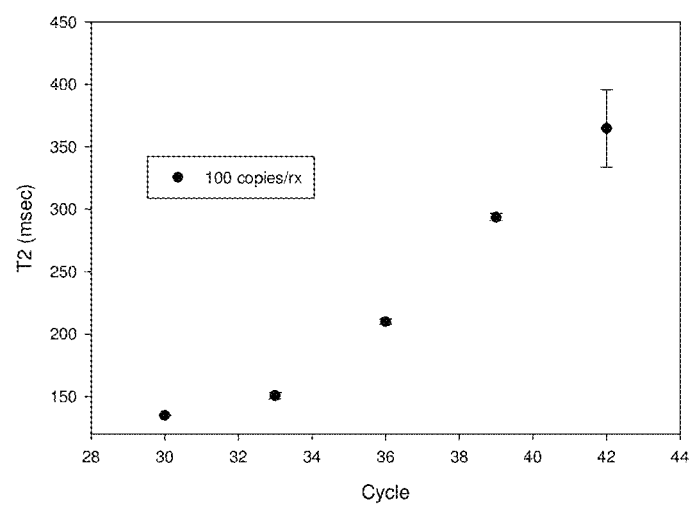
FIG. 52 is a graph depicting the change in $T_2$ signal with PCR cycling (see Example 18). The results demonstrate that the methods and systems of the invention can be used to perform real time PCR and provide quantitative information about the amount of target nucleic acid present in a sample.

The systems and methods of the invention can be used to perform real time PCR and provide quantitative information about the amount of target nucleic acid present in a sample (see FIG. 52 and Example 18). Methods for conducting quantitative real time PCR are provided in the literature (see for example: RT-PCR Protocols. Methods in Molecular Biology, Vol. 193. Joe O'Connell, ed. Totowa, N.J.: Humana Press, 2002, 378 pp. ISBN 0-89603-875-0.). Example 18 describes use of the methods of the invention for real time PCR analysis of a whole blood sample.

The systems and methods of the invention can be used to perform real time PCR directly in opaque samples, such as whole blood, using magnetic nanoparticles modified with capture probes and magnetic separation. Using real-time PCR allows for the quantification of a target nucleic acid without opening the reaction tube after the PCR reaction has commenced.

In one approach, biotin or avidin labeled primers can be used to perform real-time PCR. These labels would have corresponding binding moieties on the magnetic particles that could have very fast binding times. This allows for a double stranded product to be generated and allows for much faster particle binding times, decreasing the overall turnaround time. The binding chemistry would be reversible, preventing the primers from remaining particle bound. In order to reverse the binding, the sample can be heated or the pH adjusted.

In another approach, the real-time PCR can be accomplished through the generation of duplex DNA with overhangs that can hybridize to the superparamagnetic particles. Additionally, LNA and/or fluorinated capture probes may speed up the hybridization times. An exemplary set of capture probes useful in this method is set forth in the table below:

| | |
|---|---|
| Pan *Candida* F Uni-Tail | 5'-CAT GAT CTG CTG CAG /iSp18/GG CAT GCC TGT TTG AGC GTC-3' (SEQ ID NO. 19) |
| Pan *Candida* R Uni-Tail | 5'-GCA GAA CTC CAG ACC /iSp18/GC TTA TTG ATA TGC TTA AGT TCA GCG GGT-3' (SEQ ID NO. 20) |
| 3'AM universal tail CP | 5'-CTG CAG CAG ATC ATG TTT TTT TTT TTT /3AmMO/-3' (SEQ ID NO. 21) |
| 5'AM universal tail CP | 5'-/5AmMC6/TT TTT TTT TTT TGG TCT GGA GTT CTG C-3' |
| Fluorinated 3'AM uni CP | 5'-CTG /i2FC/AG /i2FC/AG /i2FA/TC /i2FA/TG TTT TTT TTT TTT/3AmMO/-3' (SEQ ID NO. 22) |
| Fluorinated 5'AM uni CP | 5'-/5AmMC12/TT TTT TTT TTT TGG T/i2FC/T G/i2FG/A G/i2FU/T CTG C-3' (SEQ ID NO. 23) |

In still another approach, the particles are designed to have a hairpin that buries the binding site to the amplicon. Heating the particles to a higher melt temperature would expose the binding site of the hairpin to allow binding to the target.

In another approach, a probe that hybridizes to an amplicon is tethering two (or more) particles. The reaction would be conducted in the presence of a polymerase with 5' exonuclease activity, resulting in the cleavage of the interparticle tether and a subsequent change in T2. The polymerase is selected to have exonuclease activity and compatibility with the matrix of choice (e.g. blood). In this approach, smaller particles (e.g., 30 nm CLIO) can be used to reduce steric hindrance of the hybridization to target or subsequent enzymatic digestion during polymerization (see, e.g., Heid et al Genome Research 1996 6: 986-994).

In another approach, two particle populations can be synthesized to bear complementary capture probes. In the absence of amplicon, the capture probes hybridize promoting particle clustering. Upon generation of amplicon, the amplicon can compete, hybridize, and displace the capture probes leading to particle declustering. The method can be conducted in the presence or absence of nanoparticles. The particles free in solution will cluster and decluster due to the thermocycling (because, e.g., the Tm can be below 95° C.). The Tm of the amplicon binding to one of the particle-immobilized capture probes can be designed such that that binding interaction is more favorable than the particle-to-particle binding interaction (by, e.g., engineering point mutations within the capture probes to thermodynamically destabilize the duplexes). In this embodiment, the particle concentration can be kept at, e.g., low or high levels. Examples of probes and primers useful in such a system are set forth in the table below.

| | |
|---|---|
| *C. albicans* ITS2 Reverse P | 5'-CCG TCT TTC AAG CAA ACC CAA GTC G-3' (SEQ ID NO. 24) |
| *C. albicans* ITS2 Forward P | 5'-TTT CTC CCT CAA ACC GCT GG-3' (SEQ ID NO. 25) |

| | |
|---|---|
| C. alb ITS2 CP1 | 5'-/5AmMC12/TT TTT TTT TTT TTT TGG TTT GGT MT GAG CAA TAC G-3' (SEQ ID NO. 26) |
| C. alb ITS2 CP2 | 5'-/5AmMC12/TT TTT TTT TTT TCG TAT TGC TCA ACA CCA AAC C-3' (SEQ ID NO. 27) |
| C. alb ITS2 Long CP1 | 5'-/5AmMC12/TT TTT TTT TTT TAC CGC TGG GTT TGG TGT TGA GCA ATA CG-3' (SEQ ID NO. 28) |
| C. alb ITS2 Long CP2 | 5'-/5AmMC12/TT TTT TTT TTT TAC CGC TGG GTT TGG TGT TGA GCA ATA CG-3' (SEQ ID NO. 29) |
| C. alb ITS2 mut 3 CP1 | 5'-/5AmMC12/TT TTT TTT TGG TTT GGC GTA GAG CCA TAC G-3' (SEQ ID NO. 30) |
| C. alb ITS2 mut 4 CP1 | 5'-/5AmMC12/TT TTT TTT TGG TCT GGC GTA GAG CCA TAC G-3' (SEQ ID NO. 31) |

Previous work showed that in some cases the presence of particles in the PCR reaction could inhibit PCR. For these inhibitory particles, it is envisioned that the particles could be pulled to the side of the tube (or other location within the container) to keep them out of solution during the PCR reaction. Methods can be used to release the particles back into suspension to allow them to hybridize to the PCR product and then pull them back out of solution.

In certain embodiments, the invention features the use of enzymes compatible with whole blood, e.g., NEB Hemoklentaq, DNAP Omniklentaq, Kapa Biosystems whole blood enzyme, Thermo-Fisher Finnzymes Phusion enzyme.

The invention also features quantitative asymmetric PCR. In any of the real-time PCR methods of the invention, the method can involve the following steps:

1. aliquoting whole blood into a prepared PCR mastermix containing superparamagnetic particles;
2. prior to the first PCR cycle, closing the tube until PCR cycling is completed;
3. loading the tube onto thermal cycler;
4. running "n" cycles of standard PCR thermal cycling;
5. conducting a T2 detection (the exact time duration and steps for this vary depending on the biochemical and particle design approach described below); and
6. repeating steps 4 and 5 until enough T2 readings have been taken for an accurate quantification of initial target concentration.

The above methods can be used with any of the following categories of detection of aggregation or disaggregation described herein, including:

| Name | Description |
|---|---|
| Clustering-based detection and magnetic separation | Particles >100 nm or magnetic-separation compatible. Particles removed from solution during PCR T2 goes up with amplicon generation Agitation during step 5 |
| Clustering-based detection with particles >100 nm | Particles >100 nm Particles do not inhibit PCR T2 goes up with amplicon generation Agitation during step 5 |
| De-clustering-based detection and magnetic separation | Particles >100 nm Particles on the side of the tube during PCR T2 goes down with amplicon generation Agitation during step 5 |
| De-clustering-based detection with particles >100 nm | Particles >100 nm Particles do not inhibit PCR T2 goes down with amplicon generation Agitation during step 5 |
| Clustering-based detection with particles <100 nm | Particles <100 nm (e.g., 30 nm particles) T2 goes down with amplicon appearance (at least for initial cycles, T2 may subsequently increase as cluster size increases) Has potential for much more rapid hybridization times No agitation required to keep particles suspended Particle concentration in nM range |
| De-clustering-based detection with particles <100 nm | Particles <100 nm (e.g., 30 nm particles) T2 goes up with amplicon appearance T2 could decrease as the cluster size increase above 100 nm No agitation required to keep particles suspended Has potential for most rapid detection times Particle concentration in nM range |

A variety of impurities and components of whole blood can be inhibitory to the polymerase and primer annealing. These inhibitors can lead to generation of false positives and low sensitivities. To reduce the generation of false positives and low sensitivities when amplifying and detecting nucleic acids in complex samples, it is desirable to utilize a thermal stable polymerase not inhibited by whole blood samples (see, e.g., U.S. Pat. No. 7,462,475) and include one or more internal PCR assay controls (see Rosenstraus et al. J. Clin Microbiol. 36:191 (1998) and Hoofar et al., J. Clin. Microbiol. 42:1863 (2004)). For example, to assure that clinical specimens are successfully amplified and detected, the assay can include an internal control nucleic acid that contains primer binding regions identical to those of the target sequence. As shown in the examples, the target nucleic acid and internal control can be selected such that each has a unique probe binding region that differentiates the internal control from the target nucleic acid. The internal control is, optionally, employed in combination with a processing positive control, a processing negative control, and a reagent control for the safe and accurate determination and identification of an infecting organism in, e.g., a whole blood clinical sample. The internal control can be an inhibition control that is designed to co-amplify with the nucleic acid target being detected. Failure of the internal inhibition control to be amplified is evidence of a reagent failure or process error. Universal primers can be designed such that the target sequence and the internal control sequence are amplified in the same reaction tube. Thus, using this format, if the target DNA is amplified but the internal control is not it is then assumed that the target DNA is present in a proportionally greater amount than the internal control and the positive result is valid as the internal control amplification is unnecessary. If, on the other hand, neither the internal control nor the target is amplified it is then assumed that inhibition of the PCR reaction has occurred and the test for that particular sample is not valid. The assays of the invention can include one or more positive processing controls in which one or more target nucleic acids is included in the assay (e.g., each included with one or more cartridges) at 3× to 5× the limit of detection. The measured T2 for each of the positive processing controls must be above the pre-determined threshold indicating the presence of the target nucleic acid. The positive processing controls can detect all reagent failures in each step of the process (e.g., lysis, PCR, and T2 detection), and can be used for quality control of the system. The assays of the invention can include one or more negative processing controls consisting of a solution free of target nucleic acid (e.g., buffer alone). The T2 measurements for the negative processing control should be below the threshold indicating a negative result while the T2 measured for the internal control is above the decision threshold indicating an internal control positive result. The purpose of the negative control is to detect carry-over contamination and/or reagent contamination. The assays of the invention can include one or more reagent controls. The reagent control will detect reagent failures in the PCR stage of the reaction (i.e. incomplete transfer of master mix to the PCR tubes). The reagent controls can also detect gross failures in reagent transfer prior to T2 detection.

Contamination Control

One of the major problems in the use of PCR as an analytical tool is the risk of having new reactions contaminated with old, amplified products. Potential sources of contamination include a) large numbers of target organisms in clinical specimens that may result in cross-contamination, b) plasmid clones derived from organisms that have been previously analyzed and that may be present in larger numbers in the laboratory environment, and c) repeated amplification of the same target sequence leading to accumulation of amplification products in the laboratory environment. A common source of the accumulation of the PCR amplicon is aerosolization of the product. Typically, if uncontrolled aerosolization occurs, the amplicon will contaminate laboratory reagents, equipment, and ventilation systems. When this happens, all reactions will be positive, and it is not possible to distinguish between amplified products from the contamination or a true, positive sample. In addition to taking precautions to avoid or control this carry-over of old products, it is necessary to include a blank reference reaction in every PCR experiment to check for carry-over. In order to be certain that all results are reliable, there must be no amplified products after the temperature cycling. A carry-over contamination will be visible on the agarose gel as faint bands. Furthermore, it is also very important to include a positive sample. If, contrary to expectation, the sample is negative, none of the results can be considered as trustworthy. (see Aslanzadeh et al., Annals of Clin Lab Science, 34:389 (2004)).

It is conceivable that the reagents used to prepare the PCR may be contaminated. After the amplification a positive sample may contain 250 ng PCR product in 50 µl. This gives a total of 3.9 1011 copies of a 600 bp double-stranded product. One thousandth of a microliter of this reaction will contain approximately 8 million copies. If a very small and invisible aerosol is formed when the PCR vessel is opened, there is a possibility that this aerosol can contain a very large number of amplified products. Furthermore, the microscopic droplets in an aerosol are able to float for a long time in the air, and if there is turbulence in the room, they can be carried a long way. Considering the fact that only one copy is enough to create a false positive reaction, it is obvious that great care must be taken to avoid this carry-over contamination.

To address the problem of contamination problem, one or more of the following protocols can be used:

(i) Replace all reagents and stock buffers with new chemicals and new water which have never been in contact with the areas of sample preparation and PCR analysis.

(ii) Physically divide the area of reagent mixing and sample preparation from the area of product analysis (Kwok & Higuchi, Nature, 339:237 (1989)).

(iii) Sample preparation workstations can be cleaned (e.g., with 10% sodium hypochlorite solution, followed by removal of the bleach with ethanol). Oxidative breakdown of nucleic acids prevents reamplification of impurities in subsequent PCR reactions.

(iv) Sterilization of the amplification products ensures that subsequent diagnostic assays are not compromised by carryover DNA, and must follow two generally accepted criteria: (a) the PCR needs to be exposed to the environment after there has been some form of modification of amplicon, and (b) the modification must not interfere with the detection method. For example, UV irradiation can effectively remove contaminating DNA (see Rys et al., J. Clin Microbiol. 3:2356 (1993); and Sarker et al., Nature, 343:27 (1990)), but the irradiation of the PCR reagents must take place before addition of polymerase, primers, and template DNA. Furthermore, this approach may be inefficient because the large numbers of mononucleotides present in the reaction will absorb much of the UV light (See Frothingham et al., BioTechniques 13:208 (1992)). UV light sterilization of the amplification products uses the property of UV light to induce thymine dimmers and other covalent modifications of the DNA that render the contaminating DNA un-amplifiable. Alternatively, incorporation of dUTP into the amplified fragments will also alter the composition of the product so that it is different from the template DNA composition (see Longo et al., Gene 93:125 (1990); and U.S. Pat. Nos. 5,035,996; 7,687,247; and 5,418,149). The enzyme Uracil-N-Glycosylase (UNG) is added together with the normal PCR enzyme to the reaction mix. The UNG enzyme will cleave the uracil base from DNA strands before amplification, and leave all the old amplified products unable to act as templates for new amplification, but will not react on unincorporated dUTP or new template. This will efficiently remove contaminating PCR products from the reaction after the PCR vessel has been closed, and thus no new contamination is possible. However, the use of dUTP in PCR reactions to prevent carry-over can cause problems when the products are used in a later hybridization study, due to the low capability of uracil to act in hybridization (Carmody et al., Biotechniques 15:692 (1993)). dUTP is incorporated instead of dTTP. When a probe rich in T's is amplified with the substitution of dTTP for dUTP in the reaction mixture, a later hybridization signal with the probe may be eliminated. To avoid the decrease in hybridization signal the probe binding site should be chosen with no more than 25% T's, and without stretches of poly-T. Furthermore, the PCR should contain equal concentrations of dUTP and dTTP and not only dUTP. In contrast to the decrease in hybridization signal is the increase in product amplification when using dUTP, especially when AT-rich target sequences are selected. This is probably because the incorporation of dUTP decreases re-annealing of formed PCR products which would prevent primers from annealing. If this approach is used to increase the product yield, the primer binding sites should be selected with a low content of T's, since primer annealing also will be inhibited by dUTP incorporation (Carmody et al., Biotechniques 15:692 (1993)). Heat labile UDG isolated from BMTU 3346 is described in Schmidt et al. Biochemica 2:13 (1996) (see also U.S. Pat. No. 6,187,575). A uracil-DNA glycosylase gene from *Psychrobacter* sp HJ147 was described in U.S. Pat. No. 7,723,093. Lastly a cod uracil-DNA glycosylase was described (U.S. Pat. No. 7,037,703).

(v) DNase digestion after PCR can be used to reduce contamination. A heat labile DNase enzyme was identified that can be used to digest ds DNA to remove any contaminating DNA prior to the PCR amplification step of the target DNA. In this case, the ds DNA is digested, the sample is heated to inactivate the DNase, and the target sample and PCR reactants are added to the reaction tube to carry out the target specific PCR. (see U.S. Pat. No. 6,541,204).

(vi) Sterilization after PCR can be used to reduce contamination. Incorporation of a photochemical reagent (isopsoralen) into the product during amplification will create a difference in composition between the template DNA and the amplified PCR products (see Rys et al., J. Clin Microbiol. 3:2356 (1993)). Furocoumarin compounds, such as isopsoralen or psoralen, are a class of planar tricylcic reagents that are known to intercalate between base pairs of nucleic acids (see U.S. Pat. No. 5,532,145). Light treatment of the closed PCR vessel will render previously formed PCR products unable to act as templates for further amplification. The hybridization abilities of the product are not changed, but the detection capabilities on agarose gel can be decreased due to reduced binding of EtBr. Isopsoralen of 25 mg/ml was shown to be ineffective at preventing contamination, and at concentrations up to 100 mg/ml, isopsoralen may have an inhibitory effect on the PCR reaction itself (see U.S. Pat. No. 5,221,608). Alternatively, primer hydrolysis can be used to sterilize a reaction after amplification. Primer hydrolysis of sterilization of amplification products relies on the uniquely synthesized chimeric primers that contain one or more ribose linkages at the 3' end. The generated amplification products containing those ribose residues are susceptible to alkaline hydrolysis at the site of the ribose molecule. The method includes exposure to 1M NaOH and incubated for 30 minutes to hydrolyze the amplification products at the sites of the incorporated ribose. Thus, if there is carryover contamination, the old amplicon has lost its primer site due to the hydrolysis of the ribose molecules and the new amplicon will have the primer binding sites. In another approach, addition of hydroxylamine hydrochloride to PCR reaction tubes after amplification sterilizes the reaction contents, and is especially effective for short (<100 bp) and GC rich amplification products. The hydroxylamine preferentially reacts with oxygen atoms in the cytosine residues and creates covalent adducts that prevent base-pairing with guanine residues in subsequent reactions. Thus, the modified amplification product are not recognized as amplification targets in subsequent PCR reactions.

(vii) Prevention of carry-over by changing the product composition from the template can reduce contamination. In one approach the DNA composition of the PCR product can be different from the natural template DNA composition. This altered composition is intended to make the PCR products sensitive to treatment that will not alter the template DNA. The treatment of the closed PCR vessel just before amplification should make the contaminating PCR product unable to participate in the amplification. Here the modification would have to be innocuous to the detection method. The types of modifications that can be useful in distinguishing contaminant amplification product will be apparent, but include introduction of a ligand, cross-linking agent, enzyme recognition site, or other cleavable moiety (See U.S. Pat. Nos. 5,427,929; 5,650,302; 5,876,976; and 6,037,152).

One or more of the methods described above can be used in conjunction with the methods of the invention to reduce the risk of contamination and false positives. Carry-over of old amplified PCR products can be a very serious risk in the nucleic acid analysis in the T2 Biosystems diagnostic platform. One way to prevent this contamination is to physically divide the PCR working areas. Alternatives to the physical separation of the PCR reaction method include UV irradiation of PCR mix and incorporation of reagents into the newly formed PCR product can be used to alter it from the template.

Reaction Kinetics

The reaction of magnetic particles and specific analytes to form aggregates can be used to produce a diagnostic signal in the assays of the invention. In many instances, incubation of the reaction mixture for a period of time is sufficient to form the aggregates. The methods, kits, cartridges, and devices of the invention can be configured to shorten the amount of time needed to capture a particular analyte, or produce aggregates of magnetic particles. While altering the overall concentration of magnetic particles would appear to be a simple and direct approach to increasing aggregation rates, this approach is complicated by (i) nonspecific aggregation that can arise with high magnetic particle concentrations, and (ii) the need to produce an observable signal change (i.e., change in relaxation signal) in response to aggregation in the presence of a low concentration of analyte. Reaction kinetics can be improved, for example, by mechanically induced aggregation, by acoustically induced aggregation, by ultrasonically induced aggregation, by electrostatically induced aggregation, or by trapping the magnetic particles in a portion of the liquid sample.

Mechanically Induced Aggregation

The kinetics of aggregation can be increased by passing the particle/analyte solution through a vessal in which there is a narrowing of the path of the fluid flow. The narrowing enhances particle-particle interactions.

Acoustically Induced Aggregation

The aggregation of magnetic particles can be accelerated by applying an acoustic standing wave to the sample (see Aboobaker et al., Journal of Environmental Engineering, 129:427 (2003) and U.S. Pat. No. 4,523,682). For example, a flow chamber with two transducers at opposite ends can be used to generate an acoustic standing wave in the sample that causes the magnetic particles to migrate (or be segregated) in a manner that increases the rate of magnetic particle aggregation.

Ultrasonically Induced Aggregation

The aggregation of magnetic particles can be accelerated by applying an ultrasonic wave to the sample (see Masudo et al., Anal. Chem. 73:3467 (2001)). In the presence of a standing plane ultrasound wave particles can move to the node of the wave along the ultrasound force gradient. This approach can be used to provide a reliable method for assisting the agglomeration reaction.

Electrostatically Induced Aggregation

The aggregation of magnetic particles can be accelerated by electrostatic interactions. Electrostatic separation or movement of the magnetic particles utilizes inherent differences in friction charge characteristics, electric conductivity, and dielectric constants. Since the magnetic particles will behave differently under the application of an electrostatic field, movement and enhanced collisions can occur. Electrostatic force exertion on the particles can be proportional to the surface area available for surface charge, so the nanoparticles will typically move in the presence of the electrostatic field when coated with varying materials, such as dextran or other large molecular coatings, and whether or not the nanoparticle has bound to one of the binding moieties a analyte. The nanoparticles must first be charged and the charge could optionally be pulsed. See, for example, Sinyagin et al., J. Phys. Chem. B 110:7500 (2006); Kretschmer et al., Langmuir 20:11797 (2004); Bernard et al., Nanotechnology 18: 235202 (2007); and Costanzo et al., Lab Chip 2005 5:606 (2005).

Trapping

The magnetic particles derivatized with a binding moiety can be held in position by an external magnetic field while sample containing the corresponding analyte is circulated past the "trapped" magnetic particles allowing for capture and/or concentrate the analyte of interest. The capture and/or aggregation can be facilitated by exposure to a magnetic field (i.e., MAA or gMAA) as described herein.

Alternatively, the kinetics of magnetic particle aggregation can be increased by sequestering the magnetic particles in a compartment defined by a porous membrane, such as a tea bag, that permits flow of analytes into and out of the compartment. The increase in the local concentration of magnetic particles can increase the reaction kinetics between magnetic particles and analytes, and the kinetics of aggregation. After mixing the solution and magnetic particles for a predetermined period of time, the magnetic particles are released from the compartment and the sample is measured.

In certain instances, the particles may be pulled to the side or bottom of the assay vessel, or a magnetizable mesh or magnetizable metal foam with appropriate pore size can be present in the reaction vessel, creating very high local magnetic gradients. The metal foam generates very high local magnetic field gradients over very short distances which can attract the derivatized magnetic particles and bring them in contact with the complementary binding partner on the metal foam and improve the chances of a specific productive interaction. An advantage of having the mesh/metal foam in the reaction vessel is that the distance each magnetic particle needs to travel to be "trapped" or "captured" can be very short, improving assay kinetics. For example, to a reaction tube can be added a magnetizable mesh foam having pores of 100 to 1000 microns, a liquid sample, and magnetic particles for detecting an analyte in the liquid sample. The reaction tube is exposed to a magnetic field to magnetize the mesh. The magnetic particles are then attracted to the magnetized mesh and become trapped within the pores of the mesh. The concentration of the magnetic particles within the mesh increases the reaction kinetics between the magnetic particles and the analyte diffusing into and out of the mesh (the reaction tube is optionally agitated to expedite the diffusion of analyte onto the trapped magnetic particles). The mesh is then demagnetized (e.g., by heating the mesh or exposing the mesh to an alternating magnetic field), thereby permitting the release of magnetic particles complexed to analyte. Larger aggregates of magnetic particles can then be formed, completing the reaction.

In an analogous approach, the kinetics of magnetic particle aggregation can be increased by centrifugally pulling the magnetic particles down to the bottom of the sample tube. The increase in the local concentration of magnetic particles can increase the aggregation kinetics. To facilitate separation by centrifugation the particles are, desirably, greater than about 30 nm in diameter.

NMR Units

Figure 1B:
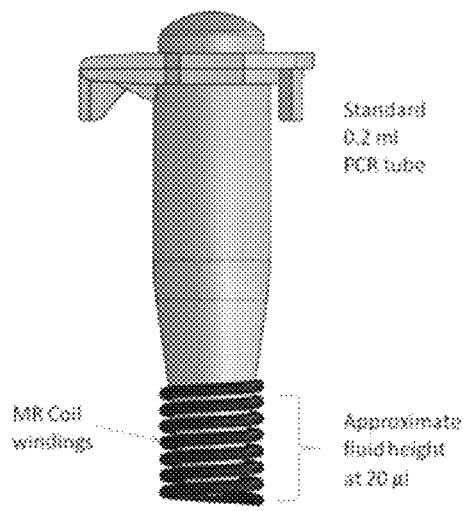
FIG. 1B depicts a typical coil configuration surrounding a sample tube for measuring a relaxation signal in a 20 μl sample.

The systems for carrying out the methods of the invention can include one or more NMR units. FIG. 1A is a schematic diagram 100 of an NMR system for detection of a signal response of a liquid sample to an appropriate RF pulse sequence. A bias magnet 102 establishes a bias magnetic field Bb 104 through a sample 106. The magnetic particles are in a liquid or lyophilized state in the cartridge prior to their introduction to a sample well (the term "well" as used herein includes any indentation, vessel, container, or support) 108 until introduction of the liquid sample 106 into the well 108, or the magnetic particles can be added to the sample 106 prior to introduction of the liquid sample into the well 108. An RF coil 110 and RF oscillator 112 provides an RF excitation at the Larmor frequency which is a linear function of the bias magnetic field Bb. In one embodiment, the RF coil 110 is wrapped around the sample well 108. The excitation RF creates a nonequilibrium distribution in the spin of the water protons (or free protons in a non-aqueous solvent). When the RF excitation is turned off, the protons "relax" to their original state and emit an RF signal that can be used to extract information about the presence and concentration of the analyte. The coil 110 acts as an RF antenna and detects a signal, which based on the applied RF pulse sequence, probes different properties of the material, for example a $T_2$ relaxation. The signal of interest for some cases of the technology is the spin-spin relaxation (generally 10-2000 milliseconds) and is called the $T_2$ relaxation. The RF signal from the coil 110 is amplified 114 and processed to determine the $T_2$ (decay time) response to the excitation in the bias field Bb. The well 108 may be a small capillary or other tube with nanoliters to microliters of the sample, including the analyte and an appropriately sized coil wound around it (see FIG. 1B). The coil is typically wrapped around the sample and sized according to the sample volume. For example (and without limitation), for a sample having a volume of about 10 ml, a solenoid coil about 50 mm in length and 10 to 20 mm in diameter could be used; for a sample having a volume of about 40 µl, a solenoid coil about 6 to 7 mm in length and 3.5 to 4 mm in diameter could be used; and for a sample having a volume of about 0.1 nl a solenoid coil about 20 µm in length and about 10 µm in diameter could be used. Alternatively, the coil may be configured as shown in any of FIGS. 2A-2E about or in proximity to the well. An NMR system may also contain multiple RF coils for the detection of multiplexing purposes. In certain embodiments, the RF coil has a conical shape with the dimensions 6 mm×6 mm×2 mm.

FIGS. 2A-2E illustrate exemplary micro NMR coil (RF coil) designs. FIG. 2A shows a wound solenoid micro coil 200 about 100 µm in length, however one could envision a coil having 200 µm, 500 µm or up to 1000 µm in length. FIG. 2B shows a "planar" coil 202 (the coil is not truly planar, since the coil has finite thickness) about 1000 µm in diameter. FIG. 2C shows a MEMS solenoid coil 204 defining a volume of about 0.02 µL. FIG. 2D shows a schematic of a MEMS Helmholz coil 206 configuration, and FIG. 2E shows a schematic of a saddle coil 220 configuration.

A wound solenoid micro coil 200 used for traditional NMR detection is described in Seeber et al., "Design and testing of high sensitivity micro-receiver coil apparatus for nuclear magnetic resonance and imaging," Ohio State University, Columbus, Ohio. A planar micro coil 202 used for traditional NMR detection is described in Massin et al., "High Q factor RF planar microcoil for micro-scale NMR spectroscopy," Sensors and Actuators A 97-98, 280-288 (2002). A Helmholtz coil configuration 206 features a well 208 for holding a sample, a top Si layer 210, a bottom Si layer 212, and deposited metal coils 214. An example of a Helmholtz coil configuration 206 used for traditional NMR detection is described in Syms et al, "MEMS Helmholz Coils for Magnetic Resonance Spectroscopy," Journal of Micromechanics and Micromachining 15 (2005) S1-S9.

The NMR unit includes a magnet (i.e., a superconducting magnet, an electromagnet, or a permanent magnet). The magnet design can be open or partially closed, ranging from U- or C-shaped magnets, to magnets with three and four posts, to fully enclosed magnets with small openings for sample placement. The tradeoff is accessibility to the "sweet spot" of the magnet and mechanical stability (mechanical stability can be an issue where high field homogeneity is desired). For example, the NMR unit can include one or more permanent magnets, cylindrically shaped and made from SmCo, NdFeB, or other low field permanent magnets that provide a magnetic field in the range of about 0.5 to about 1.5 T (i.e., suitable SmCo and NdFeB permanent magnets are available from Neomax, Osaka, Japan). For purposes of illustration and not limitation, such permanent magnets can be a dipole/box permanent magnet (PM) assembly, or a hallbach design (See Demas et al., Concepts Magn Reson Part A 34A:48 (2009)). The NMR units can include, without limitation, a permanent magnet of about 0.5 T strength with a field homogeneity of about 20-30 ppm and a sweet spot of 40 µL, centered. This field homogeneity allows a less expensive magnet to be used (less tine fine-tuning the assembly/shimming), in a system less prone to fluctuations (e.g. temperature drift, mechanical stability over time-practically any impact is much too small to be seen), tolerating movement of ferromagnetic or conducting objects in the stray field (these have less of an impact, hence less shielding is needed), without compromising the assay measurements (relaxation measurements and correlation measurements do not require a highly homogeneous field).

The coil configuration may be chosen or adapted for specific implementation of the micro-NMR-MRS technology, since different coil configurations offer different performance characteristics. For example, each of these coil geometries has a different performance and field alignment. The planar coil 202 has an RF field perpendicular to the plane of the coil. The solenoid coil 200 has an RF field down the axis of the coil, and the Helmholtz coil 206 has an RF field transverse to the two rectangular coils 214. The Helmholtz 206 and saddle coils 220 have transverse fields which would allow the placement of the permanent magnet bias field above and below the well. Helmholtz 206 and saddle coils 220 may be most effective for the chip design, while the solenoid coil 200 may be most effective when the sample and MRS magnetic particles are held in a micro tube.

The micro-NMR devices may be fabricated by winding or printing the coils or by microelectromechanical system (MEMS) semiconductor fabrication techniques. For example, a wound or printed coil/sample well module may be about 100 µm in diameter, or as large as a centimeter or more. A MEMS unit or chip (thusly named since it is fabricated in a semiconductor process as a die on a wafer) may have a coil that is from about 10 µm to about 1000 µm in characteristic dimension, for example. The wound or printed coil/sample well configuration is referenced herein as a module and the MEMS version is referenced herein as a chip. For example, the liquid sample 108 may be held in a tube (for example, a capillary, pipette, or micro tube) with the coil wound around it, or it may be held in wells on the chip with the RF coil surrounding the well. Alternatively, the sample is positioned to flow through a tube, capillary, or cavity in the proximity to the RF coil.

The basic components of an NMR unit include electrical components, such as a tuned RF circuit within a magnetic field, including an MR sensor, receiver and transmitter electronics that could be including preamplifiers, amplifiers and protection circuits, data acquisitions components, pulse programmer and pulse generator.

Systems containing NMR units with RF coils and micro wells containing magnetic particle sensors described herein may be designed for detection and/or concentration measurement of specific analyte(s) of interest by development of a model for particle aggregation phenomena and by development of an RF-NMR signal chain model. For example, experiments can be conducted for analyte/magnetic particle systems of interest by characterizing the physics of particle aggregation, including, for example, the effects of affinities, relevant dimensions, and concentrations. Also, experiments can be conducted to characterize the NMR signal(s) ($T_2$, $T_1$, $T_2^*$, $T_{2rho}$, $T_{1rho}$ and/or other signal characteristics, such as T1/T2 hybrid signals and may also include but are not limited to diffusion, susceptibility, frequency) as functions of particle aggregation or depletion and magnetic particle characteristics. Signal characteristics specific to the MRS (magnetic resonance switch) phenomenon in a given system can be used to enhance detection sensitivity and/or otherwise improve performance.

The NMR system may include a chip with RF coil(s) and electronics micromachined thereon. For example, the chip may be surface micromachined, such that structures are built on top of a substrate. Where the structures are built on top of the substrate and not inside it, the properties of the substrate are not as important as in bulk micromachining, and expensive silicon wafers used in bulk micromachining can be replaced by less expensive materials such as glass or plastic. Alternative embodiments, however, may include chips that are bulk micromachined. Surface micromachining generally starts with a wafer or other substrate and grows layers on top. These layers are selectively etched by photolithography and either a wet etch involving an acid or a dry etch involving an ionized gas, or plasma. Dry etching can combine chemical etching with physical etching, or ion bombardment of the material. Surface micromachining may involve as many layers as is needed.

In some cases, an inexpensive RF coil maybe integrated into a disposable cartridge and be a disposable component. The coil could be placed in a manner that allows electrical contact with circuitry on the fixed NMR setup, or the coupling could be made inductively to a circuit.

Where the relaxation measurement is $T_2$, accuracy and repeatability (precision) will be a function of temperature stability of the sample as relevant to the calibration, the stability of the assay, the signal-to-noise ratio (S/N), the pulse sequence for refocusing (e.g., CPMG, BIRD, Tango, and the like), as well as signal processing factors, such as signal conditioning (e.g., amplification, rectification, and/or digitization of the echo signals), time/frequency domain transformation, and signal processing algorithms used. Signal-to-noise ratio is a function of the magnetic bias field (Bb), sample volume, filling factor, coil geometry, coil Q-factor, electronics bandwidth, amplifier noise, and temperature.

In order to understand the required precision of the $T_2$ measurement, one should look at a response curve of the assay at hand and correlate the desired precision of determining the analyte concentration and the precision of the measurable, e.g., $T_2$ for some cases. Then a proper error budget can be formed.

For example, to obtain a 10-fold improvement in the 0.02 ng/mL detection limit for Troponin (10-fold increase in sensitivity), it would be necessary to discern a delta-T, less than about 5.6 milliseconds from a traditional (non-MRS-measured) $T_2$ of about 100 milliseconds. The minimum signal-to-noise ratio (S/N) would need to be about 20 to detect this difference.

The NMR units for use in the systems and methods of the invention can be those described in U.S. Pat. No. 7,564,245, incorporated herein by reference.

The NMR units of the invention can include a small probehead for use in a portable magnetic resonance relaxometer as described in PCT Publication No. WO09/061,481, incorporated herein by reference.

The systems of the invention can be implantable or partially implantable in a subject. For example, the NMR units of the invention can include implantable radiofrequency coils and optionally implantable magnets as described in PCT Publication Nos. WO09/085214 and WO08/057578, each of which is incorporated herein by reference.

The systems of the invention can include a polymeric sample container for reducing, partly or completely, the contribution of the NMR signal associated with the sample container to the nuclear magnetic resonance parameter of the liquid sample as described in PCT Publication No. WO09/045354, incorporated herein by reference.

The systems of the invention can include a disposable sample holder for use with the MR reader that is configured to permit a predetermined number of measurements (i.e., is designed for a limited number of uses). The disposable sample holder can include none, part, or all, of the elements of the RF detection coil (i.e., such that the MR reader lacks a detection coil). For example, the disposable sample holder can include a "read" coil for RF detection that is inductively coupled to a "pickup" coil present in the MR reader. When the sample container is inside the MR reader it is in close proximity to the pickup coil and can be used to measure NMR signal. Alternatively, the disposable sample holder includes an RF coil for RF detection that is electrically connected to the MR reader upon insertion of the sample container. Thus, when the sample container is inserted into the MR reader the appropriate electrical connection is established to allow for detection. The number of uses available to each disposable sample holder can be controlled by disabling a fusable link included either in the electrical circuit within the disposable sample holder, or between the disposable sample holder and the MR reader. After the disposable sample holder is used to detect an NMR relaxation in a sample, the instrument can be configure to apply excess current to the fusable link, causing the link to break and rendering the coil inoperable. Optionally, multiple fusable links could be used, working in parallel, each connecting to a pickup on the system, and each broken individually at each use until all are broken and the disposable sample holder rendered inoperable.

Cartridge Units

The systems for carrying out the methods of the invention can include one or more cartridge units to provide a convenient method for placing all of the assay reagents and consumables onto the system. For example, the system may be customized to perform a specific function, or adapted to perform more than one function, e.g., via changeable cartridge units containing arrays of micro wells with customized magnetic particles contained therein. The system can include a replaceable and/or interchangeable cartridge containing an array of wells pre-loaded with magnetic particles, and designed for detection and/or concentration measurement of a particular analyte. Alternatively, the system may be usable with different cartridges, each designed for detection and/or concentration measurements of different analytes, or configured with separate cartridge modules for reagent and detection for a given assay. The cartridge may be sized to facilitate insertion into and ejection from a housing for the preparation of a liquid sample which is transferred to other units in the system (i.e., a magnetic assisted agglomeration unit, or an NMR unit). The cartridge unit itself could potentially interface directly with manipulation stations as well as with the MR reader(s). The cartridge unit can be a modular cartridge having an inlet module that can be sterilized independent of the reagent module.

For handling biological samples, such as blood samples, there are numerous competing requirements for the cartridge design, including the need for sterility for the inlet module to prevent cross contamination and false positive test results, and the need to include reagents in the package which cannot be easily sterilized using standard terminal sterilization techniques like irradiation. An inlet module for sample aliquoting can be designed to interface with uncapped vacutainer tubes, and to aliquot two a sample volume that can be used to perform, for example, a *candida* assay (see FIGS. 7D-7F). The vacutainer permits a partial or full fill. The inlet module has two hard plastic parts, that get ultrasonically welded together and foil sealed to form a network of channels to allow a flow path to form into the first well overflow to the second sample well. A soft vacutainer seal part is used to for a seal with the vacutainer, and includes a port for sample flow, and a venting port. To overcome the flow resistance once the vacutainer is loaded and inverted, some hydrostatic pressure is needed. Every time sample is removed from a sample well, the well will get replenished by flow from the vacutainer.

A modular cartridge can provide a simple means for cross contamination control during certain assays, including but not limited to distribution of PCR products into multiple detection aliquots. In addition, a modular cartridge can be compatible with automated fluid dispensing, and provides a way to hold reagents at very small volumes for long periods of time (in excess of a year). Finally, pre-dispensing these reagents allows concentration and volumetric accuracy to be set by the manufacturing process and provides for a point of care use instrument that is more convenient as it can require much less precise pipetting.

Figure 6:
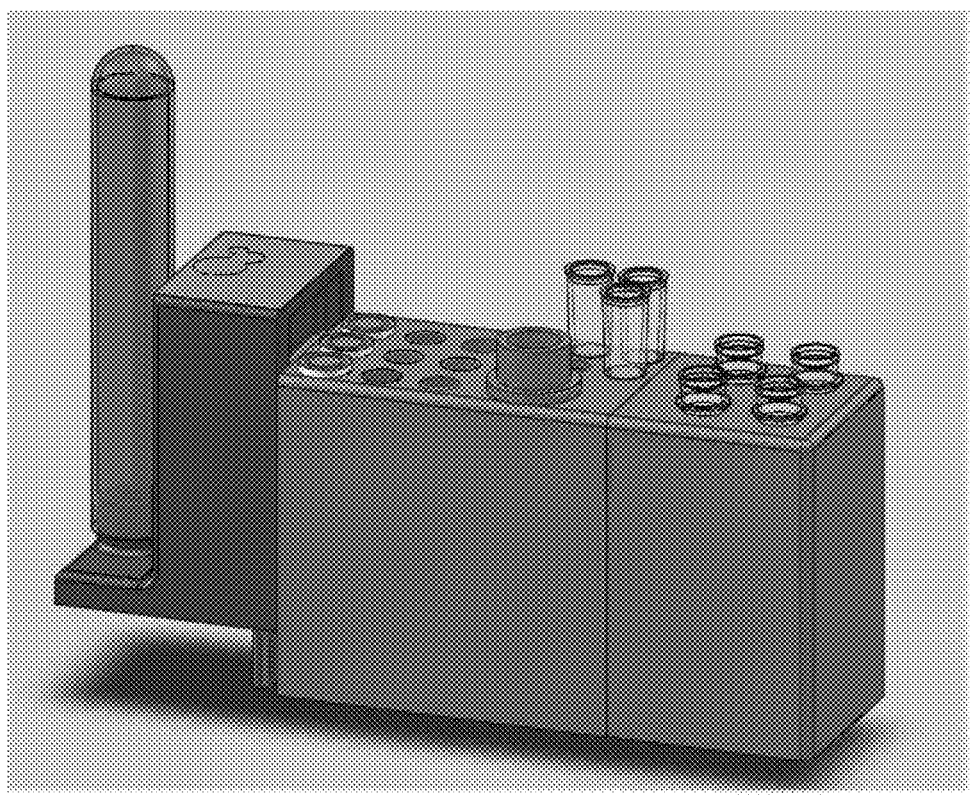
FIG. 6 illustrates a modular cartridge concept in sections that can be packaged and stored separately. This is done, for example, so that the inlet module (shown elevated with inverted Vacutainer tube attached) can be sterilized while the reagent holding module in the middle is not. This allows the component containing reagents to be the only refrigerated component.

The modular cartridge of the invention is a cartridge that is separated into modules that can be packaged and if necessary sterilized separately. They can also be handled and stored separately, if for example the reagent module requires refrigeration but the detection module does not. FIG. 6 shows a representative cartridge with an inlet module, a reagent module and a detection module that are snapped together. In this embodiment, the inlet module would be packaged separately in a sterile package and the reagent and detection modules would be pre-assembled and packaged together.

Figure 7A:
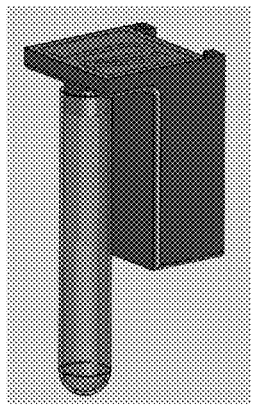
FIGS. 7A-7F depict a Vacutainer inlet module.
Figure 7B:
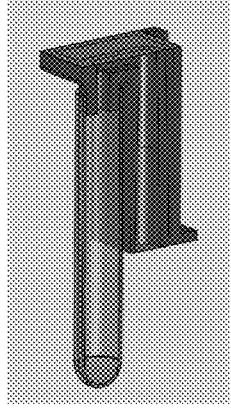
Figure 7C:
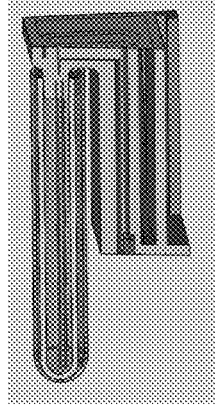
Figure 7D:
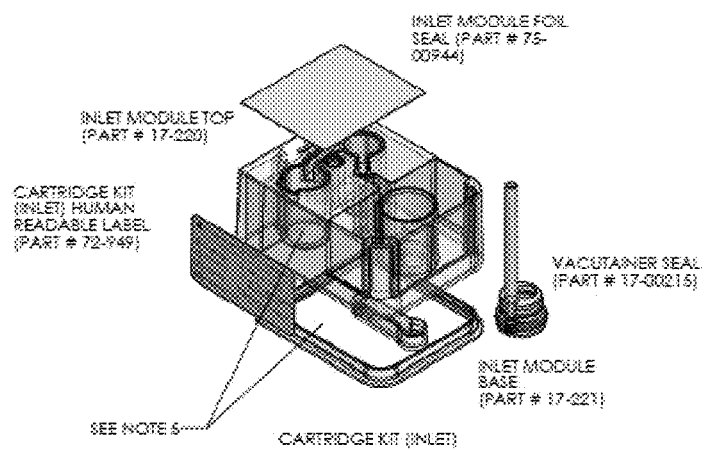
Figure 7E:
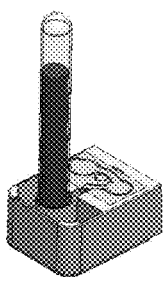
Figure 7F:
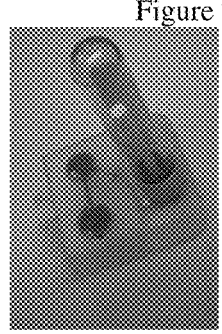
Figure 8:
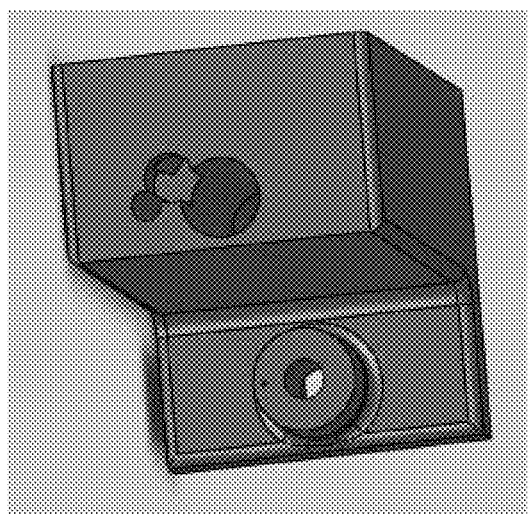
FIG. 8 depicts the sample inlet module with the foil seal removed. On the top, one can see the small air inlet port to the left, the larger sample well in the center and a port which connects them together. This port provides a channel through which air can flow once the foil seal is pierced. It also provides an overflow into the body of the module to allow excess blood to drain away and not spill over. This effectively meters the blood sample to the volume contained in the sample well.

During storage, the reagent module could be stored in a refrigerator while the inlet module could be stored in dry storage. This provides the additional advantage that only a very small amount of refrigerator or freezer space is required to store many assays. At time of use, the operator would retrieve a detection module and open the package, potentially using sterile technique to prevent contamination with skin flora if required by the assay. The Vacutainer tube is then decapped and the inverted inlet module is placed onto the tube as shown in FIG. 7A. This module has been designed to be easily moldable using single draw tooling as shown in FIGS. 7B and 7C and the top and bottom of the cartridge are sealed with foil to prevent contamination and also to close the channels. Once the tube has been re-sealed using the inlet module, the assembly is turned right side up and snapped onto the remainder of the cartridge. The inlet section includes a well with an overflow that allows sample tubes with between 2 and 6 ml of blood to be used and still provide a constant depth interface to the system automation. It accomplishes this by means of the overflow shown in FIG. 8, where blood that overflows the sampling well simply falls into the cartridge body, preventing contamination.

Figure 9A:
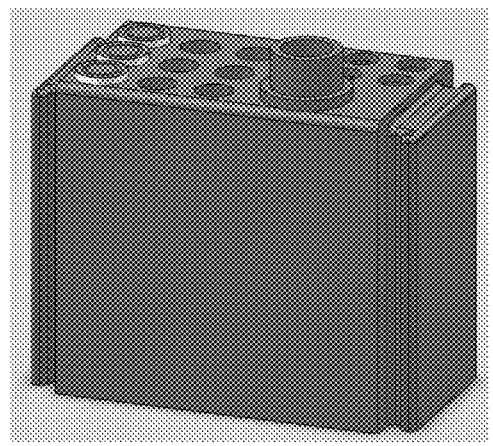
FIGS. 9A-9C depict a reagent module.
Figure 9B:
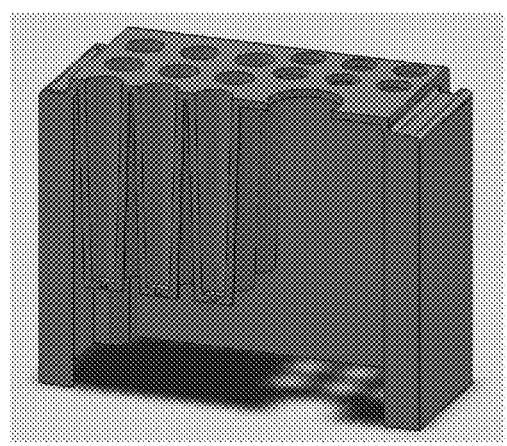
Figure 9C:
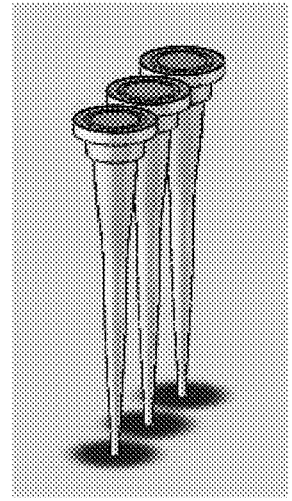

FIGS. 9A-9C show the means of storing precisely pipetted small volume reagents. The reagents are kept in pipette tips that are shown in FIG. 9C. These are filled by manufacturing automation and then are placed into the cartridge to seal their tips in tight fitting wells which are shown in a cutaway view FIG. 9B. Finally, foil seals are placed on the back of the tips to provide a complete water vapor proof seal. It is also possible to seal the whole module with a seal that will be removed by the operator, either in place of or in addition to the aforementioned foils. This module also provides storage for empty reaction vessels and pipette tips for use by the instrument while the detection module provides storage for capped 200 μl PCR vials used by the instrument to make final measurements from.

FIGS. 10-13C show an alternative embodiment of the detection module of the cartridge which is design to provide for contamination control during, for example, pipetting of post-PCR (polymerase chain reaction) products. This is required because the billion fold amplification produced by PCR presents a great risk of cross contamination and false positives. However, it is desirable to be able to aliquot this mixture safely, because low frequency analytes will have been amplified up and can be distributed for separate detection or identification. There are three ways in which this portion of the cartridge aids in contamination control during this aliquoting operation.

Figure 10A:
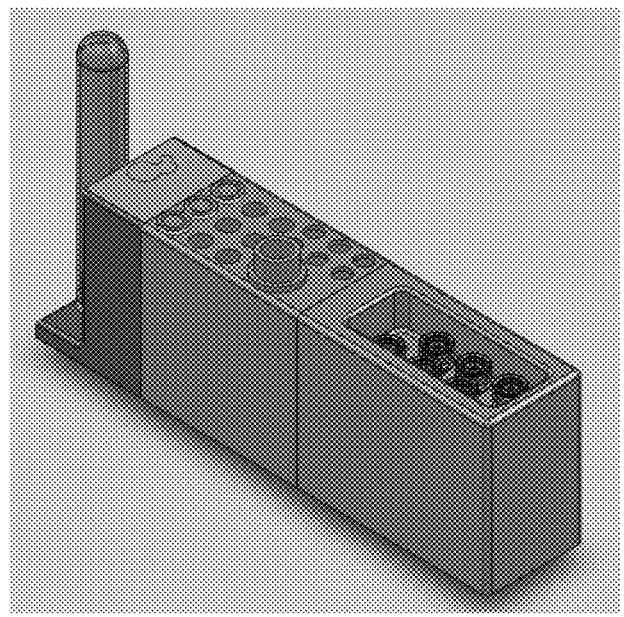
FIGS. 10A and 10B depict an alternative design of the modular cartridge, showing a detection module with a recessed well for use in assays that require PCR. Cross-contamination from PCR products is controlled in two ways. First, the seals that are on the detection tubes are designed to seal to a pipette tip as it penetrates. Second, the instrument provides air flow through the recessed well by means of holes in the well to ensure that any aerosol is carried down and does not travel throughout the machine.
Figure 10B:
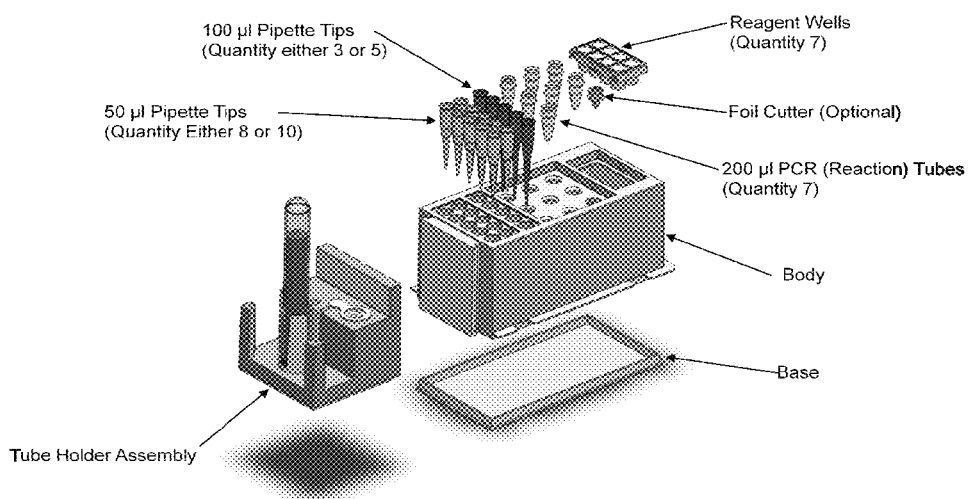
Figure 11:
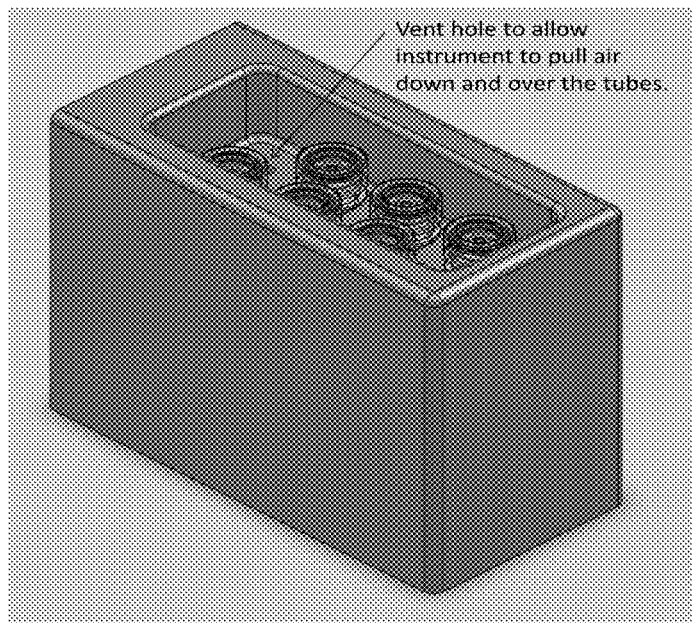
FIG. 11 depicts a detection module of cartridge showing detection tubes and one of the holes used to ensure air flow down and over the tubes during pipetting to help prevent aerosol escape.
Figure 12:
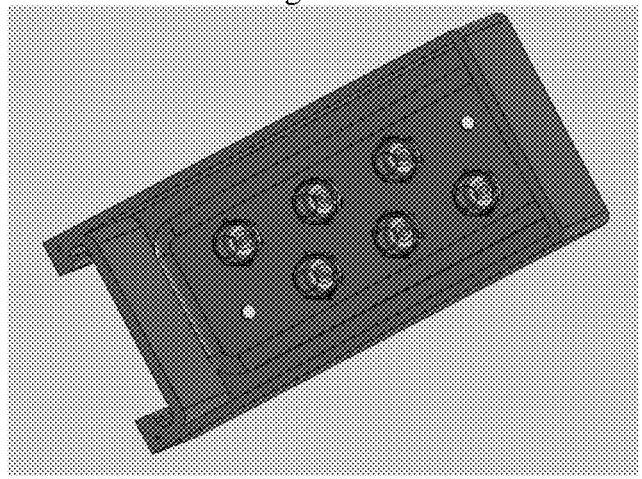
FIG. 12 depicts a bottom view of the detection module, showing the bottom of the detection tubes and the two holes used to ensure airflow. An optional filter can be inserted here to capture any liquid aerosol and prevent it from entering the machine. This filter could also be a sheet of a hydrophobic material like Gore-tex that will allow air but not liquids to escape.
Figure 13A:
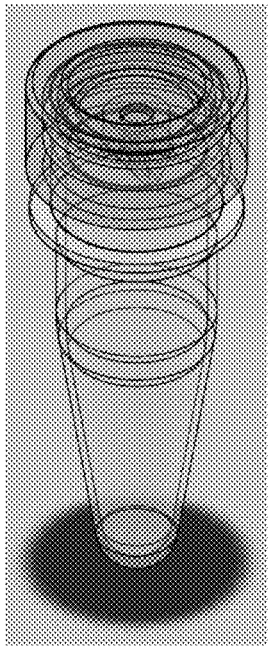
FIGS. 13A-13C depict a detection tube.
Figure 13B:
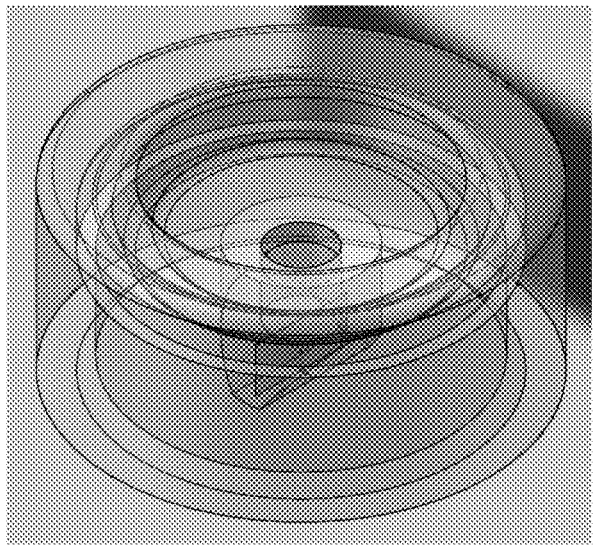
Figure 13C:
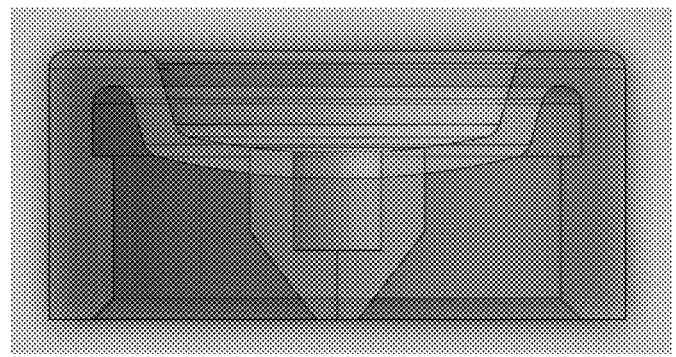

First, the cartridge contains a recessed well to perform the transfer operations in as shown in FIGS. 10A and 10B. Second, the machine provides airflow through this well and down into the cartridge through holes in the bottom of the well, as shown in FIG. 11. The depth of the well is such that a pipette tip will remain in the airflow and prevent any aerosol from escaping. FIG. 12 depicts a bottom view of the detection module, showing the bottom of the detection tubes and the two holes used to ensure airflow. An optional filter can be inserted here to capture any liquid aerosol and prevent it from entering the machine. This filter could also be a sheet of a hydrophobic material like Gore-tex that will allow air but not liquids to escape. Finally, there is a special seal cap on each 200 ul tube to provide a make then break seal for each pipette tip as it enters the vessel, as shown in FIGS. 13A-13C. It is contemplated that the pipette tip used for aliqouting be stored in this well at all, thus making it possible for the tip never to leave the controlled air flow region.

Figure 14A:
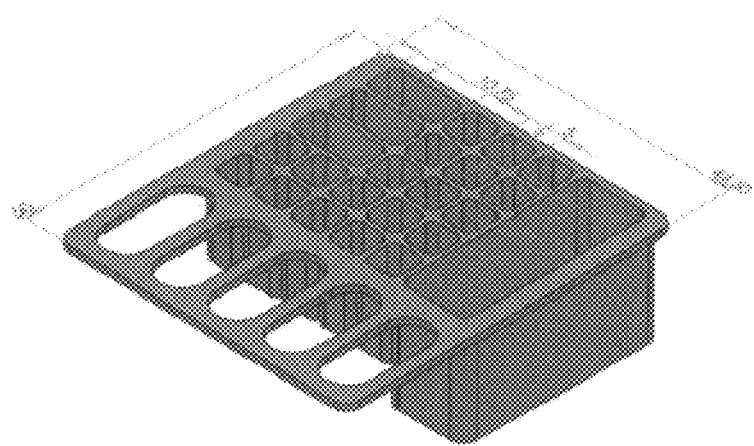
FIGS. 14A-14C depict a cartridge for performing a multiplexed assay.
Figure 14B:
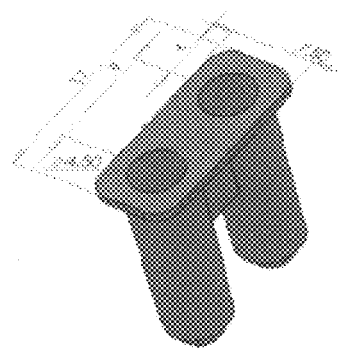
Figure 14C:
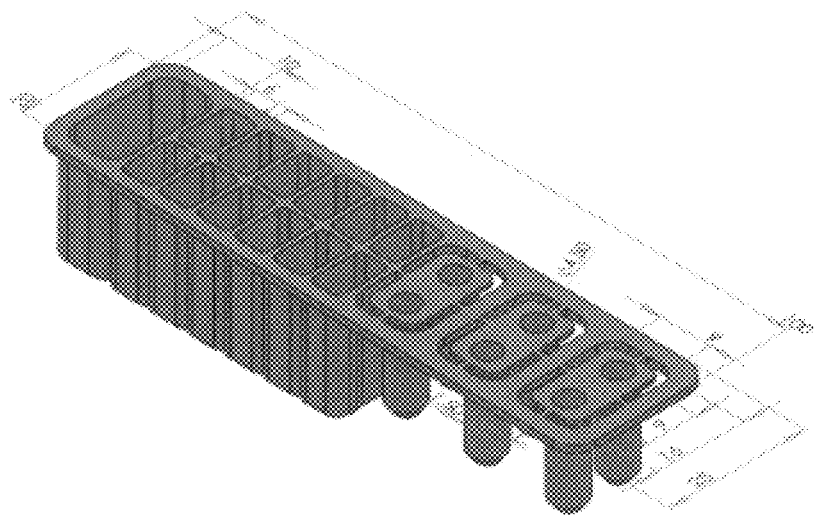

Alternatively, the modular cartridge is designed for a multiplexed assay. The challenge in multiplexing assays is combining multiple assays which have incompatible assay requirements (i.e., different incubation times and/or temperatures) on one cartridge. The cartridge format depicted in FIGS. 14A-14C allows for the combination of different assays with dramatically different assay requirements. The cartridge features two main components: (i) a reagent module (i.e., the reagent strip portion) that contains all of the individual reagents required for the full assay panel, and (ii) the detection module. The detection modules contain only the parts of the cartridge that carry through the incubation, and can carry single assays or several assays, as needed. The detection module depicted in FIG. 14B includes two detection chambers for a single assay, the first detection chamber as the control and the second detection chamber for the sample. This cartridge format is expandable in that additional assays can be added by including reagents and an additional detection module.

The operation of the module begins when the user inserts the entire or a portion of the cartridge into the instrument. The instruments performs the assay actuation, aliquoting the assays into the separate detection chambers. These individual detection chambers are then disconnected from the reagent strip and from each other, and progress through the system separately. Because the reagent module is separated and discarded, the smallest possible sample unit travels through the instrument, conserving internal instrument space. By splitting up each assay into its own unit, different incubation times and temperatures are possible as each multiplexed assay is physically removed from the others and each sample is individually manipulated.

The cartridge units of the invention can include one or more populations of magnetic particles, either as a liquid suspension or dried magnetic particles which are reconstituted prior to use. For example, the cartridge units of the invention can include a compartment including from $1 \times 10^6$ to $1 \times 10^{13}$ magnetic particles (e.g., from $1 \times 10^6$ to $1 \times 10^8$, $1 \times 10^7$ to $1 \times 10^9$, $1 \times 10^8$ to $1 \times 10^{10}$, $1 \times 10^9$ to $1 \times 10^{11}$, $1 \times 10^{10}$ to $1 \times 10^{12}$, $1 \times 10^{11}$ to $1 \times 13$, or from $1 \times 10^7$ to $5 \times 10^8$ magnetic particles) for assaying a single liquid sample.

MAA Units

The systems for carrying out the methods of the invention can include one or more magnetic assisted agglomeration (MAA) units to expedite agglomeration of the magnetic particles, allowing the assay reactions to reach completion (i.e., a stable reading) more quickly. The methods of the invention utilize functionalized magnetic particles to interact with analytes or multivalent binding agents (with multiple binding sites). Agglomeration of the magnetic particles alters the spin-spin relaxation rate of the sample when exposed to a magnetic field with a subsequent change in $T_2$ relaxation time.

For example, a field gradient can be used to sweep magnetic particles (MPs) through the liquid sample, allowing the magnetic particles to bind to either specific antibody (analyte-coated magnetic particles) or analyte (antibody-coated magnetic particles), and then concentrating the magnetic particles in a portion of the reaction chamber so as to facilitate particle-particle interactions that lead to specific, ligand/analyte induced agglomeration. The magnetic particles can optionally be allowed to diffuse in the absence of a magnetic field, sonicated, vortexed, shaken, or subjected to ultrasonic mixing to break apart non-specific magnetic particle interactions and re-distribute the magnetic particles back into the liquid sample. The process can be repeated to promote further specific agglomeration. This cycling of magnetic particles between being dispersed in the liquid sample and then concentrated at the side or bottom of the reaction vessel can be repeated as many times as necessary to maximize specific agglomeration, and consequently maximize the assay signal. The agglomeration state of the magnetic particles can be determined using an NMR relaxation measurement.

The MAA method of the invention can employ a gradient magnetic field in order to promote rapid magnetic particle-particle interactions. In one example, analyte coated magnetic particles are added to a solution with a multimeric-analyte specific ligand and placed in a gradient magnetic field. The magnetic field causes particles to concentrate on the side or bottom of a reaction vessel (highest magnetic field strength) resulting in enhanced particle-particle interaction and subsequent aggregation. Aggregation is measured by observing a change in, for example, $T_2$ signal. Improvements of 10 to 1000 percent signal change (e.g., from 10 to 30%, from 20% to 50%, from 40% to 80%, from 50% to 200%, from 100% to 500%, or from 500% to 1000% signal change) can be observed.

Traditional homogenous MAA takes advantage of dipole-dipole forces for assisting particle-particle interactions while particle dipoles are aligned with the magnetic field of the hMAA unit throughout the liquid sample. In contrast, gradient MAA rapidly concentrates magnetic particles to a locus, thereby greatly facilitating particle-particle interactions.

The cycling MAA approach described herein can accelerate the kinetics of magnetic particle-analyte clustering by (i) reducing the spatial entropy of the binding interaction step by maintaining local concentration of the magnetic particles, (ii) introducing localized mixing by magnet mediated transportation of the pellet from position to position, (iii) reducing shearing of the specific-bound clusters by reducing the need for more energetic dispersion methods, such as vortexing, and/or (iv) changing the magnetic field direction, and thereby causing a local dispersion and re-aggregation of magnetically clustered particles as they re-align their dipoles with the new magnetic field direction, and allowing the locally dispersed magnetic particles to form specific binding interactions involving the target analyte.

Figure 15:
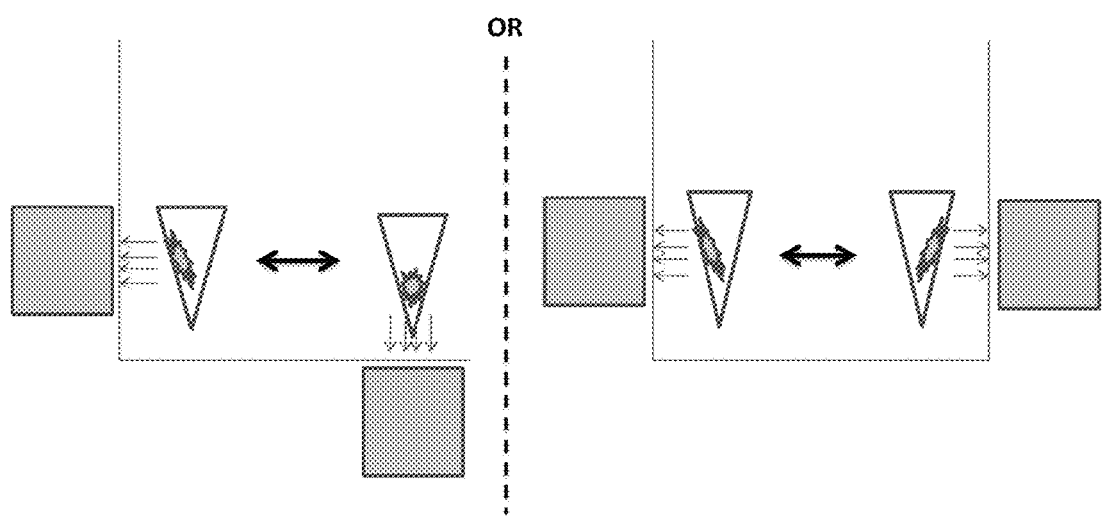
FIG. 15 is a scheme depicting one embodiment of the cycling gradient magnetic assisted agglomeration (gMAA) method of the invention. Two magnets are placed in two positions such that if the sample tube is placed close to the a region of strong magnetic field gradient produced by the first magnet, the magnetic particles will be drawn towards the direction of the field gradient produced by the first magnet, the sample tube is then placed next to the second magnet producing a field gradient, and the magnetic particles are drawn to the direction of the field gradient produced by second magnet. The cycle can be repeated until the aggregation reaction reaches a steady state (as observed by the change in the NMR relaxation rate of the sample); a smaller number of cycles can be used as well. A single magnet used to produce a field gradient can also be used, while for cycling the sample tube can be moved relative to the magnetic field gradient.

In one example, magnet assemblies producing a magnetic field gradient are placed in two positions relative to the assay tube, one to the side of the tube and one at the bottom of the tube (side-bottom configuration). Alternatively, the second magnet position can be located on a different side of the tube (side-side configuration). The tube then is moved to ensure exposure to one magnet followed by exposure to the other magnet (see FIG. 15). This has also been observed to produce a similar enhancement in clustering.

An alternate methodology is to rotate the liquid sample within a gradient magnetic field (or to rotate the magnetic field gradient about the sample) to simultaneously effect a re-orientation of particles within the pellet (relative to the remainder of the liquid sample) and to sweep the pellet through the liquid sample. The rate of rotation can be slow to allow the pellet of magnetic particles to largely remain held in proximity to the gradient magnet (rather than moving in concert with the solvent and analytes in liquid sample). For example, the rotation is typically slower than 0.0333 Hz (e.g., from 0.000833 Hz to 0.0333 Hz, from 0.00166 Hz to 0.0333 Hz, or from 0.00333 Hz to 0.0333 Hz), such that the particles are retained adjacent to the magnetic field source, while the remaining contents in the tube are rotated.

A single gradient magnet can be used, while the sample can be moved around the magnet (or use the same location close to the magnet and alternate with a position removed from the field of the single magnet. The magnet could be moved to the proximity or away from the sample.

The sample can be placed between magnets of the same field orientation for a "field averaging" effect in alternating fashion, in order to simplify the fabrication of a gMAA system (i.e., eliminate the need to carefully select magnets that generate same field profiles). For example a plurality of such magnets could be placed in a circular setup, and samples rotated via a carousel setup, from the first magnet to a null (small magnetic field exposure) to the second magnet etc. The rotary gMAA device can include a fixed baseplate to which an electric motor is attached, with a number of magnets mounted around it in a circular pattern. The magnets are spaced such that there is minimal magnetic interference between positions. A carousel capable of holding sample vials is attached to the motor shaft such that it rotates with the motor, exposing the samples to different magnetic field orientations from one position to the next. Any combination of side-oriented magnets, bottom-oriented magnets and positions with very low residual field (null) can be used. See FIG. 56A.

Figure 16:
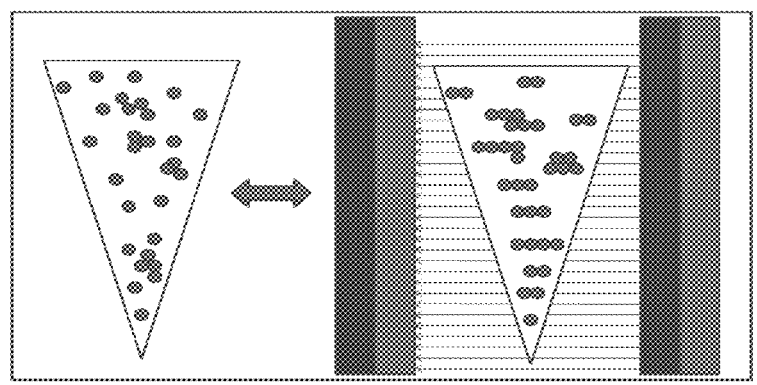
FIG. 16 is a scheme depicting a homogenous magnetic assisted agglomeration (hMAA) setup. On the left hand side, the magnetic particles are shown as dots in a partially clustered state. When exposed to a homogeneous magnetic field, as depicted on the right hand side, clustering of the magnetic particles is promoted as the magnetic particles form chains along the direction of the field produced by the hMAA setup. On the right hand side, the two magnets are represented by bars, to depict the formation of a standard dipole field. hMAA can also be used to evaluate the non-specific reversibility of a magnetic particle to assess its utility in an assay of the invention.

In another example, a homogenous field is used to expedite the agglomeration of magnetic particles in an assay of the invention. We have observed that hMAA is not as effective as exposure to field gradients in terms of concentrating particles and sweeping them through the sample, for timescales relevant to applications. However hMAA has advantages over the field gradient assisted agglomeration method. Using hMAA the magnetic particles are not enticed to move towards a specific location in the tube (see FIG. 16), minimizing non-specific trapping of particles within specific cluster fragments. Agitation after hMAA appears to minimize the non-specific binding. The hMAA treatment appears to enhance analyte induced clustering by increasing the collision frequency (a possible result of decreasing the particle's position and rotational entropies due to localization in an ordered state). The magnetic particles can subsequently be sonicated, vortexed, shaken (i.e., energy additions) to break apart any non-specific particle interactions and re-distribute the particles back into the sample. Additional mixing or gentle agitation during this process would potentially further increase the analyte-specific binding events for enhancement of the overall assay signal. The agglomeration/clustering state of the magnetic particles can be determined by monitoring changes in an NMR relaxation rate. It is also possible to rotate the liquid sample within a homogenous magnetic field (or to rotate a homogenous magnetic field about the sample) to expedite the aggregation of magnetic particles in a liquid sample.

We have observed that longer MAA times leads to increased changes in $T_2$, presumably from an increased fraction of clustered particles. We have found that cycled magnetic separation and resuspension leads to increased changes in $T_2$ and increased clustering. All of these observations point towards a system that must be driven to a steady state or completion (e.g., maximally clustered).

Figure 17:
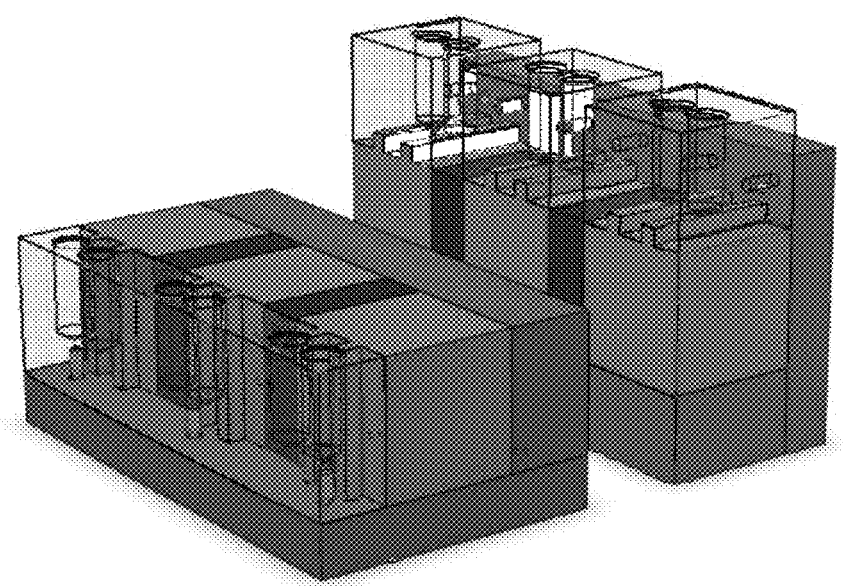
FIG. 17 depicts a gradient MAA unit configured to apply a gradient magnetic field to the side and to the bottom of a sample. The specific setup has magnets with a surface field of approximately 0.7 T, while the produced gradient is in the order of 0.25 T/mm. Similar gMAA units, covering a much bigger range of fields and gradients can be used.
Figure 18A:
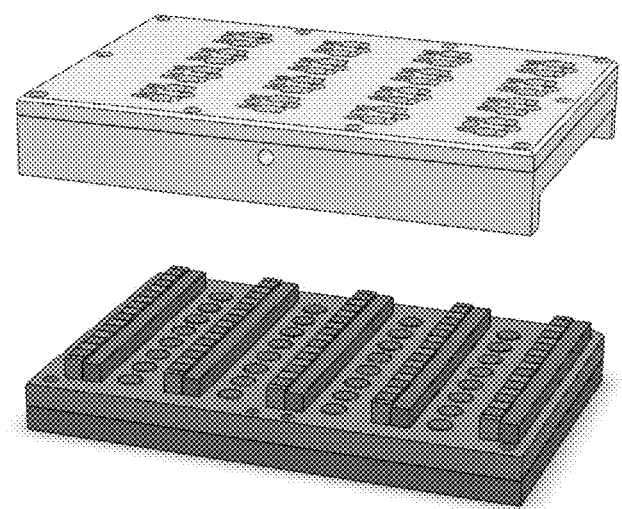
FIGS. 18A-18C depict a gradient MAA unit configured to apply a gradient magnetic field to the side and to the bottom of an array of samples.
Figure 18B:
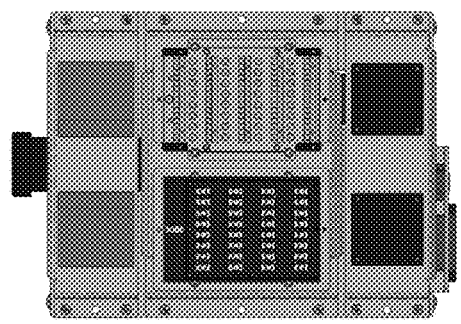
Figure 18C:
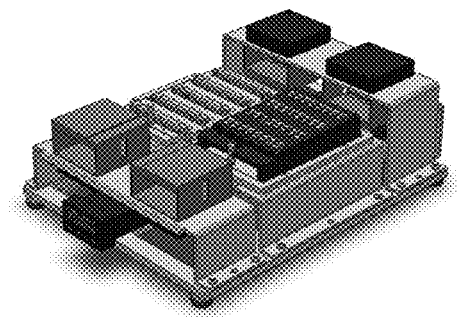
Figure 19A:
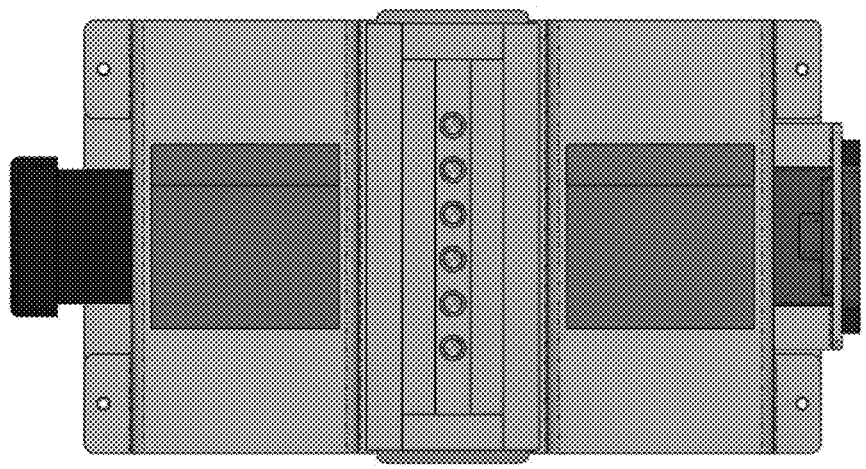
FIGS. 19A-19B depict a top view (FIG. 19A) and side view (FIG. 19B) of a homogenous MAA unit configured to apply a homogenous magnetic field to an array samples. Field strengths from 0.2-0.7 T can be used with homogeneity from 500 to 5000 ppm over the sample tube region.
Figure 19B:
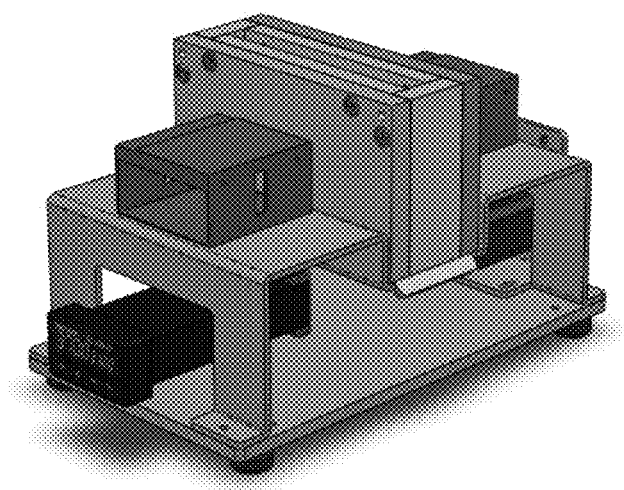

The systems of the invention can include one or more MAA units. For example, the MAA unit can be one or more magnets configured to apply a gradient magnetic field in a first direction relative to the liquid sample, and, after repositioning the sample chamber, apply a gradient magnetic field in a second direction relative to the liquid sample (see FIG. 17). Alternatively, the MAA unit can be an array of magnets configured to apply a gradient magnetic field to, e.g., the side of a liquid sample, and, after repositioning the sample chamber, to, e.g., the bottom of the liquid sample (see FIGS. 18A-18C). The systems of the invention can include an MAA unit configured to apply a homogenous magnetic field to one or more liquid samples (see FIGS. 19A and 19B).

Agitation Units

The systems for carrying out the methods of the invention can include one or more agitation units to break apart non-specific magnetic particle interactions and re-distribute the magnetic particles back into the liquid sample, or to simply agitate the sample tube to completely mix the assay reagents. For example, the agitation units can include a sonication, vortexing, shaking, or ultrasound station for mixing one or more liquid samples. Mixing could be achieved by aspiration dispensing or other fluid motion (e.g., flow within a channel). Also, mixing could be provided by a vibrating pipette or a pipette that moves from side to side within the sample tube.

The agitation unit can be vortexer or a compact vortexer each of which can be designed to provide a stable motion for the desired sample mixing.

Figure 20:
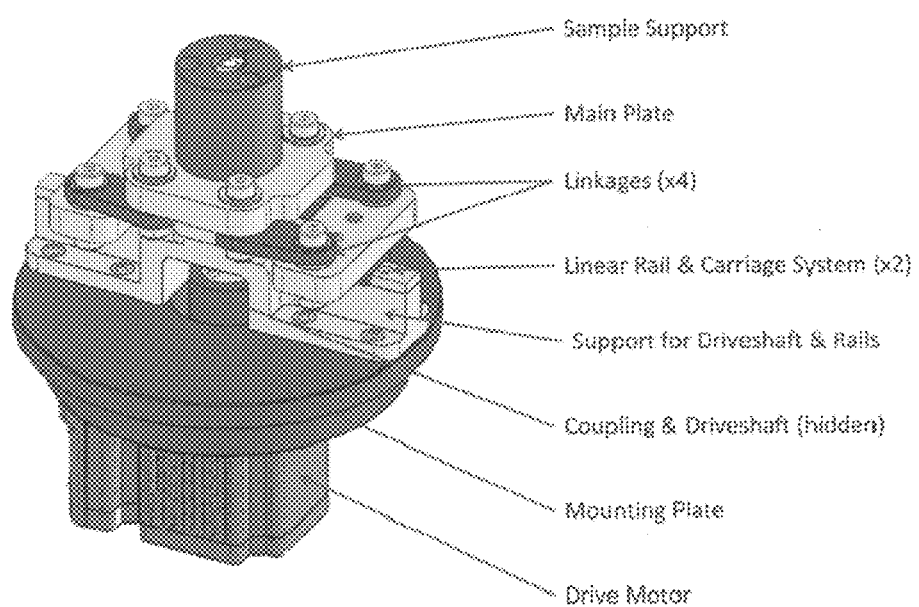
FIG. 20 is a drawing of a vortexer which includes the following components: (i) a sample support, (ii) a main plate, (iii) four linkages, (iv) linear rail and carriage system (×2), (v) a support for driveshaft and rails, (vi) coupling and driveshaft, (vii) a mounting plate, and (viii) a drive motor.

The vortexer includes the following components: (i) a sample support, (ii) a main plate, (iii) four linkages, (iv) linear rail and carriage system (×2), (v) a support for driveshaft and rails, (vi) coupling and driveshaft, (vii) a mounting plate, and (viii) a drive motor (see FIG. 20).

Figure 21:
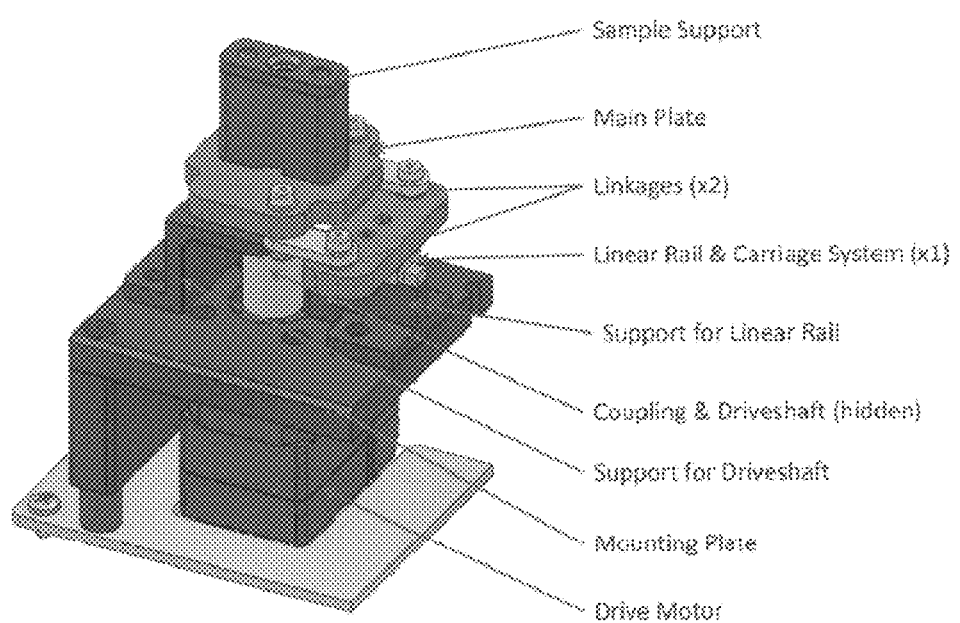
FIG. 21 is a drawing of a compact vortexer which includes the following components: (i) a sample support, (ii) a main plate, (iii) two linkages, (iv) linear rail and carriage system, (v) a support for linear rail, (vi) support for driveshaft, (vii) coupling and driveshaft, (viii) a mounting plate, and (ix) a drive motor.

The compact vortexer includes the following components: (i) a sample support, (ii) a main plate, (iii) two linkages, (iv) linear rail and carriage system (×1), (v) a support for linear rail, (vi) support for driveshaft, (vii) coupling and driveshaft, (viii) a mounting plate, and (ix) a drive motor (see FIG. 21).

The basic principle of motion for a vortexer is as follows: the driveshaft including one axis coaxial to the motor shaft, and a second that is offset and parallel to the motor shaft. When the motor shaft is attached to the driveshaft (typically through a helical coupling) and rotated, the offset axis of the driveshaft is driven in an orbital path. The typical offset is ¼" to produce a vortex in a single 0.2 mL sample tube, but this can be easily modified to effectively mix different sample volumes in other tube geometries.

Figure 23A:
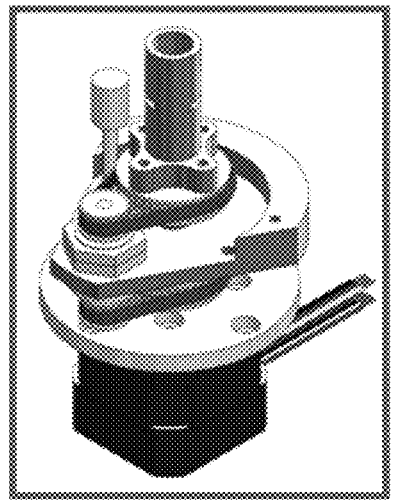
FIGS. 23A-23C are a series of drawings depicting a vortexer utilizing a planetary belt drive.
Figure 23B:
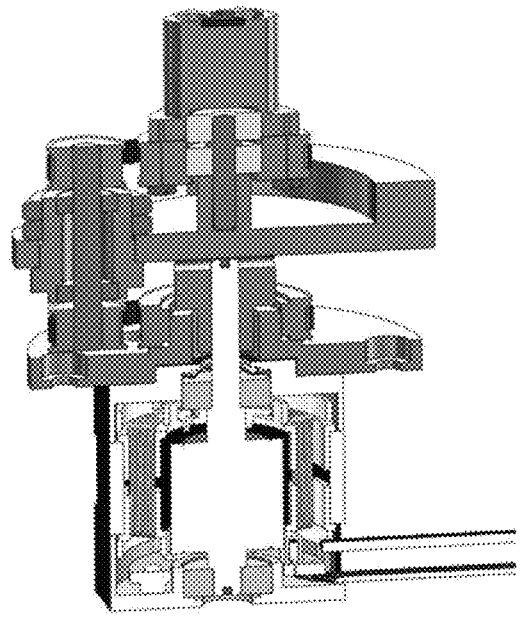
Figure 23C:
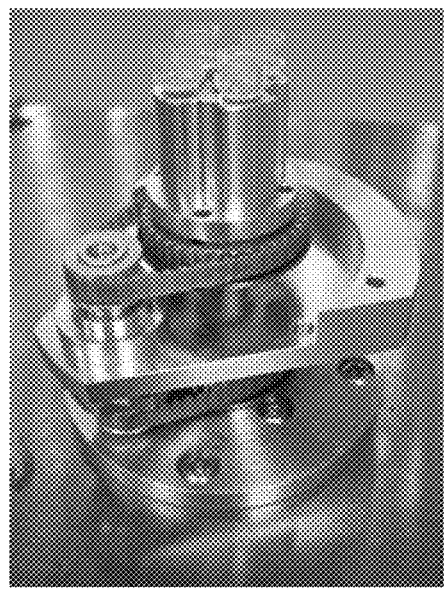

Alternatively, the vortexer can be of the type utilizing a planetary belt drive (see FIGS. 23A-23C). FIG. 23A is an overall view showing the vortexer configured for 1 large tube. FIG. 23B is a section view showing 2 tube holders for small tubes. FIG. 23C is an overall view of vortexer showing 4 tubes and a close-up of planetary belt drive mechanism.

The drive motor is typically a servo or stepper with an encoder. These motors have an "index" mark that allows the motor to find a specific point in its rotation. These index marks are used to home the system, and ensure that the sample can be returned to a known position after mixing. Knowing the exact position of the sample in the vortex station allows theses vortexers to be easily accessed by robotic actuators and thus integrated into an automated system. In lieu of index marks, sensing devices external could be employed (see FIG. 22A). These could be mechanical, magnetic, optical or other sensor that is capable of resolving the sample's position at any point along the system's path or at a fixed "home" position. In order to access a vortexers or centrifuge via a robotic sample holder/positioned, the system can include using an index mark or external switch to "home" the system to a set position after running, using a sensor which tracks the sample motion at all times, so that wherever the system stops the robot knows the position, and using a "find" method that includes finding a sample after running that would employ a vision system that tracks the sample. The guide mechanism is depicted in FIG. 22B. The main plate is connected to the offset axis of the drive shaft and is free to rotate. The plate follows the orbital path around and dictated by the motor shaft. One end of a linkage is connected to the main plate, and is free to rotate. Therefore in this way, the connected linkage is then connected to the orbital rotation of the drive shaft. The other end of the linkage is connected to a carriage of the linear rail system and is free to rotate. Thus this end of the linkage follows the linear path of the rail. Having two linkages connected to both the carriage and main plate in this way prevents the main plate from rotating around its own center. In the vortexer, two linkages are used on two sides of the main plate (4 in total) to balance and stabilize the entire system.

The two vortexers differ because of their use and design requirements. The compact version is designed to occupy less space, and requires less durability than this version because it is run at a lower speed, as limited by its smaller motor. For these reasons only two linkages are used to connect to a single linear rail system in the compact vortexer. This version needs to be capable of higher speeds, and a nearly continuous utilization due to the large throughput capability of this system. For these reasons a second carriage and set of linkages is added to balance the system, and increase its durability.

Systems

Figure 42:
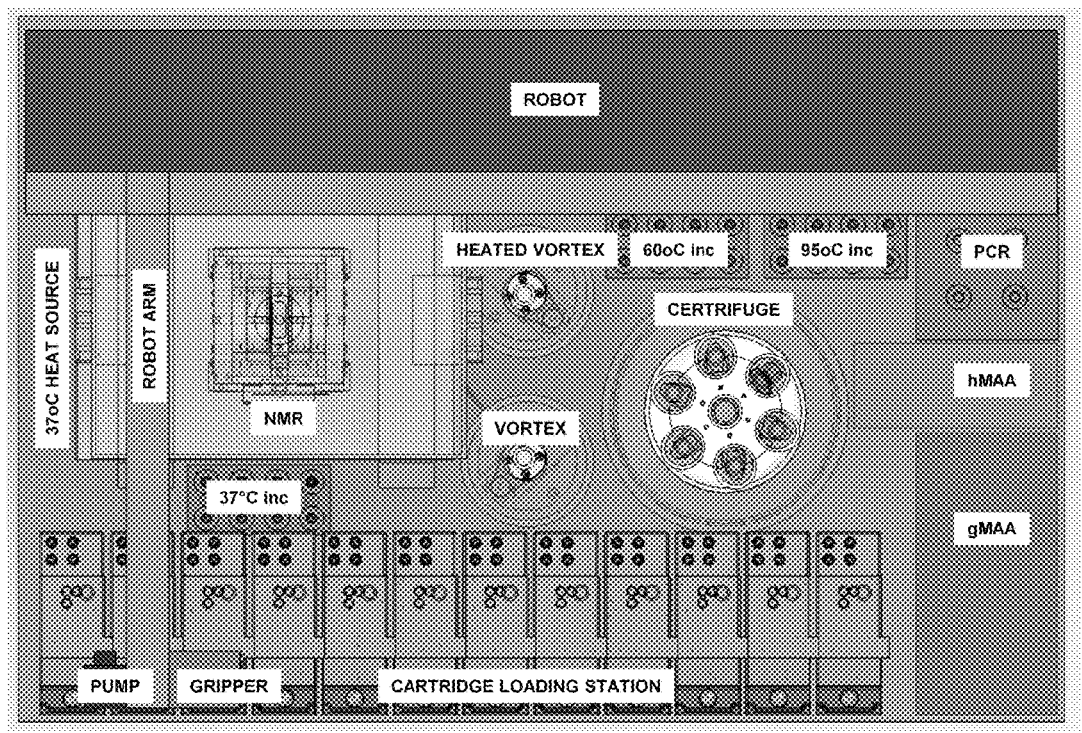
FIG. 42 is a sketch of a system of the invention including an NMR unit, a robotic arm, a hMAA unit, a gMAA unit, two agitation units, a centrifuge, and a plurality of heating blocks.

The systems for carrying out the methods of the invention can include one or more NMR units, MAA units, cartridge units, and agitation units. Such systems may further include other components for carrying out an automated assay of the invention, such as a PCR unit for the detection of oligonucleotides; a centrifuge, a robotic arm for delivery an liquid sample from unit to unit within the system; one or more incubation units; a fluid transfer unit (i.e., pipetting device) for combining assay reagents and a biological sample to form the liquid sample; a computer with a programmable processor for storing data, processing data, and for controlling the activation and deactivation of the various units according to a one or more preset protocols; and a cartridge insertion system for delivering pre-filled cartridges to the system, optionally with instructions to the computer identifying the reagents and protocol to be used in conjunction with the cartridge. See FIG. 42.

The systems of the invention can provide an effective means for high throughput and real-time detection of analytes present in a bodily fluid from a subject. The detection methods may be used in a wide variety of circumstances including, without limitation, identification and/or quantification of analytes that are associated with specific biological processes, physiological conditions, disorders or stages of disorders. As such, the systems have a broad spectrum of utility in, for example, drug screening, disease diagnosis, phylogenetic classification, parental and forensic identification, disease onset and recurrence, individual response to treatment versus population bases, and monitoring of therapy. The subject devices and systems are also particularly useful for advancing preclinical and clinical stage of development of therapeutics, improving patient compliance, monitoring ADRs associated with a prescribed drug, developing individualized medicine, outsourcing blood testing from the central laboratory to the home or on a prescription basis, and monitoring therapeutic agents following regulatory approval. The devices and systems can provide a flexible system for personalized medicine. The system of the invention can be changed or interchanged along with a protocol or instructions to a programmable processor of the system to perform a wide variety of assays as described herein. The systems of the invention offer many advantages of a laboratory setting contained in a desk-top or smaller size automated instrument.

The systems of the invention can be used to simultaneously assay analytes that are present in the same liquid sample over a wide concentration range, and can be used to monitor the rate of change of an analyte concentration and/or or concentration of PD or PK markers over a period of time in a single subject, or used for performing trend analysis on the concentration, or markers of PD, or PK, whether they are concentrations of drugs or their metabolites. For example, if glucose were the analyte of interest, the concentration of glucose in a sample at a given time as well as the rate of change of the glucose concentration over a given period of time could be highly useful in predicting and avoiding, for example, hypoglycemic events. Thus, the data generated with the use of the subject fluidic devices and systems can be utilized for performing a trend analysis on the concentration of an analyte in a subject.

For example, a patient may be provided with a plurality of cartridge units to be used for detecting a variety of analytes at predetermined times. A subject may, for example, use different cartridge units on different days of the week. In some embodiments the software on the system is designed to recognize an identifier on the cartridge instructing the system computer to run a particular protocol for running the assay and/or processing the data. The protocols on the system can be updated through an external interface, such as an USB drive or an Ethernet connection, or in some embodiments the entire protocol can be recorded in the barcode attached to the cartridge. The protocol can be optimized as needed by prompting the user for various inputs (i.e., for changing the dilution of the sample, the amount of reagent provided to the liquid sample, altering an incubation time or MAA time, or altering the NMR relaxation collection parameters).

A multiplexed assay can be performed using a variety of system designs. For example, a multiplexed assay can performed using any of the following configurations: (i) a spatially-based detection array can be used to direct magnetic particles to a particular region of a tube (i.e., without aggregation) and immobilize the particles in different locations according to the particular analyte being detected. The immobilized particles are detected by monitoring their local effect on the relaxation effect at the site of immobilization. The particles can be spatially separated by gravimetric separation in flow (i.e., larger particles settling faster along with a slow flow perpendicular to gravity to provide spatial separation based on particle size with different magnetic particle size populations being labeled with different targets). Alternatively, of capture probes can be used to locate magnetic particles in a particular region of a tube (i.e., without aggregation) and immobilize the particles in different locations (i.e., on a functionalized surface, foam, or gel). Optionally, the array is flow through system with multiple coils and magnets, each coil being a separate detector that has the appropriate particles immobilized within it, and the presence of the analyte detected with signal changes arising from clustering in the presence of the analyte. Optionally, once the particles are spatially separated, each individual analyte in the multiplexed assay can be detected by sliding a coil across the sample to read out the now spatially separated particles. (ii) A microfluidic tube where the sample is physically split amongst many branches and a separate signal is detected in each branch, each branch configured for detection of a separate analyte in the multiplexed assay. (iii) An array of 96 wells (or less or more) where each well has its own coil and magnet, and each well is configured for detection of a separate analyte in the multiplexed assay. (iv) A sipper or flow through device with multiple independently addressable coils inside one magnet or inside multiple mini magnets that can be used for sequential readings, each reading being a separate reaction for detection of a separate analyte in the multiplexed assay. (v) A sipper or flow through device with multiple independently addressable wells on a plate inside one magnet or inside multiple mini magnets that can be used for sequential readings using a single sided coil that can be traversed along the plate, each reading being a separate reaction for detection of a separate analyte in the multiplexed assay. (vi) A tube containing two compartments read simultaneously, resulting in one relaxation curve which is then fit using bi-exponential fitting to produce the separate readings for the multiplexed array. (vii) A microfluidics system where each droplet of liquid is moved around individually, to produce readings for the multiplexed array. (viii) Sequential measurements using magnetic separation and resuspension requires novel binding probes or the ability to turn them on and off. This method would be used for nucleic acid analytes in which turn on/off mechanism is based mostly on melting temperature (at higher temperatutres hairpin loops relax, denaturation of double strand binding), and hybridization will occur at different temperatures. (ix) Individual capillaries, each equipped with dried particles within them, allow for small volume rapid multiplexing of one small aliquot. The dried particles are spatially separated, and this spatial separation permits the MR Reader to read each capillary tube independently. (x) Binding moieties conjugated to nanoparticles are placed in a gel or other viscous material forming a region and analyte specific viscous solution. The gel or viscous solution enhances spatial separation of more than one analyte in the starting sample because after the sample is allowed to interact with the gel, the target analyte can readily diffuse through the gel and specifically bind to a conjugated moiety on the gel or viscous solution held nanoparticle. The clustering or aggregation of the specific analyte, optionally enhanced via one of the described magnetic assisted agglomeration methods, and detection of analyte specific clusters can be performed by using a specific location NMR reader. In this way a spatial array of nanoparticles, and can be designed, for example, as a 2d array. (xi) Magnetic particles can be spotted and dried into multiple locations in a tube and then each location measured separately. For example, one type of particle can be bound to a surface and a second particle suspended in solution, both of which hybridize to the analyte to be detected. Clusters can be formed at the surface where hybridization reactions occur, each surface being separately detectable. (xii) A spotted array of nucleic acids can be created within a sample tube, each configured to hybridize to a first portion of an array of target nucleic acids. Magnetic particles can be designed with probes to hybridize to a second portion of the target nucleic acid. Each location can be measured separately. Alternatively, any generic beacon or detection method could be used to produce output from the nucleic acid array. (xiii) An array of magnetic particles for detecting an array of targets can be included in a single sample, each configured (e.g., by size, or relaxation properties) to provide a distinct NMR relaxation signature with aggregate formation. For example, each of the particles can be selected to produce distinct T2 relaxation times (e.g., one set of particles covers 10-200 ms, a second set from 250-500 a third set from 550-1100, and so on). Each can be measured as a separate band of relaxation rates. (xiv) For detection of analytes of various size or magnetic particles, or aggregates of various size, a single sample with multiple analytes and magnetic particles can undergo separation in the presence of a magnetic or electric field (i.e., electrophoretic separation of magnetic particles coated with analytes), the separate magnetic particles and/or aggregates reaching the site of a detector at different times, accordingly. (xv) The detection tube could be separated into two (or more) chambers that each contain a different nanoparticle for detection. The tube could be read using the reader and through fitting a multiple exponential curve such as $A*\exp(T2\_1)+B*\exp(T2\_2)$, the response of each analyte could be determined by looking at the relative size of the constants A and B and $T2\_1$ and $T2\_2$. (xvi) Gradient magnetic fields can be shimmed to form narrow fields. Shim pulses or other RF based Shimming within a specific field can be performed to pulse and receive signals within a specific region. In this way one could envision a stratification of the Rf pulse within a shim and specific resonance signals could be received from the specific shim. While this method relies on shimming the gradient magnetic field, multiplexing would include then, to rely on one of the other methods described to get different nanoparticles and the clusters to reside in these different shims. Thus there would be two dimensions, one provided by magnetic field shims and a second dimension provided by varying nanoparticle binding to more than one analyte. Nanoparticles having two distinct NMR relaxation signals upon clustering with an analyte may be employed in a multiplexed assay. In this methods, the observation that small particles (30-200 nm) cause a decrease in T2 with clustering whereas large particles (>800 nm) cause an increase with clustering. The reaction assay is designed as a competitive reaction, so that with the addition of the target it changes the equilibrium relaxation signal. For example, if the T2 relaxation time is shorter, clusters forming of analyte with small particles are forming. If on the other hand, the T2 relaxation becomes longer, clusters of analyte with larger particles are forming. It's probably useful to change the density/viscosity of the solution with additives such as trehalose or glucose or glycerol to make sure the big particles stay in solution. One nanoparticle having binding moieties to a specific analyte for whose T2 signal is decreased on clustering may be combined with a second nanoparticle having a second binding moiety to a second analyte for whose T2 signal is increased on clustering. In the case for which the sample is suspected to have both analytes and the clustering reaction may cancel each other out (the increased clustering cancels the decreased clustering), one could envision an ordering of the analysis, i.e. addition of competitive binding agents to detect a competitive binding and thus T2 signal that would be related to the presence/absence of the analyte of interest in the sample. Alternatively, if the increased clustering cancels the decreased clustering in this multiplexing format, one could envision use of different relaxation pulse sequences or relaxation determinants to identify the presence/absence or concentration of analyte in the sample. (xvii) Precipitation measurement of particles. In this method, multiple types of particles designed to capture different target sequences of nucleic acid are designed So that the particle size is small enough that the particles bound with analyte remain suspended in solution. Sequential addition of an "initiator" sequence that is complementary to a nucleic acid sequence conjugated to a second set of particles (a larger particle, not necessarily having magnetic properties) and contains a complementary sequence to the captured target DNA sequence. After hybridization, clusters will form if the target DNA sequence is present, e.g. the magnetic nanoparticle conjugated with probe anneals to one specific sequence on the target analyte and the other particle binds to another sequence on the target nucleic acid sequence. These clusters will be big enough to precipitate (this step may require a centrifugation step). In the same reaction, and simulataneously, one could design an additional magnetic particle, second particle set to anneal with a second nucleic acid sequence for which formation of the magnetic nanoparticle-analyte-second particle clusters do not precipitate. In this way sequential addition of particles can result in differential signaling. (xvii) One possible different detection technique includes phase separated signals, which would stem from differing RF coil pulse sequences that are optimized for the conjugated nanoparticle-analyte interaction. Optimally, this could be achieved with multiple coils in an array that would optimize the ability of the different RF pulses and relaxation signal detection to be mapped and differentiated to ascertain the presence/absence of more than one analyte. Multiplexing may also employ the unique characteristic of the nanoparticle-analyte clustering reaction and subsequent detection of water solvent in the sample, the ability of the clusters to form various "pockets" and these coordinated clusters to have varying porosity. For example, linkers having varying length or conformational structures can be employed to conjugate the binding moiety to the magnetic nanoparticle. In this way, more than one type of cluster formed in the presence of an analyte could be designed having the ability of differing solvent water flow, and thus relaxation signal differences, through the aggregated nanoparticle-analyte-nanoparticle formation. In this way, two or more linker/binding moiety designs would then allow for detection of more than one analyte in the same sample. (xviii) The methods of the invention can include a fluorinated oil/aqueous mixture for capturing particles in an emulsion. In this design one hydrophobic capture particle set and an aqueous capture set are used, the hydrophic capture particle set is designed to bind and aggregate more readily in an hydrophobic environment, whereas the aqueous capture particle set is designed to bind and aggregate in an aqueous environment. Introduction of an analyte containing sample having specific analytes that will bind to either the hydrophic or aqueous particle, and subsequent mixing in the detection tube having both hydrophobic and aqueous solvents, binding and clustering would then result in a physical separation of analytes to either the aqueous or hydrophobic phase. The relaxation signal could be detected in either solution phase. In the event that the analytes and nanoparticles designed in this manner are physically found in an emulsion created by the mixing of the hydrophic/aqueous phases, relaxation curves would be distinguishable in the emulsion phase. The detection tube may have a capsular design to enhance the ability to move the capsules through an MR detector to read out the signal. Further, additional use of a fluorescent tag to read out probe identity may be employed, i.e. in the case of two different analytes in the same aqueous or hydrophic phase, the addition of a fluorescent tag can assist determination of the identify of the analyte. This method is amenable in samples for which limited isolation or purification of the target analyte away from the other material in the sample because the described resonance signals are independent of sample quality. Further, the addition of the fluorescent tag can be added in much higher concentrations that usually added in typical fluorescent studies because these tags will never interfere with the relaxation measurements. In this method, oligonucleotide capture probes that are conjugated to the magnetic nanoparticles are designed so that specific restriction endonuclease sites are located within the annealed section. After hybridization with the sample forming nanoparticle-analyte clusters, a relaxation measurement then provides a base signal. Introduction of a specific restriction endonuclease to the detection tube and incubation will result in a specific reduction of the nanoparticle/analyte cluster after restriction digestion has occurred. After a subsequent relaxation measurement, the pattern of signal and restriction enzyme digestion, one can deduce the target. (xix) In a combined method, a magnetic nanoparticle is conjugated with two separate and distinct binding moieties, i.e. an oligonucleotide and an antibody. This nanoparticle when incubated with a sample having both types of analytes in the sample will form nanoparticle-analyte complexes, and a baseline T2 relaxation signal will be detectable. Subsequent addition of a known concentration of one of the analytes can be added to reduce the clustering formed by that specific analyte from the sample. After known analyte addition a subsequent T2 relaxation signal is detected and the presence/absence of the sample analyte can be surmised. Further, a second analyte can be added to compete with the analyte in the sample to form clusters. Again, after a subsequent T2 relaxation signal detection the presence/absence of the second sample analyte can be surmised. This can be repeated.

Broadly a multiplexed assay employing the methods of this invention can be designed so that the use of one non-superparamagnetic nanoparticle to generate clusters with analyte from a sample, will reduce the overall Fe2+ in assay detection vessel and will extend the dynamic range so that multiple reactions can be measured in the same detection vessel.

Multiplexing nucleic acid detection can make use of differing hybridization qualities of the conjugated magnetic nanoparticle and the target nucleic acid analyte. For example, capture probes conjugated to magnetic nanoparticles can be designed so that annealing the magnetic nanoparticle to the target nucleic acid sequence is different for more than one nucleic acid target sequence. Factors for the design of these different probe-target sequences include G-C content (time to form hybrids), varying salt concentration, hybridization temperatures, and/or combinations of these factors. This method then would entail allowing various nucleic acid conjugated magnetic nanoparticles to interact with a sample suspected of having more than one target nucleic acid analyte. Relaxation times detected after various treatments, i.e. heating, addition of salt, hybridization timing, would allow for the ability to surmise which suspected nucleic acid sequence is present or absent in the sample.

Use complimentary amplicons to block one reaction and allow serial hybridizations. In this method, universal amplification primers are used to amplify more than one specific nucleic acid sequence in the stargin sample, forming an amplicon pool. Specific oligonucleotide conjugated to magnetic nanoparticles are added to the sample and a relaxation measurement is taken. The sample is then exposed to a temperature to melt the oligonucleotide-analyte interaction and addition of a oligonucleotide that is not attached to a magnetic nanoparticle is added to compete away any analyte binding to the magnetic nanoparticle. A second magnetic nanoparticle having a second oligonucleotide conjugated to it is then added to form clusters with a second specific target nucleic acid analyte. Alternatively, the method could have a step prior to the addition of the second magnetic nanoparticle that would effectively sequester the first magnetic nanoparticle from the reaction vessel, i.e. exposing the reaction vessel to a magnetic field to move the particles to an area that would not be available to the second, or subsequent reaction.

Each of the multiplexing methods above can employ a step of freezing the sample to slow diffusion and clustering time and thus alter the measurement of the relaxation time. Slowing the diffusion and clustering of the method may enhance the ability to separate and detect more than one relaxation time Each of the multiplexing methods above can make use of sequential addition of conjugated nanoparticles followed by relaxation detection after each addition. After each sequential addition, the subsequent relaxation baseline becomes the new baseline from the last addition and can be used to assist in correlating the relaxation time with presence/absence of the analyte or analyte concentration in the sample.

Hidden capture probes. In this method of multiplexing, oligonucleotides conjugated to the magnetic nanoparticles are designed so that secondary structure or a complementary probe on the surface of the particle hides or covers the sequence for hybridization initially in the reaction vessel. These hidden hybridization sequences are then exposed or revealed in the sample vessel spatially or temporally during the assay. For example, as mentioned above, hybridization can be affected by salt, temperature and time to hybridize. Thus, in one form of this method, secondary or complementary structures on the oligonucleotide probe conjugated to the magnetic nanoparticle can be reduced or relaxed to then expose or reveal the sequence to hybridize to the target nucleic acid sample. Further, secondary structures could be reduced or relaxed using a chemical compound, e.g. DMSO. Another method to selectively reveal or expose a sequence for hybridization of the oligonucleotide conjugated nanoparticle with the target analyte is to design stem-loop structures having a site for a restriction endonuclease; subsequent digestion with a restriction endonuclease would relax the stem-loop structure and allow for hybridization to occur. Alternatively, a chemical cut of the stem-loop structure, releasing one end could make the sequence free to then hybridize to the target nucleic acid sequence.

Where the multiplexed array is configured to detect a target nucleic acid, the assay can include a multiplexed PCR to generate different amplicons and then serially detect the different reactions.

The multiplexed assay optionally includes a logical array in which the targets are set up by binary search to reduce the number of assays required (e.g., gram positive or negative leads to different species based tests that only would be conducted for one group or the other).

The systems of the invention can run a variety of assays, regardless of the analyte being detected from a bodily fluid sample. A protocol dependent on the identity of the cartridge unit being used can be stored on the system computer. In some embodiments, the cartridge unit has an identifier (ID) that is detected or read by the system computer, or a bar code (1D or 2D) on a card that then supplies assay specific or patient or subject specific information needed to be tracked or accessed with the analysis information (e.g., calibration curves, protocols, previous analyte concentrations or levels). Where desired, the cartridge unit identifier is used to select a protocol stored on the system computer, or to identify the location of various assay reagents in the cartridge unit. The protocol to be run on the system may include instructions to the controller of the system to perform the protocol, including but not limited to a particular assay to be run and a detection method to be performed. Once the assay is performed by the system, data indicative of an analyte in the biological sample is generated and communicated to a communications assembly, where it can either be transmitted to the external device for processing, including without limitation, calculation of the analyte concentration in the sample, or processed by the system computer and the result presented on a display readout.

For example, the identifier may be a bar code identifier with a series of black and white lines, which can be read by a bar code reader (or another type of detector) upon insertion of the cartridge unit. Other identifiers could be used, such as a series of alphanumerical values, colors, raised bumps, RFID, or any other identifier which can be located on a cartridge unit and be detected or read by the system computer. The detector may also be an LED that emits light which can interact with an identifier which reflects light and is measured by the system computer to determine the identity of a particular cartridge unit. In some embodiments, the system includes a storage or memory device with the cartridge unit or the detector for transmitting information to the system computer.

Thus, the systems of the invention can include an operating program to carry out different assays, and cartridges encoded to: (i) report to the operating program which pre-programmed assay was being employed; (ii) report to the operating program the configuration of the cartridges; (iii) inform the operating system the order of steps for carrying out the assay; (iv) inform the system which pre-programmed routine to employ; (v) prompt input from the user with respect to certain assay variables; (vi) record a patient identification number (the patient identification number can also be included on the Vacutainer holding the blood sample); (vii) record certain cartridge information (i.e., lot #, calibration data, assays on the cartridge, analytic data range, expiration date, storage requirements, acceptable sample specifics); or (viii) report to the operating program assay upgrades or revisions (i.e., so that newer versions of the assay would occur on cartridge upgrades only and not to the larger, more costly system).

The systems of the invention can include one or more fluid transfer units configured to adhere to a robotic arm (see FIGS. 43A-43C). The fluid transfer unit can be a pipette, such as an air-displacement, liquid backed, or syringe pipette. For example, a fluid transfer unit can further include a motor in communication with a programmable processor of the system computer and the motor can move the plurality of heads based on a protocol from the programmable processor. Thus, the programmable processor of a system can include instructions or commands and can operate a fluid transfer unit according to the instructions to transfer liquid samples by either withdrawing (for drawing liquid in) or extending (for expelling liquid) a piston into a closed air space. Both the volume of air moved and the speed of movement can be precisely controlled, for example, by the programmable processor. Mixing of samples (or reagents) with diluents (or other reagents) can be achieved by aspirating components to be mixed into a common tube and then repeatedly aspirating a significant fraction of the combined liquid volume up and down into a tip. Dissolution of reagents dried into a tube can be done is similar fashion.

A system can include one or more incubation units for heating the liquid sample and/or for control of the assay temperature. Heat can be used in the incubation step of an assay reaction to promote the reaction and shorten the duration necessary for the incubation step. A system can include a heating block configured to receive a liquid sample for a predetermined time at a predetermined temperature. The heating block can be configured to receive a plurality of samples.

Figure 44A:
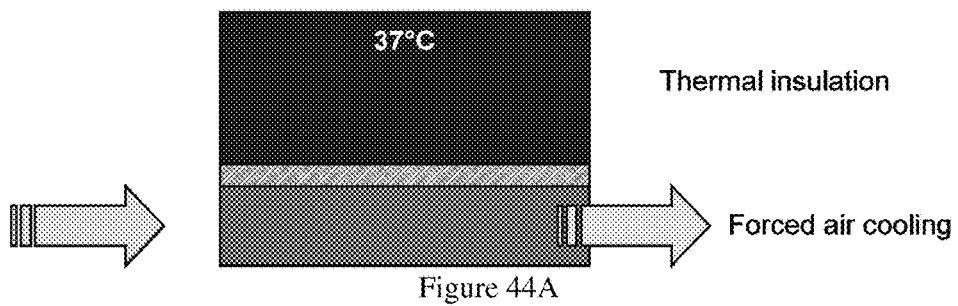
FIGS. 44A and 44B are sketches showing how a system of the invention can be designed to regulate the temperature of the working space.
Figure 44B:

The system temperature can be carefully regulated. For example, the system includes a casing kept at a predetermined temperature (i.e., 37° C.) using stirred temperature controlled air. Waste heat from each of the units will exceed what can be passively dissipated by simple enclosure by conduction and convection to air. To eliminate waste heat, the system can include two compartments separated by an insulated floor. The upper compartment includes those portions of the components needed for the manipulation and measurement of the liquid samples, while the lower compartment includes the heat generating elements of the individual units (e.g., the motor for the centrifuge, the motors for the agitation units, the electronics for each of the separate units, and the heating blocks for the incubation units). The lower floor is then vented and forced air cooling is used to carry heat away from the system. See FIGS. 44A and 44B.

Figure 45A:
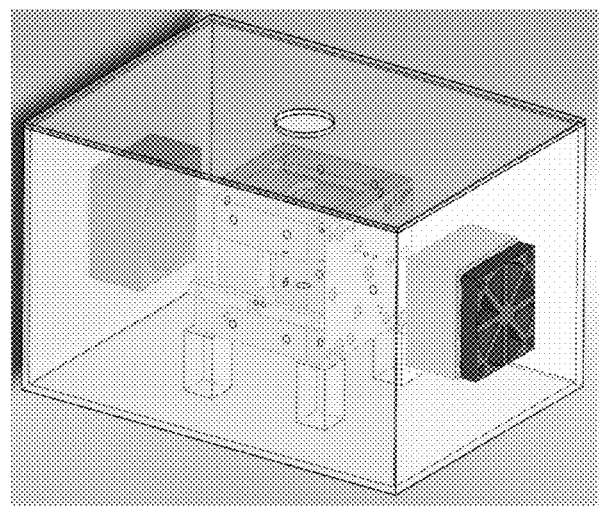
FIGS. 45A and 45B are sketches depicting an NMR unit having a separate casing for regulation of the temperature at the site of the NMR measurement, and useful where tight temperature control is needed for precision of the measurement. The temperature control configuration depicted in this figure is one of many different ways to control temperature.
Figure 45B:
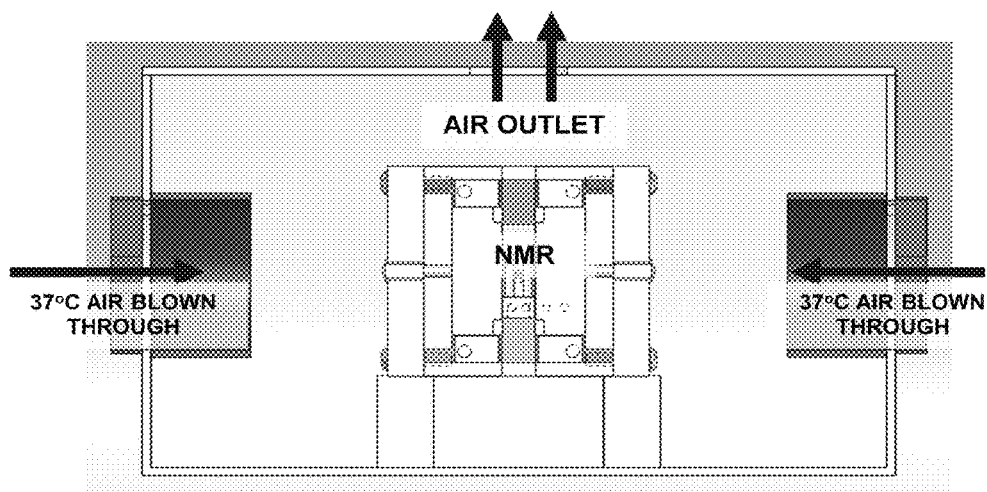

The MR unit may require more closely controlled temperature (e.g., ±0.1° C.), and so may optionally include a separate casing into which air heated at a predetermined temperature is blown. The casing can include an opening through which the liquid sample is inserted and removed, and out of which the heated air is allowed to escape. See FIGS. 45A and 45B. Other temperature control approaches may also be utilized.

The following examples are put forth so as to provide those of ordinary skill in the art with a complete disclosure and description of how the devices, systems, and methods described herein are performed, made, and evaluated, and are intended to be purely exemplary of the invention and are not intended to limit the scope of what the inventors regard as their invention.

Example 1. Preparation of Coated Particles

Briefly, 1 mg of substantially monodisperse carboxylated magnetic particles were washed and resuspended in 100 µl of activation buffer, 10 mM MES. 30 µl of 10 mg/ml 10 kDa amino-dextran (Invitrogen) was added to activation buffer and incubated on a rotator for 5 minutes at room temp. For coupling of the carboxyl groups to amines on the dextran, 30 µl of 10 mg/ml 1-Ethyl-3-[3-dimethylaminopropyl]carbodiimide Hydrochloride (EDC) was added and incubated on rotator for 2 hours at room temperature. Particles were washed away from free dextran 3× in 1 ml of PBS using magnetic separation, then resuspended in 1 ml of PBS. 100 µl of a 100 mM solution of Sulfo-NHS-biotin (Invitrogen) was used to decorate the amino groups on the dextran surface with biotin. After 30 minutes of incubation, particles were washed 3× in 1 ml activation buffer. Next, a protein block of 100 µl of 0.5 mg/ml of bovine serum albumin (BSA) (Sigma) and 30 µl of 10 mg/ml EDC was introduced and incubated overnight (Sigma). Prepared particles were washed 3× in 1 ml PBS and resuspended to the desired concentration.

Figure 37:
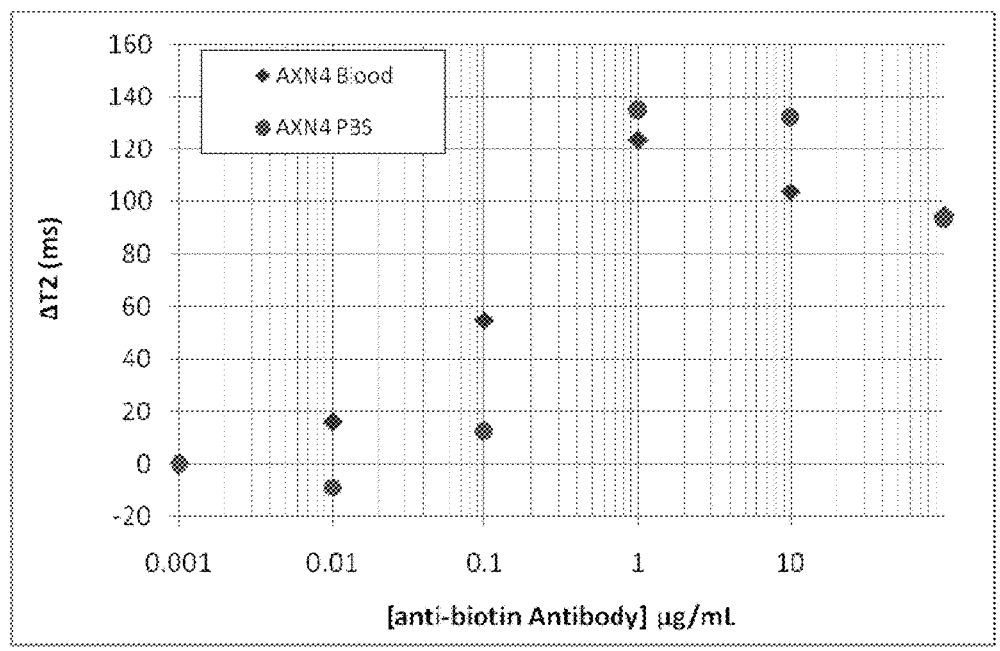
FIG. 37 is a graph depicting the results of $T_2$ assays for detecting anti-biotin antibody using prepared magnetic particles in blood and PBS matrices as described in Example 1.

Prepared particles synthesized with this protocol have been shown to give similar results in $T_2$ assays for detection of analyte, whether samples include buffer or 20% lysed blood (see FIG. 37). Variations of the preparations wherein pre-biotinylated amino dextran was conjugated directly to particles in one step have also resulted in similar performance in $T_2$ assays in both blood and buffer samples.

Example 2. Assessment of Particles Prepared with and without a Protein Block

Briefly, biotin decorated amino-dextran magnetic particles prepared according to the method described in Example 1 were assayed in PBS and in 20% lysed blood samples in an anti-biotin titration $T_2$ assay.

The assay was performed with the following procedure. 50 µL of matrix, either PBS or 20% Lysed blood sample, 50 µL of varying concentrations of Anti-biotin antibody, and 50 µL of 1.0 µg/ml secondary antibody were added to a 5 mm NMR Tube. 150 µL of 0.02 mM Fe particles were then added to each tube (i.e., $2.7 \times 10^8$ particles per tube). The samples were then vortexed for 4 seconds and incubated in a 37° C. heat block for 2 minutes. Each sample was then revortexed for 4 seconds, and incubated for an additional minute in the 37° C. heat block. Following incubation, each sample was placed into a Bruker Minispec for 10 minutes, under a magnetic field. After 10 minutes, the sample was removed from the magnet, vortexed for 4 seconds, and incubated in 37° C. heat block for 5 minutes. After 5 minutes, each sample was revortexed and incubated in a 37° C. heat block for an additional 1 minute. $T_2$ values were taken using the Bruker Minispec program with the following parameters:

Scans: 1
Gain: 75
Tau: 0.25
Echo Train: 3500
Total Echo Train: 4500
Dummy Echos: 2

$\Delta T_2$ values were calculated: $T_2-(T_2)_0$, and results are depicted in FIG. 37.

Figure 38:
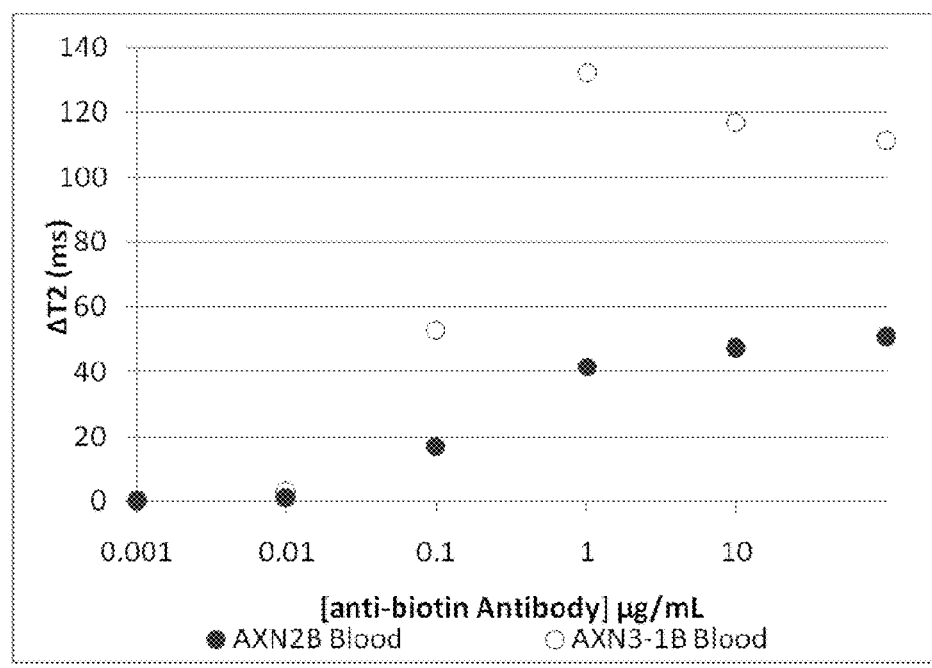
FIG. 38 is a graph depicting results of $T_2$ assays for detecting anti-biotin antibody using prepared magnetic particles with (open circle) and without (filled circle) a protein block as described in Examples 8 and 9.

Particles synthesized with a protein block, AXN4, gave nearly equal performance in blood and buffer (FIG. 37). The graph depicted in FIG. 38 compares particles prepared with (open circle) and without (filled circle) a protein blocking step. We have thus found the protein block may be needed to achieve similar functionality in blood matrices.

Figure 39:
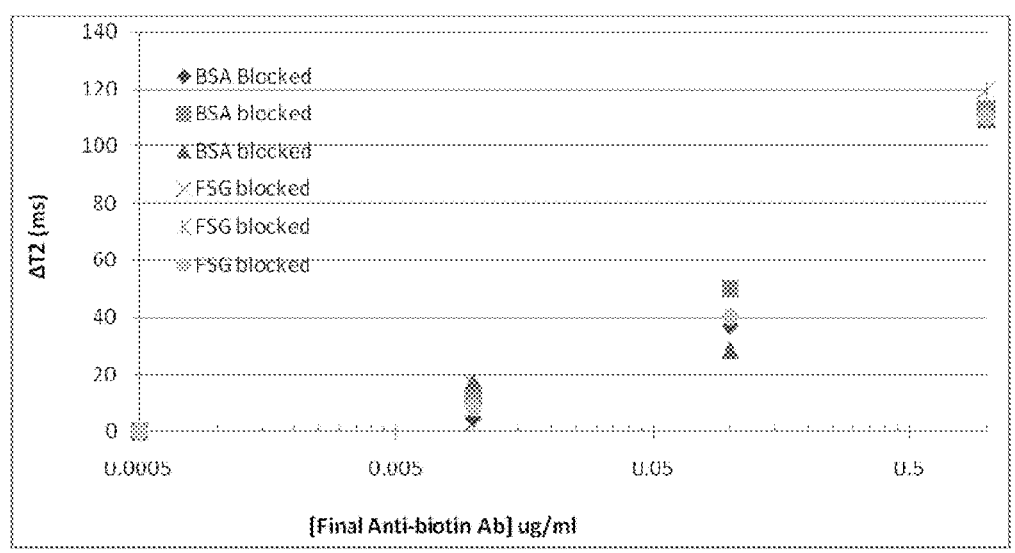
FIG. 39 is a graph depicting results of $T_2$ assays for detecting anti-biotin antibody using prepared magnetic particles having a BSA block (dark filled diamond, square, triangle) or an FSG block (light gray X's and circle) as described in Example 2.

Additional protein blocks including but not limited to fish skin gelatin have also been successful. Particles were prepared according to the method described above, with the exception that in lieu of using BSA as the protein block, fish skin gelatin (FSG) was substituted. The graph depicted in FIG. 39 shows results of a $T_2$ assay (as described above) using antibody titration for particles blocked with BSA and compared to FSG. The data indicates that there is little or no difference between the two protein blocking methods (see FIG. 39). However, BSA has proven to be a more reliable block.

Example 3. Determination of Amount of Dextran Coating

Figure 40A:
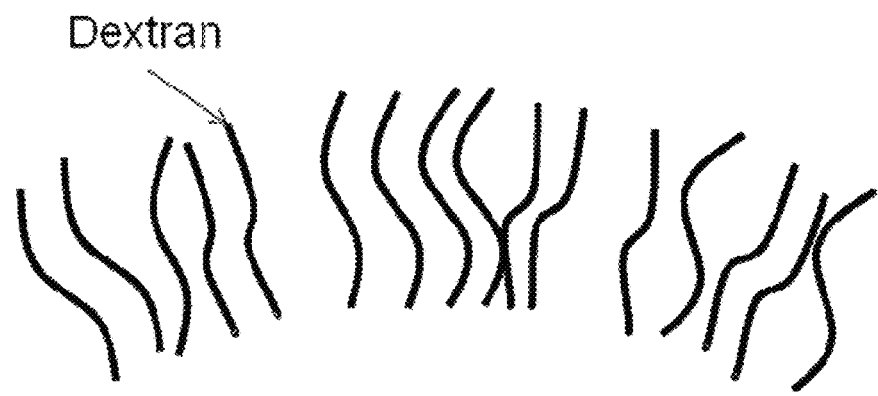
FIGS. 40A-40B are schematics of provided particle coatings.
Figure 40B:
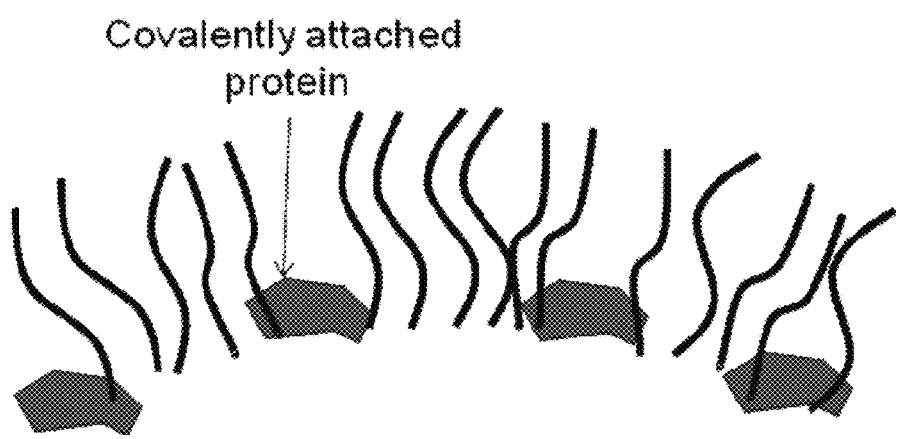
Figure 41A:
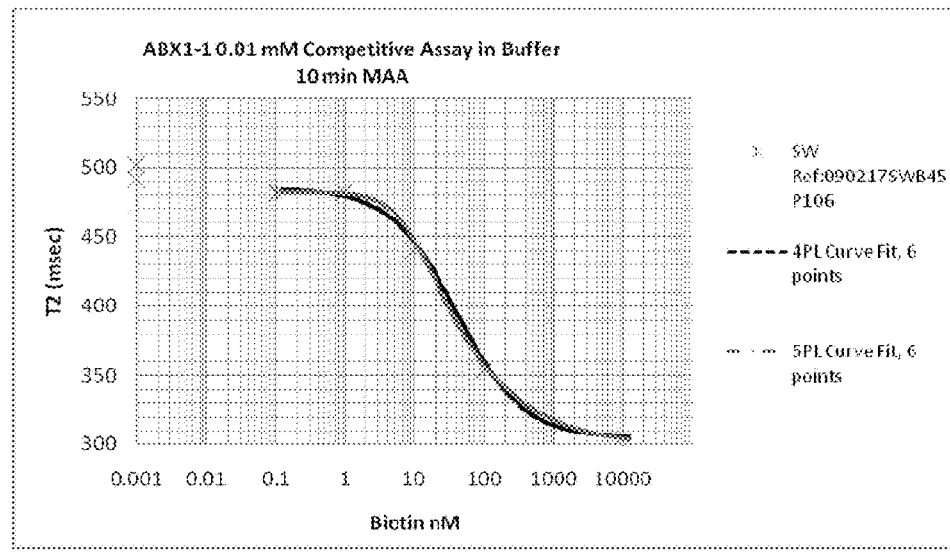
FIGS. 41A-41B depict results of $T_2$ assays for detecting biotin in a competitive assay format described in Example 4.
Figure 41B:
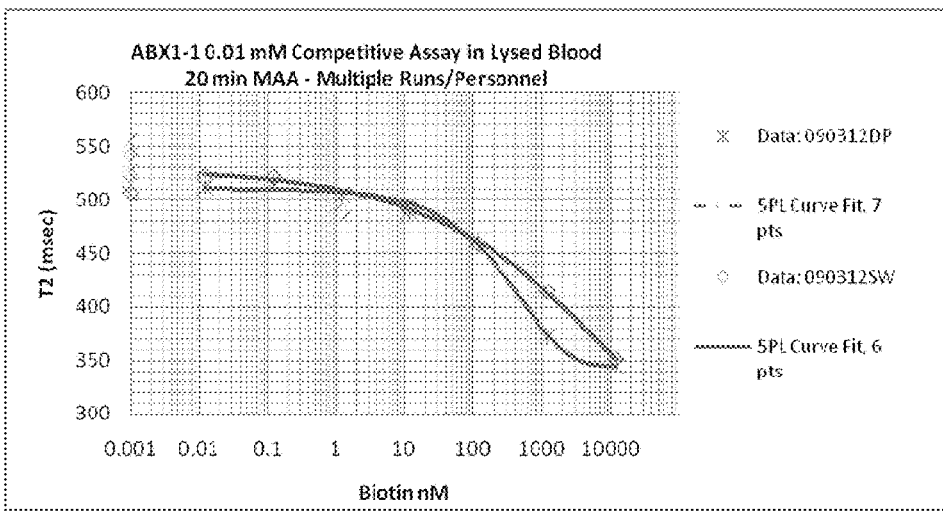

Attempts to increase dextran coating density on particles have been found to reduce functionality of prepared particles in blood. The preparation of particles described in Example 1 above that demonstrated nearly equivalent buffer/blood performance used a 10× excess of dextran base upon a space filling model to determine amount of dextran to include in coating experiments. In an attempt to functionalize particles with a higher fidelity, increasing the dextran coating to a 1000-10000× excess of dextran in coating experiments generated particles having a thicker dextran coating which yielded a reduced response in blood as compared to buffer. We conclude that a moderate density of dextran with a protein block may be desirable to produce a particle coating that functions well in $T_2$ assays in the presence of blood sample (see FIGS. 40A and 40B).

Example 4. Detection of a Small Molecule Analyte in Whole Blood Samples

Materials and Methods:
Jackson Immuno Research Labs Mouse Anti-Biotin Monoclonal Antibody (200-002-211)
Jackson Immuno Research Labs Sheep Anti-Mouse (515-005-071)
Tween 20
Bovine Serum Albumin (Sigma Product #: B4287-256)
1×PBS Tablets (Sigma P4417)
PEG FITC Biotin Analyte
100 mM Tris HCl in dH$_2$O
0.1% Tween®
EDTA Whole blood lysed 1:5 with 1× Trax buffer
Superparamagnetic, iron oxide, COOH-coated particles
Equipment:
Bruker Minispec
Variable Speed Vortexer (VWR)
5 mm NMR Tubes
37° C. Heat block with custom made NMR Tube slots Buffer/Analyte Preparation: 0.1% BSA, 0.1% Tween® in 1×PBS: A 10% Tween® 20 solution by weight was prepared. Briefly, Tween® in 1×PBS was prepared. 500 mL of 0.2% Tween solution was prepared by adding 10 mL of 10% Tween® to 490 mL of 1×PBS. A 2% solution of BSA was prepared in 1×PBS solution by weight. A 0.2% solution of BSA solution was prepared by adding 50 mL of 2% BSA in PBS to 450 mL of 1×PBS. Dilutions were combined to make a final volume of 1 L and a final buffer concentration of 0.1% BSA, 0.1% Tween® in 1×PBS.

PEG-FITC-Biotin Analyte: 100 µl of a 0.5 mM solution was prepared from 1 mM Tris HCl. 40 µl of PEG FITC biotin was mixed with 40 µl of 0.5 mM Tris HCl, and incubated for 15 minutes at room temperature. After 15 minutes, 70 µl of PEG-FITC-Biotin in 0.5 mM Tris HCl was added to 630 µl of 0.1% Tween® to make a 100 µM stock solution. Stock solution was vigorously mixed by vortexing. 200 µl of 100 µM solution was added to 900 µl of 0.1% Tween® to make 20,000 nM analyte. 10 fold dilutions were prepared down to 0.02 nM Procedure:
25 µl of appropriate analyte and 50 µl of 1:5 Lysed blood matrix were pipetted directly into a 5 mm NMR tube. Samples were vortexed for 4 seconds. 25 µl of primary Anti-biotin antibody (0.18 µg/ml diluted in 0.1% Tween 20, 0.1% BSA, 1×PBS) was added, followed by a 37° C. incubation for 15 minutes. After 15 minutes, 50 µl of 3.0 µg/ml Secondary Anti-Mouse antibody (diluted in 0.1% Tween, 0.1% BSA, 1×PBS) and 150 µl of 0.02 mM Fe particles (2.7×10$^8$ particles per tube) were added to the NMR Tube. The sample was then vortexed for 4 seconds and incubated for 5 minutes at 37° C. The sample was placed in a Bruker Minispec for 10 minutes, under magnetic field. After 10 minutes, the sample was removed from the magnet and incubated for an additional 5 minutes. The sample was again vortexed for 4 seconds and incubated for an additional 1 minute. $T_2$ values were taken using the Bruker Minispec program with the following parameters:

Scans: 1
Gain: 75
Tau: 0.25
Echo Train: 3500
Total Echo Train: 4500
Dummy Echos: 2

Example 5. Synthesis of Antibody Decorated Particles

Amino dextran coated magnetic particles prepared as described in Example 1 can be further functionalized with antibodies via an SMCC-SATA linkage (SMCC=succinimidyl 4-[N-maleimidomethyl]cyclohexane-1-carboxylate; SATA=N-succinimidyl-5-acetylthioacetate). The carboxylated magnetic particles are first conjugated to 10 kDa amino dextran via EDC chemistry as described above. The dextran coated particles are further modified with an excess of sulfo-SMCC to provide a maleimide functional group. Antibodies are modified with a SATA linker, which primarily binds to the amines on the antibody. The SATA linkage is controlled to minimize over-functionalization of the antibody which may lead to cross-linking of the particles or reduced affinity of the antibody. After deacetylation, the SATA linker exposes a thiol functional group which can be used to directly attach to the malemide functionalized particles forming a thioether bond. The number of antibodies conjugated to each particle can be measured using a BCA protein assay (Pierce). Linkers that provide similar functionality to SATA have been used successfully, such as SPDP (N-Succinimidyl 3-[2-pyridyldithio]-propionate).

Antibody coated magnetic particles can also be prepared using the chemistries described above, but with direct covalent linkage to the base carboxylated particle. In some instances it may necessary to add additional coating to the particle surface, such as dextran, or a blocking agent. Similar chemistries can be used with alternate coatings to the amino dextran, such as PEG or BSA.

Example 6. Creatinine Assay

Briefly, the assay includes the following: a target sample is incubated in the presence of a magnetic particle that has been decorated with creatinine, which is linked to the surface of the magnetic particles. The creatinine decorated magnetic particles are designed to aggregate in the presence of the creatinine antibody. Each of the creatinine decorated magnetic particles and creatinine antibody is added to the liquid sample containing creatinine, which competes with the magnetic particles for the creatinine antibody. Thus, the binding of the creatinine to the antibody blocks agglomeration of the magnetic particles, and low levels of creatinine are marked by the formation of agglomerates. These agglomerates alter the spin-spin relaxation rates of sample when exposed to a magnetic field and the change in the $T_2$ relaxation times (measuring a change in the magnetic resonance signal from the surrounding water molecules) can be directly correlated to presence and/or concentration of the analyte in the target sample.

Creatinine Antibody

In establishing an antibody generation program for creatinine, a modified creatinine molecule was devised (COOH-creatinine) and conjugated to transferrin for immunization in BALB-C and AJ mice.

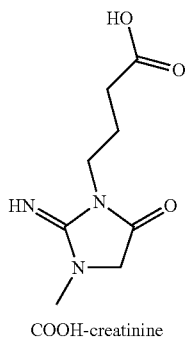

COOH-creatinine

Thirty four stable antibody producing clones were generated. These clones arose from either BALB-C (spleen cells) (n=17) or AJ mice (n=17). The two genetically different mouse lines were selected for the known genetic differences in their immune systems. Criteria and a selection process were developed for screening and identification of an optimal monoclonal antibody for use in the assay. The antibody selection process included screening for binding to BSA-creatinine by ELISA, antibody affinity/sensitivity/specificity by ELISA competitive assays using free creatinine and potential interferents, determination of the ability of the antibody to be conjugated to the magnetic particle and functionality in a $T_2$ magnetic relaxation switch assay.

Using the established antibody selection criteria outlined above, seven monoclonal antibodies were identified and selected as potential candidates in the assay.

Creatinine-Coated Magnetic Particles

Substantially monodisperse carboxylated magnetic particles were washed and resuspended in 100 µl of coupling buffer (50 mM MES, pH=4.75). Sulfo-NHS (55 µmol in 200 µl MES buffer) was added and the mixture vortexed. To the mixture was added EDC (33.5 µmol in 200 µl MES buffer). The solution was briefly vortexed and placed on an end over end mixer for 1 hour at room temperature, allowed to settle, and the supernatant removed. To the resulting solids was added 1 mL of 1% BSA in PBS, and again the mixture was vortexed and placed on an end over end mixer for 15-18 hours at room temperature. The particles were allowed to settle and the supernatant removed.

The BSA-coated particles were suspended in 0.5 mL PBS-0.01% T20 (10 mM phosphate buffer, pH=7.4, 150 mM NaCl, with 0.01% Tween® 20). Unreacted carboxyl groups were subjected to Methyl-PEG4-amine (20 µl of 10% v/v in DMSO) as a blocking agent. The mixture was vortexed and placed on an end over end mixer for 8 hours at room temperature. The resulting BSA-coated particles were repeatedly washed with 0.5 mL PBS-0.01% T20.

COOH-creatinine (66 µmol), EDC (140 µmol), and NHS (260 µmol) were combined with 300 µl of dry DMSO to form a slurry, which cleared as the reaction reached completion. BSA-coated particles were suspended in 0.5 mL PBS-0.01% T20 (pH=8), followed by the addition of the activated COOH-creatinine solution. The resulting mixture was vortexed and placed on an end over end mixer for 4 hours at room temperature. The resulting particles were washed 3× each with sonication using 1:15 and 1:30 DMSO:PBS-0.01% T20 (vol/vol). The particles were then washed 3× each with sonication using PBS-0.01% T20. The particles were resuspended in PBS-0.1% T20 (pH=8) and 2 mg of NHS-PEG 2K in 200 PBS-0.01% T20 was added. The mixture was placed on an end over end mixer for 12-20 hours at room temperature. The particles were then washed 3× each with sonication using PBS-0.01% T20 to produce creatinine-conjugated magnetic particles with sequential BSA, creatinine coating, PEG cap and block.

The creatinine coated particles were resuspended in assay buffer (100 mM glycine (pH=9.0), 150 mM NaCl, 1% BSA, 0.05% ProClin®, and 0.05% Tween®).

Figure 24:
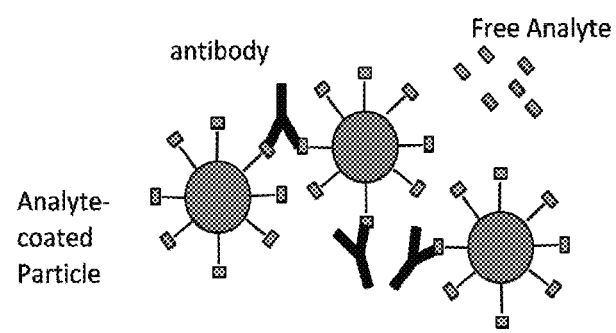
FIG. 24 is a drawing depicting the components of the creatinine competitive assay of Example 6. A magnetic particle decorated with creatinine is used in combination with a creatinine antibody to form an aggregating system. The creatinine present in a liquid sample competes with the magnetic particles for the antibody, leading to a reduction in aggregation with increasing creatinine concentration. The change in aggregation is observed as a change in the $T_2$ relaxation rate of the hydrogen nuclei in the water molecules of the liquid sample. By comparing the observed $T_2$ relaxation rate of the liquid sample to a standard curve, the concentration of creatinine is determined.

The creatinine assay protocol was performed using creatinine conjugated particles and soluble creatinine antibody with detection using the $T_2$ signal was generated/completed. The creatinine competitive assay architecture is depicted in FIG. 24.

Solutions of magnetic particles, antibody, and liquid sample were, where indicated, subject to dilution with an assay buffer that included 100 mM Tris pH 7.0, 800 mM NaCl, 1% BSA, 0.1% Tween®, and 0.05% ProClin®.

The creatinine-coated magnetic particles were diluted to 0.4 mM Fe (5.48×10$^9$ particles/ml) in assay buffer, vortexed thoroughly, and allowed to equilibrate for 24 hours at 4-8° C.

The anti-creatinine mouse monoclonal antibody (described above) was employed as a multivalent binding agent for the creatinine-conjugated magnetic particles. The antibody was diluted to a concentration of 0.8 µg/ml in assay buffer and vortexed thoroughly.

Samples and calibrators were diluted 1 part sample to 3 parts assay buffer. The upper assay range is ca. 4 mg/dL creatinine. For samples with expected creatinine levels>4 mg/dL an additional sample dilution was performed using 1 part initial diluted sample to 4 parts assay buffer.

The pre-diluted sample, assay buffer, magnetic particle, and antibody solutions were each vortexed. 10 µL of each solution added to a tube, and the tube was vortexed for 5 seconds.

Figure 25A:
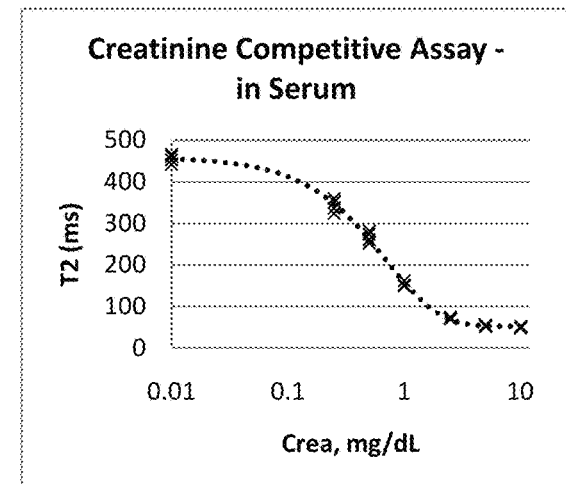
FIGS. 25A-25C are a series of graphs showing the response curve for creatinine competitive assays.

The tube was then subjected to 12 minutes of gMAA, incubated for 5 minutes at 37° C., placed in the MR Reader ($T_2$ MR, Reader with 2200 Fluke Temperature Controller, with NDxlient software 0.9.14.1/hardware Version 0.4.13 Build 2, Firmware Version 0.4.13 Build 0) to measure the $T_2$ relaxation rate of the sample, and the $T_2$ relaxation rate of the sample was compared to a standard curve (see FIG. 25A) to determine the concentration of creatinine in the liquid sample.

Performance of Modified Creatinine Antibodies

Figure 25B:
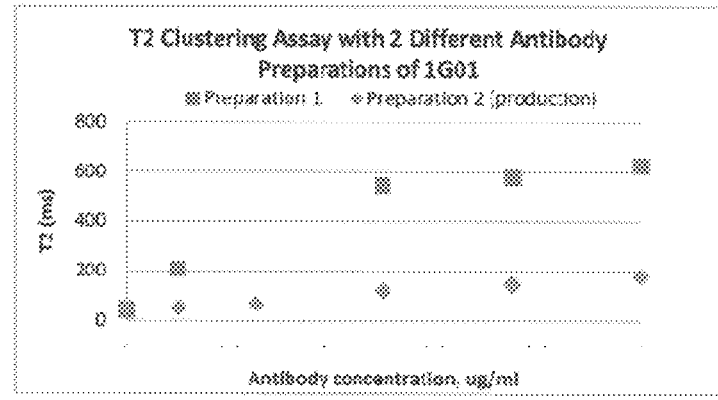
Figure 25C:
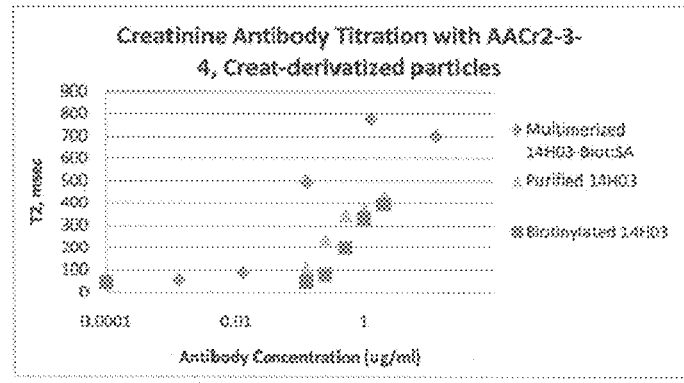

Different creatinine antibodies were tested in the assay to ascertain the effect of the antibody on agglomeration. We observed that the performance of the creatinine antibodies varied in their performance characteristics when combined with creatinine-coated magnetic particles (see FIG. 25B). SDS-PAGE gel analysis of the two preparations revealed significantly enhanced aggregation in preparation 1, believed to arise from an increase in the creatinine binding valency for this antibody, which is aggregated due to its purification process. For comparison, we multimerized another creatinine monoclonal antibody (14HO3) by biotinylating the antibody and multimerizing the antibody in the presence of streptavidin. The monomeric, biotinylated monomeric, and multimerized forms were then tested with creatinine-coated magnetic particles to assess the effect of increased valency on $T_2$ time. The results are depicted in FIG. 25C, showing the multimerized antibody forms clusters at much lower concentrations that the non-multimerized antibodies. This valency enhancement for particle clustering has also been observed using IgM antibodies.

Example 7. Creatinine Antibody-Coated Magnetic Particle

Using an alternative assay architecture, the assay includes the following: a target sample is incubated in the presence of (i) a magnetic particle that has been decorated with creatinine antibody; and (ii) a multivalent binding agent including multiple creatinine conjugates. The magnetic particles are designed to aggregate in the presence of the multivalent binding agent, but aggregation is inhibited by competition with creatinine in the liquid sample. Thus, the binding of the creatinine to the antibody-coated particle blocks agglomeration of the magnetic particles in the presence of the multivalent binding agent, and low levels of creatinine are marked by the formation of agglomerates. These agglomerates alter the spin-spin relaxation rates of sample when exposed to a magnetic field and the change in the $T_2$ relaxation times (measuring a change in the magnetic resonance signal from the surrounding water molecules) can be directly correlated to presence and/or concentration of the analyte in the target sample.

Substantially monodisperse carboxylated magnetic particles were washed and resuspended in 300 µl of coupling buffer (50 mM MES, pH=4.75), and sulfo-NHS (46 mmol) EDC (25 µmol) were added to the particles. The solution was briefly vortexed and placed on an end over end mixer for 1 hour at room temperature. The activated particles were washed with mL PBS-0.01% T20, and resuspended in 1 mL of 10% w/v solution of amine-PEG-amine in PBS-0.01% T20. The mixture was vortexed and placed on an end over end mixer for 2 hours at room temperature, and then washed 3× with PBS-0.01% T20.

BSA can be substituted for amine-PEG-amine as an alternate chemistry. The BSA-coated magnetic particles were prepared as described in example 6, in the section describing creatinine coated magnetic particles.

The particles were resuspended in 260 µl PBS-0.01% T20 and reacted with 198 µl sulfo SMCC (5 mg/mL in PBS-0.01% T20). The solution was briefly vortexed and placed on an end over end mixer for 1 hour at room temperature, and then washed 3× with PBS-0.01% T20 with 10 mM EDTA to produce SMCC-coated particles.

SATA-labeled antibody was prepared by combining SATA (30 nmol in DMSO) with antibody (2 nmol in PBS, pH=7.4). The solution was placed on an end over end mixer for 1 hour at room temperature. Blocked sulfhydryl groups on SATA-labeled antibody were deprotected by treatment with deacetylation buffer (0.5M hydroxylamine hydrochloride in pH 7.4, 10 mM phosphate, 150 mM sodium chloride, 10 mM EDTA) for 1 hour and purified through a desalting column using PBS containing 10 mM EDTA prior to use.

As an alternate to SATA, SPDP-labeled antibody can be used. SPDP-labeled antibody was prepared by adding SPDP (10 mmol in DMSO) with antibody (2 nmol in PBS, pH 7.4). The solution was incubated for 1 hour at room temperature and purified through a desalting column. The disulfide linkage of SPDP on the SPDP-labeled antibody was cleaved in a reaction with 5 mM mercaptoethyamine and incubated for 10 minutes at ambient temperature. The disulfide bond-cleaved SPDP-labeled antibody was purified through a desalting column prior to use.

The SMCC-functionalized particles with PEG- or BSA- coating and deacetylated SATA-modified antibody were combined and placed on an end over end mixer for overnight at room temperature, washed 3× with PBS-0.05% Tween® 80, and resuspended in PBS-0.01% T20 with 10 mM EDTA. A blocking agent (m-PEG-SH 2K) was added, the solution was placed on an end over end mixer for 2 hours, washed 2× with PBS-0.05% Tween® 80, and resuspended in PBS-0.05% Tween® 80, 1% BSA, and 0.05% ProClin® to produce antibody-coated magnetic particles.

The SMCC-functionalized BSA-coated particles and disulfide-bind cleaved SPDP-labeled antibody were combined and placed on an end over end mixer for 2 hours at room temperature, washed 2 times with PBS-0.01% Tween® 20, 10 mM EDTA, and resuspended in PBS, 0.01% T20, and 10 mM EDTA. A blocking agent, m-PEG-SH 2K (1 mole), was added, and the solution was placed on an end over end mixer for 2 hours. A second blocking agent, n-ethyl maleimide (5 µmole), was added. The particles were mixed for 15 minutes, washed twice with PBS-0.01% Tween® 20, and resuspended in pH 9, 100 mM Tris, 0.05% Tween® 80, 1% BSA, and 0.05% ProClin® to produce antibody coated magnetic particles.

The procedure outlined above can be used with creatinine antibodies, or the creatinine antibodies can be coupled directly to the surface of the carboxylated magnetic particles via EDC coupling.

Creatinine Multivalent Binding Agents

Figure 33:
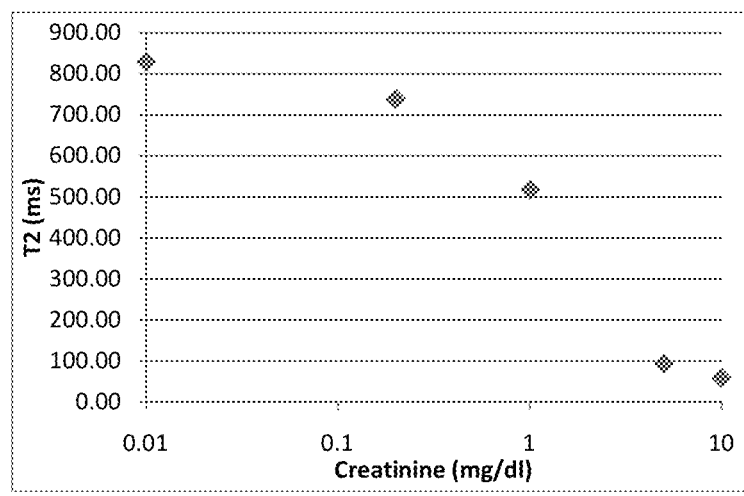
FIG. 33 is a graph depicting a creatinine inhibition curve (see Example 7) for using an antibody coated particle and an amino-dextran-creatinine multivalent binding agent to induce clustering by competing with any target analyte (creatinine) present in the sample to cause particle clustering. The binding agent used is a 40 kDa dextran with ~10 creatinines per dextran molecule.

COOH-creatinine was conjugated to 3 amino-dextran compounds (Invitrogen; MW 10 k, 40 k, and 70 k with 6.5, 12, and 24 amino groups per molecule of dextran respectively) and BSA via EDC coupling. The resulting BSA-creatinine and amino-dextran-creatinine multivalent binding agents can be used in the competitive inhibition assay described above. Degrees of substitution between 2-30 creatinines per dextran moiety were achieved. An example creatinine inhibition curve is shown in FIG. 33. The binding agent used is a 40 kDa dextran with ~10 creatinines per dextran molecule.

Example 8. Preparation of Tacrolimus Multivalent Binding Agents

Tacrolimus conjugates were prepared using dextran and BSA. FK-506 was subjected to the olefin metathesis reaction using Grubbs second generation catalyst in the presence of 4-vinylbenzoic acid as depicted below in Scheme 1. The crude product mixture was purified by normal phase silica gel chromatography.

Scheme 1

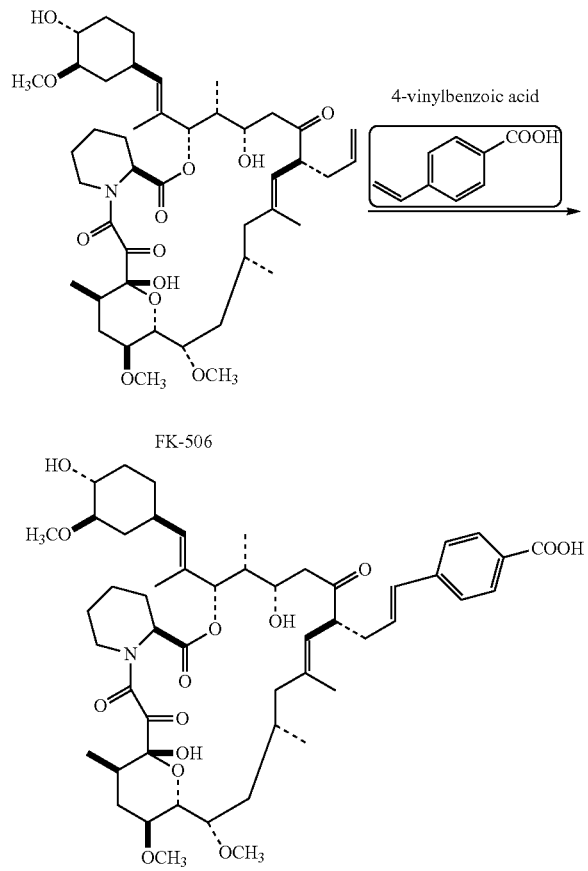

FK-506

Dextran Conjugates

Dextran-tacrolimus conjugates were prepared using three different molecular weight amino-dextrans, each with a different amino group substitution.

2.78 mL of EDC solution (40 mg/mL EDC hydrochloride) and 2.78 mL of sulfo-NHS solution (64 mg/mL sulfo-NHS) were combined with stirring. To this mixture was added 0.96 mL of tacrolimus-acid derivative (C21) solution (28.8 mg/mL in DMSO) and the contents stirred for 30 minutes at room temperature to form the activated tacrolimus-acid derivative (activated Tac solution 4.6 mM). The activated tacrolimus was used immediately.

Various amino-dextran polymers were dissolved in 100 mM sodium phosphate buffer (pH 8.0) to make a 9.5 mg/mL stock solution.

Activated Tac solution was added drop-wise with stirring at room temperature to the stock solution of amino-dextran in the ratios tabulated below. Each reaction was stirred vigorously for at least 2 hours.

TABLE 6

| Reaction | Amino Dextran m.w. | Ratio of Amine:Tac | Amino Dextran (µL) | Volume Tac (µL) | Estimated Tac:Dextran molar ratio |
|---|---|---|---|---|---|
| 1 | 70K | 1:0.2 | 1000 | 70.8 | Not tested |
| 2 | 70K | 1:0.4 | 1000 | 141.6 | Not tested |
| 3 | 70K | 1:0.8 | 1000 | 283.2 | 4.1 |
| 4 | 70K | 1:1.6 | 1000 | 566.4 | Not tested |

TABLE 6-continued

| Reaction | Amino Dextran m.w. | Ratio of Amine:Tac | Amino Dextran (µL) | Volume Tac (µL) | Estimated Tac:Dextran molar ratio |
|---|---|---|---|---|---|
| 5 | 70K | 1:3.2 | 1000 | 1132.8 | Not tested |
| 6 | 70K | 1:5 | 1000 | 1770 | 15.8 |
| 7 | 10K | 1:0.8 | 1000 | 283 | 1.0 |
| 8 | 10K | 1:5 | 1000 | 1766 | 2.2 |
| 9 | 40K | 1:0.8 | 1000 | 287 | 2.0 |
| 10 | 40K | 1:5 | 1000 | 1793 | 8.2 |

The resulting Tac-dextran conjugates were purified using a 5-step serial dialysis of each reaction product ($1^{st}$—15% (v/v) aqueous DMSO; $2^{nd}$—10% (v/v) aqueous methanol; $3^{rd}$ to $5^{th}$—high purity water; at least 2 hours for each step; using a 3,500 MWCO dialysis membrane for the 10K MW amino-dextran and a 7K MWCO dialysis membrane for the 40K and 70K amino-dextran).

Following purification, each of the samples was lyophilized and the dry weight determined. The multivalent binding agents were reconstituted prior to use.

After reconstitution, the tacrolimus substitution ratios were estimated based upon the absorbance at 254 nm.

Figure 34:
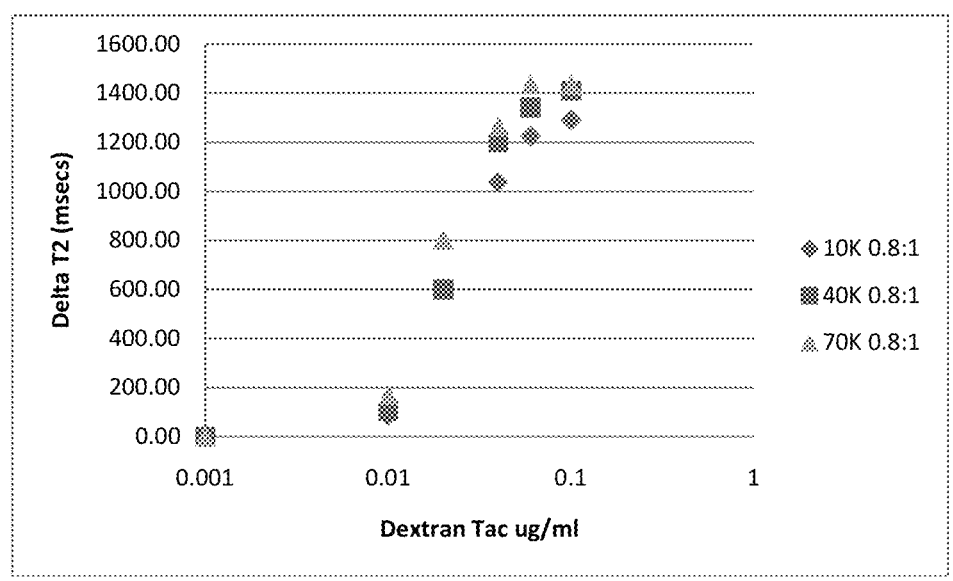
FIG. 34 is a graph depicting the evaluation of Tac-dextran conjugates for clustering ability (see Example 8) by performing a titration. As observed, that increased molecular weight of Tac-dextran results in the improved $T_2$ signal.
Figure 35:
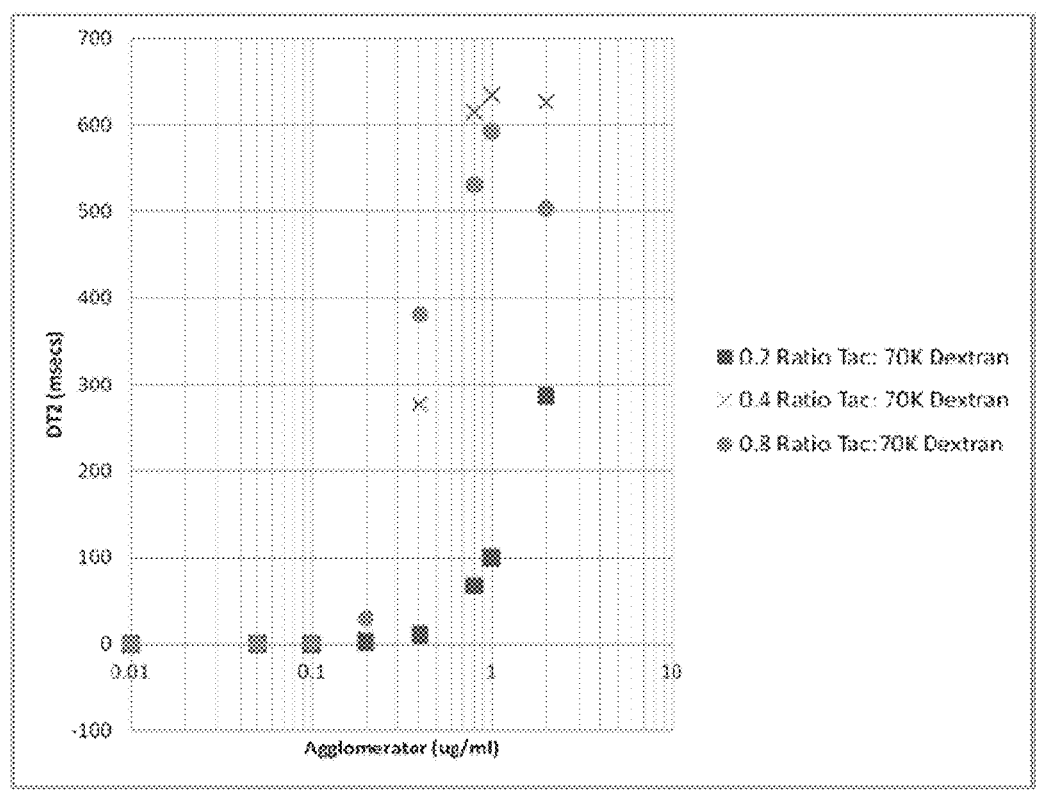
FIG. 35 is a graph depicting the evaluation of Tac-dextran conjugates for clustering ability (see Example 8) by performing a titration. As observed, higher substitution improved $T_2$ signal.

Experiments were performed to determine which size dextran provided the most optimal agglomerative performance. Briefly, 10 µL of 10% MeOH, 1% BSA in PBS pH 6.3 buffer, 20 µL of Dextran Tac agglomerator, 10K, 40K, 70K, at varying concentrations, and 10 µL of Anti-Tacrolimus coated magnetic particles at 0.2 mM Fe was added to a 200 µL PCR Tube ($2.7 \times 10^9$ particles per tube). The sample was vortexed using a plate mixer at 2000 rpm for 2 minutes, preheated for 15 minutes at 37° C. in an incubation station, exposed to a side and bottom magnet for 1 minute each, repeated for 6 cycles, vortexed again for 2 minutes at 2000 rpm, incubated for 5 minutes in 37° C. incubator containing PCR tube designed heat block, and the $T_2$ was read on the MR Reader. Data indicates that increased molecular weight/varied substitution ratios of dextran Tac can result in the improved $T_2$ signal (see FIG. 34). In addition, higher substitution also resulted in improved response (see FIG. 35).

BSA Conjugates

BSA-tacrolimus conjugates were prepared with varying degrees of tacrolimus substitution. 34.5 µL of NHS solution (66.664 mg/mL in acetonitrile) and 552 µL of EDC (6.481 mg/mL in 50 mM MES pH 4.7) were combined with stirring. 515.2 µL of this EDC NHS mixture was added drop-wise to 220.8 µL. of tacrolimus-acid derivative (C21) solution (33.33 mg/mL in acetonitrile) and the contents stirred for 1 hour at room temperature to form the activated tacrolimus-acid derivative. The activated tacrolimus was used immediately.

BSA was dissolved in phosphate buffered saline and acetonitrile to form a solution containing 5 mg/mL BSA in 40% acetonitrile.

Activated Tac solution was added drop-wise with stirring at room temperature to the BSA solution in the ratios tabulated below. Each reaction was stirred vigorously for at least 2 hours.

TABLE 7

| Reaction | Ratio of Tac:BSA | BSA (µL) | Volume Tac (µL) |
|---|---|---|---|
| 1 | 5:1 | 1000 | 35 |
| 2 | 10:1 | 1000 | 70 |
| 3 | 20:1 | 1000 | 140 |
| 4 | 30:1 | 1000 | 210 |
| 5 | 50:1 | 1000 | 350 |

The resulting Tac-BSA conjugates were purified using a PD10 size exclusion column pre-equilibrated with 40% acetonitrile. The eluent was collected in 1 mL fractions and monitored for absorbance at 280 nm to identify fractions containing BSA.

The BSA-containing fractions were combined and the acetonitrile removed under vacuum.

Figure 36:
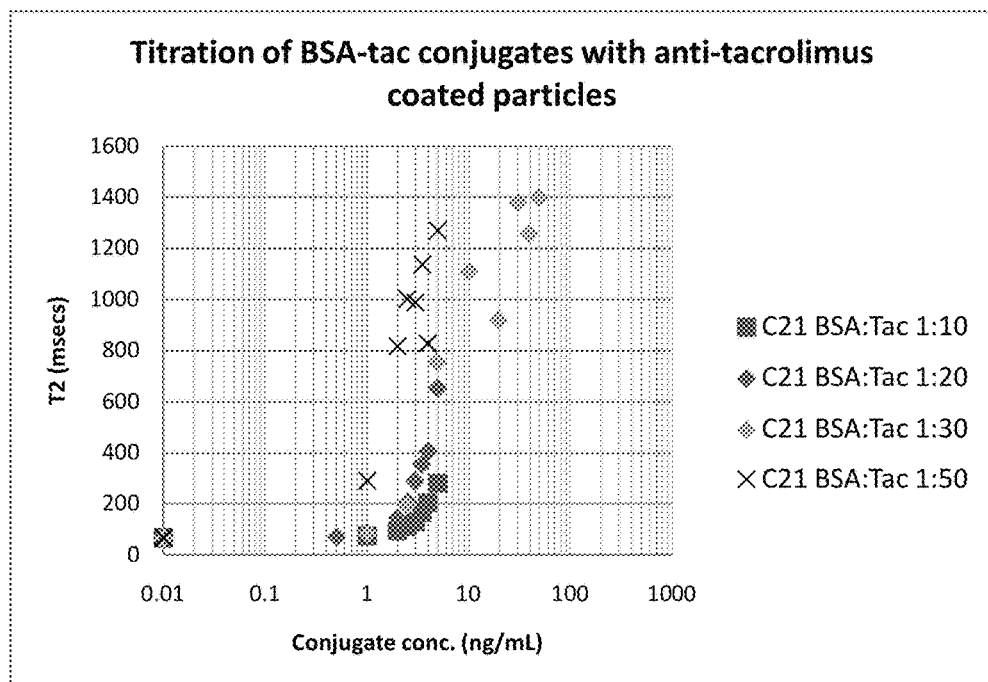
FIG. 36 is a graph depicting the evaluation of Tac-BSA conjugates for clustering ability (see Example 8) by performing a titration similar to that used for the Tac-dextran conjugates. As observed, clustering performance varies with the tacrolimus substitution ratio.

Tac-BSA conjugates were evaluated for clustering ability by performing a titration similar to that used for the dextran-tacrolimus conjugates. As observed, clustering performance differs with Tac substitution ratio (see FIG. 36).

Example 9. Tacrolimus Competitive Assay Protocol (Antibody on Particle Architecture)

Figure 28:
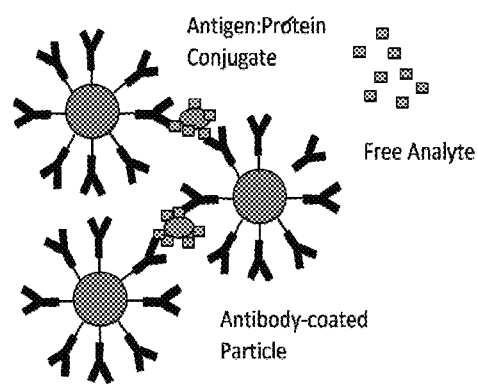
FIG. 28 is a drawing depicting the tacrolimus competitive assay architecture of Example 9.

A tacrolimus assay was developed using anti-tacrolimus antibody conjugated particles and BSA-tacrolimus multivalent binding agent with detection using an MR Reader (see Example 6). This assay was designed for testing whole blood samples that have been extracted to release tacrolimus from the red blood cells and binding proteins (the extraction of hydrophobic analyte from a sample can be achieved, for example, using the methodology described in U.S. Pat. No. 5,135,875). The tacrolimus competitive assay architecture is depicted in FIG. 28.

Solutions of magnetic particles and multivalent binding agent were, where indicated, subject to dilution with an assay buffer that included 100 mM Glycine pH 9, 0.05% Tween® 80, 1% BSA, 150 mM NaCl, 0.1% CHAPS.

A base particle with COOH functionality was modified by sequential aminated coating (PEG or BSA), antibody covalent attachment, PEG cap and PEG/protein block (as described in the examples above). The antibody-coated magnetic particles were diluted to 0.4 mM Fe ($5.48 \times 10^9$ particles/ml) in assay buffer, and vortexed thoroughly.

The multivalent binding agent was formed from COOH-modified tacrolimus covalently conjugated to BSA (as described in Example 8). The multivalent binding agent was diluted to 0.02 µg/ml in assay buffer, and vortexed thoroughly.

The extracted sample solution (10 µL) and the magnetic particle solution (10 µL) were combined and vortexed for five seconds and incubated at 37° C. for 15 minutes. To this mixture was added 20 µL of the multivalent binding agent and the resulting mixture vortexed for five seconds and incubated at 37° C. for 5 minutes.

Several samples were prepared as described above. All samples were placed into the gMAA unit for 1 minute. All samples were then placed into a tray removed from the magnetic field. Each sample was vortexed for at least five seconds and returned to the tray. All samples were again placed into the gMAA unit for 1 minute, followed by vortexing. This process was repeated twelve times for each sample.

Figure 29:
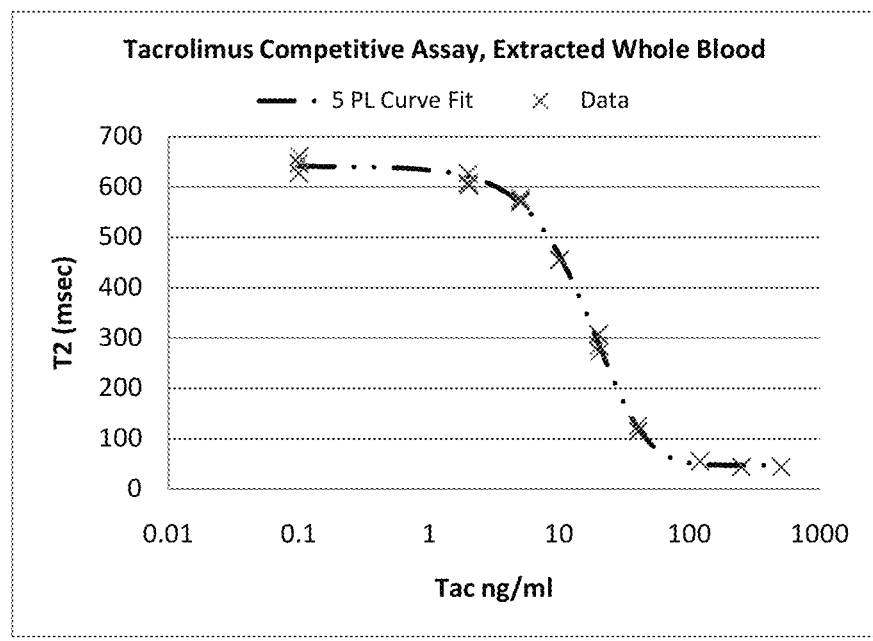
FIG. 29 is a graph showing a standard curve for the tacrolimus competitive assay of Example 9 correlating the observed $T_2$ relaxation rate observed for a liquid sample with the concentration of tacrolimus in the liquid sample.

The sample was incubated for 5 minutes at 37° C., placed in the MR Reader (see Example 6) to measure the $T_2$ relaxation rate of the sample, and the $T_2$ relaxation rate of the sample was compared to a standard curve (see FIG. 29) to determine the concentration of tracrolimus in the liquid sample.

Tacrolimus Antibody

Several antibody development programs were pursued to create a high-affinity tacrolimus antibody including traditional mouse monoclonal models, in vitro phage display strategies, and rabbit models. C21 derivatives of tacrolimus were used as the haptens for the immunogen and screening conjugates used in these programs. A set of criteria was developed for screening and identification of an optimal antibody for use in the assay. The criteria include the ability to bind tacrolimus-protein conjugates, the inhibition of that binding in the presence of nanomolar levels of free tacrolimus, all while exhibiting little or no affinity for the metabolites of tacrolimus (depicted below).

Using the established antibody selection criteria outlined above, several monoclonal antibodies, polyclonal antibodies, and Fab fragments have been identified and selected as potential candidates in a tacrolimus assay.

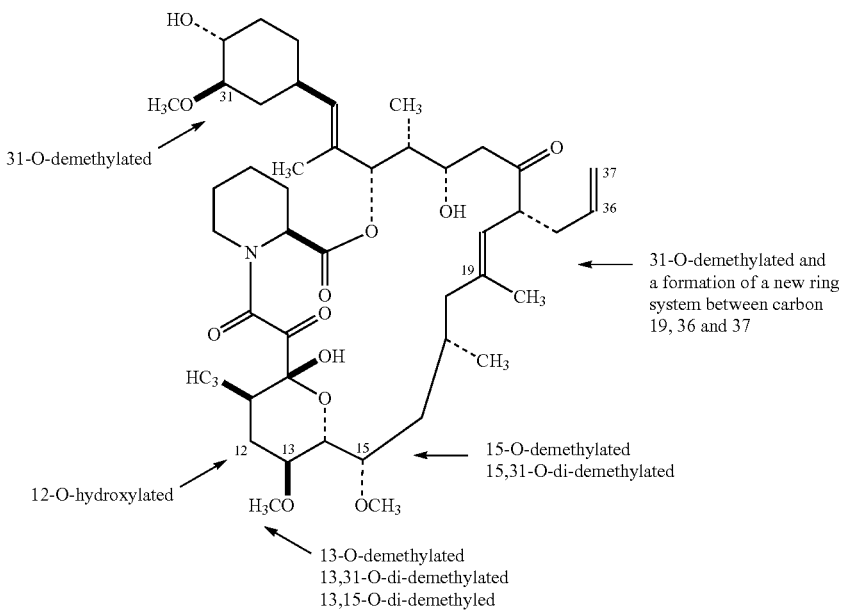

Example 10. Side-Side Gradient Magnetic Assisted Agglomeration (gMAA)

An evaluation of alternative methods of gMAA was performed using the creatinine immunoassay described in Example 6 with sample containing no analyte to compete with the particle-antibody specific agglomeration.

Several identical samples were prepared as described in Example 6. All samples were placed into the gMAA unit for 1 minute. All samples were then placed into a tray removed from the magnetic field. Each sample was vortexed for at least five seconds and returned to the tray. All samples were again placed into the gMAA unit for 1 minute. This process was repeated twelve times for each sample, to obtain replicate measurements.

After the last gMAA cycle, the sample was vortexed for 5 seconds, incubated for 5 minutes at 37° C., and placed in the MR Reader to measure the $T_2$ relaxation rate of the sample.

Figure 26:
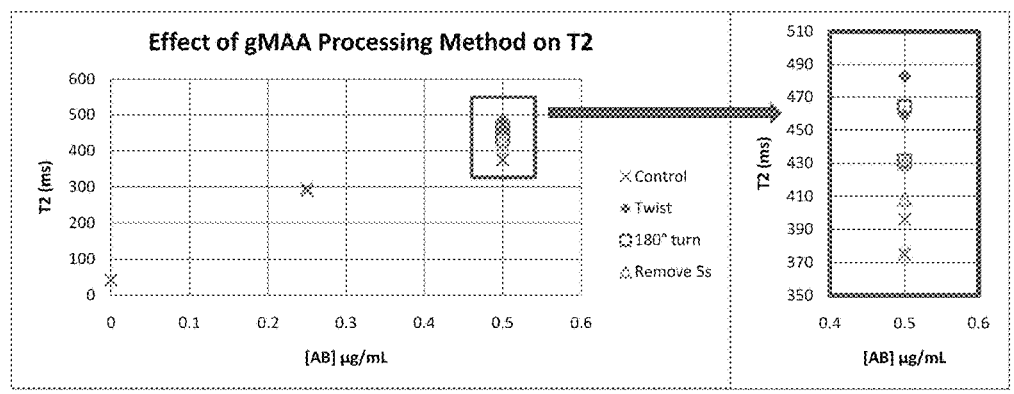
FIG. 26 is a graph showing the specific clustering achieved, as determined via $T_2$ relaxation rates, with various methods of gMAA as described in Example 10.

The specific aggregation achieved with various methods of gMAA are depicted in FIG. 26, wherein (i) "control" is gMAA (magnet exposure+vortex, repeat) in which the relative position of the sample and the magnetic field direction are unchanged with each cycle; (ii) "twist is gMAA (magnet exposure+rotation within magnet, repeat) with rotating tube ca. 90° relative to the gradient magnet with each cycle; (iii) "180 turn" is gMAA (magnet exposure+remove tube from magnet, rotate, place back in magnet, repeat) with rotating tube ca. 180° relative to the gradient magnet with each cycle; and (iv) "remove 5 s" is =removal of tube from magnet, 5 sec rest (no rotation), repeat.

In the pulsed (cycled) magnetic assisted agglomeration of the invention, the liquid sample is exposed to magnetic fields from different directions in an alternating fashion. As shown in FIG. 26, the rate at which a steady state degree of agglomeration, and stable $T_2$ reading, is achieved is expedited by cycling between the two or more positions over a series of gMAA treatments.

Example 11. Side-Bottom Gradient Magnetic Assisted Agglomeration (gMAA)

An evaluation of "side-bottom" gMAA was performed using the creatinine basic immunoassay described in Example 6. For this evaluation, creatinine antibody was diluted to 1 µg/ml and serum calibrators were diluted 1:5 prior to the assay. 10 µl of diluted calibrator, 10 µL of particle reagent and 20 µL of antibody reagent were pipetted into the reaction well. The tube was preheated to 37° C. for 5 minutes and then processed through gMAA with a 60 sec exposure in the side magnet, followed by 60 sec in the bottom magnet. This was completed for 6 total cycles or 12 minutes total. A final mix using a vortex for 60 sec was performed prior to the reading operation.

Figure 27:
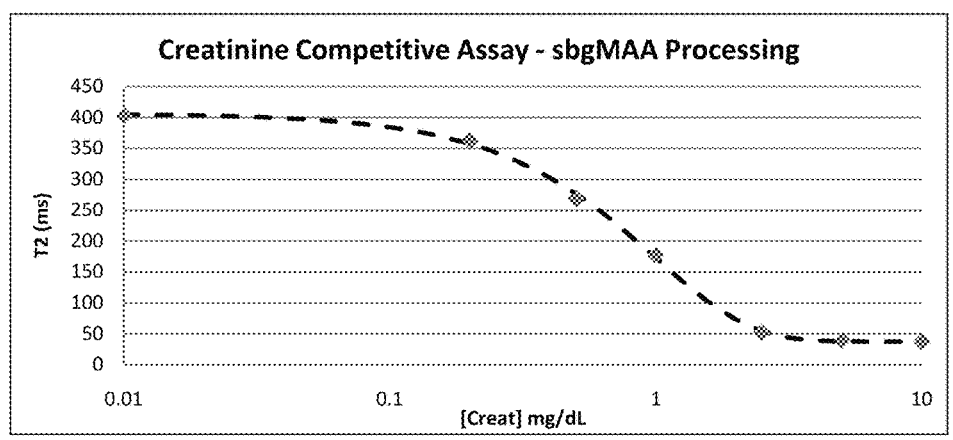
FIG. 27 is a graph showing the response curve for the creatinine competitive assay for samples processed with alternating side-bottom magnet gMAA as described in Example 11.

A standard curve for the competitive creatinine creatinine assay with alternating side-bottom gMAA is shown in FIG. 27 demonstrating good response with the side-bottom gMAA configuration.

Example 12. Effect of Varying the gMAA Dwell Time and Temperature

An evaluation of gMAA dwell time and temperature on assisted agglomeration was performed.

Figure 30A:
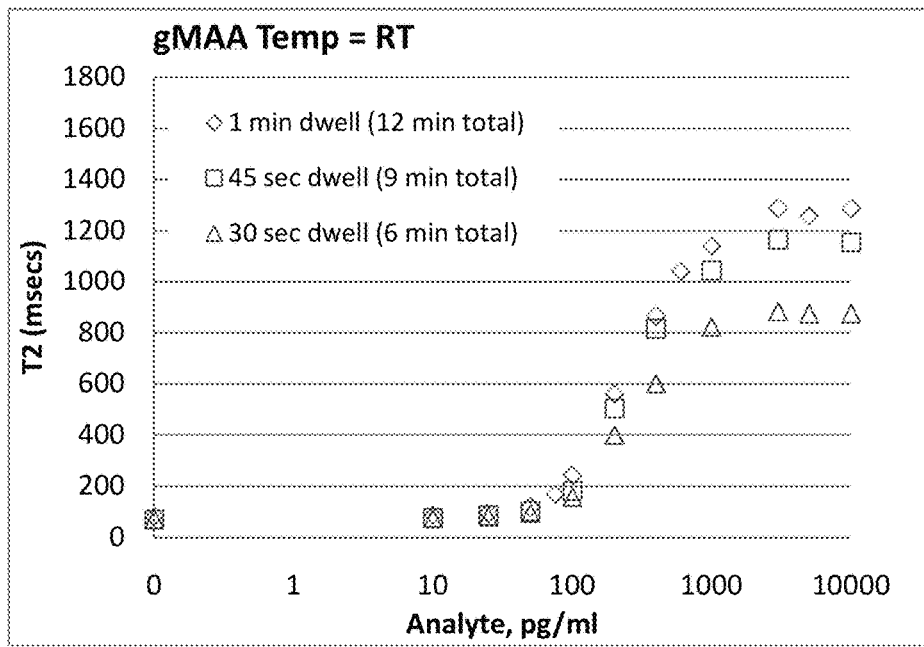
FIGS. 30A-30B are graphs depicting the degree to which gMAA assisted aggregation is dependent upon temperature and dwell time in the assay of Example 11.
Figure 30B:
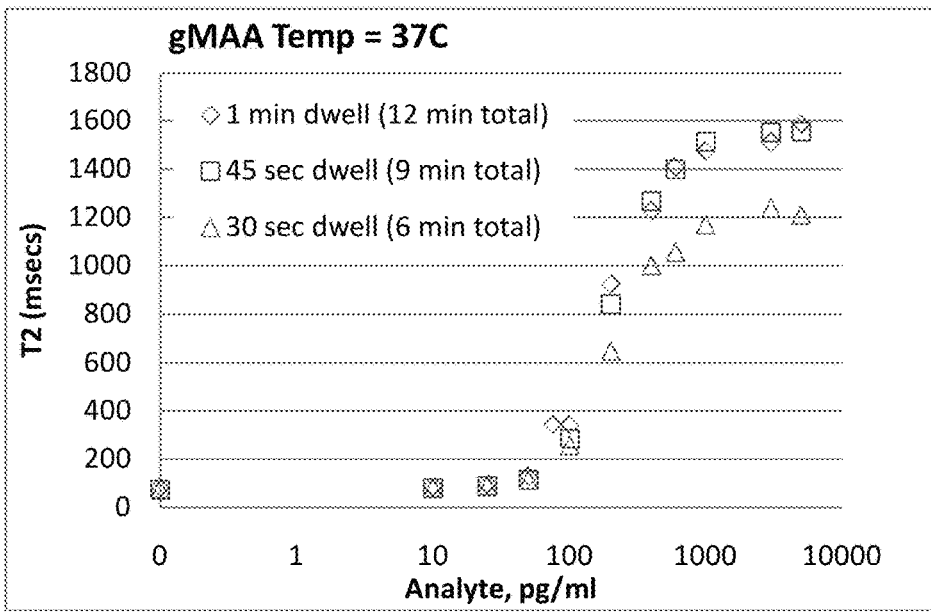

The following conditions were tested to determine the most optimal temperature and dwell time for $T_2$ performance: Alterations—6, 12, 24, 48; for each number of alterations the following dwell time was evaluated: 30, 60, 120 seconds. A fixed magnet time of 6 minutes with the following dwell times was also evaluated: 30, 60, 120 seconds. Samples were prepared by adding 20 µL of varied concentrations of Protein A (a target protein) and 20 µL Anti-Protein A antibody coated magnetic particles at 0.08 mM Fe to a PCR Tube ($1.2 \times 10^9$ particles per tube). Samples were placed into a 32 position tray, vortexed in a plate shaker for 2 minutes at 2000 rpm and incubated in a 37° C. incubation station for 15 minutes. Samples were then exposed to the aforementioned dwell and alteration conditions between alternating magnetic fields. Following gMAA treatment, samples were vortexed manually for 5 minutes, incubated in a 37° C. heat block compatible with PCR Tubes, and the $T_2$ was read using the MR Reader (see Example 6). Data in FIGS. 30A and 30B show that $T_2$ response is directly proportional to temperature and dwell time. Therefore, increased temperature and dwell time/total time results in improved $T_2$ response.

Example 13. Effect of Varying the Number of gMAA Cycles

An evaluation of varying the number of gMAA cycles was performed using the system and procedure of Example 12.

Figure 31:
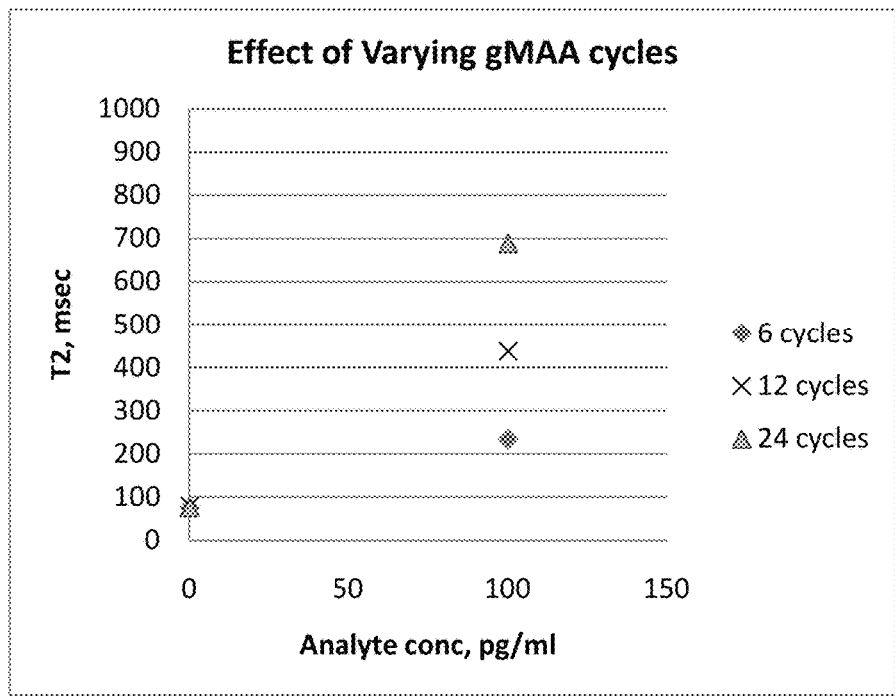
FIG. 31 is a graph showing that the degree of aggregation as determined by measuring the $T_2$ response of the sample is increased with increasing the number of gMAA cycles in the assay of Example 13.

The following conditions were tested for effect on $T_2$ performance: cycles—3, 6, 12, 24; for each cycle the following dwell time were evaluated: 30, 60, 120 seconds. A cycle consists of dwell in the side, followed by bottom. 6 cycles=12 total alterations. Samples were prepared as described in Example 12. As shown in FIG. 31, the degree of aggregation is directly proportional to number of gMAA cycles. It was also found that when magnet exposure time reaches or exceeds 24 minutes, there is an increase in non-specific aggregation that cannot be dispersed with vortex (not shown here).

Example 14. *Candida* Assay

Figure 32:
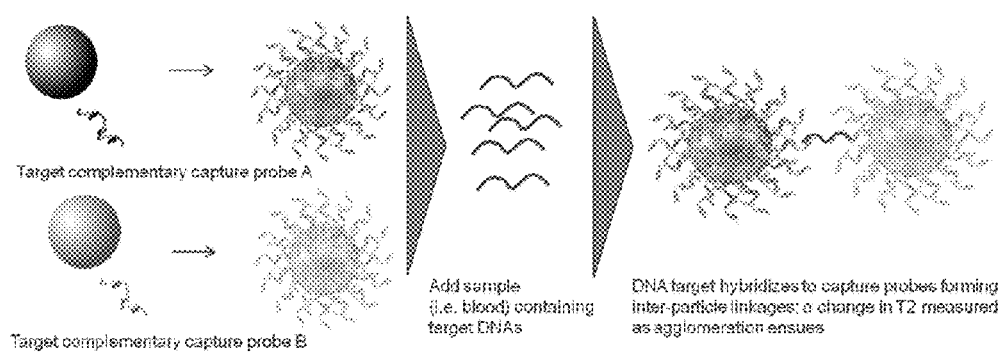
FIG. 32 is a drawing depicting the *Candida* agglomerative sandwich assay architecture of Example 14.

In the assay used for *Candida*, two pools of magnetic particles are used for detection of each *Candida* species. In the first pool, a species specific *Candida* capture oligonucleotide probe is conjugated to the magnetic particles. In the second pool, an additional species-specific capture oligonucleotide probe is conjugated to the magnetic particles. Upon hybridization, the two particles will hybridize to two distinct species-specific sequences within the sense strand of the target nucleic acid, separated by approximately 10 to 100 nucleotides. (Alternatively, the two capture oligonucleotides can be conjugated to a single pool of particles, resulting in individual particles having specificity for both the first and second regions). The oligonucleotide-decorated magnetic particles are designed to aggregate in the presence of nucleic acid molecules from a particular species of *Candida*. Thus, unlike the inhibition assays used for creatinine and tacrolimus, the *Candida* assay features an increase in agglomeration in the presence of the target *Candida* nucleic acid molecules. The hybridization-mediated agglomerative assay architecture is depicted in FIG. 32.

Carboxylated magnetic particles are used in the *Candida* assays. Magnetic particles were conjugated to oligonucleotide capture probes to create oligonucleotide-particle conjugates. For each target amplicon, two populations of oligonucleotide-particle conjugates were prepared. Oligonucleotide-particle conjugates were prepared using standard EDC chemistry between aminated oligonucleotides and carboxylated particles, or, optionally, by coupling biotin-TEG modified oligonucleotides to streptavidin particles. Coupling reactions were typically performed at a particle concentration of 1% solids.

Post-conjugation, functional oligonucleotide densities were measured by hybridizing Cy5-labeled complements to the particles, washing the particles three times to remove non-hybridized oligo; and eluting by heating to 95° C. for 5 minutes. The amount of Cy5 labeled oligonucleotide was quantified via fluorescence spectroscopy.

The coupling reactions were performed at 37° C. overnight with continuous mixing using a rocker or roller. The resulting particle conjugates were washed twice with 1× reaction volume of Millipore water; twice with 1× reaction volume of 0.1 M Imidazole (pH 6.0) at 37° C. for 5 minutes; three times with 1× reaction volume of 0.1 M sodium bicarbonate at 37° C. for 5 minutes; then twice with 1× reaction volume of 0.1 M sodium bicarbonate at 65° C. for 30 minutes. The resulting particle conjugates were stored at 1% solids in TE (pH 8), 0.1% Tween®20).

The panel of *Candida* species detected includes *C. albicans, C. glabrata, C. krusei, C. tropicalis*, and *C. parapsilosis*. The sequences are amplified using universal primers recognizing highly conserved sequence within the genus *Candida*. The capture oligonucleotides were designed to recognize and hybridize to species-specific regions within the amplicon.

An aliquot of a blood sample was first subjected to lysis as follows:

(i) A whole blood sample was mixed with an excess (1.25×, 1.5×, or 2×) volume of ammonium chloride hypotonic lysis solution. Addition of lysis solution disrupts all RBCs, but does not disrupt WBC, yeast, or bacteria cells. The cellular matter was centrifuged at 9000 rpm for 5 minutes and lysate was removed. Intact cells were reconstituted with 100 µl TE (tris EDTA, pH=8) to a final volume of about 100 µl; and (ii) To the approximately 100 µl sample, 120 mg of 0.5 mm beads were added. The sample was agitated for 3 minutes at about 3K rpm, thereby forming a lysate.

An aliquot of ca. 50 µl of lysate was then subjected to PCR amplification by addition of the lysate to a PCR master mix including nucleotides; buffer (5 mM $(NH_4)SO_4$, 3.5 mM $MgCl_2$, 6% glycerol, 60 mM Tricine, pH=8.7 at 25° C.; primers (forward primer in 4× excess (300 mM forward; 0.75 mM reverse) to allow for asymmetric single strand production in the final product); and thermostable polymerase (HemoKlenTaq (New England Biolabs)). After an initial incubation at 95° C. for 3 minutes, the mixture is subjected to PCR cycles: 62° C. annealing; 68° C. elongation; 95° C.—for 40 cycles. Note: there is a 6° C. difference in the annealing and elongation temperatures; the annealing and elongation may be combined into a single step to reduce the total amplification turn-around time.

The PCR amplicon, now ready for detection, is combined with two populations of particles in a sandwich assay.

The PCR primers and capture probes which can be used in the *Candida* assay are provided below in Table 8.

TABLE 8

| PCR Primers | |
|---|---|
| Pan *Candida*-PCR Forward Primer | GGC ATG CCT GTT TGA GCG TC (SEQ ID NO. 1) |
| Pan *Candida*-PCR Reverse Primer | GCT TAT TGA TAT GCT TAA GTT CAG CGG GT (SEQ ID NO. 2) |
| Capture Probes | |
| *Candida albicans* Probe #1 | ACC CAG CGG TTT GAG GGA GAA AC (SEQ ID NO. 3) |

TABLE 8-continued

| *Candida albicans* Probe #2 | AAA GTT TGA AGA TAT ACG TGG TGG ACG TTA (SEQ ID NO. 4) |
|---|---|
| *Candida krusei* Probe #1 | CGC ACG CGC AAG ATG GAA ACG (SEQ ID NO. 5) |
| *Candida krusei* Probe #2 | AAG TTC AGC GGG TAT TCC TAC CT (SEQ ID NO. 6) |
| *Candida krusei* probe | AGC TTT TTG TTG TCT CGC AAC ACT CGC (SEQ ID NO. 32) |
| *Candida glabrata* Probe #1 | CTA CCA AAC ACA ATG TGT TTG AGA AG (SEQ ID NO. 7) |
| *Candida glabrata* Probe #2 | CCT GAT TTG AGG TCA AAC TTA AAG ACG TCT G (SEQ ID NO. 8) |
| *Candida parapsilosis/tropicalis* Probe #1 | AGT CCT ACC TGA TTT GAG GTC NitInd[1]AA (SEQ ID NO. 9) |
| *Candida parapsilosis/tropicalis* Probe #2 | CCG NitInd[1]GG GTT TGA GGG AGA AAT (SEQ ID NO. 10) |
| *Candida tropicalis* | AAA GTT ATG AAATAA ATT GTG GTG GCC ACT AGC (SEQ ID NO. 33) |
| *Candida tropicalis* | ACC CGG GGGTTT GAG GGA GAA A (SEQ ID NO. 34) |
| *Candida parapsilosis* | AGT CCT ACC TGA TTT GAG GTC GAA (SEQ ID NO. 35) |
| *Candida parapsilosis* | CCG AGG GTT TGA GGG AGA AAT (SEQ ID NO. 36) |
| inhibition control 5' | GG AAT AAT ACG CCG ACC AGC TTG CAC TA (SEQ ID NO. 37) |
| inhbition control 3' | GGT TGT CGA AGG ATC TAT TTC AGT ATG ATG CAG (SEQ ID NO. 38) |

[1]NitInd is 5' 5-Nitroindole, a base that is capable of annealing with any of the four DNA bases.
[2]Note that oligo Ts are added as spacers Optionally, the assay is carried out in the presence of a control sequence, along with magnetic particles decorated with probes for confirming the presence of the control sequence.

Example 15. Non-Agglomerative Methods

This process has been demonstrated using aminosilane-treated nickel metal foam with 400 µm pores decorated with anti-creatinine antibodies and shown to specifically bind creatinine-detivatized magnetic particles. A 1 cm square piece of nickel metal foam (Recemat RCM-Ni-4753.016) was washed by incubating at room temperature for 1 hr in 2M HCL, rinsed thoroughly in deionized water, and dried at 100° C. for 2 hours. The nickel foam was then treated with 2% 3-aminopropyltriethoxysilane in acetone at room temp overnight. The nickel metal foam was then washed extensively with deionized water and dried for 2 hours at 100° C. The aminosilane-treated nickel metal foam was treated with 2% gluteraldehyde in water for 2 hours at room temp and washed extensively with deionized water. Next, the metal foam was exposed to 100 µg/ml of anti-creatinine antibody (14HO3) (see Example 6) in PBS overnight, washed extensively with PBS, and treated with Surmodics Stabilguard to stabilize and block non-specific binding. Two mm square pieces of the derivatized metal foam were cut using a fresh razor blade being careful not to damage the foam structure. A piece of the derivatized metal foam was place into a PCR tube in 20 µl assay buffer (100 mM glycine (pH=9.0), 150 mM NaCl, 1% BSA, 0.05% ProClin®, and 0.05% Tween®). Twenty microliters of control particles (that should not bind to the metal foam ABX1-11) at 0.2 mMFe were added to the tube to bring the final volume to 40 ul and final particle concentration to 0.1 mM Fe ($1\times10^6$-$1\times10^8$ particles/tube). A separate PCR tube with the exact particle and buffer, without the metal foam was also prepared. The PCR tube containing the derivatized metal foam and control particles was placed in a gMAA fixture (side pull 6 position) for one minute and removed touched with a hand demagnetizer, and placed back into the gMAA fixture for another minute, removed touched with a hand demagnetizer and placed back into the gMAA fixture for another minute and vortexed (three 1 minute magnetic exposures). Thirty µl of sample was removed from both PCR tubes, heated to 37° C. in a grant block heater for 5 minutes and the $T_2$ read using the MR Reader (see Example 6). The $T_2$ from the sample with no foam read 39.2, and the samples from the PCR tube containing the foam read 45.1, demonstrating a low level of particle depletion due to NSB. The derivatized metal foam was de-magnetized, vortexed and rinsed in assay buffer. It was placed in a new PCR tube with 20 µl of assay buffer and 20 µl of AACr2-3-4 particles derivatized with creatinine with a final particle concentration of 0.1 mMFe. A duplicate PCR tube without the derivatized metal foam was also set up as in the control experiment. The PCR tube with the metal foam was cycled twice through the gMAA device exactly as the control experiment (3 one minute exposures with demag after each exposure, and final vortex). Thirtly µl samples from both tubes were removed and heated to 37° C. for 5 minutes and then read on the MR reader. The sample from the PCR tube with the derivatized metal foam read 41.5, and the sample from the PCR tube with the metal foam derivatized with the anti-creatinine antibody read 324.2, thus demonstrating specific binding/depletion of the appropriate creatinine-derivatized magnetic particles from the aqueous volume read by the MR reader.

Example 16. Detection of Single Nucleotide Polymorphisms

There are numerous methods by which $T_2$ measurements could detect single nucleotide polymorphisms.

The simplest application would involve discrimination of mismatches via a thermophilic DNA ligase (Tth ligase). This assay would require lysis of the sample material followed by DNA shearing. Adaptors could be ligated onto the sheared DNA if a universal amplification of the genomic DNA was needed. The SNP would be detected by engineering superparamagnetic particle bound capture probes which flank the SNP such that the 5' end of the 3' aminated capture probe would be perfectly complementary to one particular SNP allele and subsequent treatment with Tth ligase would result in the ligation of the two particle-bound capture probes. Ligation would therefore lock the particles into an agglomerated state. Repeated melt, hybridization cycles will result in signal amplification in cases where genomic DNA amplification is not desired because of the amplification bias risk. The same 5' aminated capture probe could be utilized in all case while the 3' aminated probe could be generated to yield 4 distinct pools (an A, G, C, or T) at the extreme 5' end. Detection would require splitting of the sample into the 4 pools to determine which nucleotide(s) were present at the polymorphic site within that particular individual. For example a strong $T_2$ switch in the G detection tube only would indicate the individual were homozygous for G at that particular sequence location, while a switch at G and A would indicate the individual is a heterozygote for G and A at that particular SNP site. The advantage of this method is Tth polymerase has been demonstrated to have superior discrimination capability even discriminating G-T mismatches (a particular permissive mismatch and also the most common) 1:200 fold against the correct complement. While ligase detection reactions as well as oligonucleotide ligase assays have been employed in the past to define nucleotide sequences at known polymorphic sites, all required amplification either before or after ligation; in this particular example the signal could be amplified via a ligation induced increase in the size of the resulting agglomerated particle complex and thereby increases in the measured relaxation times ($T_2$).

A modification to this procedure could include hybridization of a particle bound capture probe flanking the hybridization of a biotinylated probe. When a perfectly complementary duplex is formed via hybridization of the particle bound probe, the ligase would covalently bind the biotin probe to the magnetic particle. Again repeated rounds of heat denaturation followed by annealing and ligation should yield a high proportion of long biotinylated oligos on the magnetic particle surface. A wash to remove any free probe would be conducted followed by the addition of a second streptavidin labeled superparamagnetic particle. Agglomeration would ensue only if the biotinylated probes were ligated onto the surface of first particle.

A hybridization discrimination approach could as well be employed. In this example, aminated oligonucleotide complements adjacent to known SNPs would be generated. These aminated oligonucleotides would be used to derivatize the surface of a 96-well plate with 1 SNP detection reaction conducted per well. Genomic DNA would then be sheared, ligated to adaptors, and asymmetrically amplified. This amplified genomic DNA would then be applied to the array as well as a short biotinylated SNP detecting probe. The amplified genomic DNA would hybridize to the well-bound capture probe and the SNP detecting probe would then bind to the tethered genomic DNA. Washing would be conducted to remove free SNP-detecting probe. A streptavidin (SA) magnetic particle would then be added to each well. Washing again would be required to remove free-SA particles. $T_2$ detection could be conducted directly within the wells by added biotinylated superparamagnetic particles to yield surface tethered agglomerated particles, or the SA magnetic particles could be eluted from each well on the array and incubated in detection reactions with biotinylated magnetic particles.

Lastly a primer extension reaction could be coupled to $T_2$ detection to discriminate which nucleotide is present at a polymorphic site. In this assay, a pool of dideoxynucleotides would be employed with one nucleotide per pool possessing a biotin (i.e., ddA, ddT, ddbiotin-C, and/or ddG). A superparamagnetic particle bearing a capture probe whose last base upon hybridization lies adjacent to a SNP would be employed.

The sheared genomic DNA would be split and incubated in four separate primer extension reactions. An exo-DNA polymerase would then catalyze the addition of a dideoxy complementary to the nucleotide present in the SNP. Again this reaction could be cycled if a thermophilic polymerase is employed to ensure that most of the capture probes on the particle will be extended. A magnetic separation followed by a wash of the particles would be conducted followed by incubation with streptavidin superparamagnetic particles. Clustering would ensue proportional to the extent of biotinylated capture probe on the surface of the first particle. If two of the dideoxypools generated a gain in $T_2$ (i.e., facilitate particle agglomeration), the patient would be a heterozygote. If only one pool yielded and increase in $T_2$, the patient would be a homozygote.

A final method to detect SNPs employs allele-specific PCR primers, in which the 3' end of the primer encompasses the SNP. Since stringent amplification conditions are employed, if the target sequence is not perfectly complementary to the primer, PCR amplification will be compromised with little or no product generated. In general, multiple forward primers would be designed (one perfectly complementary to each allele) along with a single reverse primer. The amplicon would be detected using two or more capture probe bound superparamagnetic particles to induce hybridization based agglomeration reactions. One advantage of this approach is that it leverages some of the work already conducted at $T_2$ on PCR within crude samples, and would merely entail primers designed to encompass known SNPs. A disadvantage in this approach is that it cannot determine de novo SNP locations.

An additional method which can be used is simply relying on the discrimination capabilities of particle-particle cross-linking due to hybridization to a short nucleic acid target. Mismatches in base pairs for oligonucleotides have been shown to dramatically shift the agglomeration state of particles, and the measured $T_2$ signal, due to reduced hybridization efficiencies from the presence of a single base mismatch.

Example 17. Diagnostic *Candida* Panel

Testing was performed over the course of 45 days. *C. albicans* and *C. krusei* reference strains as well as *C. albicans* clinical isolates were cultivated and maintained for the duration of the study.

Materials:

*C. albicans* and *C. krusei* nanoparticles: Two particle populations were generated for each species, the particles bearing covalently conjugated to oligos complementary to species-specific sequences within the ITS2 region (see Example 14). The particles were stored at 4-8° C. in TE (pH 8), 0.1% Tween and were diluted to 0.097 mM Fe in DNA hybridization buffer immediately before use.

*Candida* strains: Panels were performed using *C. albicans* reference strain MYA 2876 (GenBank FN652297.1), *C. krusei* reference strain 24210 (GenBank AY939808.1), and *C. albicans* clinical isolates. The five *C. albicans* isolates used were cultivated on YPD at room temperature. Single colonies were selected, washed 3 times with PBS, and then quantified via hemocytometer for preparation of whole blood spikes. The samples were stored as frozen glycerol stocks as −80° C.

Human whole blood: Whole blood was collected from healthy donors and treated with $K_2$EDTA and spiked with washed serially diluted *Candida* cells at concentrations spanning 1E5 to 5 cells/mL. Cell spikes prepared in fresh blood were stored at −20° C.

Erythrocyte Lysis buffer: A hypotonic lysis buffer containing 10 mM potassium bicarbonate, 155 mM ammonium chloride, and 0.1 mM EDTA was filter sterilized and stored at room temperature prior to use. Alternatively an erythrocyte lysis agent can be used, such as a non-ionic detergent (e.g., a mixture of Triton-X 100 and igepal, or Brij-58).

PCR master mix: A master mix containing buffer, nucleotides, primers, and enzyme was prepared (20 µL 5× reaction buffer, 22 µL water, 2 µL 10 mM dNTP, 3 µL 10 µM forward primer, 3 µL 2.5 µM reverse primer, 10 µL HemoKlenTaq, and 40 µL bead beaten lysate) and stored at room temperature.

Particle hybridization master mix: A master mix consisting of nanoparticle conjugates, salts, surfactant, and formamide was prepared (78 µL formamide, 78 µL 20×SSC, 88.3 µL 1×TE+0.1% Tween, 7.5 µL CP 1-3', and 8.2 µL CP 3-5') immediately before use.

Glass beads (0.5 mm), used in mechanical lysis of *Candida*, were washed in acid and autoclaved and stored at room temperature prior to use.

Figure 47:
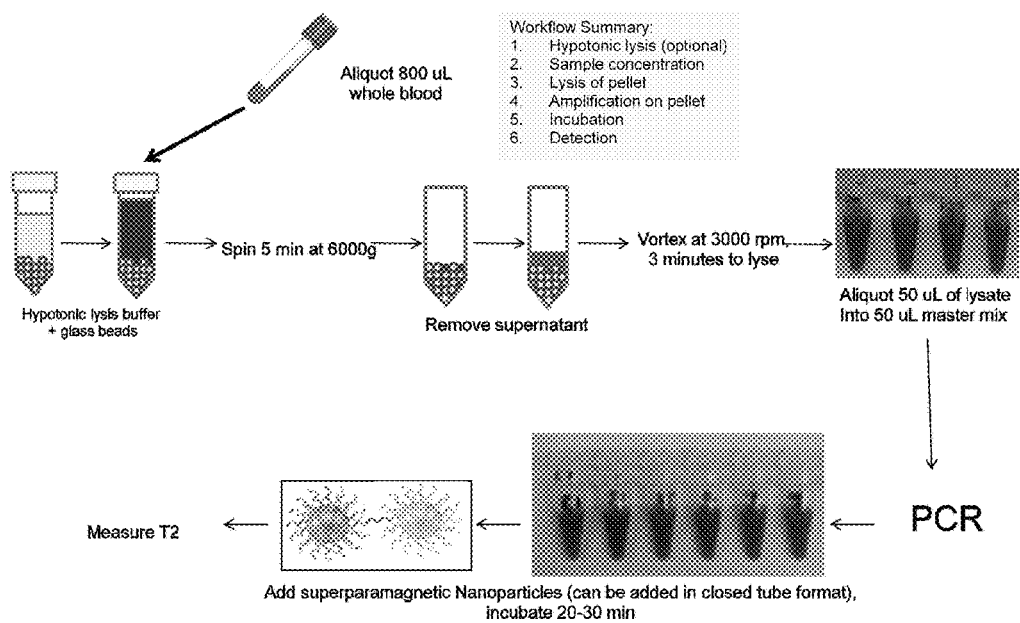
FIG. 47 is a scheme describing the work flow for detection of a bacterial or fungal pathogen in a whole blood sample (see Examples 14 and 17).

PCR Protocol:

A general scheme of the workflow for detection of a pathogen (e.g., *Candida*) in a whole blood sample is shown in FIG. 47. The protocol was as follows: (i) human whole blood spiked samples were allowed to warm to room temperature (~30 minutes); (ii) 1 mL of erythrocyte lysis buffer was aliquoted into each tube; (iii) each tube was centrifuged at 9000 g for 5 minutes and the lysed blood discarded; (iv) 100 µL of 0.2 micron filtered TE was aliquoted into each tube; (v) 120 mg of acid washed glass beads were added to each tube; (vi) each tube was vortexed for 3 minutes at maximum speed (~3000 rpm); (vii) 50 µL of lysed sample was aliquoted into a tube containing PCR master mix (viii) cycle PCR reactions as follows: (initial denaturation: 95° C., 3 minutes; 30-40 cycles at 95° C., 20 seconds; 30-40 cycles at 62° C., 30 seconds; 30-40 cycles at 68° C., 20 seconds; final extension: 68° C., 10 minutes; final soak: 4° C.); (ix) each of the samples was briefly centrifuged after thermocycling to form pellet clotted blood; (x) 5 µL of particle master mix was aliquoted into the tube for every 10 µL of amplified sample; (xi) the resulting mixture was well mixed and the sample denatured at 95° C. for 3 minutes; (xii) the sample was hybridized at 60° C. for 1 hour with gentle agitation; (xiii) the sample was then diluted to 150 uL with particle dilution buffer, and equilibrated to 37° C. in a heat block for 1 minute; and (xiv) the $T_2$ of the sample was measured using a $T_2$ MR reader.

Test Results

Repeatability of *Candida albicans* detection in human whole blood: To determine the repeatability of the $T_2$ measurement on *C. albicans* infected human whole blood, we conducted an eight day study in which the same donor spiked and amplified sample was hybridized to the superparamagnetic particles (n=3) each day and the resulting $T_2$ values were recorded.

Figures 46A, 46B:
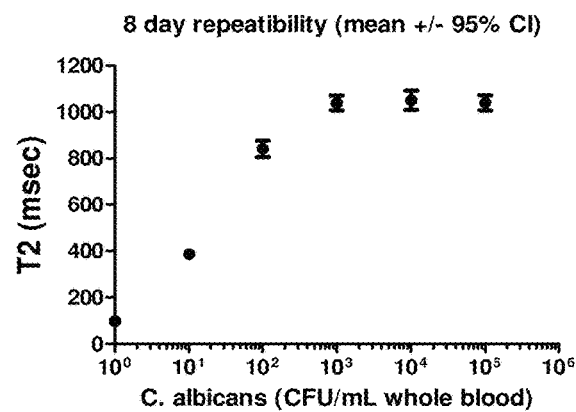
FIGS. 46A is a table and 46B is a graph depicting the repeatability of *Candida* measurements by methods of the invention over a period of eight days. To determine the repeatability of the T2 measurement on *C. albicans* infected human whole blood, we conducted an eight day study in which the same donor spiked and amplified sample was hybridized to the superparamagnetic particles (n=3) each day and the resulting T2 values were recorded (see Example 17). The within run precision is shown in FIG. 46A and in general is tight with the CV's of all measurands less than 12%. The repeatability observed over the course of eight days is shown in FIG. 46B (Mean T2 values+/-the 95% confidence intervals measured from the same donor spiked and amplified samples over the course of eight days) with the CVs less than 10% across the range of *Candida* concentrations and 6% for the negative control.

The within run precision is shown in FIG. 46A and in general is tight with the CV's of all measurands less than 12%. The repeatability observed over the course of eight days is shown in FIG. 46B with the CVs less than 10% across the range of *Candida* concentrations and 6% for the negative control. Importantly, a two population two-tailed Student's T-test was applied to determine if the difference in means between the mock *Candida* infected blood at 10 cells/mL and the healthy donor blood was significant. The results are summarized in Table 9.

TABLE 9

The difference in means between 10 cells/mL infected blood and negative control is significant (p value < 0.0001)

| | |
|---|---|
| P value | < 0.0001 |
| Are means signif. different? (P < 0.05) | Yes |
| One- or two-tailed P value? | Two-tailed |
| t, df | t = 40.69 df = 23 |
| Number of pairs | 24 |
| Mean of differences | 287.7 |
| 95% confidence interval | 273.0 to 302.3 |
| R square | 0.9863 |

Figure 48A:
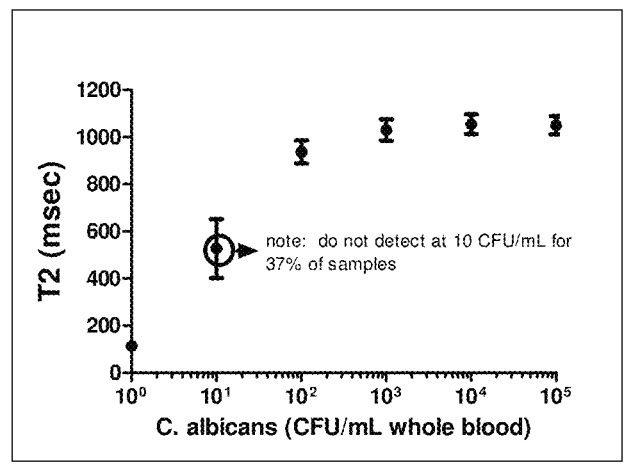
FIGS. 48A and 48B are graphs depicting results from donor samples.

Influence of sample matrix on *Candida albicans* and *Candida krusei* detection and reproducibility: Healthy blood from 6 donors was spiked with a range of *C. albicans* or *C. krusei* cells (1E5 cells/mL to 0 cells/mL). From the *Candida albicans* spiked blood, sixteen independent experiments were conducted. Each experiment consisted of PCR amplification of the 1E5 to 0 cells/mL spiked blood with each amplification reaction subjected to three replicate $T_2$ detection experiments; thus for *C. albicans* a total of 48 $T_2$ values were recorded at each tested concentration (see FIG. 48A). At the lowest test concentration (10 cells/mL), we failed to detect *Candida albicans* 37% of the time (6 out of 16 experiments); however at 100 cells/mL *Candida albicans* was detected 100% of the time. This suggests the LOD for *C. albicans* is above 10 cells/mL but below 100 cells/mL. More concentrations will be tested between the 10 CFU to 100 cells/mL to better define the LOD; however we do not expect to observe any major matrix effects on assay performance. This is evidenced by the CVs of the $T_2$ measurements which are as follows: 12.6% at 1E5 cells/mL in 6 donor bloods, 13.7% at 1E4 cells/mL, 15% at 1E3 cells/mL, 18% at 1E2 cells/mL, and 6% at 0 cells/mL. This suggests the assay can robustly detect at *C. albicans* concentrations greater than or equal to 100 cells/mL with no major inhibition of performance introduced through the donor blood samples.

Figure 48B:
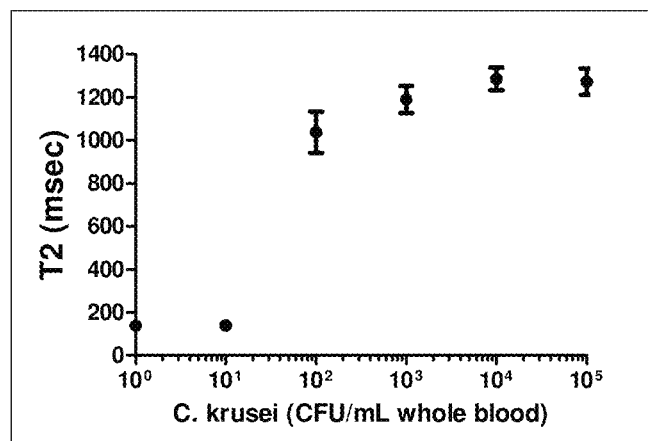

The same experiment was conducted using a reference strain of *C. krusei*. In this case 7 independent experiments were conducted as the remaining spiked blood was reserved for blood culture analysis. We did not detect at 10 cells/mL in any of the experimental runs but detected at 100 cells/mL for all experimental runs. This suggests the LOD between 10 and 100 cells/mL. Again a titration of cell concentrations between 100 and 10 cells/mL will need to be conducted to better define the LOD. The CV's of the measurements across the range of concentrations was: 10.5% at 1E5, 9% at 1E4, 12% at 1E3, 20% at 1E2, 6.4% at 10, and 5.2% at 0 cells/mL. The results are shown in FIG. 48B.

Figure 49:
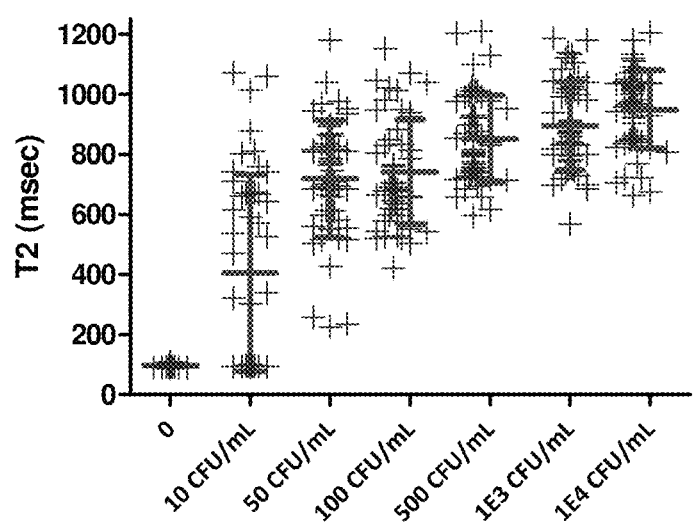
FIG. 49 is a dot diagram showing the T2 values measured for five *C. albicans* clinical isolates spiked into 400 µL whole blood at concentrations spanning 0 to 1E4 cells/mL. The plotted results are the mean+/-1 SD. The data indicates despite the scatter of absolute T2 values obtained among the different isolates, at 50 cells/mL all values are above that of the no *Candida* control (3 replicate measurements from 20 independent assays, total of 60 different clustering reactions).

Preliminary determination of limit of detection: Five *Candida albicans* clinical isolates were spiked into 6 different donor blood samples at concentrations of 1E4, 1E3, 5E2, 1E2, 50, 10, 5, and 0 cells/mL. Each isolate was spiked into a minimum of two different donor blood samples. Amplification reactions were detected via $T_2$ measurement with the results plotted in FIG. 49. It is important to note that no data was removed for cause within this study. We did not detect *C. albicans* 50% of the time at 5 cells/mL or 10 cells/mL; however at 50 cells/mL *C. albicans* was detected 95% of the time. These data were generated using different clinical isolates; each isolate contains a different number of rDNA repeats and the number of these repeats can vary as much as 4-fold from strain to strain (i.e. ~50 units to 200 units). Since the input target copy numbers will vary slightly from strain to strain and certainly from species to species, there will be subtle differences in the absolute $T_2$ values observed at very low cell numbers (i.e. 10 cells/mL). Based on our very preliminary study, the data suggests a cut-off of 10 cells/mL; however this determination cannot be made in the absence of final formulations of reagents as well as the instrument/cartridge. It does suggest that defining the C5-C95 interval will be difficult because at 10 cells/mL each reaction contains only 4 cells. Titrating at cell numbers lower than this becomes challenging with this input volume of blood. Using the Poisson distribution to calculate the number of reactions that would contain 0 cells at 10 cells/mL indicates only 2% of the reactions would not contain cells; however at 5 cells/mL, 13% of the reactions will contain no *Candida* cells, and at 2 cells/mL, ~37% of the reactions would not contain *Candida* cells. To increase the assay's sensitivity to 95% at 10 cells/mL, we could increase the amount of lysate added to the PCR reactions from 40 μL to 50 μL and increase the amount of patient blood from 400 μL to 800 μL/reaction.

Preliminary determination of sensitivity/specificity: Initially, quantification of input *Candida* colony forming units was conducted using a hemocytometer; however in this case the operator counted budding daughter cells as separate cells. As our data is reported in colony forming units/mL and not cells/mL, buds should not be quantified. Because of this error, fewer cells/mL of *Candida* are present at the various spike concentrations and our sensitivity at 10 cells/mL was only 90%, while our specificity was 100%. At 25 cells/mL or greater we observe 100% sensitivity and 100% specificity. In all cases, blood culture vials inoculated with *Candida* cells were blood culture positive by day 8. It should be noted that the default setting for blood culture is incubation for 5 days; however we needed to extend this incubation time as many of our inoculums required >5 days incubation. As an example, Table 10A shows the time from inoculation to culture positive recorded for four different *C. albicans* clinical isolates inoculated into blood culture.

The results of $T_2$ measurements conducted on 800 μL aliquots from these spiked whole blood samples is shown in Table 10B. In all cases we were able to detect at 25 cells/mL, or greater, however we were unable to detect clinical isolate C3 at 12 cells/mL. It is important to note the CFU's were quantified via hemocytometer and not Coulter counter for this particular method compare experiment. In total 51 blood culture bottles were inoculated with hemocytomer quantified *Candida albicans* clinical isolates and 35 negative blood culture vials were included in the experiment. The results for inoculums greater than 25 cells/mL are shown in the contingency table in Table 11.

TABLE 10A

Time to blood culture positive results for 4 different *Candida albicans* clinical isolates.

| C. albicans isolate | 100 CFU/mL | 25 CFU/mL | 12 CFU/mL | 0.0 | 0.0 |
|---|---|---|---|---|---|
| C1 | 161 hrs +/− 12 | 161 hrs +/− 12 | 161 hrs +/− 12 | 192 hrs | 192 hrs |
| C2 | 40 hrs +/− 12 | 65 hrs +/− 12 | 47.5 hrs | 192 hrs | 192 hrs |
| C3 | 69.5 hrs | 161 hrs +/− 12 | 161 hrs +/− 12 | 192 hrs | 192 hrs |
| C4 | 40 hrs +/− 12 | 43 hrs | 47.5 hrs | 192 hrs | 192 hrs |

*Note:
all blood culture negative vials were negative and discarded at t = 8 days

TABLE 10B

T$_2$ values obtained following PCR amplification and
T2 detection on the pre-culture in vitro spiked
blood samples shown above (assay time ~3 hrs).

| C. albicans isolate | 100 CFU/mL | 25 CFU/mL | 12 CFU/mL | 0.0 | 0.0 |
|---|---|---|---|---|---|
| C1 | 739.0 | 409.0 | 632.5 | 112.7 | 112.8 |
| C2 | 983.2 | 1014.5 | 997.6 | 117.4 | 114.8 |
| C3 | 912.7 | 510.5 | 113.3 | 116.2 | 112.0 |
| C4 | 807.6 | 741.2 | 665.2 | 119.1 | 115.9 |

T2 values (in msec) are the mean n = 3 with CV's less than 10% for replicate measurements

TABLE 11

Contingency Table used to calculate sensitivity/specificity
at > 25 cells/mL C. albicans.

| Positive | 51 (true positive) | 0 (false positive) | 51 (TP + FP) |
|---|---|---|---|
| Negative | 0 (false negative) | 35 (true negative) | 35 (FN + TN) |
| Total | 51 (TP + FN) | 35 (FP + TN) | 86 (N) |

Estimated Sensitivity = 100 × [TP/(TP + FN)] = 100% (95% confidence interval = 93 to 100%)
Estimated Specificity = 100 × [TN/(FP + TN)] = 100% (95% confidence interval = 90 to 100%)

Standardization of CFU quantification has improved our assay sensitivity and reproducibility. Preliminary results from 27 blood culture bottles are shown in Table 12. These preliminary results indicate we have 100% sensitivity and specificity at 10 cells/mL or greater. We have additionally begun method comparisons using *C. krusei*. Preliminary results (from 36 vials) are shown in Table 13. The results indicate we have a sensitivity/specificity of 88%/100% at 10 cells/mL or greater and 00% sensitivity/100% specificity at 33 cells/mL or greater for *Candida krusei*. Another important change which was instituted prior to the new blood culture agreement comparisons was the employment of a multi-probe particle. In this case the T$_2$ clustering reactions for *C. albicans* detection were conducted using albicans/parapsilosis/tropicalis multi-functional particles while *C. krusei* was detected using the glabrata/krusei multi-functional particles.

TABLE 12

Contingency Table used to calculate sensitivity/specificity
at >10 cells/mL C. albicans.

| Positive | 18 (true positive) | 0 (false positive) | 18 (TP + FP) |
|---|---|---|---|
| Negative | 0 (false negative) | 6 (true negative) | 6 (FN + TN) |
| Total | 18 (TP + FN) | 6 (FP + TN) | 24 (N) |

Estimated Sensitivity = 100 × [TP/(TP + FN)] = 100% (95% confidence interval = 81.4 to 100%)
Estimated Specificity = 100 × [TN/(FP + TN)] = 100% (95% confidence interval = 54 to 100%)

TABLE 13

Contingency Table used to calculate sensitivity/specificity
at >10 cells/mL Candida krusei.

| Positive | 24 (true positive) | 0 (false positive) | 24 (TP + FP) |
|---|---|---|---|
| Negative | 3 (false negative) | 9 (true negative) | 12 (FN + TN) |
| Total | 27 (TP + FN) | 9(FP + TN) | 36 (N) |

Estimated Sensitivity = 100 × [TP/(TP + FN)] = 89% (95% confidence interval = 71 to 98%)
Estimated Specificity = 100 × [TN/(FP + TN)] = 100% (95% confidence interval = 66 to 100%)

Figure 50A:
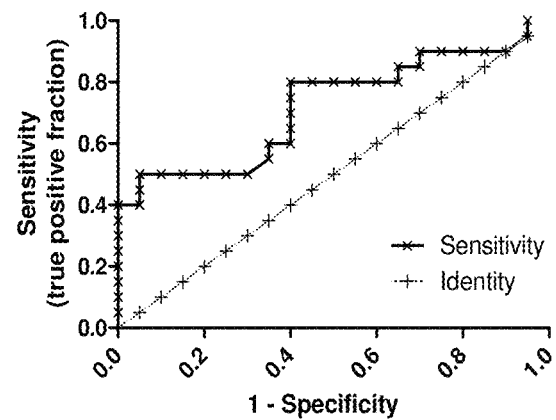
FIGS. 50A and 50B are ROC plots of T2 results generated at 10 cells/mL (FIG. 50A) and 50 cells/mL (FIG. 50B). The area under the curve at 10 cells/mL is 0.72 (95CI=0.56 to 0.88) while at 50 cells/mL the area under the curve is 0.98 (95CI=0.95 to 1.001). The area under the curve is often used to quantify the diagnostic accuracy; in this case our ability to discriminate between a Candidemic patient with an infection of 10 cells/mL or 50 cells/mL versus a patient with no Candidemia. At 10 cells/mL the area under the curve is 0.72 which means that if the T2 assay was run on a randomly chosen person with Candidemia at a level of infection of 10 cells/mL, there is an 72% chance their T2 value would be higher than a person with no Candidemia. The clinical accuracy of the test is much higher at 50 cells/mL with the area under the curve at 0.98. Again indicating that in a person with Candidemia at this level of infection, the T2 assay would give a value higher than a sample from a patient without Candidemia 98% of the time. See Example 17.
Figure 50B:
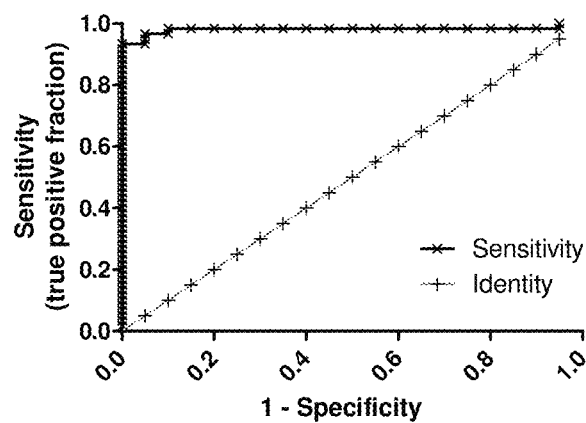

Preliminary assessment of clinical accuracy: Clinical accuracy is defined as the ability to discriminate between two or more clinical states, for example Candidemia versus no Candidemia. Receiver Operator Characteristic (ROC) plots describe the test's performance graphically illustrating the relationship between sensitivity (true positive fraction) and specificity (true negative fraction). The clinical accuracy (sensitivity/specificity pairs) is displayed for the entire spectrum of decision levels. Using the data generated from the 10 cells/mL and 50 cells/mL clinical isolate spiked whole blood samples, two ROC plots were generated and are shown in FIGS. 50A and 50B. The area under the curve is often used to quantify the diagnostic accuracy; in this case our ability to discriminate between a Candidemic patient with an infection of 10 cells/mL or 50 cells/mL versus a patient with no Candidemia. At 10 cells/mL the area under the curve is 0.72 which means that if the T$_2$ assay was run on a randomly chosen person with Candidemia at a level of infection of 10 cells/mL, there is an 72% chance their T$_2$ value would be higher than a person with no Candidemia. The clinical accuracy of the test is much higher at 50 cells/mL with the area under the curve at 0.98. Again indicating that in a person with Candidemia at this level of infection, the T$_2$ assay would give a value higher than a sample from a patient without Candidemia 98% of the time. This is excellent clinical accuracy for infection levels of 50 cells/mL. ROC plots were not prepared for the 100 cells/mL samples or higher as the area would be translating to 100% clinical diagnostic accuracy. Final clinical accuracy is determined from real patient samples on the clinical platform.

Figure 51:
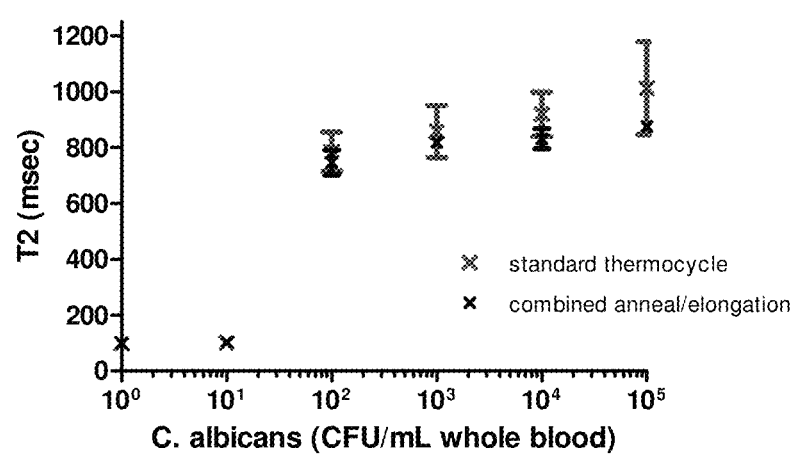
FIG. 51 is a graph depicting the sensitivity of the assay using the standard thermocycle (~3 hours turnaround time) and a process that combines the annealing/elongation steps (~2 hours, 13 minutes turnaround time). Combining the annealing and elongation step in the thermocycling reduces the total assay TAT to 2.25 hours without compromising assay sensitivity.

Assay turnaround time: The primary assay steps with estimated times are: (i) hypotonic lysis/centrifugation/bead beating (8 min); (ii) PCR (120 min.); (iii) hybridization of amplicon to particles (30 min.); (iv) hMAA (10 min.); and (v) transfer and read (10 sec.). The processing time for the assay is estimated at ~178 minutes (~3 hrs), excluding reagent and equipment preparation. This is the workflow used for qualification; however we have demonstrated that the following modified work-flow with shorter PCR and hybridization steps does yield the same detection sensitivity (see FIG. 51) (albeit with a reduction in the amount of amplicon generated for some *Candida* species (i.e., glabrata) and hence a smaller delta T$_2$ between diseased and normal): (i) hypotonic lysis/centrifugation/bead beating (8 min.); (ii) PCR (70 min.); (iii) hybridization of amplicon to particles (30 min.); (iv) hMAA (10 min.); and (v) transfer and read (10 sec.). This modified flow generates a TAT of 133 minutes or 2 hours and 13 minutes (and this is without migration to a faster thermocycler).

Conclusions

This testing demonstrates a current T$_2$ based molecular diagnostic assay for Candidemia with the following metrics: (i) detection of *Candida albicans* within whole blood at a range spanning 5-1E5 cells/mL (5-log); (ii) detection of *Candida krusei* within whole blood at a range spanning 10 cells/mL to 1E5 cells/mL; (iii) sensitivity/specificity of 100%/100% at >25 cells/mL; (iv) diagnostic accuracy of greater than 98% for concentrations >50 cells/mL; (v) assay compatibility with whole blood (no major matrix effects observed using twelve different donor blood samples); (vi) repeatability of T$_2$ measurements (less than 12% within the same day and less than 13% across eight days); and (vii) reduced total assay turnaround time to 2 hours 3 minutes.

We have tested higher input volumes of human blood and found that efficient hypotonic lysis is achievable with these larger blood volumes; further it has increased the reproducibility of detection at 10 cells/mL.

Contamination was observed within 2 samples of the 50 titrations. To reduce contamination issues, the PCR steps may be separated from the detection steps. Further, chemical/biochemical methods may be used to render the amplicons unamplifiable. For example, uracils may be incorporated into the PCR product, and a pre-PCR incubation may be conducted with uracil N glycosylase.

The advantages of the systems and methods of the invention include the ability to assay whole blood samples without separating proteins and non-target nucleic acids from the sample. Because no losses in target nucleic acids are incurred through DNA purification (e.g., running Qiagen column after lysis and prior to amplification results in >10× loss in sensitivity; and use of whole blood interferes with optical detection methods at concentrations above 1%), sample-to-sample variability and biases (which can be introduced by DNA purification) are minimized and sensitivity is maximized.

Over 10% of septic shock patients are carriers of *Candida*; this is the third most prevalent pathogen after *S. aureus* & *E. coli*, and there is an approximately 50% mortality rate for septic shock patients infected with *Candida*. *Candida* is the fourth leading cause of hospital acquired infections. Rapid identification of these patients is critical to selecting proper treatment regimens.

Example 18. Viral Assay

CMV genomic DNA was spiked into CMV-free healthy donor blood samples, 40 µL of this spiked blood was aliquoted into a 100 µL total volume PCR reaction. Amplification was conducted using a whole blood compatible thermophilic DNA polymerase (T2 Biosystems, Lexington, Mass.) and exemplary universal primers that were designed as follows: 24 mer end—C6 linker—CMV specific sequence, the exact sequences were as follows:

```
                  (SEQ ID NO. 11, universal tail probe #1)
5'-CAT GAT CTG CTG GAG TCT GAC GTT A-3'

(SEQ ID NO. 12, universal tail probe #2)
5'-GCA GAT CTC CTC AAT GCG GCG-3'

(SEQ ID NO. 14, CMV US8 reverse primer)
5'-CGT GCC ACC GCA GAT AGT AAG-3'

(SEQ ID NO. 14, CMV US8 reverse primer)
5'-GAA TAC AGA CAC TTA GAG CTC GGG-3'
```

The primers were designed such that the capture probes (i.e., the nucleic acid decorating the magnetic particle) would anneal to the 10mer region (10mers are different on either 5' or 3' end). The final primer concentration in the reaction tube was 300 nM and PCR master mix which included 5 mM $(NH_4)_2SO_4$, 3.5 mM $MgCl_2$, 6% glycerol, 60 mM Tricine (pH 8.7)). Five separate sample reaction tubes were set up. Cycle PCR reactions followed an initial denaturation of 95° C. for 3 minutes, and each cycle consisted of 95° C., 20 seconds; 55° C., 30 seconds; and 68° C., 20 seconds. At 30, 33, 36, 39, and 42 cycles reaction tubes were removed and maintained at 4° C. Once all samples were ready, 5 µL of particle master mix (6×SSC, 30% formamide, 0.1% Tween) was aliquoted into the tube for every 10 µL of amplified sample; the resulting mixture was well mixed and the sample denatured at 95° C. for 3 minutes; the sample was hybridized at 45° C. for 1 hour with gentle agitation; the sample was then diluted to 150 µL with particle dilution buffer (PBS, 0.1% Tween, 0.1% BSA), placed into a temperature controlled hMAA magnet for 10 minutes, and equilibrated to 37° C. in a heat block for 1 minute; and the $T_2$ relaxation time for each of the five separate samples was measured using a $T_2$ MR reader (see FIG. 52).

The primers were designed to allow the magnetic particles decorated with capture probes to anneal to the 10mer region (10mers are different on either 5' or 3' end), providing particles with a universal architecture for aggregation with specific amplification primers.

The results provided in FIG. 52 show that the methods and systems of the invention can be used to perform real time PCR and provide quantitative information about the amount of target nucleic acid present in a whole blood sample.

Example 19. Real-Time PCR

Figure 53:
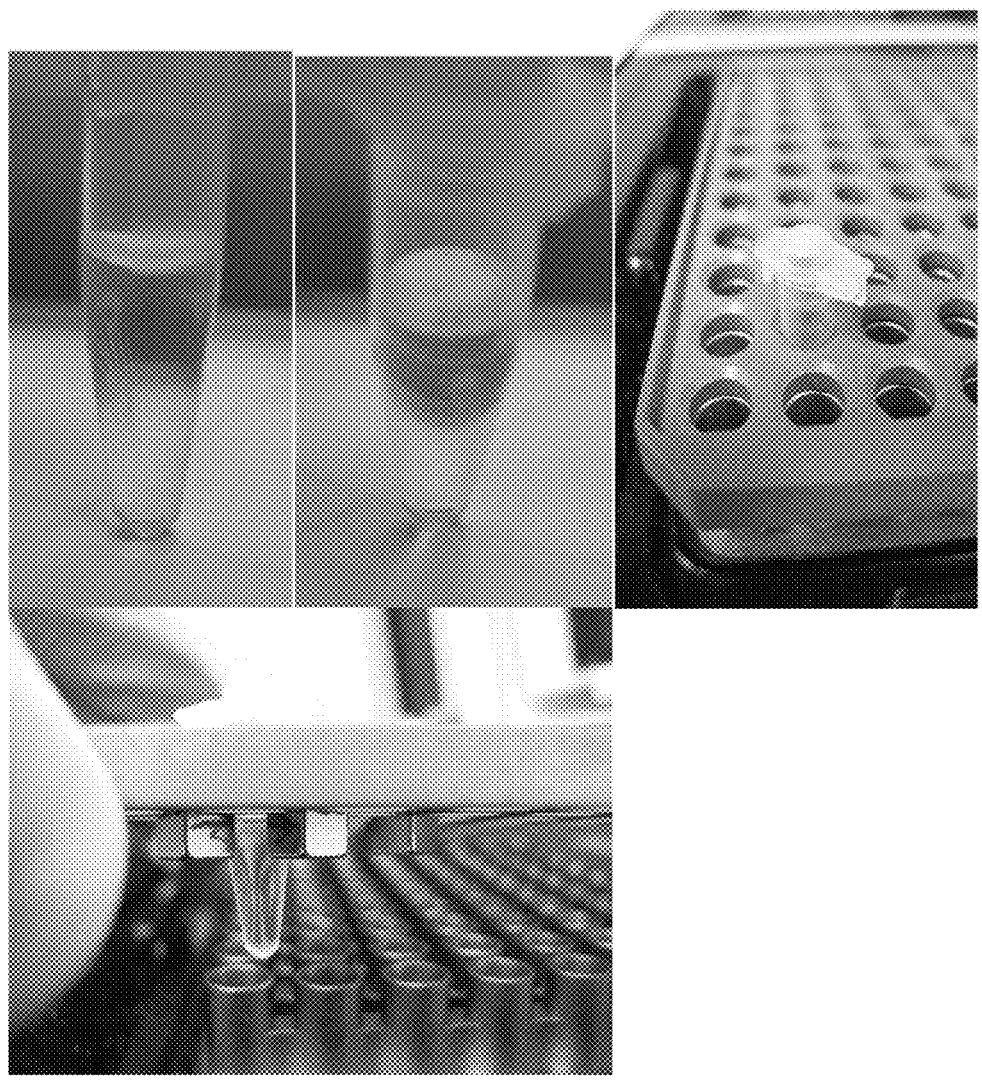
FIG. 53 is a series of photographs showing a simple magnetic separator/PCR block insert.

Previous results showed that when particles were present in the PCR reaction the amplicon production was inhibited. We hypothesize that moving the particles to the side of the reaction tube during the thermocycling will allow production of amplicon. A simple magnetic separator/PCR block insert (FIG. 53) was designed to keep nanoparticles on the side walls during PCR reaction, thus minimizing interference and particle exposure to the PCR reaction components. Upon removal of the magnetic field, particles can be completely resuspended into the reaction mixture.

In one experiment, we tested the rate at which particles could be sequestered to the side of the tube and returned to solution. In this experiment, 100 µL of the *C. albicans* (3' and 5') particle mix in 1×TE (~150 msec unclustered T2 baseline) went three times through clustering/unclustering process at 95° C. This was followed by the following protocol 1. vortex, incubate at 37° C. for 1 min, measure T2;
2. heat at 95° C. for 5 min on the magnetic PCR insert;
3. incubate at 37° C. for 1 min, measure T2;
4. vortex 15 sec, incubate at 37° C. for 1 min, measure T2; and
5. go to step 2.

The results of this experiment are shown in Table 14 below.

TABLE 14

| cycle # | 1 | 2 | 3 | 4 | | | |
|---|---|---|---|---|---|---|---|
| tube 1 | 147.1 | 150.8 | 154.9 | 140.9 | T2 unclustered | | |
| | 2198.6 | 1965.6 | 2161.4 | | T2 clustered at 95° C. | | |
| % T2 incr. | 1494.2 | 1303.5 | 1395.1 | | | avrg. % | 1397.6 |
| tube 2 | 143.5 | 147.4 | 150.4 | 144.2 | T2 unclustered | | |
| | 2240.7 | 2141.3 | 2086.5 | | T2 clustered at 95° C. | | |
| % T2 incr. | 1561.4 | 1452.9 | 1386.9 | | | avrg. % | 1467.1 |

As shown in Table 14, fully reversible nanoparticle clustering was demonstrated at 95° C. when using the tested magnetic separator. Particles are stable at 95° C. for at least 3 clustering/unclustering cycles.

We next tested PCR efficiency in the presence of nanoparticles in reaction solution. PCR was performed under two conditions: (1) nanoparticles are fully dispersed in solution;

and (2) nanoparticles are concentrated on the PCR test tube side walls using magnetic insert.

Three PCR reactions (with nanoparticles concentrated on the test tube wall; fully dispersed in solution; and no nanoparticles) were set up using C. albicans genomic DNA as a starting material.

Successful target DNA amplification was validated using gel electrophoresis. Capture-probe decorated Seramag particles were used.

Figure 54:
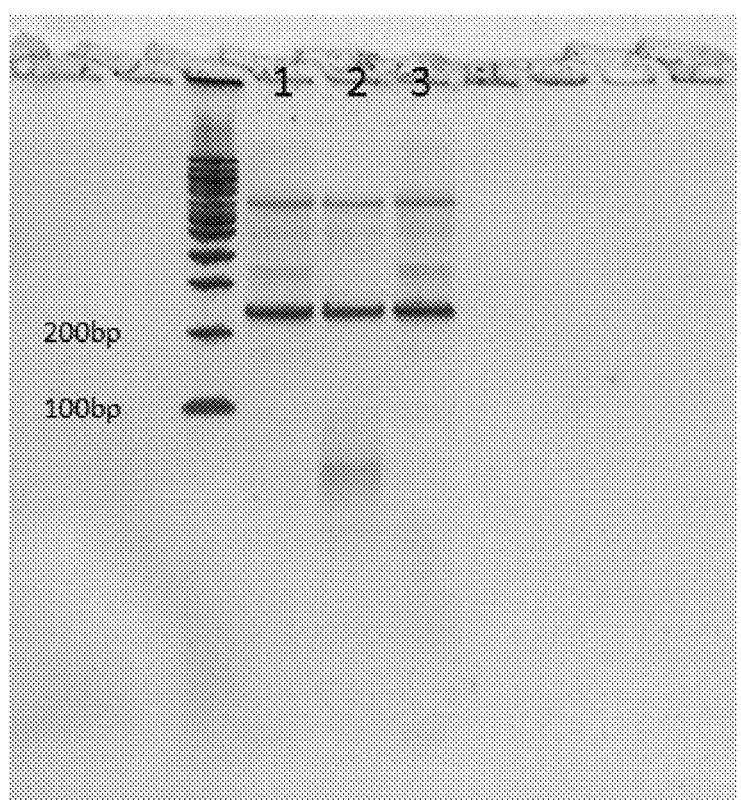
FIG. 54 is an image showing the quantity of DNA generated by amplification of (1) 100 copies of genomic *C. albicans* amplified in the presence of 3' and 5' *C. albicans* single probe nanoparticles; particles were held on the side wall during PCR via magnetic field, (2) 100 copies of genomic *C. albicans* amplified without nanoparticles, and (3) 100 copies of genomic *C. albicans* amplified in the presence of 3' and 5' *C. albicans* single probe nanoparticles; no magnetic field.
Figures 55A, 55B, 55C, 55D:
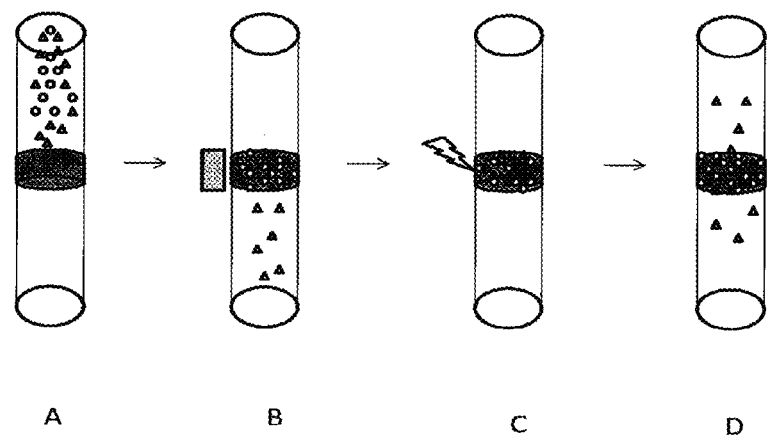
FIGS. 55A-55E are schematic views of a sample tube containing an immobilized portion of magnetizable metal foam (shaded), magnetic particles (circles), and analyte (triangles). a magnetizable metal foam, e.g., made of nickel, may be inserted into a conduit and immobilized by exposure to heat, which shrinks the conduit around the metal foam, resulting in a tight seal. A sample containing magnetic particles and analytes is then introduced at one end of the conduit (FIG. 55A). Next, the conduit is exposed to a magnet (FIG. 55B), and the magnetic particles are attracted to the metal foam and become magnetically trapped within its pores, or crevices. The average diameter of the pores in the metal foam is, e.g., between 100-1000 microns. Analyte molecules can be carried to the metal foam via binding to a magnetic particle, or the fluid can be forced through the metal foam to reach trapped magnetic particles. While trapped in the metal foam, the magnetic particles have enhanced interactions, as they are now confined and are closer to other magnetic particles, and cluster formation is enhanced. The metal foam is then demagnetized (FIG. 55C), i.e., the magnetic field of the metal foam becomes negligible. The magnetic particles and analyte cluster complexes largely remain in the metal foam, as the diffusion of magnetic particle clusters is relatively low, although some natural diffusion of the analyte in to and out of the metal foam occurs (FIG. 55D). Alternatively, the magnetizable metal foam (hollow cylinder) is free floating in the sample tube with the magnetic particles (circles), and analyte (stars). The magnetization and demagnetization of the free floating metal foam is used to increase the rate of aggregate formation.
Figure 55E:
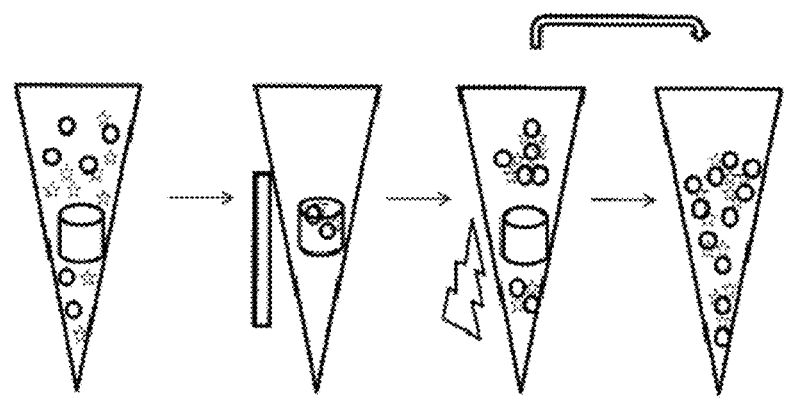

Asymmetric (4:1) PCR reactions were setup using pre-made PCR mix and 100 copies of genomic C. albicans DNA as a starting material. C. albicans capture particle mix (3' and 5') in 1×TE was added to reactions (1) and (3) (baseline ~150 msec). Control reaction (2) did not have nanoparticles added (FIG. 54).

No difference was observed in PCR product formation when nanoparticles were present in solution (dispersed in solution or concentrated on test tube side walls via magnetic field) during PCR. Therefore, nanoparticles modified with capture probes do not interfere with PCR. Comparable amounts of product were generated in the reactions with and without nanoparticles present in solution as evidenced by gel electrophoresis. Also, magnetic concentration of nanoparticles on test tube side walls during PCR process does not have an effect on the PCR.

Example 20. Internal Controls for C. Albicans

A variety of impurities and components of whole blood can be inhibitory to the polymerase and primer annealing. These inhibitors can lead to generation of false positives and low sensitivities. To assure that clinical specimens are successfully amplified and detected, the assay can include an internal control nucleic acid that contains primer binding regions identical to those of the target sequence. The target nucleic acid and internal control are selected such that each has a unique probe binding region that differentiates the internal control from the target nucleic acid. The internal control can be an inhibition control that is designed to co-amplify with the nucleic acid target being detected. Failure of the internal inhibition control to be amplified is evidence of a reagent failure or process error. Universal primers can be designed such that the target sequence and the internal control sequence are amplified in the same reaction tube. Thus, using this format, if the target DNA is amplified but the internal control is not it is then assumed that the target DNA is present in a proportionally greater amount than the internal control and the positive result is valid as the internal control amplification is unnecessary. If, on the other hand, neither the internal control nor the target is amplified it is then assumed that inhibition of the PCR reaction has occurred and the test for that particular sample is not valid.

The already amplified and detected Candida albicans sequence was examined for use in generating an internal control. The universal primer sequences were removed from the 5' and 3' ends. The residual internal sequence was subjected to a random sequence generator and a random sequence was generated. The universal primer sequences were replaced at the ends and the full internal control sequence was cloned into pCR2.1-TOPO and was sequence verified.

In designing these internal controls, the following criteria and features for use in diagnostic PCR assays were employed: 1) the target and internal control DNA share the same primers; 2) the internal control and target DNA are easily distinguishable (i.e. different capture probes); 3) the amplification efficiencies of the target and internal control have been tested and are acceptable; 4) the source of the internal control is a plasmid DNA carrying the cloned internal control sequence; 5) the internal control is detected by sequence dependent hybridization; 6) the internal control plasmid is highly purified; 7) the concentration of the internal control is determined by titration; 8) the internal control plasmid is added to the PCR mix to ensure equal distribution to all of the PCR tubes; 9) it has been determined the amount of internal control in the assay reaction tubes is 100-1000 copies/reaction and this concentration has been determined to be the lowest amount that still elicits a signal via amplification. See Hoofar et al., J. Clin. Microbiol. 42:1863 (2004).

The internal inhibition control for the Candida assay was designed to co-amplify with the Pan Candida PCR primers and contain a unique intervening sequence of similar length and base composition as the Candida species. The intervening sequence was developed by applying a sequence randomizing algorithm to the C. ablicans amplicon sequence. Four randomized sequences were then thermodynamically and bioinformatically characterized. A nucleotide mega-BLAST search was conducted for each sequence using both the human genomic+transcript database as well as the nr database. No significant alignments were identified with the four query sequences in either database. Each sequence was then subjected to UNAfold analysis to determine the extent of secondary structure present at the hybridization concentration of monovalent cation (600 mM) at a temperature of 60 degrees C. Two sequences were excluded at this point due to the presence of extensive stems under these hybridization conditions. Two were further characterized to determine if capture probes could be designed complementary to the 5' and 3' ends of the strand amplified in excess that would be devoid of poly-G tracts, and have low probabilities of forming homo and heterodimers. One sequence met all the criteria and was ordered as a PAGE purified synthetic oligonucleotide and its respective complement from IDT Technologies (Coralville, Iowa). The sequence of the internal control that will be amplified in excess is:

(SEQ ID NO. 15)
5-GGC ATG CCT GTT TGA GCG TCC TGC ATC ATA CTG

AAA TAG ATC CTT CGA CAA CCT CGG TAC ACT GGG AAC

AAG GCC TCA AAC ATT GAT GCT CGA CTA CAC GTA GGG

CAATGC GTC TTG CTA GAA GCG AAA TCT GTG GCT TGC

TAG TGC AAG CTG GTC GGC GTA TTA TTC CAA CCC GCT

GAA CTT AAG CAT ATC AAT AAG CA-3

The annealed complementary sequence is:

(SEQ ID NO. 16)
5-GCT TAT TGA TAT GCT TAA GTT CAG CGG GTT GGA

ATA ATA CGC CGA CCA GCT TGC ACT AGC AAG CCA CAG

ATT TCG CTT CTA GCA AGA CGC ATT GCC CTA CGT GTA

GTC GAG CAT CAA TGT TTG AGG CCT TGT TCC CAGTGT

ACC GAG GTT GTC GAA GGATCT ATT TCA GTA TGA TGC

AGG ACG CTC AAA CAG GCATGC CA-3

5 uM of the annealed duplex in 2×SSC was sent to SeqWright for subcloning and sequencing. The annealed duplexes contain 3' adenosine overhangs to facilitate cloning into a TA cloning vector. This construct was cloned into pCR2.1-TOPO. Upon transformation, 5 clones were selected and sequenced to confirm the presence of the correct insert. Upon verification of the correct cloned insert, the mini-prepped plasmid DNA should be digested with EcoRV and HindIII and the insert subcloned into pBR322. From this transformation, 5 transformants were selected and the insert verified via sequencing. Two E. coli hosts bearing the pBR322-IC were frozen in 30% glycerol+LB amp. A plasmid maxi-prep was conducted using the Qiagen and yielded ~1 mg of purified plasmid DNA.

Capture probes were designed to hybridize nested to the Pan *Candida* PCR primer sequences. A 3' aminated capture probe with a T-9 linker was designed to complementary to the 5' end of the strand amplified in excess. A 5' aminated capture probe with a C12 T-9 linker was designed complementary to the 3' end of the strand amplified in excess. These sequences are shown below:

```
                                             (SEQ ID NO. 17)
GGT TGT CGA AGG ATC TAT TTC AGT ATG ATG CAG-TTT
TTT TTT-3'Amino (SEQ ID NO. 18)
5'Amino-C12-TTT TTT TTT-TGG AAT AAT ACG CCG ACC
AGC TTG CAC TA
```

The predicted melting temperatures (Allawi, 1997) were 75 and 78° C., respectively.

Example 21. Rotary gMAA

Figure 56A:
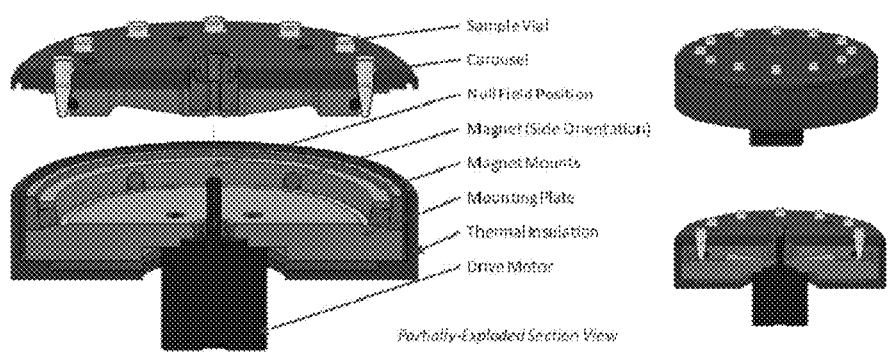
FIG. 56A depicts a rotary gMAA configuration. The Rotary gMAA can include three configurations for varying magnetic field exposures—side-bottom; side-null and bottom-null (see Example 21).

Three prototype rotary gMAA configurations were designed, built and tested with comparison to the conventional plate based gMAA (see FIG. 56A). The three configurations included varying magnetic field exposures—side-bottom; side-null and bottom-null. The plate based gMAA used for comparison is the standard side-bottom. Assay functional performance (non-specific binding and clustering) was evaluated using the Creatinine agglomerative assay system. Particles derivatized with creatinine antibody were mixed with 1:5 diluted serum and creatinine dextran agglomerator. The agglomerator was tested at 6 concentrations to provide a titration curve. Each concentration level was tested in triplicate. The T2 of samples with no agglomerator was measured before and after gMAA to assess non-specific binding. gMAA was performed at room temperature for a total of 12 minutes with 1 minute dwells at the magnet stations.

With respect to non-specific binding, all rotary configurations yielded acceptable results (<10% difference) and were comparable to the conventional plate gMAA.

Figure 56B:
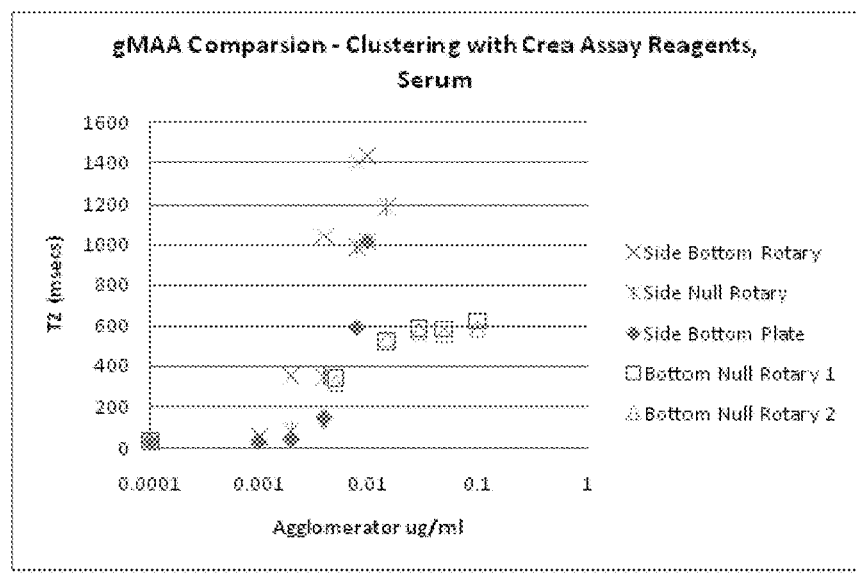
FIG. 56B is a graph comparing T2 signal as a function of various rotary gMAA configurations for varying magnetic field exposures to a sample at a given agglomerator concentration. The rotary side-bottom configuration provided the highest T2 signal at a given agglomerator concentration, followed by the comparison side-bottom plate configuration. Rotary side-null provides equivalent signal to the plate side-bottom; and the bottom-null produces the lowest signal (see Example 21).

With respect to aggregate formation, all rotary gMAA devices produced aggregation. The rotary side-bottom configuration provided the highest T2 signal at a given agglomerator concentration, followed by the comparison side-bottom plate configuration. Rotary side-null provides equivalent signal to the plate side-bottom; and the bottom-null produces the lowest signal (see FIG. 56B).

Example 22. *Candida* Assay and Clinical Data

A rapid, accurate, and reproducible molecular diagnostic test was developed for the detection of five *Candida* species directly within human whole blood with a limit of detection (LOD) of 10 cells/mL and a time to result of less than 2 hours. The assay's clinical performance was determined using 32 blinded clinical specimens and in this study we observed 100% positive and 100% negative agreement with blood culture while accurately identifying the causative *Candida* species within 100% of the candidemic patient samples. We further applied the assay to blood specimens drawn from *Candida* positive patients and observed a decrease in *Candida* detection concordant with the time course of antifungal treatment. This diagnostic method is rapid, amenable to automation, and offers clinicians the opportunity to detect multiple human pathogens within complex biological specimens.

Magnetic Resonance Relaxometer

A compact magnetic resonance (MR) system was designed and constructed for precise T2 relaxation measurements in order to perform the intended assay under the described conditions. This system was held at 37° C. via temperature control and contains a samarium cobalt permanent magnet of approximately 0.5 T, corresponding to a proton frequency of operation of 22-24 MHz. All standard MR components: radio frequency probe, low-noise preamplifier and transmitter electronics, spectrometer board, as well as the temperature control hardware are packaged in the system. The system uses standard AC power input and connects to an external computer via Ethernet. A user friendly graphical user interface allows users to set experimental parameters.

The system has been designed to accept samples in standard 0.2 ml PCR tubes. The electronics as well as the coil were optimized to improve the measurement precision of the applicable sample volumes, allowing us to achieve single-scan run to run CVs in T2 of less than 0.1%. Instrument to instrument variability is under 2% with minimal tolerance requirements on the system components and without calibration.

Nanoparticle Sensor Conjugation and Characterization 800 nm carboxylated iron oxide superparamagnetic particles, consisting of numerous iron oxide nanocrystals embedded in a polymer matrix including a total particle diameter of 800 nm (see Demas et al., New J. Phys. 13:1 (2011)), were conjugated to aminated DNA oligonucleotides using standard carbodiimide chemistry. DNA-derivatized nanoparticles were stored at 4° C. in 1× Tris-EDTA (pH 8), 0.1% Tween-20. Iron concentration of nanoparticle conjugates were measured by dissolving the particle with 6M HCl followed by addition of hydroxylamine hydrochloride and 1,10 O-phenanthroline and subsequent spectrophotometric detection as described in Owen et al., J Immunol Methods, 73:41 (1984). Oligonucleotide derivatized particles are then subjected to a functional performance test by conducting hybridization induced agglomeration reactions using diluted synthetic oligonucleotide targets identical in sequence to the fungal ITS2 sequences from the five different *Candida* species within a sodium phosphate hybridization buffer 4×SSPE (600 mM NaCl, 40 mM sodium phosphate, 4 mM EDTA). Reversibility of the agglomeration reaction was confirmed by subjecting agglomerated reactions to a 95° C. heat denaturation step, conducting a T2 measurement, and repeat hybridization at 60° C. followed by a second T2 measurement.

PCR Primer and Nanoparticle Capture Probe Design

Universal Pan *Candida* PCR primers were designed complementary to 5.8S and 26S rRNA sequences that amplify the intervening transcribed spacer 2 (ITS2) region of the *Candida* genome. A pair of oligonucleotide capture probes was designed complementary to nested sequences at the 5' and 3' end respectively of the asymmetrically amplified PCR product. The capture probe that hybridizes to the 5' end of the amplicon was 3' aminated while the capture probe that hybridizes to the 3' end of the amplicon was 5' aminated. A poly-T linker (n=9 to 24) is added between the amino group and the first nucleotide base of the capture probe sequence. HPLC purified PCR primers and capture probes were procured from IDT Technologies (Coralville, Iowa).

Inhibition Control Design

A PCR inhibition control was designed to co-amplify with the Candida species and monitor factors within the whole blood specimens that inhibit PCR amplification. A synthetic template was designed to contain 30 nucleotide flanking sequences identical in sequence to the 5.8S and 26S regions of the Candida rRNA operon. The internal sequence within this template consists of a randomly scrambled C. albicans amplicon. Capture probes were designed complementary to the strand amplified in excess within the asymmetric Candida PCR reactions. Synthetic oligonucleotide ultramers were procured from IDT (Coralville, Iowa) identical in sequence to the inhibition control. The oligonucleotides were annealed at a concentration of 5 µM in 2×SSC and cloned into HindIII/EcoRV digested pBR322 (NEB, Ipswich, Mass.) using standard methods. Transformation was conducted via electroporation of 1 µL of the ligation reaction into electrocompetant E. coli K12 cells and the transformants were plated onto Luria Bertani (LB) agar plates containing 100 µg/mL ampicillin. Two ampicillin resistant colonies were selected and cultivated in 2 mL LB ampicillin media. Plasmid mini-preps were conducted followed by restriction enzyme mapping to confirm the clones contained the correct insert. Sanger dideoxy sequencing was then conducted (SeqWright, Houston, Tex.) to confirm successful cloning of the control and DNA maxi-preps were conducted on correct insert bearing clones. Titrations of the inhibition control in the presence of increasing concentrations of all 5 species of Candida were conducted to determine the lowest concentration of inhibition control that could be reproducibly detected. Confirmation of the function of the inhibition control was demonstrated by conducting PCR reactions in the presence of titrations of known PCR interferents (SDS, heparin, ethanol) and demonstrating that amplification of the control was inhibited.

Candida Cultivation and In-Vitro Spiked Sample Preparation

MYA-2876, ATCC 2001, ATCC 24210, ATCC 66029, and ATCC 22019 were the C. albicans, C. glabrata, C. krusei, C. tropicalis, and C. parapsilosis laboratory reference strains (ATCC, Manassas, Va.) used to prepare the in-vitro spiked whole blood specimens. Yeasts were cultivated on yeast peptone dextrose agar plates (YPD) and incubated at 25° C. Single colonies were selected and suspended in phosphate buffered saline (PBS). The species were verified via ITS2 sequencing at Accugenix (Newark, Del.). The cells were then subjected to a low speed centrifugation (3000 g for 2 minutes) and washed three times with fresh PBS. An aliquot of the PBS washed cells was then diluted in ISOTON II diluent (Beckman Coulter, Brea, Calif.) within a 20 mL Accuvette and cells were quantified on a Multisizer 4 Coulter Counter (Beckman Coulter, Brea, Calif.) following the manufacturers instruction. Cells were then serially diluted to concentrations ranging from 500 to 5 cells/100 µL PBS buffer. Fresh human healthy donor blood drawn by sterile collection in K2EDTA vacutainer tubes (BD Diagnostics, Franklin Lakes, N.J.) was obtained from ProMedX. Typically five milliliters of human blood was spiked with 100 mL of quantified Candida cells. Whole blood spiked samples are then used immediately in the assay.

Whole Blood PCR

Erythrocyte lysis was conducted within 1 mL of the whole blood sample using previously described methods (see Bramley et al., Biochimica et Biophysica Acta (BBA)—Biomembranes, 241:752 (1971) and Wessels J M, Biochim Biophys Acta., 2:178 (1973)), a low speed centrifugation is then conducted and the supernatant was removed and discarded. One hundred uL of Tris EDTA (TE) buffer pH 8.0 containing 1500 copies of the inhibition control was then added to the harvested pellets and the suspension was subjected to mechanical lysis (see Garver et al., Appl. Microbiol., 1959. 7:318 (1959); Hamilton et al., Appl. Microbiol., 10: 577 (1962); and Ranhand, J. M., Appl. Microbiol., 28:66 (1974)). Fifty µL of lysate was then added to 50 µL of an asymmetric PCR master mix containing a deoxynucleotides, PCR primers and a whole blood compatible thermophilic DNA polymerase (T2 Biosystems, Lexington, Mass.). Thermocycling was conducted using the following cycle parameters: heat denaturation at 95° C. for 5 minutes, 40 cycles consisting of a 30 second 95° C. heat denaturation step, a 20 second 62° C. annealing step, and a 30 second 68° C. elongation step, and a final extension at 68° C. for 10 minutes.

Hybridization Induced Agglomeration Assays

Fifteen microliters of the resulting amplification reaction was aliquoted into 0.2 mL thin walled PCR tubes and incubated within a sodium phosphate hybridization buffer (4×SSPE) with pairs of oligonucleotide derivatized nanoparticles at a final iron concentration of 0.2 mM iron per reaction. Hybridization reactions were incubated for 3 minutes at 95° C. followed by 30 minutes incubation at 60° C. within a shaking incubator set at an agitation speed of 1000 rpm (Vortemp, LabNet International). Hybridized samples are then placed in a 37° C. heating block to equilibrate the temperature to that of the MR reader for 3 minutes. Each sample is then subjected to a 5 second vortexing step (3000 rpm) and inserted into the MR reader for T2 measurement.

Candida Patient Sample Collection Protocol.

Blood specimen discards that had been drawn in K2EDTA vacutainers (BD) on the same day as specimens drawn for blood culture (T=0) were obtained from the clinical hematology laboratory at the Massachusetts General Hospital (MGH) or Houston University Hospital. Specimens were collected and catalogued from patients having blood culture positive results. Samples were stored within the original vacutainer at −80° C. and the blinded specimen collection was shipped overnight on dry ice to T2 Biosystems. Clinical sample collection protocols were reviewed by the appropriate Human Research Committees.

Statistical Analyses

For each species, the limit of detection was determined with the use of probit modeling. For each species, the 90% level of detection and 95% fiducial intervals were calculated. Each raw T2 signal was transformed as T2 msec over the assay's background. SAS v. 9.1.3 (Cary, N.C.) was used in the statistical calculations for the analyses for limit of detection, agreement of spiked specimens with culture, sensitivity and specificity in clinical specimens, and serial assays to measure Candida clearance.

Agreement of T2 MR Detection of Candida with Blood Culture

The current gold standard for Candida diagnosis is blood culture. In vitro spiked healthy donor whole blood specimens were prepared using laboratory reference strains for C. albicans and C. krusei and clinical isolates of C. albicans at concentrations of 0, 33, and 100 cells/mL. Pediatric BACTEC blood culture vials (BACTEC Peds Plus/F vials, Beckton Dickenson) were inoculated with an aliquot of the in-vitro spiked specimens evaluated by T2MR. Blood culture vials inoculated with Candida cells were blood culture positive by day 8 in all cases. In total, 133 blood culture bottles were inoculated with 90 *Candida* spiked blood samples (inoculum of 33 cells/mL) or 43 negative blood samples. Ninety eight percent positive agreement and 100% negative agreement was observed between T2MR and blood culture.

Clinical Specimen Data

Figure 57:
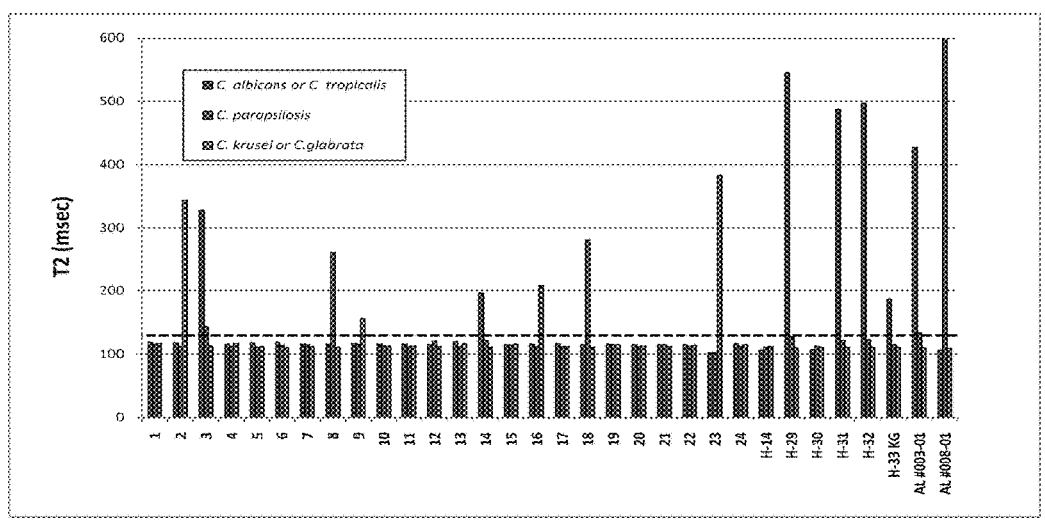
FIG. 57 is a table depicting the T2MR results for 32 clinical specimens indicates fourteen specimens are *Candida* positive. The test identifies four specimens containing *C. krusei* or *C. glabrata*, seven specimens containing *C. albicans* or *C. tropicalis*, and three containing *C. parapsilosis*. A solid black line indicates the decision threshold (T2=128 msec) (see Example 22).

K2 EDTA whole blood patient specimens were obtained to test the clinical performance of the T2MR *Candida* assay. The patients presented with symptoms of septicemia and blood was drawn for culture. Blood sample retains were stored at 4° C. in the hematology lab and selected for T2MR if the outcome was blood culture positive for *Candida*, blood culture positive for bacteremia, or blood culture negative to better represent the spectrum of samples that would be run on the platform. Fourteen of the samples were from candidemic patients, eight were from bacteremic patients, and ten were from blood-culture negative patients. FIG. 57 shows the measured T2 values for all 32 patient samples. A single PCR reaction was conducted using 1 mL of each specimen. 750 copies of the internal inhibition control were added to each PCR reaction. Among *Candida* negative samples the average internal control (IC) signal was 279 ms with a CV across the 18 *Candida* negative specimens of 25%. In no cases was the IC signal below the decision threshold (128 ms, 5 standard deviations added to the mean T2 measured in *Candida* negative detection reactions) suggesting that all negatives were true negatives and no inhibitory substances were present with the whole blood samples. The detection reactions were multiplexed based on IDSA guidelines, such that three results were reported as follows: *C. albicans* or *C. tropicalis* positive; *C. krusei* or *C. glabrata* positive; and *C. parapsilosis* positive. The average T2 measured in the *Candida* negative specimens is 114 ms, the CV for these measurements was 2.4%, and the decision threshold (calculated by addition of five times the standard deviation measured in the *Candida* negative detection reactions plus the mean T2 measured in *Candida* negative specimens) was 128 ms. In specimens positive for *Candida*, the IC signal was suppressed due to competition for the amplification reagents. In instances of high *C. albicans*, some cross-reactivity was observed for detection with the *C. parapsilosis* particles (e.g. patient sample #3) however this signal is not significantly above the cut-off (20 ms) and does not lead to a difference in antifungal therapy as both *C. albicans* and *C. parapsilosis* are susceptible to fluconazole.

T2MR successfully identified fourteen samples of *C. albicans*, *C. parapsilosis*, or *C. krusei* which were confirmed positive by blood culture followed by the Vitek 2 biochemical card. Furthermore, the detection was specific for *Candida* spp. as bacteremic patient samples with *Escherichia coli*, *Enterococcus* sp., *Staphylococcus aureus*, *Klebsiella pneumoniae*, coagulase negative *Staphylococcus*, or alpha hemolytic *Streptococcus* remained negative.

Figure 3:
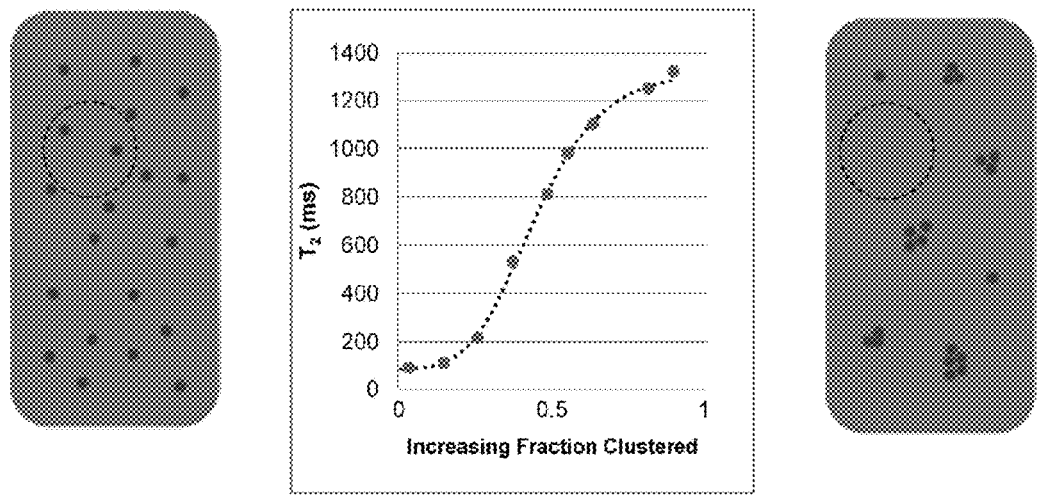
FIG. 3 is a drawing depicting an aggregation assay of the invention. The magnetic particles (dots) are coated with a binding agent (i.e., antibody, oligo, etc) such that in the presence of analyte, or multivalent binding agent, aggregates are formed. The dotted circles represent the diffusion sphere or portion of the total fluid volume that a solution molecule may experience via its diffusion during a $T_2$ measurement (the exact path traveled by a water molecule is random, and this drawing is not to scale). Aggregation (right hand side) depletes portions of the sample from the microscopic magnetic non-uniformities that disrupt the water's $T_2$ signal, leading to an increase in $T_2$ relaxation.

Serially drawn samples were tested from two patients who exhibited symptoms suggestive of candidemia, such as persistent fever after receiving antibiotics to demonstrate the assay's utility in monitoring *Candida* clearance. Blood draws for T2MR occurred the same day as blood draws for blood culture. Surveillance cultures were then drawn over a course of nine days for Patient A and over a course of five days for Patient B. FIG. 3 shows the results obtained with the T2MR method for both patients. Patient A had blood drawn for culture (t=0), was diagnosed with candidemia and administered intravenous micafungin (*C. glabrata*) the following day via blood culture (t=1). Whole blood specimens were tested with T2MR at t=0 days, t=3 days, t=7 days, t=8 days, t=9 days. The T2MR values obtained were 320 ms at t=0, 467 ms at t=3, 284 ms at t=7, 245 ms at t=8, and 117 ms (below cut-off) for t=9. Subsequent blood culture draws on day 3 and day 8 took 24 and 48 hours to culture positive, respectively. A series of serially drawn specimens were obtained from Patient B. *C. albicans* was correctly detected with T2MR on day 0 (T2=426 ms). Blood culture came up positive on day 2 with subsequent *C. albicans* identification. One day after the patient was administered micafungin, a sharp decrease in *C. albicans* T2MR was evident (T2=169 ms) and three or more days after antifungal treatment was initiated no detectable *C. albicans* was observed. All tests were completed in a total processing time of two hours, using a fast block PCR thermocycler and three step thermocycling procedure that was not optimized for speed.

Conclusions

We have developed and validated a whole blood T2MR *Candida* assay capable of detecting five clinically important species of *Candida* that leverages the advantages of non-optical detection to eliminate analyte purification, thus enabling enable more rapid turn-around times and more reproducible results. Asymmetric PCR was used to specifically amplify the ITS2 region of the *Candida* genome directly in whole blood to achieve clinically relevant detection sensitivities. A T2 detection method was developed in which two pools of oligonucleotide derivatized nanoparticles hybridize to each end of the single stranded amplicon. The amplicons thus serve as interparticle tethers and induce nanoparticle agglomeration which yields a measurable and reproducible change in the spin-spin relaxometry (T2) of the protons in water molecules. We further constructed and implemented an internal inhibition control to monitor for PCR inhibitors that may be present in the patient samples.

The assay was evaluated using reference strains and clinical isolates quantified by Coulter Counter and spiked into healthy donor whole blood. Assay repeatability was measured using *C. albicans* spiked blood (same sample, same operator, same instrument) over the course of 10 days and we observe CV's less than 12.8% (n=30) over the entire dynamic response range (0 to 1E5 cells/mL). The analytical sensitivity and limit of detection of <10 cells/mL were measured for *C. albicans*, *C. tropicalis*, *C. krusei*, and *C. parapsilosis* and >10 cells/mL with 92.5% detected at 10 cells/mL for *C. glabrata*. Although not proven, a possible cause of the higher LoD observed in *C. glabrata* may be that the rDNA operon copy number is reduced in *C. glabrata* as compared to the other queried *Candida* spp since it is known that *C. glabrata* exists in nature as a haploid while the other *Candida* species are diploids. Agreement with the gold standard for *Candida* diagnosis was high with 98% positive and 100% negative agreement observed for 133 in vitro spiked *C. albicans* and *C. krusei* samples. It should be noted that the time to result was 2 hours for the T2 *Candida* test while the time to blood culture positivity was typically 2 days for *C. albicans* and ~1 day (18-24 hours) for *Candida krusei*.

The 32 clinical specimens are similar to blood culture results. The measured T2 was above a cut-off established at five standard deviations of the T2 values measured in the *Candida* negative specimens added to their mean. In this case the threshold was 128 ms (n=54). In no cases did we observe inhibition of the PCR reaction, as the internal control was detected within all 32 reactions with a reduced IC signal observed in *Candida* positive patients and a CV of 25% (mean T2 of 279 ms) across the *Candida* negative specimens (n=18). The assay is highly specific for *Candida* detection as no cross-reactivity was observed with any of the bacteremic specimens (n=8). *Candida* positive specimens were accurately identified, the causative *Candida* spp. was accurately identified, and all within a time to answer of 2 hours.

The potential for this assay to provide a rapid detection of *Candida* clearance after administration of antifungal therapy was also demonstrated. Two sets of patient samples were drawn and subjected to T2MR (FIG. 3). Moderate to high T2 signals for *C. glabrata* were observed in patient A at day 0 and day 3 with antifungal agents administered at day 1. A decrease in *C. glabrata* signal was observed over subsequent days with none detectable after eight days of anti-fungal treatment. A strong *C. albicans* signal was measured for patient B at day 0, and a sharp decline (delta T2 of 306 ms) in T2 signal was observed one day after antifungal administration with none detectable after two days of anti-fungal treatment. Although preliminary, this data suggests the test could be used to monitor treatment effectiveness and *Candida* clearance in a real-time fashion.

In conclusion, we have developed a sensitive and specific test for the diagnosis of candidemia caused by the five most commonly encountered *Candida* species. Early clinical results were encouraging and show that rapid diagnosis and species identification is achievable and could not only facilitate early treatment with the appropriate antifungal but also provide a means to monitor *Candida* clearance. We anticipate that this nanoparticle-based T2MR method can be broadly applied to infectious disease diagnoses in a variety of specimen types and pathogens.

Example 23. Tacrolimus Assay Utilizing Fab

The tacrolimus assay is a homogeneous competitive immunoassay performed using an EDTA whole blood sample extracted to release tacrolimus from the red blood cells and binding proteins. A key component of the assay is a high affinity tacrolimus antibody, a reliable extraction method, and improvement of the buffer systems selected to promote specific aggregation and minimize non-specific aggregation. This version of the assay utilizes a recombinant monovalent Fab with high affinity for tacrolimus.

The tacrolimus assay was assessed using whole blood calibrators, commercial whole blood controls, spiked samples and patient samples.

Assay reagents included: (a) 244 nm particle conjugated with sequential BSA, and monovalent Fab antibody and blocked with mPEG-thiol+NEM (particle is diluted to 0.2 mM Fe in assay buffer); (b) C22 modified tacrolimus conjugated to BSA at tacrolimus to BSA input ratio of 10:1 (diluted to 600 ng/ml in assay buffer); (c) assay buffer of 100 mM Glycine pH 9.0, 1% BSA, 0.05% Tween 80, 150 mM NaCl, and 0.05% Proclin; and (d) extraction reagent of 70% MeOH, 60 mM $ZnSO_4$ in $dH_2O$.

Whole blood calibrators were prepared using 1 mg/ml Sigma FK506 Stock in 100% MeOH. EDTA whole blood was spiked at varying levels with the tacrolimus solution. The spiked blood was incubated at 37° C. with gentle mixing and then stored overnight at 4° C. prior to aliquoting and freezing. Target levels were 0, 1, 2, 5, 10, 20, 50, 100, and 250 ng/ml of tacrolimus. The calibrators were provided to an external lab for value assignment by the Architect Tacrolimus assay. The samples were assayed by mass spectroscopy. Results show a correlation of 0.9998 for theoretical versus actual value assignment Quality controls consisted of 3 levels of UTAK Immunosuppressant Matrix Controls. Patient samples were obtained from transplant patients on tacrolimus therapy.

The testing protocol was as follows:

(i) Allow all samples, calibrators, QC and reagents to equilibrate to room temperature, mix by gentle inversion.

(ii) Pipette 200 μL of sample, calibrator, or QC material into a 1.5 mL microfuge tube. Add 200 uL of extraction reagent and vortex for 30 secs. Allow the sample to incubate for 2 minutes at room temperature, and centrifuge for 5 minutes at 10,000 rpm. Transfer the clean supernatant to a clean tube and prepare a 2.5× dilution using assay buffer.

(iii) pipette 10 μL of the diluted extract and 10 μL of diluted particle into the reaction tube, vortex mix and incubate for 15 minutes at 37° C. Pipette 20 μL of BSA-tac conjugate into the reaction tube, vortex mix and incubate for 15 minutes at 37° C. Perform gMAA for 6 cycles (12 min.). Vortex mix, incubate for 5 minutes at 37° C. and read in the T2 reader at 37° C.

Calibrators were tested in triplicate for each test run (6 total runs). Individual run data were fit with a 5PL model using GraphPad Prism 5 for Windows, version 5.02, GraphPad Software, San Diego Calif. USA. The 0 calibrator was entered as 0.01 ng/ml and used in the curve model. The resulting calibration curves (Run Calibration) were used to back-calculate the tacrolimus concentration for all calibrators, whole blood spikes, QC and patient samples contained in the run.

In addition, a Master Calibration curve was obtained by fitting data across the entire 3-day study (n=18) for each calibrator. All samples were back-calculated using the Master Curve and the resulting tacrolimus levels compared to those obtained using the Run Calibration.

A reproducibility panel consisting of 13 members (9 calibrators, 3 controls and 1 spiked whole blood sample) was tested in triplicate for 3 days with 2 runs per day for a total of 18 replicates. Calibrators were stored at −80° C. while the controls and whole blood spike were stored at 4-8° C. for the duration of the study.

Sample concentrations were predicted using the run calibration curve, as well as the master curve in GraphPrism. Within-run, within-day, day-to-day and total precision were calculated by ANOVA using MiniTab 15.

Data predicted using the Run Calibration method showed total imprecision <25% CV across a tacrolimus concentration range from ~3-210 ng/ml.

Analytical sensitivity was calculated by the 2SD method. The standard deviation of 18 replicates of the 0 calibrator was determined. The tacrolimus level at the maximum T2 (top asymptote of the curve fit)—2SD was then calculated and the concentration predicted using the Master Calibration Curve. Analytical sensitivity is 0.8 ng/ml.

During tacrolimus antibody development and screening, antibody specificity was evaluated against five tacrolimus metabolites. ELISA inhibition was performed with each of the 5 metabolites and compared to free tacrolimus for five affinity matured clones and seven clones with additional affinity maturation by cross-cloning. Data for two of the cross-clones and a state-of-the-art murine monoclonal RUO antibody are shown below. The only cross-reactivity observed was slight reactivity to the 15-O-desmethyl metabolite.

A summary of the tacrolimus assay performance is tabulated below.

| Requirement | Results |
| --- | --- |
| Reportable range: | ~3.5-200 ng/ml based on calibrator % CV <30% and 90-110% recovery. |
|  | ~2 to >200 ng/ml based on calibrator % CV <30% and 85-115% recovery. |
| Analytical Sensitivity (2SD): | 0.8 ng/ml |
| Precision: | @ 2.8 ng/ml: 22% CV |
|  | @ 6.9 ng/ml: 14% CV |
|  | @ 14.6 ng/ml: 4% CV |
| Time to result: | 56 minutes |
| Specimen type: | Whole Blood |
| Pre-treatment: | Solvent-based extraction process demonstrated using functionality planned on instrument |
| Sample volume: | 200 μL |

Example 24. Preparation of Nanoparticles for Detection of Nucleic Acid Analytes Preparation of single probe particles: 800 nm carboxylated iron oxide superparamagnetic particles, consisting of numerous iron oxide nanocrystals embedded in a polymer matrix including a total particle diameter of 800 nm (see Demas et al., New J. Phys. 13:1 (2011)) were washed using a magnetic rack prior to use. The magnetic particles were resusupended in 66 µL of nuclease-free water, 20 µL of 250 mM MES buffer pH 6, and 4 µL of aminated probe (obtained from IDT), at 1 mM concentration per mg of particle to be prepared. A 3' aminated probe particle and a 5' aminated probe particle were prepared (e.g., the probe for *C. parapsilosis*). The probe was added to the particle and the suspension was vortexed using a vortexer equipped with a foam holder to hold the tube. The vortexer was set to a speed that keeps the particles well-suspended without any splashing. N-ethyl-N'-(3-dimethylaminopropyl) carbodiimide hydrochloride (EDC) was then dissolved in water and immediately added to the vortexing particle-probe mixture. The tube was then closed and incubated with rotation in an incubator at 37° C. for 2 hours. The tube was then placed in a magnetic rack and the reaction fluid was removed. The particles were washed with a series of washes (125 µL/mg particle) as follows: water, water, 0.1M imidazole, pH 6.0 with a 5 minute incubation with rotation at 37° C., water, 0.1 M sodium bicarbonate, pH 8.0 with a 5 minute incubation with rotation at 37° C. water. The particles were then subjected to a 1 hour heat-stress at 60-65° C. in 0.1M sodium bicarbonate pH 8.0 with rotation. After the heat-stress, the bicarbonate was removed by placing the tube in a magnetic rack. The particles were then resuspended in the storage buffer (Tris-EDTA, 0.1% tween 20) and vortexed. The storage buffer was removed and a final 100 µl of storage buffer was added to the particle preparation. The particles were stored at 2-8° C., qualified using an iron test to determine the iron concentration of the particles, and tested against target nucleic acid (e.g., *C. paraplsilosis* ITS2 oligo titration). In the *Candida* assay, the particles are diluted in 8×SSPE supplemented with 0.09% sodium azide as a preservative.

Preparation of dual probe particles: For the preparation of a dual probe particle, the procedure is the same as above, except that equal volumes of a second probe (e.g., 3' aminated *C. albicans*) and the first probe (e.g., 3' aminated *C. tropicalis*) were mixed prior to addition to the magnetic particles. Similarly, equal volumes of the 5' aminated probes were mixed prior to addition to the magnetic particles.

Example 25. *Candida* Assay Improvements

The limit of detection for the *Candida* assay of Example 22 was improved by washing the pellet. 2.0 mL of whole blood was combined with 100 µL of TRAX erythrocyte lysis buffer (i.e., a mixture of nonyl phenoxy-polyethoxylethanol (NP-40) and 4-octylphenol polyethoxylate (Triton-X 100)) and incubated for about 5 minutes. The sample was centrifuged for 5 minutes at 6000 g and the resulting supernatant was removed and discarded. To wash the pellet, the pellet was mixed with 200 µL of Tris EDTA (TE) buffer pH 8.0 and subjected to vortexing. The sample was again centrifuged for 5 minutes at 6000 g and the resulting supernatant was removed and discarded. Following the wash step the pellet was mixed with 100 µL TE buffer and subjected to bead beating (e.g., such as with 0.5 mm glass beads, 0.1 mm silica beads, 0.7 mm silica beads, or a mixture of differently sized beads) with vigorous agitation. The sample was again centrifuged. Fifty µL of the resulting lysate was then added to 50 µL of an asymmetric PCR master mix containing a deoxynucleotides, PCR primers and a whole blood compatible thermophilic DNA polymerase (T2 Biosystems, Lexington, Mass.). Thermocycling and hybridization induced agglomeration assays were conducted as described in Example 22 to produce T2 values characteristic of the presence of *Candida* in the blood sample. The assay can produce (i) a coefficient of variation in the T2 value of less than 20% on *Candida* positive samples; (ii) at least 95% correct detection at less than or equal to 5 cells/mL in samples spiked into 50 individual healthy patient blood samples; (iii) at least 95% correct detection less than or equal to 5 cells/mL in samples spiked into 50 individual unhealthy patient blood samples; and/or (iv) greater than or equal to 80% correct detection in clinically positive patient samples (i.e., *Candida* positive by another technique, such as by cell culture) starting with 2 mL of blood.

This application claims priority to U.S. application Ser. No. 12/910,594, filed Oct. 22, 2010, and claims benefit of U.S. Provisional Patent Application No. 61/414,141, filed Nov. 16, 2010, U.S. Provisional Patent Application No. 61/418,465, filed Dec. 1, 2010, and U.S. Provisional Patent Application No. 61/497,374, filed Jun. 15, 2011, each of which is incorporated herein by reference.

Other Embodiments

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A method of detecting a pathogen in a whole blood sample, said method comprising the following steps:
   (a) contacting a whole blood sample obtained from a subject with an erythrocyte lysis agent, thereby lysing red blood cells;
   (b) centrifuging the product of step (a) to form a supernatant and a pellet;
   (c) discarding some or all of the supernatant of step (b) and resuspending the pellet to form an extract, optionally washing the pellet prior to resuspending the pellet, and optionally repeating the centrifuging, discarding, and resuspending steps of (b) and (c);
   (d) combining the extract of step (c) with beads to form a mixture and agitating the mixture to form a lysate, said lysate containing both subject cell nucleic acid and pathogen nucleic acid;
   (e) amplifying a target nucleic acid in said lysate of step (d) specific to said pathogen by polymerase chain reaction (PCR) to form an amplified lysate solution;
   (f) following step (e), adding to the amplified lysate solution from $1\times10^6$ to $1\times10^{13}$ magnetic particles per milliliter of the amplified lysate solution to form a detection mixture, wherein the magnetic particles have a mean diameter of from 700 nm to 950 nm and binding moieties on their surface, the binding moieties operative to alter aggregation of the magnetic particles in the presence of the target nucleic acid, wherein said magnetic particles have a T2 relaxivity per particle of from $1\times10^9$ to $1\times10^{12}$ mM$^{-1}$s$^{-1}$;
   (g) exposing the detection mixture to a bias magnetic field and an RF pulse sequence, thereby producing a signal;
   (h) following step (g), measuring the signal from the detection mixture; and
   (i) on the basis of the result of step (h), detecting the target nucleic acid, thereby determining whether the pathogen was present in the sample.

2. The method of claim 1, wherein said amplification of step (e) is carried out in the presence of whole blood proteins and non-target oligonucleotides.

3. The method of claim 1, wherein said pathogen is a fungal pathogen.

4. The method of claim 3, wherein said fungal pathogen is a species of *Candida*.

5. The method of claim 4, wherein the species of *Candida* is *Candida glabrata*.

6. The method of claim 1, wherein said detection occurs within four hours of step (a).

7. The method of claim 1, wherein the pellet of step (b) comprises white blood cells suspected of containing the pathogen.

8. The method of claim 1, wherein said sample is between 1.25 and 4 mL.

9. The method of claim 8, wherein said sample is between 1.25 and 2 mL.

10. The method of claim 1, wherein step (h) comprises measuring the $T_2$ relaxation response of the detection mixture, and wherein increasing agglomeration in the detection mixture produces an increase in the observed $T_2$ relaxation time of the detection mixture.

11. The method of claim 1, wherein the magnetic particles are substantially monodisperse.

12. The method of claim 1, wherein the magnetic particles comprise two populations, a first population bearing a first probe on its surface, and a second population bearing a second probe on its surface, the first probe operative to bind a first segment of the amplified target nucleic acid and the second probe operative to bind a second segment of the amplified target nucleic acid, wherein the magnetic particles form aggregates in the presence of the amplified target nucleic acid.

13. The method of claim 1, wherein the magnetic particles have a mean particle diameter of between 700 and 850 nm.

14. The method of claim 1, wherein the pathogen is a bacterial pathogen.

15. The method of claim 14, wherein the bacterial pathogen is a bacterium selected from *Acinetobacter* sp., *Bacteroides fragilis*, *Burkholderia cepacia*, *Campylobacter jejuni/coli*, *Clostridium pefringens*, coagulase-negative *Staphylococcus* sp., *Enterobacter aeraogenes*, *Enterobacter cloacae*, Enterobacteriaceae, *Enterococcus faecalis*, *Enterococcus faecium*, *Escherichia coli*, *Haemophilus influenzae*, *Kingella kingae*, *Klebsiella oxytoca*, *Klebsiella pneumoniae*, *Listeria monocytogenes*, Methicillin-resistant *Staphylococcus aureus* (MRSA), *Morganella morganii*, *Neisseria meningitidis*, non-*meningitidis Neisseria* sp., *Prevotella buccae*, *Prevotella intermedia*, *Prevotella melaninogenica*, *Propionibacterium acnes*, *Proteus mirabilis*, *Proteus vulgaris*, *Pseudomonas aeruginosa*, *Salmonella enterica*, *Serratia marcescens*, *Staphylococcus aureus*, *Staphylococcus haemolyticus*, *Stenotrophomonas maltophilia*, *Staphylococcus saprophyticus*, *Streptococcus agalactie*, *Streptococcus bovis*, *Streptococcus dysgalactiae*, *Streptococcus mitis*, *Streptococcus mutans*, *Streptococcus pneumoniae*, *Streptococcus pyogenes*, and *Streptococcus sanguinis*.

16. The method of claim 14, wherein the bacterial pathogen is *Borrelia burgdorferi*.

17. The method of claim 15, wherein the bacterium is selected from the group consisting of *Enterococcus faecalis*, *Enterococcus faecium*, *Staphylococcus aureus*, *Klebsiella pneumoniae*, *Acinetobacter* sp., and *Pseudomonas aeruginosa*.

18. The method of claim 15, wherein the bacterium is *Escherichia coli*.

* * * * *

SEQUENCE LISTING

<160> NUMBER OF SEQ ID NOS: 39

<210> SEQ ID NO 1
<211> LENGTH: 20
<212> TYPE: DNA
<213> ORGANISM: Artificial Sequence
<220> FEATURE:
<223> OTHER INFORMATION: Pan Candida- PCR Forward Primer

<400> SEQUENCE: 1
ggcatgcctg tttgagcgtc                                          20

<210> SEQ ID NO 2
<211> LENGTH: 29
<212> TYPE: DNA
<213> ORGANISM: Artificial Sequence
<220> FEATURE:
<223> OTHER INFORMATION: Pan Candida- PCR Reverse Primer

<400> SEQUENCE: 2
gcttattgat atgcttaagt tcagcgggt                                29

<210> SEQ ID NO 3
<211> LENGTH: 23
<212> TYPE: DNA
<213> ORGANISM: Artificial Sequence
<220> FEATURE:
<223> OTHER INFORMATION: Candida albicans Probe #1

<400> SEQUENCE: 3
acccagcggt ttgagggaga aac                                      23

<210> SEQ ID NO 4
<211> LENGTH: 30
<212> TYPE: DNA
<213> ORGANISM: Artificial Sequence
<220> FEATURE:
<223> OTHER INFORMATION: Candida albicans Probe #2

<400> SEQUENCE: 4
aaagtttgaa gatatacgtg gtggacgtta                               30

<210> SEQ ID NO 5
<211> LENGTH: 21
<212> TYPE: DNA
<213> ORGANISM: Artificial Sequence
<220> FEATURE:
<223> OTHER INFORMATION: Candida krusei Probe #1

<400> SEQUENCE: 5
cgcacgcgca agatggaaac g                                        21

<210> SEQ ID NO 6
<211> LENGTH: 23
<212> TYPE: DNA
<213> ORGANISM: Artificial Sequence
<220> FEATURE:
<223> OTHER INFORMATION: Candida krusei Probe #2

<400> SEQUENCE: 6
aagttcagcg ggtattccta cct                                      23

<210> SEQ ID NO 7
<211> LENGTH: 26
<212> TYPE: DNA
<213> ORGANISM: Artificial Sequence
<220> FEATURE:
<223> OTHER INFORMATION: Candida glabrata Probe #1

<400> SEQUENCE: 7
ctaccaaaca caatgtgttt gagaag                                   26

<210> SEQ ID NO 8

```
<211> LENGTH: 31
<212> TYPE: DNA
<213> ORGANISM: Artificial Sequence
<220> FEATURE:
<223> OTHER INFORMATION: Candida glabrata Probe #2

<400> SEQUENCE: 8
cctgatttga ggtcaaactt aaagacgtct g                               31

<210> SEQ ID NO 9
<211> LENGTH: 24
<212> TYPE: DNA
<213> ORGANISM: Artificial Sequence
<220> FEATURE:
<223> OTHER INFORMATION: Candida parapsilosis/tropicalis Probe #1
<220> FEATURE:
<221> NAME/KEY: misc_feature
<222> LOCATION: (22)..(22)
<223> OTHER INFORMATION: n is 5' 5-Nitroindole

<400> SEQUENCE: 9
agtcctacct gatttgaggt cnaa                                       24

<210> SEQ ID NO 10
<211> LENGTH: 21
<212> TYPE: DNA
<213> ORGANISM: Artificial Sequence
<220> FEATURE:
<223> OTHER INFORMATION: Candida parapsilosis/tropicalis Probe #2
<220> FEATURE:
<221> NAME/KEY: misc_feature
<222> LOCATION: (4)..(4)
<223> OTHER INFORMATION: n is 5' 5-Nitroindole

<400> SEQUENCE: 10
ccgngggttt gagggagaaa t                                          21

<210> SEQ ID NO 11
<211> LENGTH: 25
<212> TYPE: DNA
<213> ORGANISM: Artificial Sequence
<220> FEATURE:
<223> OTHER INFORMATION: universal tail probe #1

<400> SEQUENCE: 11
catgatctgc tggagtctga cgtta                                      25

<210> SEQ ID NO 12
<211> LENGTH: 21
<212> TYPE: DNA
<213> ORGANISM: Artificial Sequence
<220> FEATURE:
<223> OTHER INFORMATION: universal tail probe #2

<400> SEQUENCE: 12
gcagatctcc tcaatgcggc g                                          21

<210> SEQ ID NO 13
<211> LENGTH: 21
<212> TYPE: DNA
<213> ORGANISM: Artificial Sequence
<220> FEATURE:
<223> OTHER INFORMATION: CMV US8 forward primer

<400> SEQUENCE: 13
cgtgccaccg cagatagtaa g                                          21
```

```
<210> SEQ ID NO 14
<211> LENGTH: 24
<212> TYPE: DNA
<213> ORGANISM: Artificial Sequence
<220> FEATURE:
<223> OTHER INFORMATION: CMV US8 reverse primer

<400> SEQUENCE: 14
gaatacagac acttagagct cggg                                             24

<210> SEQ ID NO 15
<211> LENGTH: 200
<212> TYPE: DNA
<213> ORGANISM: Artificial Sequence
<220> FEATURE:
<223> OTHER INFORMATION: Synthetic Construct

<400> SEQUENCE: 15
ggcatgcctg tttgagcgtc ctgcatcata ctgaaataga tccttcgaca acctcggtac      60
actgggaaca aggcctcaaa cattgatgct cgactacacg tagggcaatg cgtcttgcta     120
gaagcgaaat ctgtggcttg ctagtgcaag ctggtcggcg tattattcca acccgctgaa     180
cttaagcata tcaataagca                                                 200

<210> SEQ ID NO 16
<211> LENGTH: 200
<212> TYPE: DNA
<213> ORGANISM: Artificial Sequence
<220> FEATURE:
<223> OTHER INFORMATION: Synthetic Construct

<400> SEQUENCE: 16
gcttattgat atgcttaagt tcagcgggtt ggaataatac gccgaccagc ttgcactagc      60
aagccacaga tttcgcttct agcaagacgc attgccctac gtgtagtcga gcatcaatgt     120
ttgaggcctt gttcccagtg taccgaggtt gtcgaaggat ctatttcagt atgatgcagg     180
acgctcaaac aggcatgcca                                                 200

<210> SEQ ID NO 17
<211> LENGTH: 42
<212> TYPE: DNA
<213> ORGANISM: Artificial Sequence
<220> FEATURE:
<223> OTHER INFORMATION: Synthetic Construct

<400> SEQUENCE: 17
ggttgtcgaa ggatctattt cagtatgatg cagttttttt tt                         42

<210> SEQ ID NO 18
<211> LENGTH: 38
<212> TYPE: DNA
<213> ORGANISM: Artificial Sequence
<220> FEATURE:
<223> OTHER INFORMATION: Synthetic Construct

<400> SEQUENCE: 18
tttttttttt ggaataatac gccgaccagc ttgcacta                              38

<210> SEQ ID NO 19
<211> LENGTH: 36
<212> TYPE: DNA
<213> ORGANISM: Artificial Sequence
<220> FEATURE:
<223> OTHER INFORMATION: Pan Candida F Uni-Tail
<220> FEATURE:
```

<221> NAME/KEY: misc_feature
<222> LOCATION: (16)..(16)
<223> OTHER INFORMATION: n is isp18

<400> SEQUENCE: 19
catgatctgc tgcagnggca tgcctgtttg agcgtc                                36

<210> SEQ ID NO 20
<211> LENGTH: 45
<212> TYPE: DNA
<213> ORGANISM: Artificial Sequence
<220> FEATURE:
<223> OTHER INFORMATION: Pan Candida R Uni-Tail
<220> FEATURE:
<221> NAME/KEY: misc_feature
<222> LOCATION: (16)..(16)
<223> OTHER INFORMATION: n is iSp18

<400> SEQUENCE: 20
gcagaactcc agaccngctt attgatatgc ttaagttcag cgggt                      45

<210> SEQ ID NO 21
<211> LENGTH: 28
<212> TYPE: DNA
<213> ORGANISM: Artificial Sequence
<220> FEATURE:
<223> OTHER INFORMATION: 3'AM universal tail CP
<220> FEATURE:
<221> NAME/KEY: misc_feature
<222> LOCATION: (28)..(28)
<223> OTHER INFORMATION: n is 3AmMO

<400> SEQUENCE: 21
ctgcagcaga tcatgttttt tttttttn                                         28

<210> SEQ ID NO 22
<211> LENGTH: 28
<212> TYPE: DNA
<213> ORGANISM: Artificial Sequence
<220> FEATURE:
<223> OTHER INFORMATION: Fluorinated 3'AM uni CP
<220> FEATURE:
<221> NAME/KEY: misc_feature
<222> LOCATION: (4)..(4)
<223> OTHER INFORMATION: n is i2fc
<220> FEATURE:
<221> NAME/KEY: misc_feature
<222> LOCATION: (7)..(7)
<223> OTHER INFORMATION: n is i2fc
<220> FEATURE:
<221> NAME/KEY: misc_feature
<222> LOCATION: (10)..(10)
<223> OTHER INFORMATION: n is i2fa
<220> FEATURE:
<221> NAME/KEY: misc_feature
<222> LOCATION: (13)..(13)
<223> OTHER INFORMATION: n is i2fa
<220> FEATURE:
<221> NAME/KEY: misc_feature
<222> LOCATION: (28)..(28)
<223> OTHER INFORMATION: n is 3AmMO

<400> SEQUENCE: 22
ctgnagnagn tcntgttttt tttttttn                                         28

<210> SEQ ID NO 23
<211> LENGTH: 28
<212> TYPE: DNA
<213> ORGANISM: Artificial Sequence
<220> FEATURE:
<223> OTHER INFORMATION: Fluorinated 5'AM uni CP

```
<220> FEATURE:
<221> NAME/KEY: misc_feature
<222> LOCATION: (1)..(1)
<223> OTHER INFORMATION: n is 5AmMC12
<220> FEATURE:
<221> NAME/KEY: misc_feature
<222> LOCATION: (17)..(17)
<223> OTHER INFORMATION: n is i2FC
<220> FEATURE:
<221> NAME/KEY: misc_feature
<222> LOCATION: (20)..(20)
<223> OTHER INFORMATION: n is i2FG
<220> FEATURE:
<221> NAME/KEY: misc_feature
<222> LOCATION: (23)..(23)
<223> OTHER INFORMATION: n is i2FU

<400> SEQUENCE: 23
nttttttttt tttggtntgn agntctgc                                          28

<210> SEQ ID NO 24
<211> LENGTH: 25
<212> TYPE: DNA
<213> ORGANISM: Artificial Sequence
<220> FEATURE:
<223> OTHER INFORMATION: C. albicans ITS2 Reverse P

<400> SEQUENCE: 24
ccgtctttca agcaaaccca agtcg                                             25

<210> SEQ ID NO 25
<211> LENGTH: 20
<212> TYPE: DNA
<213> ORGANISM: Artificial Sequence
<220> FEATURE:
<223> OTHER INFORMATION: C. albicans ITS2 Forward P

<400> SEQUENCE: 25
tttctccctc aaaccgctgg                                                   20

<210> SEQ ID NO 26
<211> LENGTH: 37
<212> TYPE: DNA
<213> ORGANISM: Artificial Sequence
<220> FEATURE:
<223> OTHER INFORMATION: C. alb ITS2 CP1
<220> FEATURE:
<221> NAME/KEY: misc_feature
<222> LOCATION: (1)..(1)
<223> OTHER INFORMATION: n is 5ammc12

<400> SEQUENCE: 26
nttttttttt tttttggtt tggtgttgag caatacg                                 37

<210> SEQ ID NO 27
<211> LENGTH: 34
<212> TYPE: DNA
<213> ORGANISM: Artificial Sequence
<220> FEATURE:
<223> OTHER INFORMATION: C.alb ITS2 CP2
<220> FEATURE:
<221> NAME/KEY: misc_feature
<222> LOCATION: (1)..(1)
<223> OTHER INFORMATION: n is 5ammc12

<400> SEQUENCE: 27
nttttttttt tttcgtattg ctcaacacca aacc                                   34

<210> SEQ ID NO 28
```

<211> LENGTH: 44
<212> TYPE: DNA
<213> ORGANISM: Artificial Sequence
<220> FEATURE:
<223> OTHER INFORMATION: C.alb ITS2 Long CP1
<220> FEATURE:
<221> NAME/KEY: misc_feature
<222> LOCATION: (1)..(1)
<223> OTHER INFORMATION: n is 5ammc12

<400> SEQUENCE: 28 ntttttttttt tttttttaccg ctgggtttgg tgttgagcaa tacg            44

<210> SEQ ID NO 29
<211> LENGTH: 44
<212> TYPE: DNA
<213> ORGANISM: Artificial Sequence
<220> FEATURE:
<223> OTHER INFORMATION: C.alb ITS2 Long CP2
<220> FEATURE:
<221> NAME/KEY: misc_feature
<222> LOCATION: (1)..(1)
<223> OTHER INFORMATION: n is 5ammc12

<400> SEQUENCE: 29 ntttttttttt tttttttaccg ctgggtttgg tgttgagcaa tacg            44

<210> SEQ ID NO 30
<211> LENGTH: 34
<212> TYPE: DNA
<213> ORGANISM: Artificial Sequence
<220> FEATURE:
<223> OTHER INFORMATION: C.alb ITS2 mut 3 CP1
<220> FEATURE:
<221> NAME/KEY: misc_feature
<222> LOCATION: (1)..(1)
<223> OTHER INFORMATION: 5ammc12

<400> SEQUENCE: 30 ntttttttttt tttggtttgg cgtagagcca tacg            34

<210> SEQ ID NO 31
<211> LENGTH: 34
<212> TYPE: DNA
<213> ORGANISM: Artificial Sequence
<220> FEATURE:
<223> OTHER INFORMATION: C.alb ITS2 mut 4 CP1
<220> FEATURE:
<221> NAME/KEY: misc_feature
<222> LOCATION: (1)..(1)
<223> OTHER INFORMATION: n is 5ammc12

<400> SEQUENCE: 31 ntttttttttt tttggtctgg cgtagagcca tacg            34

<210> SEQ ID NO 32
<211> LENGTH: 27
<212> TYPE: DNA
<213> ORGANISM: Artificial Sequence
<220> FEATURE:
<223> OTHER INFORMATION: Candida Krusei probe

<400> SEQUENCE: 32 agcttttttgt tgtctcgcaa cactcgc            27

<210> SEQ ID NO 33
<211> LENGTH: 33
<212> TYPE: DNA
<213> ORGANISM: Candida tropicalis

<400> SEQUENCE: 33
aaagttatga aataaattgt ggtggccact agc                          33

<210> SEQ ID NO 34
<211> LENGTH: 22
<212> TYPE: DNA
<213> ORGANISM: Candida tropicalis

<400> SEQUENCE: 34
acccgggggt ttgagggaga aa                                      22

<210> SEQ ID NO 35
<211> LENGTH: 24
<212> TYPE: DNA
<213> ORGANISM: Candida parapsilosis

<400> SEQUENCE: 35
agtcctacct gatttgaggt cgaa                                    24

<210> SEQ ID NO 36
<211> LENGTH: 21
<212> TYPE: DNA
<213> ORGANISM: Candida parapsilosis

<400> SEQUENCE: 36
ccgagggttt gagggagaaa t                                       21

<210> SEQ ID NO 37
<211> LENGTH: 28
<212> TYPE: DNA
<213> ORGANISM: Artificial Sequence
<220> FEATURE:
<223> OTHER INFORMATION: inhibition control 5'

<400> SEQUENCE: 37
ggaataatac gccgaccagc ttgcacta                                28

<210> SEQ ID NO 38
<211> LENGTH: 33
<212> TYPE: DNA
<213> ORGANISM: Artificial Sequence
<220> FEATURE:
<223> OTHER INFORMATION: inhibition control 3'

<400> SEQUENCE: 38
ggttgtcgaa ggatctattt cagtatgatg cag                          33

<210> SEQ ID NO 39
<211> LENGTH: 28
<212> TYPE: DNA
<213> ORGANISM: Artificial Sequence
<220> FEATURE:
<223> OTHER INFORMATION: 5'AM universal tail CP
<220> FEATURE:
<221> NAME/KEY: misc_feature
<222> LOCATION: (1)..(1)
<223> OTHER INFORMATION: n is 5ammc6

<400> SEQUENCE: 39
nttttttttt tttggtctgg agttctgc                                28